US010450354B2

(12) United States Patent
Poma et al.

(10) Patent No.: US 10,450,354 B2
(45) Date of Patent: Oct. 22, 2019

(54) CD20-BINDING IMMUNOTOXINS FOR INDUCING CELLULAR INTERNALIZATION AND METHODS USING SAME

(71) Applicant: Molecular Templates, Inc., Georgetown, TX (US)

(72) Inventors: Eric Poma, New York, NY (US); Erin Willert, Round Rock, TX (US); Jason Kim, Austin, TX (US); Jack Higgins, Georgetown, TX (US); Sangeetha Rajagopalan, Round Rock, TX (US)

(73) Assignee: Molecular Templates, Inc., Austin, TX (US)

( * ) Notice: Subject to any disclaimer, the term of this patent is extended or adjusted under 35 U.S.C. 154(b) by 347 days.

(21) Appl. No.: 14/774,609

(22) PCT Filed: Mar. 11, 2014

(86) PCT No.: PCT/US2014/023198
§ 371 (c)(1),
(2) Date: Sep. 10, 2015

(87) PCT Pub. No.: WO2014/164680
PCT Pub. Date: Oct. 9, 2014

(65) Prior Publication Data

US 2016/0017047 A1 Jan. 21, 2016

Related U.S. Application Data

(60) Provisional application No. 61/777,130, filed on Mar. 12, 2013.

(51) Int. Cl.

| | |
|---|---|
| *C07K 16/28* | (2006.01) |
| *A61K 38/00* | (2006.01) |
| *C07K 14/25* | (2006.01) |
| *C07K 16/08* | (2006.01) |
| *C07K 16/20* | (2006.01) |
| *C07K 16/30* | (2006.01) |
| *C07K 16/32* | (2006.01) |
| *C07K 14/245* | (2006.01) |
| *C07K 16/40* | (2006.01) |
| *A61K 39/00* | (2006.01) |

(52) U.S. Cl.
CPC ............ *C07K 14/25* (2013.01); *C07K 14/245* (2013.01); *C07K 16/085* (2013.01); *C07K 16/20* (2013.01); *C07K 16/2863* (2013.01); *C07K 16/2866* (2013.01); *C07K 16/2887* (2013.01); *C07K 16/2896* (2013.01); *C07K 16/30* (2013.01); *C07K 16/32* (2013.01); *C07K 16/40* (2013.01); *A61K 38/00* (2013.01); *A61K 2039/505* (2013.01); *C07K 2317/56* (2013.01); *C07K 2317/569* (2013.01); *C07K 2317/622* (2013.01); *C07K 2317/73* (2013.01); *C07K 2317/77* (2013.01); *C07K 2317/92* (2013.01); *C07K 2319/00* (2013.01); *C07K 2319/33* (2013.01); *C07K 2319/55* (2013.01)

(58) Field of Classification Search
CPC ................ C07K 16/2887; C07K 16/46; C07K 2317/622; C07K 2319/55; C07K 2319/56; C07K 2319/33; C07K 2317/73; C07K 2317/77; C07K 2319/00; A61K 2039/505; A61K 38/00
See application file for complete search history.

(56) References Cited

U.S. PATENT DOCUMENTS

| | | | |
|---|---|---|---|
| 5,668,255 | A | 9/1997 | Murphy |
| 6,022,950 | A | 2/2000 | Murphy |
| 7,267,973 | B2 | 9/2007 | Backer |
| 7,527,787 | B2 | 5/2009 | Chang |
| 7,700,557 | B2 | 4/2010 | Backer |
| 7,713,915 | B1 | 5/2010 | Gariepy |

(Continued)

FOREIGN PATENT DOCUMENTS

| | | |
|---|---|---|
| GB | 2519786 | 5/2015 |
| JP | 2001500730 | 1/2001 |

(Continued)

OTHER PUBLICATIONS

Paul, Fundamental Immunology, (textbook), pp. 292-295 (Year: 1993).*

(Continued)

*Primary Examiner* — Phuong Huynh
(74) *Attorney, Agent, or Firm* — Nixon Peabody LLP; Mark J. FitzGerald; Teresa A. Ptashka

(57) ABSTRACT

The present invention provides CD20-binding proteins that bind to and rapidly internalize CD20 antigens from a cell surface location to the interior of a cell. CD20-binding proteins of the invention comprise a CD20 binding region and a Shiga toxin effector region. Certain of the disclosed CD20-binding proteins kill cells that express CD20 on their surface. Further, the presently disclosed CD20-binding proteins can comprise additional exogenous materials and are capable of targeted delivery of these additional exogenous materials into the interior of CD20 expressing cells. Such additional materials may include peptides, antigens, enzymes, and polynucleotides. These CD20-binding proteins have uses in methods of internalizing themselves, targeted killing of CD20 expressing cells, delivering exogenous materials into CD20 expressing cells, and treating a variety of diseases involving CD20 expressing cells, such as cancers and immune disorders.

40 Claims, 6 Drawing Sheets

Specification includes a Sequence Listing.

(56) References Cited

U.S. PATENT DOCUMENTS

| | | | |
|---|---|---|---|
| 8,147,832 | B2 | 4/2012 | Carr |
| 2002/0168370 | A1 | 11/2002 | McDonald |
| 2003/0166196 | A1 | 9/2003 | Better |
| 2004/0166565 | A1 | 8/2004 | Backer |
| 2005/0054835 | A1 | 3/2005 | Better |
| 2005/0069545 | A1 | 3/2005 | Carr |
| 2009/0023649 | A1 | 1/2009 | Backer |
| 2012/0251542 | A1 | 10/2012 | Turner |
| 2015/0259428 | A1 | 9/2015 | Poma et al. |

FOREIGN PATENT DOCUMENTS

| | | |
|---|---|---|
| JP | 2002544173 | 12/2002 |
| JP | 2003531588 | 10/2003 |
| JP | 2008533977 | 8/2008 |
| JP | 2009502936 | 1/2009 |
| JP | 2012044997 | 3/2012 |
| JP | 2012070737 | 4/2012 |
| KR | 2011-0033233 | 3/2011 |
| KR | 2011-0119725 | 11/2011 |
| WO | WO-1991009871 | 7/1991 |
| WO | WO-1994026910 | 11/1994 |
| WO | WO-1998011229 | 3/1998 |
| WO | WO-2000004926 | 2/2000 |
| WO | WO-2000067795 | 11/2000 |
| WO | 2001/077342 | 3/2001 |
| WO | WO-2001070945 | 9/2001 |
| WO | WO 03/066854 | 8/2003 |
| WO | WO-2004056312 | 7/2004 |
| WO | WO-2004058158 | 7/2004 |
| WO | WO-2005016969 | 2/2005 |
| WO | WO-2005092917 | 10/2005 |
| WO | WO-2006099875 | 9/2006 |
| WO | WO-2007014238 | 2/2007 |
| WO | WO-2007033497 | 3/2007 |
| WO | WO-2008080218 | 8/2008 |
| WO | WO-2009032954 | 3/2009 |
| WO | WO-2009064815 | 5/2009 |
| WO | WO-2010011697 | 1/2010 |
| WO | WO-2010085539 | 7/2010 |
| WO | WO-2011009624 | 1/2011 |
| WO | WO-2012022985 | 2/2012 |
| WO | WO-2012093158 | 7/2012 |
| WO | WO-2012101235 | 8/2012 |
| WO | WO-2012104344 | 8/2012 |
| WO | WO-2012154530 | 11/2012 |
| WO | WO-2013080147 | 6/2013 |
| WO | WO-2014164693 | 10/2014 |
| WO | WO-2015113005 | 7/2015 |
| WO | WO-2015113007 | 7/2015 |
| WO | WO-2015120058 | 8/2015 |
| WO | WO-2015138435 | 9/2015 |
| WO | WO-2015138452 | 9/2015 |

OTHER PUBLICATIONS

Rudikoff et al., Proc. Natl. Acad. Sci. USA vol. 79 p. 1979 (Year: 1982).*

Wargalla et al., Proc Natl. Acad. Sci. USA 86: 5146-5150 (Year: 1989).*

Yu et al., Investigative Ophthalmology & Visual Science 49(2): 522-527 (Year: 2008).*

Jubala et al., Vet Pathol 42: 468-476, 2005 (Year: 2005).*

Beers, SA, et al., "CD20 as a Target for Therapeutic Type I and II Monoclonal Antibodies", Seminars in Hematology, 47(2), (2010), 107-114.

Cao, Y, et al., "Design optimization and characterization of Her2/neu-targeted immunotoxins: comparative in vitro and in vivo efficacy studies", Oncogene, 33(4), (2014), 429-439.

Hexham, JM, et al., "Influence of relative binding affinity on efficacy in a panel of anti-CD3 scFv immunotoxins", Molecular Immunology, 38(5), (2001), 397-408.

Lyu, MA, et al., Cell-Targeting Fusion Constructs Containing Recombinant Gelonin, Methods in Enzymology, 502, (2012), 167-214.

Ewers, H., and Helenius, A., "Lipid-Mediated Endocytosis", Cold Spring Harbor Perspectives in Biology 3 (8), (2011), 1-14.

Burgess, BJ, et al., "Proteolytic cleavage at arginine residues within the hydrophilic disulphide loop of the Escherichia coli Shiga-like toxin I A subunit is not essential for cytotoxicity", Molecular Microbiology, 10(1), (1993), 171-179.

Lea, N, et al., "Proteolytic cleavage of the a subunit is essential for maximal cytotoxicity of Escherichia coli O157:H7 Shiga-like toxin-1", Microbiology, 145(5), (1999), 999-1004.

Gannon, VP, et al., "Molecular cloning and nucleotide sequence of another variant of the Escherichia coli Shiga-like toxin II family", Journal of General Microbiology 136(6), (1990), 1125-1135.

Casalini, P., et al., "Use of Combination of Monoclonal Antibodies Directed Against Three Distinct Epitopes of a Tumor-Associated Antigen: Analysis of Cell Binding and Internalization", International Journal of Cancer 48 (2), (1991), 284-290.

Ackerman, R, et al., "SLT-VEGF Reduces Lung Metastases, Decreases Tumor Recurrence, and Improves Survival in an Orthotopic Melanoma Model", Toxins (Basel), 2(9), (2010), 224-257.

Al-Jaufy, AY, et al., "Cytotoxicity of a Shiga Toxin A Subunit-CD4 Fusion Protein to Human Immunodeficiency Virus-Infected Cells", Infection and Immunity, 62(3), (1994), 956-960.

Al-Jaufy, AY, et al., "Purification and Characterization of a Shiga Toxin A Subunit-CD4 Fusion Protein Cytotoxic to Human Immunodeficiency Virus-Infected Cells", Infection and Immunity, 63(8), (1995), 3073-3078.

Backer, MV, et al., "Shiga-like toxin-VEGF fusion proteins are selectively cytotoxic to endothelial cells overexpressing VEGFR-2", Journal of Controlled Release, 74(1-3), (2001), 349-355.

Backer, MV, Backer JM, "Targeting Endothelial Cells Overexpressing VEGFR-2: Selective Toxicity of Shiga-like Toxin—VEGF Fusion Proteins", Bioconjugate Chemistry, 12(6), (2001), 1066-1073.

Beers, SA, et al., "Type II (tositumomab) anti-CD20 monoclonal antibody out performs type I (rituximab-like) reagents in B-cell depletion regardless of complement activation", Blood, 112, (2008), 4170-4177.

Beers, SA, et al., "Antigenic modulation limits the efficacy of anti-CD20 antibodies: implications for antibody selection", Blood, 115(25), (2010), 5191-5201.

Beum, PV, et al., "The Shaving Reaction: Rituximab/CD20 Complexes Are Removed from Mantle Cell Lymphoma and Chronic Lymphocytic Leukemia Cells by THP-1 Monocytes", Journal of Immunology, 176(4), (2006), 2600-2609.

Beum, PV, et al., "Loss Of CD20 and Bound CD20 Antibody from Opsonized B Cells Occurs More Rapidly Because Of Trogocytosis Mediated by Fc Receptor-Expressing Effector Cells Than Direct Internalization by the B Cells", Journal of Immunology, 187(6), (2011), 3438-3447.

Boross, P, et al., "Both activating and inhibitory Fc gamma receptors mediate rituximab-induced trogocytosis of CD20 in mice", Immunology Letters, 143(1), (2012), 44-52.

Boross, P, et al., "Mechanisms of action of CD20 antibodies", American Journal of Cancer Research, 2(6), (2012), 676-690.

Braslawsky, GR, et al., "Adriamycin(hydrazone)-antibody conjugates require internalization and intracellular acid hydrolysis for antitumor activity", Cancer Immunology, Immunotherapy 33, (1991), 367-374.

Cheung, MC, et al., "An evolved ribosome-inactivating protein targets and kills human melanoma cells in vitro and in vivo", Molecular Cancer, 9(28), (2010).

Cizeau, JPA, et al., "8th Fabisch-Symposium, 3rd Targeted Tumor Therapies, Berlin 2012", Mar. 21, 2012.

Cragg, MS, et al., "Apparent modulation of CD20 by rituximab: an alternative explanation", Blood, 103(10), (2004), 3989-3990.

Goulet, AC, et al., "Conjugation of Blocked Ricin to an Anti-CD19 Monoclonal Antibody Increases Antibody-Induced Cell Calcium Mobilization and CD19 Internalization", Blood, 90(6), (1995), 2364-2375.

(56) References Cited

OTHER PUBLICATIONS

Hiraga, J, et al., "Down-regulation of CD20 expression in B-cell lymphoma cells after treatment with rituximab-containing combination chemotherapies: its prevalence and clinical significance", Blood, 113(20), (2009), 4885-4893.

Hotz, B, et al., "Specific Targeting of Tumor Endothelial Cells by a Shiga-like Toxin-Vascular Endothelial Growth Factor Fusion Protein as a Novel Treatment Strategy for Pancreatic Cancer", Neoplasia, 12(10), (2010), 797-806.

"International Application Serial No. PCT/US2014/023231, International Search Report dated Oct. 24, 2014 and published Dec. 4, 2014", 3 pgs.

"International Application Serial No. PCT/US2014/023231, Written Opinion dated Oct. 24, 2014", 4 pgs.

Jilani, I, et al., "Transient down-modulation of CD20 by rituximab in patients with chronic lymphocytic leukemia", Blood, 102(10), (2003), 3514-3520.

Jilani, I, et al., "Anti-idiotype versus anti-mouse Ig for detecting rituximab", Blood, 103(10), (2004), 3990.

Lambert, J, et al., "Purified Immunotoxins That Are Reactive with Human Lymphoid Cells: Monoclonal antibodies conjugated to the ribosome-inactivating proteins gelonin and the pokeweed antiviral proteins", Journal of Biological Chemistry, 260(22), (1985), 12035-12041.

Law, CL, et al., "Efficient Elimination of B-Lineage Lymphomas by Anti-CD20-Auristatin Conjugates", Clinical Cancer Research, 10(23), (2004), 7842-7851.

Li, H, et al., "The CD20 Calcium Channel Is Localized to Microvilli and Constitutively Associated with Membrane Rafts: Antibody binding increases the affinity of the association through an epitope-dependent cross-linking-independent mechanism", Journal of Biological Chemistry, 279(19), (2004), 19893-19901.

Lim, SH, et al., "Fc gamma receptor IIb on target B cells promotes rituximab internalization and reduces clinical efficacy", Blood, 118(9), (2011), 2530-2540.

Luqman, M, et al., "The antileukemia activity of a human anti-CD40 antagonist antibody, HCD122, on human chronic lymphocytic leukemia cells", Blood, 112(3), (2008), 711-720.

Michel, RB, et al., "Intracellular Accumulation of the Anti-CD20 Antibody 1F5 in B-Lymphoma cells", Clinical Cancer Research, 8(8), (2002), 2701-2713.

Noakes, K, et al., "Exploiting retrograde transport of Shiga-like toxin 1 for the delivery of exogenous antigens into the MHC class I presentation pathway", FEBS Letters 543, (1999) 95-99.

Oloomi, M, et al., "In vivo Characterization of Fusion Protein Comprising of A1 Subunit of Shiga Toxin and Human GM-CSF: Assessment of Its Immunogenicity and Toxicity", Iranian Biomedical Journal, 14(4), (2010), 136-141.
Pastan, I, et al., "Immunotoxin Treatment of Cancer", Annual Review of Medicine 58, (2007), 221-237.
Pirie, CM, et al., "Convergent Potency of Internalized Gelonin Immunotoxins across Varied Cell Lines, Antigens, and Targeting Moieties", Journal of Biological Chemistry, 286(6), (2011), 4165-4172.
Polito, L, et al., "The conjugate Rituximab/saporin-S6 completely inhibits clonogenic growth of CD20-expressing cells and produces a synergistic toxic effect with Fludarabine", Leukemia, 18(7), (2004), 1215-1222.
Polson, AG, et al., "Antibody-Drug Conjugates for the Treatment of Non-Hodgkin's Lymphoma: Target and Linker-Drug Selection", Cancer Research, 69(6), (Jan. 1, 2009), 2358-2364.
Poma, Eric, "Proteins Comprising Binding Regions, Shiga Toxin a Subunit Effector Regions, and Carboxy-Terminal, Endoplasmic Reticulum Localization Signal Motifs", International Application Serial No. PCT/US2015/019684, Filed on Mar. 10, 2015.
Poma, Eric, "Proteins Comprising Amino-Terminal Proximal Shiga Toxin a Subunit Effector Regions and Cell-Targeting Immunoglobulin-Type Binding Regions", International Application Serial No. PCT/US2015/019708, Filed Mar. 10, 2015.
Poma, Eric, "Protease-Cleavage Resistant, Shiga Toxin a Subunit Effector Polypeptides and Cell-Targeted Molecules Comprising the Same", International Application Serial No. PCT/US2015/035179, Filed on Jun. 10, 2015.
Press, OW, et al., "Endocytosis and Degradation of Monoclonal Antibodies Targeting Human B-Cell Malignancies", Cancer Research, 49(17), (1989), 4906-4912.
Press, OW, et al., "Retention of B-Cell—Specific Monoclonal Antibodies by Human Lymphoma Cells", Blood, 83(5), (1994), 1390-1397.
Protein ID ABM97743, European Molecular Biology Laboratory (EMBL), Oloomi, M, et al., "synthetic construct partial A1-GMCSF chimeric protein", Sep. 10, 2007.
Rajagopalan, S, et al., "CD2O-Specific Engineered Toxin Body Demonstrates Direct Cell Kill Of Multiple B-Cell Non-Hodgkin's Lymphoma Types", Blood, 122(21), (2013), 5152.
Rajagopalan, S, et al., "CD20-specific Engineered Toxin Body demonstrates direct cell kill of multiple B-cell Non-Hodgkin's lymphoma types", Proceedings: American Association for Cancer Research (AACR) Annual Meeting 2014, Abstract #647, (Apr. 5-9, 2014).
Roudkenar, MH, et al., "Selective cytotoxicity of recombinant STXA1-GM-CSF protein in hematopoetic cancer cells", Cell Biology and Toxicology, 22(3), (2006), 213-219.
Sieber, T, et al., "Selective internalization of monoclonal antibodies by B-cell chronic lymphocytic leukaemia cells", 121(3), (2003), 458-461.
Su, H, et al., "Clinical grade production and characterization of a fusion protein comprised of the chemokine CCL2-ligand genetically fused to a mutated and truncated form of the Shiga A1 subunit", Protein Expression and Purification, 66(2), (Jan. 1, 2009), 149-157.
Vallera, DA, et al., "Bioengineering a Unique Deimmunized Bispecific Targeted Toxin That Simultaneously Recognizes Human CD22 and CD19 Receptors in a Mouse Model of B-Cell Metastases", Molecular Cancer Therapeutics, 9(6), (2010), 1872-1883.
Wirth, R, et al., "Engineered Toxin Body demonstrating CD20-specific binding and cell kill in B-Cell Non-Hodgkin lymphoma vells", Proceedings: American Association for Cancer Research (AACR) 104th Annual Meeting 2013, Abstract #5477, (Apr. 6-10, 2013).
U.S. Appl. No. 14/965,882, filed Dec. 10, 2015, Molecular Templates, Inc.
Bera, TK, et al., "A Bivalent Disulfide-stabilized Fv with Improved Antigen Binding to erbB2", Journal of Molecular Biology, 281(3), (1998), 475-483.
Cuesta, AM, et al., "Multivalent antibodies: when design surpasses evolution", Trends in Biotechnology, 28(7), (2010), 355-362.
Hamlin, PA, et al., "Safety and Efficacy of Anti-CD20 Immunotoxin MT-3724 in Relapsed/Refractory B-cell Non-Hodgkin Lymphoma (NHL) in a Phase 1 Study", 2018 American Society of Clinical Oncology Annual Meeting, Abstract 7580, (Jun. 4, 2018).
Hooijberg, E, et al., "Characterization of a Series of Isotype Switch Variants of a New CD20 Monoclonal Antibody", Hybridoma 15(1), (1996), 23-31.
"U.S. Appl. No. 14/643,619, Office Action dated Jun. 27, 2018", 48 pgs.
Vervoordeldonk, SF, et al., "Preclinical Studies with Radiolabeled Monoclonal Antibodies for Treatment of Patients with B-Cell Malignancies", Cancer 73(3), (1994), 1006-1011.
Bevan, N., et al., Real-time 96-well antibody internalization assays using IncuCyte® FabFluor Red Antibody Labeling Reagent, Application Note, Sartorius, 2017 Essen BioScience.

* cited by examiner

Figure 1. Schematic Drawing of the General Architecture of Exemplary CD20-Binding Proteins

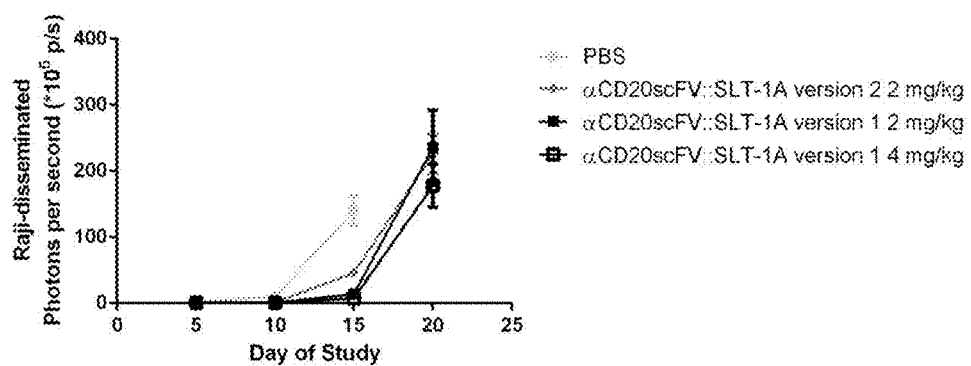
Figure 2. Disseminated Tumor Xenograft Results: Exemplary CD20-binding proteins reduced disseminated tumor volumes *in vivo*

Figure 3. Disseminated Tumor Xenograft Results: Exemplary CD20-binding proteins extended lifespan
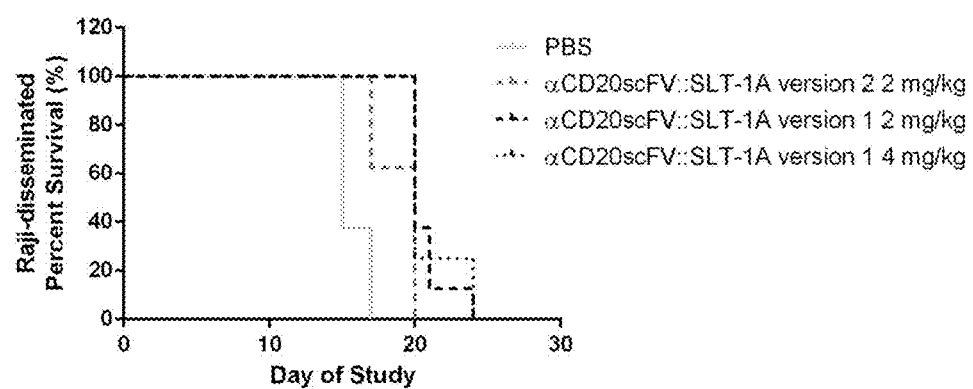

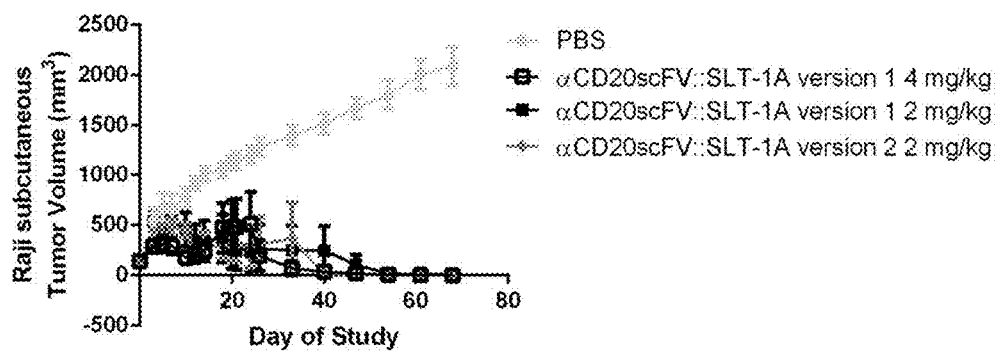
Figure 4. Subcutaneous Xenograft Results: the majority of mice displayed complete regression of tumor volume by day 54

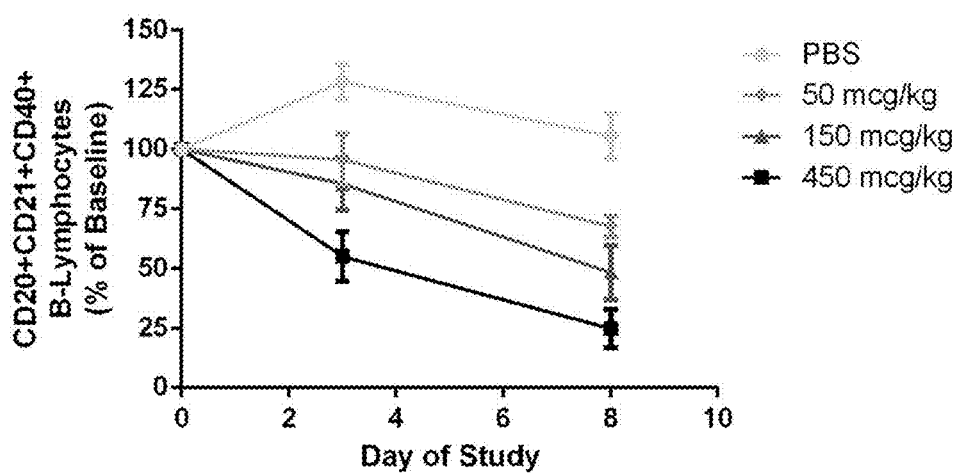
Figure 5. Non-Human Primate Results: Following parenteral administration of an exemplary CD-20 binding protein, dose-dependent depletion of peripheral blood B-cells was observed over time Figure 6. Non-Human Primate Results: Following parenteral administration of an exemplary CD-20 binding protein, dose-dependent depletion of peripheral blood B-cells was observed over time
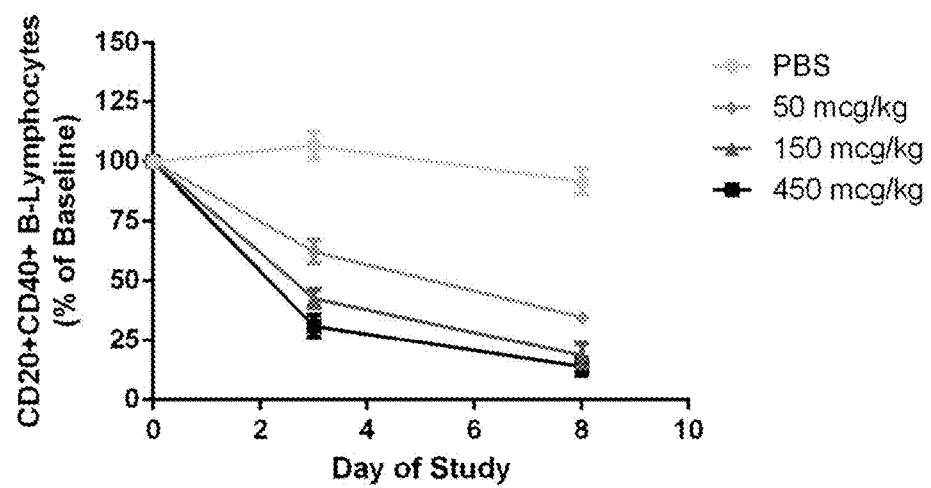

CD20-BINDING IMMUNOTOXINS FOR INDUCING CELLULAR INTERNALIZATION AND METHODS USING SAME

SEQUENCE LISTING

The instant application contains a Sequence Listing which has been submitted electronically in ASCII format and is hereby incorporated by reference in its entirety. Said ASCII copy, created on Mar. 24, 2014, is named 13-03PCT SL.txt and is 170,964 bytes in size.

FIELD OF THE INVENTION

The present invention relates to CD20-binding proteins with the ability of binding to and forcing the rapid internalization of CD20 antigens from a cell surface location to the cell interior. These CD20-binding proteins have uses as therapeutic molecules for treatment of a variety of diseases, including cancer and immune disorders.

BACKGROUND OF THE INVENTION

An immunotoxin is a chimeric molecule which combines a cell surface binding region, such as from an immunoglobulin domain, and a toxin region typically derived from a naturally occurring protein toxin, such as those found in bacteria or plants. The potency of an immunotoxin greatly depends on its efficiency in transiting from the cell surface to the cytosol, a process that begins with cell internalization (see Pirie C et al., *J Biol Chem* 286: 4165-72 (2011)).

CD20 is a member of a family of polypeptides known as the membrane-spanning 4A (MS4A) family that includes at least 26 proteins in humans and mice (Ishibashi K et al., *Gene* 264: 87-93 (2001)). As with all MS4A members, the CD20 sequence predicts three hydrophobic regions forming a transmembrane molecule that spans the membrane four times, a structural characteristic believed central to its function. Also predicted is a single extracellular loop between the proposed third and fourth transmembrane domains and intracellular amino- and carboxy-terminal regions (Tedder T et al., *Proc Natl Acad Sci* 85: 208-12 (1988)). It is within this extracellular loop of approximately 40 amino acids that the majority of anti-CD20 monoclonal antibodies (mAbs), such as rituximab, are believed to bind with alanine-170 and proline-172 being the most critical residues. A crystal structure of an antibody binding a peptide fragment of CD20 using amino acids 163-187 of CD20 has confirmed amino acids 170 (alanine) through amino acids 173 (serine) as antigen-antibody interaction points for rituximab and CD20 (Du J et al., *J Biol Chem* 282: 15073-80 (2007)).

CD20 is believed to be present on the cell surface as a homo-multimer, likely a tetramer, and electron microscopy has shown that 90% of complexed CD20 is present in the membrane in lipid rafts and microvilli (Li H et al., *J Biol Chem* 279: 19893-901 (2004)). Lipid rafts are micro-domains found in the plasma membrane which have high polypeptide, sphingolipid, and cholesterol concentrations (Brown D, London E, *Annu Rev Cell Dev Biol* 14: 111-36 (1998)). Microvilli, or microvillar channels, are cell extensions from the plasma membrane surface (Reaven E et al., *J Lipid Res* 30: 1551-60 (1989)). Some antibodies to CD20 are known to bind only when the molecule is present in lipid rafts, such as FMC7 (Polyak M et al., *Leukemia* 17:1384-89 (2003)) and others, such as rituximab, are known to increase association of CD20 to rafts (Li H et al, supra). It is hypothesized that raft association is important to the proposed function of CD20 as an amplifier of calcium signals that are transduced through the B-cell antigen receptor (BCR), another protein commonly located within lipid rafts and found associated with CD20 multimers (Polyak M et al., *J Biol Chem* 283: 18545-52 (2008)).

Antibody-based therapies targeting a CD20 antigen are numerous (see Boross P, Leusen J, *Am J Cancer Res* 2: 676-90 (2012), for review). One of the attractive characteristics of CD20 as a target for therapies based on a mechanism in which the therapeutic remains on the cell surface in order to function is the lack of CD20 cellular internalization after being bound by antibody-based therapeutics (Anderson K et al., *Blood* 63: 1424-33 (1984); Press 0 et al., *Blood* 69: 584-91 (1987)). Although this has proven to be both cell-type and antibody-type specific, in general, CD20 appears to internalize at a much lower rate than do other cell surface antigens (Beers S et al., *Sem Hematol* 47: 107-14 (2010)).

There is a question in the art as to the utility of CD20 antigens as a target for therapies that require the therapeutic to internalize into a target cell after binding in order to be effective because of the general finding that CD20 does not readily internalize (Anderson K et al., *Blood* 63: 1424-33 (1984); Press 0 et al., *Blood* 69: 584-91 (1987); Beers S et al., *Sem Hematol* 47: 107-14 (2010)). Thus, there is an unsolved problem in targeting CD20 antigens with immunoglobulin-type therapeutics that require cell internalization for efficacy—how to force the CD20 bound therapeutic into the target cell's interior after binding. For example, therapies based on the delivery of an immunotoxin that targets a CD20 antigen are predicted to be ineffective based on insufficient CD20 internalization efficiency. Thus, there is a need in the art to develop effective compositions, therapeutics, and therapeutic methods that target cell-surface antigens which do not natively internalize at an efficient rate or upon binding by an immunoglobulin-type domain, like CD20.

In particular, there remains a need in the art to identify and develop CD20-targeted compositions that trigger rapid and efficient cellular internalization of the complex of the composition bound to CD20. For example, cytotoxic CD20-binding proteins comprising toxin-derived regions that induce cellular internalization of native CD20 molecules are desirable for the development of effective cancer and immuno-modulatory therapeutic molecules that target cells of B-cell lineages.

SUMMARY OF THE INVENTION

The present invention provides various CD20-binding proteins for inducing rapid cellular internalization of CD20, which comprise 1) a CD20 binding region, such as an immunoglobulin domain, and 2) a Shiga toxin effector region, such as a truncation of SLT-1A. Upon binding a CD20 antigen on the surface of a cell, the CD20-binding proteins of the invention are capable of inducing rapid cellular internalization of the complex comprising of the CD20-binding protein and a CD20 antigen into the interior of a eukaryotic cell. The linking of CD20 binding regions with Shiga-toxin-Subunit-A-derived polypeptides enables the engineering of cytotoxic Shiga-toxin based molecules that are capable of inducing rapid cellular internalization of natively expressed CD20, as well as capable of delivering additional exogenous materials into the interior of CD20 expressing cells. The CD20-binding proteins of the invention have uses, e.g., for targeted killing of CD20 positive cell types, delivering exogenous materials, as diagnostic agents, and as therapeutics for the treatment of a variety of conditions in patients such as cancers, tumors, and immune disorders related to B-cell lineages.

A CD20-binding protein of the invention comprises (a) a CD20 binding region comprising an immunoglobulin-type binding region and capable of specifically binding an extracellular part of CD20 and (b) a Shiga toxin effector region comprising a polypeptide derived from the amino acid sequence of the A Subunit of at least one member of the Shiga toxin family; whereby upon administration of the CD20-binding protein to a cell expressing CD20 on a cellular surface, the CD20-binding protein is capable of inducing rapid cellular internalization of a protein complex comprising the CD20-binding protein bound to CD20.

For certain embodiments of the CD20-binding proteins of the present invention, the CD20 binding region comprises an immunoglobulin-type binding region comprising a polypeptide selected from the group consisting of: a complementary determining region 3 fragment, constrained FR3-CDR3-FR4 polypeptide, single-domain antibody fragment, single-chain variable fragment, antibody variable fragment, antigen-binding fragment, Fd fragment, fibronectin-derived 10$^{th}$ fibronectin type III domain, tenascin type III domain, ankyrin repeat motif domain, low-density-lipoprotein-receptor-derived A-domain, lipocalin, Kunitz domain, Protein-A-derived Z domain, gamma-B crystalline-derived domain, ubiquitin-derived domain, Sac7d-derived polypeptide, Fyn-derived SH2 domain, engineered antibody mimic, and any genetically manipulated counterparts of any of the foregoing that retain CD20 binding functionality.

For certain embodiments, the CD20-binding proteins are capable of inducing rapid cellular internalization of a CD20 natively present on the surface of a cell. In certain further embodiments, the CD20-binding proteins are capable of inducing, in less than about one hour, cellular internalization of a CD20 natively present on the surface of a cell. In certain further embodiments, the CD20-binding proteins are capable of inducing, in less than about one hour, cellular internalization of a CD20 natively present on the surface of a member of a B-cell lineage.

For certain embodiments, upon administration of the CD20-binding protein to a cell which expresses CD20 on a cellular surface, the CD20-binding protein is capable of causing the death of the cell. In certain other embodiments, the CD20-binding proteins comprise Shiga toxin effector regions that lack catalytic activity and are not capable of causing the death of a cell.

For certain embodiments, upon administration of the CD20-binding protein to a first population of cells whose members express CD20, and a second population of cells whose members do not express CD20, the cytotoxic effect of the CD20-binding protein to members of the first population of cells relative to members of the second population of cells is at least 3-fold greater.

For certain embodiments, the CD20-binding proteins comprise the Shiga toxin effector region comprising or consisting essentially of amino acids 75 to 251 of SEQ ID NO:1, SEQ ID NO:25, or SEQ ID NO:26. Further embodiments are CD20-binding proteins in which the Shiga toxin effector region comprises or consists essentially of amino acids 1 to 241 of SEQ ID NO:1, SEQ ID NO:25, or SEQ ID NO:26; amino acids 1 to 251 of SEQ ID NO:1, SEQ ID NO:25, or SEQ ID NO:26; and/or amino acids 1 to 261 of SEQ ID NO:1, SEQ ID NO:25, or SEQ ID NO:26.

For certain embodiments, the CD20-binding protein comprises or consists essentially of amino acids of SEQ ID NO:4, SEQ ID NO:12, SEQ ID NO:14, or SEQ ID NO:16.

In certain embodiments, the CD20-binding proteins comprise the CD20 binding region comprising: (a) a heavy chain variable domain comprising HCDR1, HCDR2, and HCDR3 amino acid sequences as shown in SEQ ID NO:6, SEQ ID NO:7, and SEQ ID NO:8, respectively, and a light chain variable domain comprising LCDR1, LCDR2, and LCDR3 amino acid sequences as shown in SEQ ID NO:9, SEQ ID NO:10, and SEQ ID NO:11, respectively; (b) a heavy chain variable domain comprising HCDR1, HCDR2, and HCDR3 amino acid sequences as shown in SEQ ID NO:21, SEQ ID NO:22, and SEQ ID NO:23, respectively, and a light chain variable domain comprising LCDR1, LCDR2, and LCDR3 amino acid sequences as shown in SEQ ID NO:24, SEQ ID NO:10, and SEQ ID NO:11, respectively; or (c) a heavy chain variable (VH) domain comprising HCDR1, HCDR2, and HCDR3 amino acid sequences as shown in SEQ ID NO:21, SEQ ID NO:22, and SEQ ID NO:27, respectively, and a light chain variable (VL) domain comprising LCDR1, LCDR2, and LCDR3 amino acid sequences as shown in SEQ ID NO:28, SEQ ID NO:10, and SEQ ID NO:29, respectively. Further embodiments are CD20-binding proteins comprising the immunoglobulin-type binding region comprising or consisting essentially of amino acids 2-245 of SEQ ID NO:4. Further embodiments are CD20-binding proteins comprising the immunoglobulin-type binding region comprising or consisting essentially of amino acids 2-245 of SEQ ID NO:4 and the Shiga toxin effector region comprising or consisting essentially of amino acids 75-251 of SEQ ID NO:1. Further embodiments are CD20-binding proteins comprising or consisting essentially of SEQ ID NO:4 or SEQ ID NO:16.

In certain embodiments, the CD20-binding proteins comprise Shiga toxin effector regions which comprise a mutation relative to a naturally occurring A Subunit of a member of the Shiga toxin family which changes the enzymatic activity of the Shiga toxin effector region, the mutation selected from at least one amino acid residue deletion or substitution.

Certain embodiments of the CD20-binding proteins can also be utilized for the delivery of additional exogenous material into a cell that expresses CD20 on a cellular surface. These embodiments comprise a CD20 binding region comprising (a) an immunoglobulin-type polypeptide capable of specifically binding an extracellular part of a CD20 molecule, (b) a Shiga toxin effector region comprising a polypeptide derived from the amino acid sequence of at least one member of the Shiga toxin family, and (c) an additional exogenous material; whereby upon administration of the CD20-binding protein to a cell expressing CD20 on a cellular surface, the CD20-binding protein is capable of inducing rapid cellular internalization of a protein complex comprising the CD20-binding protein bound to CD20 and capable of delivering the additional exogenous material into the interior of the cell. In certain further embodiments, the CD20-binding proteins comprise the CD20 binding region comprising: (a) a heavy chain variable domain comprising HCDR1, HCDR2, and HCDR3 amino acid sequences as shown in SEQ ID NO:6, SEQ ID NO:7, and SEQ ID NO:8, respectively, and a light chain variable domain comprising LCDR1, LCDR2, and LCDR3 amino acid sequences as shown in SEQ ID NO:9, SEQ ID NO:10, and SEQ ID NO:11, respectively; or (b) a heavy chain variable domain comprising HCDR1, HCDR2, and HCDR3 amino acid sequences as shown in SEQ ID NO:21, SEQ ID NO:22, and SEQ ID NO:23, respectively, and a light chain variable domain comprising LCDR1, LCDR2, and LCDR3 amino acid sequences as shown in SEQ ID NO:24, SEQ ID NO:10, and SEQ ID NO:11, respectively; or (c) a heavy chain variable (VH) domain comprising HCDR1, HCDR2, and HCDR3 amino acid sequences as shown in SEQ ID NO:21, SEQ ID NO:22, and SEQ ID NO:27, respectively, and a light chain variable (VL) domain comprising LCDR1, LCDR2, and LCDR3 amino acid sequences as shown in SEQ ID NO:28, SEQ ID NO:10, and SEQ ID NO:29, respectively.

In certain embodiments, the additional exogenous material is selected from the group consisting of peptides, polypeptides, proteins, and polynucleotides. In certain embodiments, the additional exogenous material comprises a protein or polypeptide comprising an enzyme. In certain other embodiments, the additional exogenous material is a nucleic acid, such as, e.g. a ribonucleic acid that functions as a small inhibiting RNA (siRNA) or microRNA (miRNA).

In certain embodiments, the additional exogenous material is a peptide and the peptide is an antigen. In certain embodiments, the additional exogenous material is an antigen derived from a bacterial protein. In certain other embodiments, the antigen is derived from a protein mutated in cancer. Further embodiments are ones in which the antigen is derived from a protein aberrantly expressed in cancer. Still further embodiments are ones in which the antigen is derived from a T-cell complementary determining region.

For certain embodiments, the antigen is included within the CD20-binding protein as part of a polypeptide fusion in which the peptide antigen is located between the binding region and the toxin effector region of a single-chain protein. In certain embodiments, the additional exogenous material is an antigen derived from a viral protein. In certain embodiments, the antigen comprises or consists essentially of SEQ ID NO:3, the influenza Matrix 58-66 antigen. In certain further embodiments, the CD20-binding protein comprises or consists essentially of SEQ ID NO:16.

The invention also includes pharmaceutical compositions comprising a CD20-binding protein of the present invention and at least one pharmaceutically acceptable excipient or carrier; and the use of such a cytotoxic protein or a composition comprising it in methods of the invention as further described herein.

The present invention also provides polynucleotides that encode the CD20-binding proteins of the invention, expression vectors that comprise the polynucleotides of the invention, as well as host cells comprising the expression vectors of the invention.

Additionally, the present invention provides a method of rapidly inducing cellular internalization of a CD20-binding protein of the present invention into a CD20 expressing cell(s), the method comprising the step of contacting the cell(s) with a CD20-binding protein of the present invention or a pharmaceutical composition thereof. Similarly, the present invention provides a method of internalizing a cell surface localized CD20 bound by a CD20-binding protein in a patient, the method comprising the step of administering to the patient a CD20-binding protein or pharmaceutical composition of the present invention.

Additionally, the present invention provides a method of killing a CD20 expressing cell(s) comprising contacting the cell(s), either in vitro or in vivo, with a CD20-binding protein or pharmaceutical composition of the present invention.

Additionally, the present invention provides a method for delivering exogenous material to the inside of a cell(s) comprising contacting the cell(s), either in vitro or in vivo, with a CD20-binding protein or pharmaceutical composition of the present invention.

The present invention further provides a method for delivering exogenous material to the inside of a cell(s) in a patient, wherein the cell expresses CD20 on its surface, the method comprising the step of administering to the patient a CD20-binding protein of the present invention.

Additionally, the present invention provides methods of killing cells comprising the step of contacting the cell with a CD20-binding protein of the invention or a pharmaceutical composition of the invention. In certain embodiments of the cell killing method, the step of contacting the cell(s) occurs in vitro. In certain other embodiments, the step of contacting the cell(s) occurs in vivo.

Also, the present invention provides a method of treating a disease, disorder, or condition in patients comprising the step of administering to a patient in need thereof a therapeutically effective amount of a CD20-binding protein of the invention or a pharmaceutical composition of the invention. In certain embodiments of the treating method, the disease, disorder, or condition to be treated using this method of the invention involves a cell(s) or cell type(s) which express CD20 on a cellular surface, such as, e.g., a cancer cell, a tumor cell, or an immune cell. A further embodiment is a method of treating a disease involving a cancer or tumor cell associated with the disease selected from the group consisting of: bone cancer, leukemia, lymphoma, melanoma, or myeloma. In certain embodiments of this method, the disorder is an immune disorder associated with a disease selected from the group consisting of: amyloidosis, ankylosing spondylitis, asthma, Crohn's disease, diabetes, graft rejection, graft-versus host disease, Hashimoto's thyroiditis, hemolytic uremic syndrome, HIV-related diseases, lupus erythematosus, multiple sclerosis, polyarteritis, psoriasis, psoriatic arthritis, rheumatoid arthritis, scleroderma, septic shock, Sjörgren's syndrome, ulcerative colitis, and vasculitis.

Among certain embodiments of the present invention is the use of a CD20-binding protein of the invention in the manufacture of a medicament for the treatment or prevention of a cancer or immune disorder. Among certain embodiments of the present invention is a cytotoxic protein or a pharmaceutical composition comprising said protein for use in the treatment or prevention of a cancer, tumor, or immune disorder.

These and other features, aspects and advantages of the present invention will become better understood with regard to the following description, appended claims, and accompanying figures. The aforementioned elements of the invention may be combined or removed freely in order to make other embodiments, without any statement to object such combination or removal hereinafter.

BRIEF DESCRIPTION OF THE FIGURES

FIG. 1 shows the general architecture of exemplary CD20-binding proteins of the present invention.

FIG. 2 graphically shows the change in total body luminescence with the administration of αCD20scFv::SLT-1A version 1 and αCD20scFv::SLT-1A version 2 in a disseminated Raji-luc xenograft model.

FIG. 3 graphically shows the increased survival of Raji-luc xenograft model mice with the administration of αCD20scFv::SLT-1A version 1 and αCD20scFv::SLT-1A version 2.

FIG. 4 graphically shows the change in tumor volume with the administration of αCD20scFv::SLT-1A version 1 and αCD20scFv::SLT-1A version 2 in a Raji subcutaneous xenograft model.

FIG. 5 shows B-cell depletion in a non-human primate study with the administration of αCD20scFv::SLT-1A version 1. Specifically, the subsets of CD20+ B-cells that expressed CD21 were analyzed.

FIG. 6 shows B-cell depletion in a non-human primate study with the administration of αCD20scFv::SLT-1A version 1. Specifically, the subsets of CD20+ B-cells that did not express CD21 were analyzed.

DETAILED DESCRIPTION OF THE INVENTION

The present invention is described more fully hereinafter using illustrative, non-limiting embodiments, and references to the accompanying figures. This invention may, however, be embodied in many different forms and should not be construed as to be limited to the embodiments set forth below. Rather, these embodiments are provided so that this disclosure is thorough and conveys the scope of the invention to those skilled in the art.

In order that the present invention may be more readily understood, certain terms are defined below. Additional definitions may be found within the detailed description of the invention.

As used in the specification and the appended claims, the terms "a," "an" and "the" include both singular and the plural referents unless the context clearly dictates otherwise.

As used in the specification and the appended claims, the term "and/or" when referring to two species, A and B, means at least one of A and B. As used in the specification and the appended claims, the term "and/or" when referring to greater than two species, such as A, B, and C, means at least one of A, B, or C, or at least one of any combination of A, B, or C (with each species in singular or multiple possibility).

Throughout this specification, the word "comprise" or variations such as "comprises" or "comprising" will be understood to imply the inclusion of a stated integer (or components) or group of integers (or components), but not the exclusion of any other integer (or components) or group of integers (or components).

Throughout this specification, the term "including" is used to mean "including but not limited to." "Including" and "including but not limited to" are used interchangeably.

The term "amino acid residue" or "amino acid" includes reference to an amino acid that is incorporated into a protein, polypeptide, or peptide. The term "polypeptide" includes any polymer of amino acids or amino acid residues. The term "polypeptide sequence" refers to a series of amino acids or amino acid residues from which a polypeptide is physically composed. A "protein" is a macromolecule comprising one or more polypeptides chains. A "peptide" is a small polypeptide of sizes less than a total of 15-20 amino acid residues.

The terms "amino acid," "amino acid residue," or polypeptide sequence include naturally occurring amino acids and, unless otherwise limited, also include known analogs of natural amino acids that can function in a similar manner as naturally occurring amino acids. The amino acids referred to herein are described by shorthand designations as follows in Table A:

TABLE A

Amino Acid Nomenclature

| Name | 3-letter | 1-letter |
|---|---|---|
| Alanine | Ala | A |
| Arginine | Arg | R |
| Asparagine | Asn | N |
| Aspartic Acid or Aspartate | Asp | D |
| Cysteine | Cys | C |
| Glutamic Acid or Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The phrase "conservative substitution" with regard to a polypeptide, refers to a change in the amino acid composition of the polypeptide that does not substantially alter the function and structure of the overall polypeptide (see Creighton, *Proteins: Structures and Molecular Properties* (W. H. Freeman and Company, New York (2nd ed., 1992)).

As used herein, the term "expressed," "expressing" or "expresses" refers to translation of a polynucleotide or nucleic acid into a polypeptide or protein. The expressed polypeptide or protein may remain intracellular, become a component of the cell surface membrane or be secreted into an extracellular space.

As used herein, the symbol "α" is shorthand for an immunoglobulin-type binding region capable of binding to the biomolecule following the symbol. The symbol "α" is used to refer to the functional characteristic of an immunoglobulin-type binding region based on its capability of binding to the biomolecule following the symbol.

The term "selective cytotoxicity" with regard to the cytotoxic activity of a CD20-binding protein refers to the relative levels of cytotoxicity between a targeted cell population and a non-targeted bystander cell population, which can be expressed as a ratio of the half-maximal cytotoxic concentration ($CD_{50}$) for a targeted cell type over the $CD_{50}$ for an untargeted cell type to show preferentiality of cell killing of the targeted cell type.

For purposes of the present invention, the term "effector" means providing a biological activity, such as cytotoxicity, biological signaling, enzymatic catalysis, subcellular routing, and/or intermolecular binding resulting in the recruit of a factors and/or allosteric effects.

For purposes of the present invention, the phrase "derived from" means the polypeptide region comprises amino acid sequences originally found in a protein and may now comprise additions, deletions, truncations, or other alterations form the original sequence such that overall function and structure are substantially conserved.

Introduction

The present invention solves problems for engineering therapeutics targeting CD20 that require cell internalization for function because Shiga-toxin-Subunit-A derived effector regions induce the cellular internalization of CD20. The present invention provides CD20-binding proteins that bind to extracellular CD20 antigens and rapidly internalize CD20 from a cell membrane location to the interior of a cell.

Certain of the disclosed CD20-binding proteins kill cells which express CD20 on their surface. Certain of the disclosed CD20-binding proteins are capable of precisely delivering additional exogenous material in the form of molecular cargos to the interior of cells which express CD20 on their surface. The present invention expands the universe of immunotoxin-drugable targets to include CD20 and enables the precise delivery of payloads to the interiors of CD20 expressing cells.

I. The General Structure of the CD20-Binding Proteins of the Invention

The present invention provides various CD20-binding proteins for the selective killing of specific cell types, each CD20-binding protein comprising 1) a CD20 binding region comprising immunoglobulin-type binding regions for cell targeting and 2) a Shiga toxin effector region for cell killing. The linking of CD20 targeting immunoglobulin-type binding regions with Shiga-toxin-Subunit-A-derived regions enables the engineering of cell-type specific targeting of the potent Shiga toxin cytotoxicity. This system is modular, in that various Shiga toxin effector regions and additional exogenous materials may be linked to the same CD20 binding region to provide diverse applications involving CD20 expressing cells. CD20-binding proteins of the invention comprise Shiga toxin effector regions derived from the A Subunits of members of the Shiga toxin family linked to immunoglobulin-type CD20 binding regions which can bind specifically to at least one extracellular part of a CD20 molecule spanning the outer cell membrane of a eukaryotic cell. This general structure is modular in that various CD20 binding regions can be linked to Shiga-toxin-Subunit-A derived effector regions at various positions or with different linkers between them to produce variations of the same general structure (see e.g. FIG. 1).

A. CD20 Binding Regions Comprising an Immunoglobulin-Type Binding Region

For purposes of the present invention, the term "CD20 binding region" refers to a polypeptide region capable of specifically binding an extracellular part of a CD20 molecule. While the name CD20 might refer to multiple proteins with related structures and polypeptide sequences from various species, for the purposes of the present invention the term "CD20" refers to the B-lymphocyte antigen CD20 proteins present in mammals whose exact sequence might vary slightly based on the isoform and from individual to individual. For example, in humans CD20 refers to the protein represented by the predominant polypeptide sequence UnitProt P11836 and NCBI accession NP 690605.1; however, different isoforms and variants may exist. The polypeptide sequence of various CD20 proteins has been described in various species, such as bats, cats, cattle, dogs, mice, marmosets, and rats, and can be predicted by bioinformatics in numerous other species based on genetic homology (e.g. CD20 has been predicted in various primates, including baboons, macaques, gibbons, chimpanzees, and gorillas) (see Zuccolo J et al., *PLoS One* 5: e9369 (2010) and NCBI protein database (National Center for Biotechnology Information, U.S.). A skilled worker will be able to identify a CD20 protein in mammals, even if it differs from the referenced sequences slightly.

An extracellular part of a CD20 molecule refers to a portion of its structure exposed to the extracellular environment when the CD20 molecule is natively present in a cell membrane. In this context, exposed to the extracellular environment means that part of the CD20 molecule is accessible by, e.g., an antibody or at least a binding moiety smaller than an antibody such as a single-domain antibody domain, a nanobody, a heavy-chain antibody domain derived from camelids or cartilaginous fishes, a single-chain variable fragment, or any number of engineered alternative scaffolds to immunoglobulins (see below). The exposure of a part of CD20 may be empirically determined by the skilled worker using methods known in the art. Note that some portion of CD20, which was predicted not to be accessible to an antibody in the extracellular space based on its location within CD20, was empirically shown to be accessible by a monoclonal antibody (Teeling J et al., *J. Immunol.* 177: 362-71 (2006)).

CD20 binding regions are commonly derived from antibody or antibody-like structures; however, alternative scaffolds from other sources are contemplated within the scope of the term. In certain embodiments, the CD20 binding region is derived from an immunoglobulin-derived binding region, such as an antibody paratope. In certain other embodiments, the CD20 binding region comprises an immunoglobulin-type binding region that is an engineered polypeptide not derived from any immunoglobulin domain. There are numerous immunoglobulin-derived binding regions contemplated as components in the present invention.

CD20-binding proteins of the invention comprise an immunoglobulin-type binding region comprising one or more polypeptides capable of selectively and specifically binding an extracellular part of CD20. The term "immunoglobulin-type binding region" as used herein refers to a polypeptide region capable of binding one or more target biomolecules, such as an antigen or epitope. Immunoglobulin-type binding regions are functionally defined by their ability to bind to target molecules, and all the immunoglobulin-type binding regions of the present invention are capable of binding CD20. Immunoglobulin-type binding regions are commonly derived from antibody or antibody-like structures; however, alternative scaffolds from other sources are contemplated within the scope of the term.

Immunoglobulin (Ig) proteins have a structural domain known as an Ig domain. Ig domains range in length from about 70-110 amino acid residues and possess a characteristic Ig-fold, in which typically 7 to 9 antiparallel beta strands arrange into two beta sheets which form a sandwich-like structure. The Ig fold is stabilized by hydrophobic amino acid interactions on inner surfaces of the sandwich and highly conserved disulfide bonds between cysteine residues in the strands. Ig domains may be variable (IgV or V-set), constant (IgC or C-set) or intermediate (IgI or I-set). Some Ig domains may be associated with a complementarity determining region (CDR), also referred to as antigen binding region (ABR), which is important for the specificity of antibodies binding to their epitopes. Ig-like domains are also found in non-immunoglobulin proteins and are classified on that basis as members of the Ig superfamily of proteins. The HUGO Gene Nomenclature Committee (HGNC) provides a list of members of the Ig-like domain containing family.

An immunoglobulin-type binding region may be a polypeptide sequence of antibody or antigen-binding fragment thereof wherein the amino acid sequence has been varied from that of a native antibody or an Ig-like domain of a non-immunoglobulin protein, for example by molecular engineering or selection by library screening. Because of the relevance of recombinant DNA techniques and in vitro library screening in the generation of immunoglobulin-type binding regions, antibodies can be redesigned to obtain desired characteristics, such as smaller size, cell entry, or other therapeutic improvements. The possible variations are many and may range from the changing of just one amino acid to the complete redesign of, for example, a variable region. Typically, changes in the variable region will be made in order to improve the antigen-binding characteristics, improve variable region stability, or reduce the potential for immunogenic responses.

There are numerous immunoglobulin-type binding regions that bind an extracellular part of CD20 contemplated in the present invention. In certain embodiments, the immunoglobulin-type binding region is derived from an immunoglobulin binding region, such as an antibody paratope capable of binding an extracellular part of CD20. In certain other embodiments, the immunoglobulin-type binding region comprises an engineered polypeptide not derived from any immunoglobulin domain but that functions like an immunoglobulin binding region by providing high-affinity binding to an extracellular part of CD20. This engineered polypeptide may optionally include polypeptide scaffolds comprising or consisting essentially of complementary determining regions from immunoglobulins as described herein.

There are numerous immunoglobulin-derived binding regions and non-immunoglobulin engineered polypeptides in the prior art that are useful for targeting the CD20-binding proteins of the invention to CD20 expressing cells. In certain embodiments, the immunoglobulin-type binding region of the present CD20-binding proteins is selected from the group which includes single-domain antibody domains (sdAb), nanobodies, heavy-chain antibody domains derived from camelids (VHH fragments), bivalent nanobodies, heavy-chain antibody domains derived from cartilaginous fishes, immunoglobulin new antigen receptors (IgNARs), VNAR fragments, single-chain variable (scFv) fragments, multimerizing scFv fragments (diabodies, triabodies, tetrabodies), bispecific tandem scFv fragments, disulfide stabilized antibody variable (Fv) fragments, disulfide stabilized antigen-binding (Fab) fragments consisting of the $V_L$, $V_H$, $C_L$ and $C_H 1$ domains, divalent F(ab')2 fragments, Fd fragments consisting of the heavy chain and $C_H1$ domains, single chain Fv-$C_H3$ minibodies, bispecific minibodies, dimeric $C_H2$ domain fragments ($C_H2D$), Fc antigen binding domains (Fcabs), isolated complementary determining region 3 (CDR3) fragments, constrained framework region 3, CDR3, framework region 4 (FR3-CDR3-FR4) polypeptides, small modular immunopharmaceutical (SMIP) domains, and any genetically manipulated counterparts of the foregoing that retain its paratope and binding function (see, Weiner L, Cell 148: 1081-4 (2012); Ahmad Z et al., Clin Dev Immunol 2012: 980250 (2012), for reviews).

In accordance with certain other embodiments, the immunoglobulin-type binding region of the CD20-binding proteins of the invention may include engineered, alternative scaffolds to immunoglobulin domains that exhibit similar functional characteristics, such as high-affinity and specific binding to CD20, and enable the engineering of improved characteristics, such as greater stability or reduced immunogenicity. For certain embodiments of the CD20-binding proteins of the invention, the immunoglobulin-type binding region is selected from the group which includes engineered, fibronectin-derived, $10^{th}$ fibronectin type III (10Fn3) domains (monobodies, AdNectins™, or AdNexins™); engineered, tenascin-derived tenascin type III domains (Centryns™); engineered, ankyrin repeat motif containing polypeptides (DARPins™); engineered, low-density-lipoprotein-receptor-derived, A domains (LDLR-A) (Avimers™); lipocalins (anticalins); engineered, protease inhibitor-derived, Kunitz domains; engineered, Protein-A-derived, Z domains (Affibodies™); engineered, gamma-B crystalline-derived scaffolds or engineered, ubiquitin-derived scaffolds (Affilins); Sac7d-derived polypeptides (Nanoffitins® or affitins); engineered, Fyn-derived, SH2 domains (Fynomers®); and engineered antibody mimics; and any genetically manipulated counterparts of the foregoing that retains its binding functionality (Wörn A, Plückthun A, J Mol Biol 305: 989-10 (2001); Xu L et al., Chem Biol 9: 933-42 (2002); Wikman M et al., Protein Eng Des Sel 17: 455-62 (2004); Binz H et al., Nat Biotechnol 23: 1257-68 (2005); Holliger P, Hudson P, Nat Biotechnol 23: 1126-36 (2005); Gill D, Damle N, Curr Opin Biotech 17: 653-8 (2006); Koide A, Koide S, Methods Mol Biol 352: 95-109 (2007)).

Nonlimiting examples of protein constructs encompassed within the term "binding region" as used herein include: (i) an Fab fragment, a monovalent fragment consisting of the VL, VH, CL and CH 1 domains; (ii) an F(ab')2 fragment, a bivalent fragment comprising two Fab fragments linked by a disulfide bridge at the hinge region; (iii) an Fd fragment consisting of the VH and CH 1 domains; (iv) an Fv fragment consisting of the VL and VH domains of a single arm of an antibody, (v) a dAb fragment, which consists of a VH domain; and (vi) an isolated CDR. Furthermore, although the two domains of the Fv fragment, VL and VH, are coded for by separate genes, they may be recombinantly joined by a synthetic linker, creating a single protein chain in which the VL and VH domains pair to form monovalent molecules (known as single chain Fv (scFv)). The most commonly used linker is a 15-residue (Gly4Ser)3 peptide, but other linkers are also known in the art. Single chain antibodies are also intended to be encompassed within the term "binding region" as used herein.

It is also anticipated that alternative scaffolds that provide binding function are within the scope of the term "binding region" as used herein. Some examples of the alternative scaffolds include diabodies, a CDR3 peptide, a constrained FR3-CDR3-FR4 peptide, a nanobody (U.S. patent application publication 2008/0107601), a bivalent nanobody, small modular immunopharmaceuticals (SMIPs), a shark variable IgNAR domain (WO 03/014161), a minibody and any fragment or chemically or genetically manipulated counterparts that retain target molecule binding function.

An "antibody-derived sequence" as used herein, means an amino acid sequence of an antibody or antigen-binding fragment thereof wherein the amino acid sequence has been varied from that of a native antibody. Because of the relevance of recombinant DNA techniques in the generation of antibodies, antibodies can be redesigned to obtain desired characteristics. The possible variations are many and range from the changing of just one or a few amino acids to the complete redesign of, for example, a variable region. Typically, changes in the variable region will be made in order to improve the antigen-binding characteristics, improve variable region stability, or reduce the risk of immunogenicity.

As used herein, the term "heavy chain variable (VH) domain" or "light chain variable (VL) domain" respectively refer to any native antibody VH or VL domain (e.g., a human VH or VL domain) as well as any derivative thereof retaining at least qualitative antigen binding ability of the corresponding native antibody (e.g., a humanized VH or VL domain derived from a native murine VH or VL domain). A VH or VL domain consists of a "framework" region interrupted by the three CDRs. The framework regions serve to align the CDRs for specific binding to an epitope of an antigen. From amino-terminus to carboxyl-terminus, both VH and VL domains comprise the following framework (FR) and CDR regions: FR1, CDR1, FR2, CDR2, FR3, CDR3, FR4. The assignment of amino acids to each domain is in accordance with the definitions of Kabat, *Sequences of Proteins of Immunological Interest* (5th ed., National Institutes of Health, Bethesda, Md., 1991), or Chothia and Lesk, *J. Mol. Biol.* 196: 901-17 (1987); Chothia et al., *Nature* 342:878-83, (1989). CDRs 1, 2, and 3 of a VH domain are also referred to herein, respectively, as HCDR1, HCDR2, and HCDR3; CDRs 1, 2, and 3 of a VL domain are also referred to herein, respectively, as LCDR1, LCDR2, and LCDR3.

In some embodiments of the CD20-binding proteins of the present invention, the binding region comprises an antibody or an antibody-derived sequence that comprises a specific set of complementarity determining regions, or CDRs. CDRs are defined sequence regions within the variable domains of antibodies that are necessary for specific binding of the antibody to its antigenic determinants. In one embodiment of the invention, the set of CDRs comprise three CDRs derived from the heavy chain of the antibody and three CDRs derived from light chain of the antibody. In some embodiments, the three heavy chain CDRs comprise: (a) a heavy chain variable domain comprising HCDR1, HCDR2, and HCDR3 amino acid sequences as shown in SEQ ID NO:6, SEQ ID NO:7, and SEQ ID NO:8, respectively, and a light chain variable domain comprising LCDR1, LCDR2, and LCDR3 amino acid sequences as shown in SEQ ID NO:9, SEQ ID NO:10, and SEQ ID NO:11, respectively; (b) a heavy chain variable domain comprising HCDR1, HCDR2, and HCDR3 amino acid sequences as shown in SEQ ID NO:21, SEQ ID NO:22, and SEQ ID NO:23, respectively, and a light chain variable domain comprising LCDR1, LCDR2, and LCDR3 amino acid sequences as shown in SEQ ID NO:24, SEQ ID NO:10, and SEQ ID NO:11, respectively; or (c) a heavy chain variable (VH) domain comprising HCDR1, HCDR2, and HCDR3 amino acid sequences as shown in SEQ ID NO:21, SEQ ID NO:22, and SEQ ID NO:27, respectively, and a light chain variable (VL) domain comprising LCDR1, LCDR2, and LCDR3 amino acid sequences as shown in SEQ ID NO:28, SEQ ID NO:10, and SEQ ID NO:29, respectively. Additionally, in certain embodiments of the invention, the binding region comprises or consists essentially of amino acids 2 to 245 of SEQ ID NO:4.

This system is modular, in that various, diverse immunoglobulin-type binding regions can be used with the same Shiga toxin effector region to target different extracellular epitopes of CD20. It will be appreciated by the skilled worker that any CD20 binding region of an immunoglobulin type capable of binding an extracellular part of CD20 may be used to design or select an immunoglobulin-type binding region to be linked to the Shiga toxin effector region to produce a CD20-binding protein of the invention.

B. Shiga Toxin Effector Regions Derived from a Subunits of Members of the Shiga Toxin Family For purposes of the present invention, the phrase "Shiga toxin effector region" refers to a polypeptide region derived from a Shiga toxin A Subunit of a member of the Shiga toxin family that is capable of inactivating ribosomes and effectuating cytotoxicity and/or cytostatic effects. A member of the Shiga toxin family refers to any member of a family of naturally occurring protein toxins which are structurally and functionally related, notably toxins isolated from *S. dysenteriae* and *E. coli* (Johannes, *Nat Rev Microbiol* 8: 105-16 (2010)). For example, the Shiga toxin family encompasses true Shiga toxin (Stx) isolated from *S. dysenteriae* serotype 1, Shiga-like toxin 1 variants (SLT1 or Stx1 or SLT-1 or Slt-I) isolated from serotypes of enterohemorrhagic *E. coli*, and Shiga-like toxin 2 variants (SLT2 or Stx2 or SLT-2) isolated from serotypes of enterohemorrhagic *E. coli*. SLT1 differs by only one residue from Stx, and both have been referred to as Verocytotoxins or Verotoxins (VTs) (O'Brien, *Curr Top Microbiol Immunol* 180: 65-94 (1992)). Although SLT1 and SLT2 variants are only about 53-60% similar to each other at the amino acid sequence level, they share mechanisms of enzymatic activity and cytotoxicity common to the members of the Shiga toxin family (Johannes, *Nat Rev Microbiol* 8: 105-16 (2010)). Over 39 different Shiga toxins have been described, such as the defined subtypes Stx1a, Stx1c, Stx1d, and Stx2a-g (Scheutz F et al., *J Clin Microbiol* 50: 2951-63 (2012)). Members of the Shiga toxin family are not naturally restricted to any bacterial species because Shiga-toxin-encoding genes can spread among bacterial species via horizontal gene transfer (Strauch E et al., *Infect Immun* 69: 7588-95 (2001); Zhaxybayeva O, Doolittle W, *Curr Biol.* 21: R242-6 (2011)). As an example of interspecies transfer, a Shiga toxin was discovered in a strain of *A. haemolyticus* isolated from a patient (Grotiuz G et al., *J Clin Microbiol* 44: 3838-41 (2006)). Once a Shiga toxin encoding polynucleotide enters a new subspecies or species, the Shiga toxin amino acid sequence is presumed to be capable of developing slight sequence variations due to genetic drift and/or selective pressure while still maintaining a mechanism of cytotoxicity common to members of the Shiga toxin family (see Scheutz, *J Clin Microbiol* 50: 2951-63 (2012)).

Shiga toxin effector regions of the invention comprise or consist essentially of a polypeptide derived from a Shiga toxin A Subunit dissociated from any form of its native Shiga toxin B Subunit. In addition, the CD20-binding proteins of the present invention do not comprise any polypeptide comprising or consisting essentially of a functional binding domain of a Shiga toxin B subunit. Rather, the Shiga toxin A Subunit derived regions are functionally associated with heterologous CD20 binding regions to effectuate cell targeting to CD20 expressing cells.

In certain embodiments, a Shiga toxin effector region of the invention may comprise or consist essentially of a full length Shiga toxin A Subunit (e.g. SLT-1A (SEQ ID NO:1), StxA (SEQ ID NO:25), or SLT-2A (SEQ ID NO:26)), noting that naturally occurring Shiga toxin A Subunits may comprise precursor forms containing signal sequences of about 22 amino acids at their amino-terminals which are removed to produce mature Shiga toxin A Subunits. One specific example of a "toxin effector region" is one that is derived from the A chain of Shiga-like toxin 1 (SLT-1) (SEQ ID NO:1). The A chain of SLT-1 is composed of 293 amino acids with the enzymatic (toxic) domain spanning residues 1 to 239. In other embodiments, the Shiga toxin effector region of the invention comprises or consists essentially of a truncated Shiga toxin A Subunit which is shorter than a full-length Shiga toxin A Subunit.

Shiga-like toxin 1 A Subunit truncations are catalytically active, capable of enzymatically inactivating ribosomes in vitro, and cytotoxic when expressed within a cell (LaPointe, *J Biol Chem* 280: 23310-18 (2005)). The smallest Shiga toxin A Subunit fragment exhibiting full enzymatic activity is a polypeptide composed of residues 1-239 of Slt1A (LaPointe, *J Biol Chem* 280: 23310-18 (2005)). Although the smallest fragment of the Shiga toxin A Subunit reported to retain substantial catalytic activity was residues 75-247 of StxA (Al-Jaufy, *Infect Immun* 62: 956-60 (1994)), a StxA truncation expressed de novo within a eukaryotic cell requires only up to residue 240 to reach the cytosol and exert catalytic inactivation of ribosomes (LaPointe, *J Biol Chem* 280: 23310-18 (2005)).

Shiga toxin effector regions may commonly be smaller than the full length A subunit. It is preferred that the Shiga toxin effector region maintain the polypeptide region from amino acid position 77 to 239 (SLT-1A (SEQ ID NO:1), StxA (SEQ ID NO:25), or SLT-2A (SEQ ID NO:26)) or the equivalent in other A Subunits of members of the Shiga toxin family. For example, in certain embodiments of the invention, a Shiga toxin effector region derived from SLT-1A may comprise or consist essentially of amino acids 75 to 251 of SEQ ID NO:1, 1 to 241 of SEQ ID NO:1, 1 to 251 of SEQ ID NO:1, or amino acids 1 to 261 of SEQ ID NO:1.

Similarly, among certain other embodiments, the Shiga toxin effector regions derived from StxA may comprise or consist essentially of amino acids 75 to 251 of SEQ ID NO:25, 1 to 241 of SEQ ID NO:25, 1 to 251 of SEQ ID NO:25, or amino acids 1 to 261 of SEQ ID NO:25. Additionally, among certain other embodiments, the Shiga toxin effector regions derived from SLT-2 may comprise or consist essentially of amino acids 75 to 251 of SEQ ID NO:26, 1 to 241 of SEQ ID NO:26, 1 to 251 of SEQ ID NO:26, or amino acids 1 to 261 of SEQ ID NO:26.

The invention further provides variants of the CD20-binding proteins of the invention, wherein the Shiga toxin effector region differs from a naturally occurring Shiga toxin A Subunit by up to 1, 2, 3, 4, 5, 6, 7, 8, 9, 10, 15, 20, 25, 30, 35, 40 or more amino acid residues (but by no more than that which retains at least 85%, 90%, 95%, 99% or more amino acid sequence identity). Thus, a polypeptide region derived from an A Subunit of a member of the Shiga toxin family may comprise additions, deletions, truncations, or other alterations from the original sequence so long as at least 85%, 90%, 95%, 99% or more amino acid sequence identity is maintained to a naturally occurring Shiga toxin A Subunit.

Accordingly, in certain embodiments, the Shiga toxin effector region comprises or consists essentially of amino acid sequences having at least 55%, 60%, 65%, 70%, 75%, 80%, 85%, 90%, 95%, 97%, 98%, 99%, 99.5% or 99.7% overall sequence identity to a naturally occurring Shiga toxin A Subunit, such as SLT-1A (SEQ ID NO:1), Stx (SEQ ID NO:25), and/or SLT-2A (SEQ ID NO:26).

Optionally, either a full length or a truncated version of the Shiga toxin A Subunit may comprise one or more mutations (e.g. substitutions, deletions, insertions or inversions). In certain embodiments that are potently cytotoxic, the Shiga toxin effector region has sufficient sequence identity to retain cytotoxicity after entry into a cell, either by well-known methods of host cell transformation, transfection, infection or induction, or by internalization mediated by the cell targeting, immunoglobulin-type binding region linked with the Shiga toxin effector region. The most critical residues for enzymatic activity and/or cytotoxicity in the Shiga toxin A Subunits have been mapped to the following residue-positions: asparagine-75, tyrosine-77, glutamate-167, arginine-170, and arginine-176 among others (Di, *Toxicon* 57: 535-39 (2011)). In any one of the embodiments of the present invention, the Shiga toxin effector region may preferably but not necessarily maintain one or more conserved amino acids at positions, such as those found at positions 77, 167, 170, and 203 in StxA, SLT-1A, or the equivalent conserved position in other members of the Shiga toxin family which are typically required for cytotoxic activity. The capacity of a CD20-binding protein of the invention to cause cell death, e.g. its cytotoxicity, may be measured using any one or more of a number of assays well known in the art.

In certain embodiments of the invention, one or more amino acid residues may be mutated or deleted in order to reduce or eliminate cytotoxic activity of the Shiga toxin effector region. The cytotoxicity of the A Subunits of members of the Shiga toxin family may be reduced or eliminated by mutation or truncation. The positions labeled tyrosine-77, glutamate-167, arginine-170, tyrosine-114, and tryptophan-203 have been shown to be important for the catalytic activity of Stx, Stx1, and Stx2 (Hovde C et al., *Proc Natl Acad Sci USA* 85: 2568-72 (1988); Deresiewicz R et al., *Biochemistry* 31: 3272-80 (1992); Deresiewicz R et al., *Mol Gen Genet* 241: 467-73 (1993); Ohmura M et al., *Microb Pathog* 15: 169-76 (1993); Cao C et al., *Microbiol Immunol* 38: 441-7 (1994); Suhan M, Hovde C, *Infect Immun* 66: 5252-9 (1998)). Mutating both glutamate-167 and arginine-170 eliminated the enzymatic activity of Slt-I A1 in a cell-free ribosome inactivation assay (LaPointe, *J Biol Chem* 280: 23310-18 (2005)). In another approach using de novo expression of Slt-I A1 in the endoplasmic reticulum, mutating both glutamate-167 and arginine-170 eliminated Slt-I A1 fragment cytotoxicity at that expression level (LaPointe, *J Biol Chem* 280: 23310-18 (2005)). A truncation analysis demonstrated that a fragment of StxA from residues 75 to 268 still retains significant enzymatic activity in vitro (Haddad, *J Bacteriol* 175: 4970-8 (1993)). A truncated fragment of Slt-I A1 containing residues 1-239 displayed significant enzymatic activity in vitro and cytotoxicity by de novo expression in the cytosol (LaPointe, *J Biol Chem* 280: 23310-18 (2005)). Expression of a Slt-I A1 fragment truncated to residues 1-239 in the endoplasmic reticulum was not cytotoxic because it could not retrotranslocate into the cytosol (LaPointe, *J Biol Chem* 280: 23310-18 (2005)).

For the purposes of the present invention, the specific order or orientation is not fixed for the Shiga toxin effector region and the CD20 binding region in relation to each other or the entire CD20-binding protein's N-terminal(s) and C-terminal(s) (see e.g. FIG. 1). In the above CD20-binding proteins, the CD20 binding regions and Shiga toxin effector regions may be directly linked to each other and/or suitably linked to each other via one or more intervening polypeptide sequences, such as with one or more linkers well known in the art.

II. Examples of Specific Structural Variations of the CD20-Binding Proteins of the Invention Among certain embodiments of the present invention, the CD20-binding proteins comprise the Shiga toxin effector region comprising or consisting essentially of amino acids 75 to 251 of SLT-1A (SEQ ID NO:1), StxA (SEQ ID NO:25), or SLT-2A (SEQ ID NO:26). Further embodiments are CD20-binding proteins in which the Shiga toxin effector region comprises or consists essentially of amino acids 1 to 241 of SLT-1A (SEQ ID NO:1), StxA (SEQ ID NO:25), and/or SLT-2A (SEQ ID NO:26). Further embodiments are CD20-binding proteins in which the Shiga toxin effector region comprises or consists essentially of amino acids 1 to 251 of SLT-1A (SEQ ID NO:1), StxA (SEQ ID NO:25), and/or SLT-2A (SEQ ID NO:26). Further embodiments are CD20-binding proteins in which the Shiga toxin effector region comprises or consists essentially of amino acids 1 to 261 of SLT-1A (SEQ ID NO:1), StxA (SEQ ID NO:25), and/or SLT-2A (SEQ ID NO:26).

For certain embodiments, the CD20-binding proteins of the present invention is one which comprises or consists essentially of the amino acid sequence of SEQ ID NO:4, SEQ ID NO:12, SEQ ID NO:14, or SEQ ID NO:16.

As used herein, the term "heavy chain variable ($V_H$) domain" or "light chain variable ($V_L$) domain" respectively refer to any antibody $V_H$ or $V_L$ domain (e.g. a human $V_H$ or $V_L$ domain) as well as any derivative thereof retaining at least qualitative antigen binding ability of the corresponding native antibody (e.g. a humanized $V_H$ or $V_L$ domain derived from a native murine $V_H$ or $V_L$ domain). A $V_H$ or $V_L$ domain consists of a "framework" region interrupted by the three CDRs. The framework regions serve to align the CDRs for specific binding to an epitope of an antigen. From aminoterminus to carboxyl-terminus, both $V_H$ and $V_L$ domains comprise the following framework (FR) and CDR regions: FR1, CDR1, FR2, CDR2, FR3, CDR3, and FR4. The assignment of amino acids to each domain is in accordance with the definitions of Kunik V et al., *PLoS Comput Biol* 8: e1002388 (2012) and Kunik V et al., *Nucleic Acids Res* 40: W521-4 (2012) or alternatively in accordance with the definitions of Kabat, *Sequences of Proteins of Immunological Interest*, (5th ed., National Institutes of Health, Bethesda, Md., 1991); or Chothia and Lesk, *J. Mol. Biol.* 196: 901-17 (1987); Chothia et al., *Nature* 342: 878-83 (1989).

In certain embodiments of the invention, the CDRs comprise three CDRs derived from a heavy chain of the antibody and three CDRs derived from a light chain of the antibody. In certain embodiments, the three heavy chain CDRs comprise SEQ ID NO: 7 (HCDR1), SEQ ID NO:8 (HCDR2), and SEQ ID NO:9 (HCR3), while the three light chain CDRs comprise SEQ ID NO:9 (LCDR1), SEQ ID NO:10 (LCDR2) and SEQ ID NO:11 (LCDR3). Additionally, in certain embodiments of the invention, the immunoglobulin-type binding region comprises or consists essentially of amino acids 2 to 245 of SEQ ID NO:4.

It is within the scope of the invention to use fragments, variants, and/or derivatives of the polypeptides of the CD20-binding proteins of the invention which contain a functional CD20 binding site to any extracellular part of CD20, and even more preferably capable of binding CD20 with high affinity (e.g. as shown by $K_D$). For example, the invention provides immunoglobulin-derived polypeptide sequences that can bind to CD20. Any polypeptide may be substituted for this region which binds an extracellular part of CD20 with a dissociation constant ($K_D$) of $10^{-5}$ to $10^{-12}$ moles/liter, preferably less than 200 nM.

Thus it is within the scope of the invention to alter the immunoglobulin-type binding site of a disclosed exemplary CD20-binding protein so long as at least one polypeptide sequence is chosen from the group consisting of the CDR1 sequences, CDR2 sequences, and CDR3 sequences that are described. In particular, but without limitation, the polypeptide sequences of the invention may consist essentially of 4 framework regions (FR1 to FR4) and three complementary determining regions (CDR1 to CDR3 respectively); or any suitable fragment of such amino acid sequence that exhibits target biomolecule binding functionality based on the presence of one or more CDRs.

In certain embodiments, the immunoglobulin-type binding region comprises (i) a heavy chain variable (VH) domain comprising CDR amino acid sequences as shown in SEQ ID NO:6, SEQ ID NO:7, and SEQ ID NO:8, and (ii) a light chain variable (VL) domain comprising CDR amino acid sequences as shown in SEQ ID NO:9, SEQ ID NO:10, and SEQ ID NO:11. In other embodiments, the immunoglobulin-type binding region comprises or consists essentially of amino acids 2 to 245 of SEQ ID NO:4.

Among certain embodiments of the present invention, the immunoglobulin-type binding region is derived from a nanobody or single domain immunoglobulin-derived region $V_{HH}$ which exhibits high affinity binding specifically to CD20. Generally, nanobodies are constructed from fragments of naturally occurring single, monomeric variable domain antibodies (sdAbs) of the sort found in camelids and cartilaginous fishes (Chondrichthyes). Nanobodies are engineered from these naturally occurring antibodies by truncating the single, monomeric variable domain to create a smaller and more stable molecule. Due to their small size, nanobodies are able to bind to antigens that are not accessible to whole antibodies.

III. The General Function of the CD20-Binding Proteins of the Invention

The present invention provides various CD20-binding proteins for the selective killing of specific cell types, the CD20 proteins comprising 1) immunoglobulin-type CD20 binding regions for cell targeting and 2) cytotoxic Shiga toxin effector regions for inducing cellular internalization and, optionally, cell killing as well. The linking of CD20 targeting immunoglobulin-type binding regions with Shiga-toxin-Subunit-A-derived regions enables the targeting of the potent Shiga toxin cytotoxicity specifically to CD20 expressing cells. In their preferred embodiments, the CD20-binding proteins of the invention are capable of binding CD20 natively present on a cell surface and entering the cell. Once internalized within a targeted cell type, certain embodiments of the CD20-binding proteins of the invention are capable of routing a cytotoxic Shiga toxin effector polypeptide fragment into the cytosol of the target cell. Once in the cytosol of a targeted cell type, certain embodiments of the CD20-binding proteins of the invention are capable of enzymatically inactivating ribosomes and eventually killing the cell. Alternatively, non-toxic variants may be used to deliver additional exogenous materials and/or label the interiors of CD20 expressing cells for diagnostic purposes.

Various types of cells which express CD20 may be targeted by the CD20-binding proteins of the invention for killing and/or receiving exogenous materials. Among the CD20 expressing cell types anticipated to internalize the CD20-binding proteins of the invention are those within the B-cell lineage. "B-cell lineage" is a term used to describe those cells that are cytologically or otherwise identified as B-cells themselves, e.g., through cell surface markers, or were once or presently derived from cells that are cytologically or otherwise identified as B-cells. The term "B-cell lineage" includes neoplastic cells derived from the B-cell lineage or precursors to the B-cell lineage. Among the CD20 expressing cell types that may be targeted are dysplastic or neoplastic cells of cell lineages which do not normally express CD20, e.g. melanoma cells. In particular, the CD20 expressing cells to be targeted with the CD20-binding proteins of the invention include neoplastic cells of B-cell lineages or non-B-cell lineages, such as neoplastic cells from a hematopoietic lineage that are not usually categorized as B-cells but which express CD20.

A. CD20-Binding Protein Capable of Inducing Rapid Internalization of CD20

The Shiga toxin effector regions of the present invention provide an internalization function, moving the CD20-binding proteins from the external surface of the target cell into the cytosol of the target cell. However, this internalization function is also an acceleration function in that the cellular internalization of CD20 is promoted or induced. As used in the specification and the claims herein, the phrase "rapid internalization" refers to a CD20-binding protein of the invention decreasing the time for CD20 cellular internalization upon binding as compared to a prior art reference molecule, such as the monoclonal antibody rituximab.

For the purposes of the present invention, cellular internalization is considered rapid if the time for internalization to occur due to the binding of the CD20-binding proteins is reduced as compared to the time for internalization of the target molecule with the binding of a well-characterized antibody recognizing a CD20 antigen, such as the 1H4 CD20 monoclonal antibody (Haisma H et al., *Blood* 92: 184-90 (1999)). For example, internalization timing for the CD20 antigen, although variable for cell type and antibody type, does not typically begin to reach maximal levels until approximately six hours after binding. Thus the term "rapid" as defined within the present specification is less than this six hour standard internalization window. In certain embodiments, rapid can be as quickly as less than about one hour, but can also encompass a range of from about 1 hour to about 2 hours, to about 3 hours, to about 4 hours, to about 5 hours; a range of about 2 hours to about 3 hours, to about 4 hours, to about 5 hours; a range of about 3 hours to about 4 hours, to about 5 hours; and a range of about 4 hours to about 5 hours.

B. Cell Kill Via Targeted Shiga Toxin Cytotoxicity

Because members of the Shiga toxin family are adapted to killing eukaryotic cells, CD20-binding proteins designed using Shiga toxin effector regions can show potent cell-kill activity. The A Subunits of members of the Shiga toxin family comprise enzymatic domains capable of killing a eukaryotic cell once in the cell's cytosol. Certain embodiments of the CD20-binding proteins of the invention take advantage of this cytotoxic mechanism.

In certain embodiments of the CD20-binding proteins of the invention, upon contacting a cell expressing CD20 such that at least a part of CD20 is accessible from the extracellular space, the CD20-binding protein is capable of causing death of the cell. CD20 positive "cell kill" may be accomplished using a CD20-binding protein of the invention under varied conditions of target cells, such as an ex vivo manipulated target cell, a target cell cultured in vitro, a target cell within a tissue sample cultured in vitro, or a target cell in vivo.

C. Selective Cytotoxicity Between CD20 Expressing Cells and Non-CD20 Expressing Cells By targeting the delivery of enzymatically active Shiga toxin regions using high-affinity immunoglobulin-type binding regions to CD20 expressing cells, this potent cell-kill activity can be restricted to preferentially killing CD20 positive cell types.

In certain embodiments, upon administration of the CD20-binding protein of the invention to a mixture of cell types, the CD20-binding protein is capable of selectively killing CD20 expressing cells displaying an extracellular CD20 target compared to cell types lacking extracellular CD20 targets. Because members of the Shiga toxin family are adapted for killing eukaryotic cells, CD20-binding proteins designed using Shiga toxin effector regions can show potent cytotoxic activity. By targeting the delivery of enzymatically active Shiga toxin regions to CD20 expressing cells using high-affinity immunoglobulin-type binding regions, this potent cell kill activity can be restricted to preferentially killing only CD20 expressing cells.

In certain embodiments, the CD20-binding protein of the invention is capable of selectively or preferentially causing the death of a specific cell type within a mixture of two or more different cell types. This enables targeting cytotoxic activity to specific cell types with a high preferentiality, such as with at least a 3-fold cytotoxic effect, over "bystander" cell types that do not express any significant amount of extracellular CD20 targets. This enables the targeted cell-killing of specific cell types expressing CD20 on cellular surfaces with a high preferentiality, such as with at least a 3-fold cytotoxic effect, over "bystander" cell types that do not express significant amounts of CD20 or are not exposing significant amounts of CD20 on a cellular surface.

In certain further embodiments, upon administration of the CD20-binding protein to two different populations of cell types, the CD20-binding protein is capable of causing cell death as defined by the half-maximal cytotoxic concentration ($CD_{50}$) on a cell population which expresses CD20 on a cellular surface at a dose at least three times lower than the $CD_{50}$ dose of the same CD20-binding protein to a cell population which does not express CD20.

In certain embodiments, the cytotoxic activity toward populations of cell types expressing CD20 on a cellular surface is at least 3-fold higher than the cytotoxic activity toward populations of cell types not physically coupled with any extracellular CD20 target of the CD20 binding region of the embodiment. According to the present invention, selective cytotoxicity may be quantified in terms of the ratio (a/b) of (a) cytotoxicity towards a population of cells expressing an extracellular CD20 target of the CD20 binding region of the embodiment to (b) cytotoxicity towards a population of cells of a cell type not physically coupled with any extracellular CD20 target of the CD20 binding region of the embodiment. In certain embodiments, the cytotoxicity ratio is indicative of selective cytotoxicity which is at least 3-fold, 5-fold, 10-fold, 15-fold, 20-fold, 25-fold, 30-fold, 40-fold, 50-fold, 75-fold, 100-fold, 250-fold, 500-fold, 750-fold, or 1000-fold higher for populations of cells or cell types expressing CD20 compared to populations of cells or cell types which do not express CD20.

This preferential cell-killing function allows a targeted cell to be killed by certain CD20-binding proteins of the invention under varied conditions and in the presence of non-targeted bystander cells, such as ex vivo manipulated mixtures of cell types, in vitro cultured tissues with mixtures of cell types, or in vivo in the presence of multiple cell types (e.g. in situ or in its native location within a multicellular organism).

In addition, catalytically inactive forms of CD20-binding proteins optionally may be used for diagnostic functions. The conjugating of additional diagnostic agents known in the art to CD20-binding proteins of the invention enable the imaging of intracellular organelles (e.g. Golgi, endoplasmic reticulum, and cytosolic compartments) of individual immune cells of the B-cell lineage or cancer cells in a patient or biopsy sample. For example, this may be useful in the diagnosis of neoplastic cell types, assaying the progression of anticancer therapies over time, and/or evaluating the presence of residual cancer cells after surgical excision of a tumor mass.

D. Delivery of Additional Exogenous Material

Because the CD20-binding protein are capable of inducing cellular internalization of CD20 after binding to an extracellular part of CD20, certain embodiments of the CD20-binding proteins of the invention may be used to deliver additional exogenous materials into the interior of CD20 expressing cells. In one sense, the entire CD20-binding protein is an exogenous material which will enter the cell; thus, the "additional" exogenous materials are materials linked to but other than the core CD20-binding protein itself.

"Additional exogenous material" as used herein refers to one or more molecules, often not generally present within a native target cell, where the CD20-binding proteins of the present invention can be used to specifically transport such material to the interior of a cell. In general, additional exogenous material is selected from peptides, polypeptides, proteins, and polynucleotides. One example of an additional exogenous material that is a peptide is an influenza virus antigen, such as the influenza Matrix 58-66 peptide (SEQ ID NO:3). One exemplary embodiment of a CD20-binding protein that may deliver that antigen into a target cell that expresses CD20 is provided in SEQ ID NO:16.

Additional exogenous material may include an interior polypeptide sequence within the core CD20-binding protein structure, such as the influenza Matrix 58-66 peptide (SEQ ID NO:3). Similarly, additional exogenous material may include a terminally-located polypeptide sequence linked to a terminal of the CD20-binding structure. Certain embodiments of the CD20-binding proteins of the invention that may deliver that antigen, as an additional exogenous material, into a target cell that expresses CD20 on a cell surface is the CD20-binding protein that comprises or consists essentially of SEQ ID NO:4, SEQ ID NO:12, SEQ ID NO:14, or SEQ ID NO:16.

Additional examples of exogenous materials that may be linked to the CD20-binding proteins of the invention include antigens such as those derived from bacterial proteins, such as those characteristic of antigen-presenting cells infected by bacteria. Further examples of additional exogenous materials are proteins mutated in cancer or proteins that are aberrantly expressed in cancer. Further examples of additional exogenous materials include T-cell complementary determining regions capable of functioning as exogenous antigens.

Further examples of exogenous materials that may be linked to the CD20-binding proteins of the invention include proteins other than antigens, such as enzymes. Further types of exogenous material are polynucleotides. Among the polynucleotides that can be transported are those formulated to have regulatory function, such as small interfering RNA (siRNA) and microRNA (miRNA).

Additional examples of exogenous materials include antigens such as those derived from bacterial proteins, such as those characteristic of antigen-presenting cells that are infected with bacteria. Further examples of exogenous antigens are ones that are derived from a protein mutated in cancer or proteins that are aberrantly expressed in cancer. T-cell complementary determining regions (CDR) can also act as exogenous antigens for the purposes of the present invention. Additional examples of exogenous material includes proteins other than antigens, such as enzymes. A further type of exogenous material is nucleic acids. Among the nucleic acids that can be transported are those formulated to have regulatory function, such as small interfering RNA (siRNA) and microRNA (miRNA).

Variations in the Polypeptide Sequence of the CD20-Binding Proteins of the Invention which Maintain Overall Structure and Function In certain of the above embodiments, the CD20-binding protein of the invention is a variant in which there are one or more conservative amino acid substitutions introduced into the polypeptide region(s). As used herein, the term "conservative substitution" denotes that one or more amino acids are replaced by another, biologically similar amino acid residue. Examples include substitution of amino acid residues with similar characteristics, e.g. small amino acids, acidic amino acids, polar amino acids, basic amino acids, hydrophobic amino acids and aromatic amino acids (see, for example, Table B below). An example of a conservative substitution with a residue normally not found in endogenous, mammalian peptides and proteins is the conservative substitution of an arginine or lysine residue with, for example, ornithine, canavanine, aminoethylcysteine, or another basic amino acid. For further information concerning phenotypically silent substitutions in peptides and proteins (see e.g. Bowie J et al., *Science* 247: 1306-10 (1990)). In the scheme below are conservative substitutions of amino acids grouped by physicochemical properties. I: neutral, hydrophilic, II: acids and amides, III: basic, IV: hydrophobic, V: aromatic, bulky amino acids.

TABLE B

Examples of Conservative Amino Acid Substitutions

| I | II | III | IV | V |
|---|----|-----|----|---|
| A | N  | H   | M  | F |
| S | D  | R   | L  | Y |
| T | E  | K   | I  | W |
| P | Q  |     | V  |   |
| G |    |     | C  |   |

In certain embodiments, a CD20-binding protein of the invention may comprise functional fragments or variants of a polypeptide region of the invention that have, at most, 20, 15, 10, 9, 8, 7, 6, 5, 4, 3, 2, or 1 amino acid substitutions compared to a polypeptide sequence recited herein, as long as it retains measurable biological activity alone or as a component of a CD20-binding protein. Variants of CD20-binding proteins are within the scope of the invention as a result of changing a polypeptide of the CD20-binding protein by altering one or more amino acids or deleting or inserting one or more amino acids, such as within the immunoglobulin-type binding region or the Shiga toxin effector region, in order to achieve desired properties, such as changed cytotoxicity, changed cytostatic effects, changed immunogenicity, and/or changed serum half-life. A polypeptide of a CD20-binding protein of the invention may further be with or without a signal sequence.

In certain embodiments, a CD20-binding protein of the invention shares at least 85%, 90%, 95%, 96%, 97%, 98%, 99% or more amino acid sequence identity to any one of the amino acid sequences of a CD20-binding protein recited herein, as long as it retains measurable biological activity, such as cytotoxicity, extracellular target biomolecule binding, enzymatic catalysis, or subcellular routing. The immunoglobulin-type binding region may differ from the amino acid sequences of a CD20-binding protein recited herein, as long as it retains binding functionality to its extracellular target biomolecule. Binding functionality will most likely be retained if the amino acid sequences of the ABRs are identical. For example, a CD20-binding protein that consists essentially of 85% amino acid identity to SEQ ID NO: 4 or SEQ ID NO:16 in which for the purposes of determining the degree of amino acid identity, the amino acid residues that form the ABR are disregarded. Binding functionality can be determined by the skilled worker using standard techniques.

In certain embodiments, the Shiga toxin effector region may be altered to change the enzymatic activity and/or cytotoxicity of the Shiga toxin effector region. This change may or may not result in a change in the cytotoxicity of a CD20-binding protein of which the altered Shiga toxin effector region is a component. Possible alterations include mutations to the Shiga toxin effector region selected from the group consisting of: a truncation, deletion, inversion, insertion and substitution.

The cytotoxicity of the A Subunits of members of the Shiga toxin family may be reduced or eliminated by mutation or truncation. The positions labeled tyrosine-77, glutamate-167, arginine-170, tyrosine-114, and tryptophan-203 have been shown to be important for the catalytic activity of Stx, Stx1, and Stx2 (Hovde C et al., *Proc Natl Acad Sci USA* 85: 2568-72 (1988); Deresiewicz R et al., *Biochemistry* 31: 3272-80 (1992); Deresiewicz R et al., *Mol Gen Genet* 241: 467-73 (1993); Ohmura M et al., *Microb Pathog* 15: 169-76 (1993); Cao C et al., *Microbiol Immunol* 38: 441-7 (1994); Suhan M, Hovde C, *Infect Immun* 66: 5252-9 (1998)). Mutating both glutamate-167 and arginine-170 eliminated the enzymatic activity of Slt-I A1 in a cell-free ribosome inactivation assay (LaPointe, *J Biol Chem* 280: 23310-18 (2005)). In another approach using de novo expression of Slt-I A1 in the endoplasmic reticulum, mutating both glutamate-167 and arginine-170 eliminated Slt-I A1 fragment cytotoxicity at that expression level (LaPointe, *J Biol Chem* 280: 23310-18 (2005)). A truncation analysis demonstrated that a fragment of StxA from residues 75 to 268 still retains significant enzymatic activity in vitro (Haddad, *J Bacteriol* 175: 4970-8 (1993)). A truncated fragment of Slt-I A1 containing residues 1-239 displayed significant enzymatic activity in vitro and cytotoxicity by de novo expression in the cytosol (LaPointe, *J Biol Chem* 280: 23310-18 (2005)). Expression of a Slt-I A1 fragment truncated to residues 1-239 in the endoplasmic reticulum was not cytotoxic because it could not retrotranslocate to the cytosol (LaPointe, *J Biol Chem* 280: 23310-18 (2005)).

The most critical residues for enzymatic activity and/or cytotoxicity in the Shiga toxin A Subunits were mapped to the following residue-positions: aspargine-75, tyrosine-77, glutamate-167, arginine-170, and arginine-176 among others (Di, *Toxicon* 57: 535-39 (2011)). In particular, a double-mutant construct of Stx2A containing glutamate-E167-to-lysine and arginine-176-to-lysine mutations was completely inactivated; whereas, many single mutations in Stx1 and Stx2 showed a 10-fold reduction in cytotoxicity. Further, truncation of Stx1A to 1-239 or 1-240 reduced its cytotoxicity, and similarly, truncation of Stx2A to a conserved hydrophobic residue reduced its cytotoxicity.

Shiga-like toxin 1 A Subunit truncations are catalytically active, capable of enzymatically inactivating ribosomes in vitro, and cytotoxic when expressed within a cell (LaPointe, *J Biol Chem* 280: 23310-18 (2005)). The smallest Shiga toxin A Subunit fragment exhibiting full enzymatic activity is a polypeptide composed of residues 1-239 of Slt1A (LaPointe, *J Biol Chem* 280: 23310-18 (2005)). Although the smallest fragment of the Shiga toxin A Subunit reported to retain substantial catalytic activity was residues 75-247 of StxA (Al-Jaufy, *Infect Immun* 62: 956-60 (1994)), a StxA truncation expressed de novo within a eukaryotic cell requires only up to residue 240 to reach the cytosol and exert catalytic inactivation of ribosomes (LaPointe, *J Biol Chem* 280: 23310-18 (2005)).

In certain embodiments derived from SLT-1A (SEQ ID NO:1), StxA (SEQ ID NO:25), or SLT-2A (SEQ ID NO:26), these changes include substitution of the asparagine at position 75, tyrosine at position 77, tyrosine at position 114, glutamate at position 167, arginine at position 170, arginine at position 176, and/or substitution of the tryptophan at position 203. Examples of such substitutions will be known to the skilled worker based on the prior art, such as asparagine at position 75 to alanine, tyrosine at position 77 to serine, substitution of the tyrosine at position 114 to alanine, substitution of the glutamate at position 167 to aspartate, substitution of the arginine at position 170 to alanine, substitution of the arginine at position 176 to lysine, and/or substitution of the tryptophan at position 203 to alanine.

CD20-binding proteins of the invention may optionally be conjugated to one or more additional agents which may include therapeutic and/or diagnostic agents known in the art.

Production, Manufacture, and Purification of a CD20-Binding Protein of the Invention The CD20-binding proteins of the invention may be produced using biochemical engineering techniques well known to those of skill in the art. For example, CD20-binding proteins of the invention may be manufactured by standard synthetic methods, by use of recombinant expression systems, or by any other suitable method. Thus, the CD20-binding proteins may be synthesized in a number of ways, including, e.g. methods comprising: (1) synthesizing a polypeptide or polypeptide component of a CD20-binding protein using standard solid-phase or liquid-phase methodology, either stepwise or by fragment assembly, and isolating and purifying the final peptide compound product; (2) expressing a polynucleotide that encodes a polypeptide or polypeptide component of a CD20-binding protein in a host cell and recovering the expression product from the host cell or host cell culture; or (3) cell-free in vitro expression of a polynucleotide encoding a polypeptide or polypeptide component of a CD20-binding protein, and recovering the expression product; or by any combination of the methods of (1), (2) or (3) to obtain fragments of the peptide component, subsequently joining (e.g. ligating) the fragments to obtain the peptide component, and recovering the peptide component.

It may be preferable to synthesize a polypeptide or polypeptide component of a CD20-binding protein of the invention by means of solid-phase or liquid-phase peptide synthesis. CD20-binding proteins of the invention may suitably be manufactured by standard synthetic methods. Thus, peptides may be synthesized by, e.g. methods comprising synthesizing the peptide by standard solid-phase or liquid-phase methodology, either stepwise or by fragment assembly, and isolating and purifying the final peptide product. In this context, reference may be made to WO 1998/11125 or, inter alia, Fields, G et al., *Principles and Practice of Solid-Phase Peptide Synthesis* (Synthetic Peptides, Gregory A. Grant, ed., Oxford University Press, U.K., 2nd ed., 2002) and the synthesis examples therein.

CD20-binding proteins of the invention may be prepared (produced and purified) using recombinant techniques well known in the art. In general, methods for preparing polypeptides by culturing host cells transformed or transfected with a vector comprising the encoding polynucleotide and recovering the polypeptide from cell culture are described in, e.g. Sambrook et al., *Molecular Cloning: A Laboratory Manual* (Cold Spring Harbor Laboratory Press, NY, U.S., 1989); Dieffenbach et al., *PCR Primer: A Laboratory Manual* (Cold Spring Harbor Laboratory Press, N.Y., U.S., 1995). Any suitable host cell may be used to produce a CD20-binding protein of the invention. Host cells may be cells stably or transiently transfected, transformed, transduced or infected with one or more expression vectors which drive expression of a polypeptide of the invention. In addition, a CD20-binding protein of the invention may be produced by modifying the polynucleotide encoding the CD20-binding protein that result in altering one or more amino acids or deleting or inserting one or more amino acids in order to achieve desired properties, such as changed cytotoxicity, changed cytostatic effects, changed immunogenicity, and/or changed serum half-life.

Accordingly, the present invention also provides methods for producing a CD20-binding protein of the invention according to above recited methods and using a polynucleotide encoding part or all of a polypeptide of the invention, an expression vector comprising at least one polynucleotide of the invention capable of encoding part or all of a polypeptide of the invention when introduced into a host cell, and/or a host cell comprising a polynucleotide or expression vector of the invention.

When a polypeptide or protein is expressed using recombinant techniques in a host cell or cell-free system, it is advantageous to separate (or purify) the desired polypeptide or protein away from other components, such as host cell factors, in order to obtain preparations that are of high purity or are substantially homogeneous. Purification can be accomplished by methods well known in the art, such as centrifugation techniques, extraction techniques, chromatographic and fractionation techniques (e.g. size separation by gel filtration, charge separation by ion-exchange column, hydrophobic interaction chromatography, reverse phase chromatography, chromatography on silica or cation-exchange resins such as DEAE and the like, chromatofocusing, and Protein A Sepharose chromatography to remove contaminants), and precipitation techniques (e.g. ethanol precipitation or ammonium sulfate precipitation. Any number of biochemical purification techniques may be used to increase the purity of a CD20-binding protein of the invention. In certain embodiments, the CD20-binding proteins of the invention may optionally be purified in homo-multimeric forms (i.e. a protein complex of two or more identical CD20-binding proteins).

In the Examples below are descriptions of non-limiting examples of methods for producing a CD20-binding protein of the invention, as well as specific but non-limiting aspects of CD20-binding protein production for the disclosed, exemplary, CD20-binding proteins.

Pharmaceutical Compositions Comprising a CD20-Binding Protein of the Invention

The present invention provides CD20-binding proteins for use, alone or in combination with one or more additional therapeutic agents, in a pharmaceutical composition, for treatment or prophylaxis of conditions, diseases, disorders, or symptoms described in further detail below (e.g. cancers, malignant tumors, non-malignant tumors, and immune disorders). The present invention further provides pharmaceutical compositions comprising a CD20-binding protein of the invention, or a pharmaceutically acceptable salt or solvate thereof, according to the invention, together with at least one pharmaceutically acceptable carrier, excipient, or vehicle. In certain embodiments, the pharmaceutical composition of the invention may comprise homo-multimeric and/or hetero-multimeric forms of the CD20-binding proteins of the invention. The pharmaceutical compositions will be useful in methods of treating, ameliorating, or preventing a disease, condition, disorder, or symptom described in further detail below. Each such disease, condition, disorder, or symptom is envisioned to be a separate embodiment with respect to uses of a pharmaceutical composition according to the invention. The invention further provides pharmaceutical compositions for use in at least one method of treatment according to the invention, as described in more detail below.

As used herein, the terms "patient" and "subject" are used interchangeably to refer to any organism, commonly vertebrates such as humans and animals, which presents symptoms, signs, and/or indications of at least one disease, disorder, or condition. These terms include mammals such as the non-limiting examples of primates, livestock animals (e.g. cattle, horses, pigs, sheep, goats, etc.), companion animals (e.g. cats, dogs, etc.) and laboratory animals (e.g. mice, rabbits, rats, etc.).

As used herein, "treat," "treating," or "treatment" and grammatical variants thereof refer to an approach for obtaining beneficial or desired clinical results. The terms may refer to slowing the onset or rate of development of a condition, disorder or disease, reducing or alleviating symptoms associated with it, generating a complete or partial regression of the condition, or some combination of any of the above. For the purposes of this invention, beneficial or desired clinical results include, but are not limited to, reduction or alleviation of symptoms, diminishment of extent of disease, stabilization (e.g. not worsening) of state of disease, delay or slowing of disease progression, amelioration or palliation of the disease state, and remission (whether partial or total), whether detectable or undetectable. "Treat," "treating," or "treatment" can also mean prolonging survival relative to expected survival time if not receiving treatment. A subject (e.g. a human) in need of treatment may thus be a subject already afflicted with the disease or disorder in question. The terms "treat," "treating," or "treatment" includes inhibition or reduction of an increase in severity of a pathological state or symptoms relative to the absence of treatment, and is not necessarily meant to imply complete cessation of the relevant disease, disorder, or condition.

As used herein, the terms "prevent," "preventing," "prevention" and grammatical variants thereof refer to an approach for preventing the development of, or altering the pathology of, a condition, disease, or disorder. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g. a human) in need of prevention may thus be a subject not yet afflicted with the disease or disorder in question. The term "prevention" includes slowing the onset of disease relative to the absence of treatment, and is not necessarily meant to imply permanent prevention of the relevant disease, disorder or condition. Thus "preventing" or "prevention" of a condition may in certain contexts refer to reducing the risk of developing the condition, or preventing or delaying the development of symptoms associated with the condition.

As used herein, an "effective amount" or "therapeutically effective amount" is an amount or dose of a composition (e.g. a therapeutic composition or agent) that produces at least one desired therapeutic effect in a subject, such as preventing or treating a target condition or beneficially alleviating a symptom associated with the condition. The most desirable therapeutically effective amount is an amount that will produce a desired efficacy of a particular treatment selected by one of skill in the art for a given subject in need thereof. This amount will vary depending upon a variety of factors understood by the skilled worker, including but not limited to the characteristics of the therapeutic compound (including activity, pharmacokinetics, pharmacodynamics, and bioavailability), the physiological condition of the subject (including age, sex, disease type, disease stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly (see e.g. *Remington: The Science and Practice of Pharmacy* (Gennaro A, ed., Mack Publishing Co., Easton, Pa., U.S., 19th ed., 1995)).

Production or Manufacture of a Pharmaceutical Composition Comprising a CD20-Binding Protein of the Invention Pharmaceutically acceptable salts or solvates of any of the CD20-binding proteins of the invention are likewise within the scope of the present invention.

The term "solvate" in the context of the present invention refers to a complex of defined stoichiometry formed between a solute (in casu, a polypeptide compound or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

CD20-binding proteins of the present invention, or salts thereof, may be formulated as pharmaceutical compositions prepared for storage or administration, which typically comprise a therapeutically effective amount of a compound of the invention, or a salt thereof, in a pharmaceutically acceptable carrier. The term "pharmaceutically acceptable carrier" includes any of the standard pharmaceutical carriers. Pharmaceutically acceptable carriers for therapeutic use are well known in the pharmaceutical art, and are described, for example, in *Remington's Pharmaceutical Sciences* (Mack Publishing Co. (A. Gennaro, ed., 1985)). As used herein, "pharmaceutically acceptable carrier" includes any and all physiologically acceptable, i.e. compatible, solvents, dispersion media, coatings, antimicrobial agents, isotonic, and absorption delaying agents, and the like. Pharmaceutically acceptable carriers or diluents include those used in formulations suitable for oral, rectal, nasal or parenteral (including subcutaneous, intramuscular, intravenous, intradermal, and transdermal) administration. Exemplary pharmaceutically acceptable carriers include sterile aqueous solutions or dispersions and sterile powders for the extemporaneous preparation of sterile injectable solutions or dispersion. Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyloleate. Proper fluidity can be maintained, for example, by the use of coating materials, such as lecithin, by the maintenance of the required particle size in the case of dispersions, and by the use of surfactants. In certain embodiments, the carrier is suitable for intravenous, intramuscular, subcutaneous, parenteral, spinal or epidermal administration (e.g. by injection or infusion). Depending on selected route of administration, the CD20-binding protein or other pharmaceutical component may be coated in a material intended to protect the compound from the action of low pH and other natural inactivating conditions to which the active CD20-binding protein may encounter when administered to a patient by a particular route of administration.

The formulations of the pharmaceutical compositions of the invention may conveniently be presented in unit dosage form and may be prepared by any of the methods well known in the art of pharmacy. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. Compositions may be formulated for any suitable route and means of administration. Subcutaneous or transdermal modes of administration may be particularly suitable for therapeutic CD20-binding proteins described herein.

The pharmaceutical compositions of the invention may also contain adjuvants such as preservatives, wetting agents, emulsifying agents and dispersing agents. Prevention of the presence of microorganisms may be ensured both by sterilization procedures, and by the inclusion of various antibacterial and antifungal agents, for example, paraben, chlorobutanol, phenol sorbic acid, and the like. Isotonic agents, such as sugars, sodium chloride, and the like into the compositions, may also be desirable. In addition, prolonged absorption of the injectable pharmaceutical form may be brought about by the inclusion of agents which delay absorption such as, aluminum monostearate and gelatin.

A pharmaceutical composition of the invention also optionally includes a pharmaceutically acceptable antioxidant. Exemplary pharmaceutically acceptable antioxidants are water soluble antioxidants such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propylgallate, alpha-tocopherol, and the like; and metal chelating agents, such as citric acid, ethylenediamine tetraacetic acid (EDTA), sorbitol, tartaric acid, phosphoric acid, and the like.

In another aspect, the present invention provides pharmaceutical compositions comprising one or a combination of different CD20-binding proteins of the invention, or an ester, salt or amide of any of the foregoing, and at least one pharmaceutically acceptable carrier.

Therapeutic compositions are typically sterile and stable under the conditions of manufacture and storage. The composition may be formulated as a solution, microemulsion, liposome, or other ordered structure suitable to high drug concentration. The carrier may be a solvent or dispersion medium containing, for example, water, alcohol such as ethanol, polyol (e.g. glycerol, propylene glycol, and liquid polyethylene glycol), or any suitable mixtures. The proper fluidity may be maintained, for example, by the use of a coating such as lecithin, by the maintenance of the required particle size in the case of dispersion and by use of surfactants according to formulation chemistry well known in the art. In certain embodiments, isotonic agents, e.g. sugars, polyalcohols such as mannitol, sorbitol, or sodium chloride may be desirable in the composition. Prolonged absorption of injectable compositions may be brought about by including in the composition an agent that delays absorption for example, monostearate salts and gelatin.

Solutions or suspensions used for intradermal or subcutaneous application typically include one or more of: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and tonicity adjusting agents such as, e.g., sodium chloride or dextrose. The pH can be adjusted with acids or bases, such as hydrochloric acid or sodium hydroxide, or buffers with citrate, phosphate, acetate and the like. Such preparations may be enclosed in ampoules, disposable syringes or multiple dose vials made of glass or plastic.

Sterile injectable solutions may be prepared by incorporating a CD20-binding protein of the invention in the required amount in an appropriate solvent with one or a combination of ingredients described above, as required, followed by sterilization microfiltration. Dispersions may be prepared by incorporating the active compound into a sterile vehicle that contains a dispersion medium and other ingredients, such as those described above. In the case of sterile powders for the preparation of sterile injectable solutions, the methods of preparation are vacuum drying and freeze-drying (lyophilization) that yield a powder of the active ingredient in addition to any additional desired ingredient from a sterile-filtered solution thereof.

When a therapeutically effective amount of a CD20-binding protein of the invention is designed to be administered by, e.g. intravenous, cutaneous or subcutaneous injection, the binding agent will be in the form of a pyrogen-free, parenterally acceptable aqueous solution. Methods for preparing parenterally acceptable protein solutions, taking into consideration appropriate pH, isotonicity, stability, and the like, are within the skill in the art. A preferred pharmaceutical composition for intravenous, cutaneous, or subcutaneous injection will contain, in addition to binding agents, an isotonic vehicle such as sodium chloride injection, Ringer's injection, dextrose injection, dextrose and sodium chloride injection, lactated Ringer's injection, or other vehicle as known in the art. A pharmaceutical composition of the present invention may also contain stabilizers, preservatives, buffers, antioxidants, or other additives well known to those of skill in the art.

As described elsewhere herein, a compound may be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art (see e.g. *Sustained and Controlled Release Drug Delivery Systems* (J. Robinson, ed., Marcel Dekker, Inc., NY, U.S., 1978)).

In certain embodiments, the pharmaceutical composition of the invention may be formulated to ensure a desired distribution in vivo. For example, the blood-brain barrier excludes many large and/or hydrophilic compounds. To target a therapeutic compound or composition of the invention to a particular in vivo location, they can be formulated, for example, in liposomes which may comprise one or more moieties that are selectively transported into specific cells or organs, thus enhancing targeted drug delivery. Exemplary targeting moieties include folate or biotin; mannosides; antibodies; surfactant protein A receptor; p120 catenin and the like.

Polynucleotides, Expression Vectors, and Host Cells

Beyond the CD20-binding proteins of the present invention, the polynucleotides which encode such CD20-binding proteins, or functional portions thereof, are within the scope of the present invention. The term "polynucleotide" is equivalent to the term "nucleic acids" both of which include polymers of deoxyribonucleic acids (DNAs), polymers of ribonucleic acids (RNAs), analogs of these DNAs or RNAs generated using nucleotide analogs, and derivatives, fragments and homologs thereof. The polynucleotide of the invention may be single-, double-, or triple-stranded. Disclosed polynucleotides are specifically disclosed to include all polynucleotides capable of encoding an exemplary CD20-binding protein, for example, taking into account the wobble known to be tolerated in the third position of RNA codons, yet encoding for the same amino acid as a different RNA codon (see Stothard P, Biotechniques 28: 1102-4 (2000)).

In one aspect, the invention provides polynucleotides which encode a CD20-binding protein of the invention, or a fragment or derivative thereof. The polynucleotides may include, e.g., nucleic acid sequence encoding a polypeptide at least 50%, 55%, 60%, 65%, 70%, 75%, 80%, 85%, 90%, 95%, 99% or more, identical to a polypeptide comprising one of the amino acid sequences of the CD20-binding protein. The invention also includes polynucleotides comprising nucleotide sequences that hybridize under stringent conditions to a polynucleotide which encodes a CD20-binding protein of the invention, or a fragment or derivative thereof, or the antisense or complement of any such sequence.

Derivatives or analogs of the polynucleotides (or CD20-binding proteins) of the invention include, inter alia, polynucleotide (or polypeptide) molecules having regions that are substantially homologous to the polynucleotides or CD20-binding proteins of the invention, e.g. by at least about 45%, 50%, 70%, 80%, 95%, 98%, or even 99% identity (with a preferred identity of 80-99%) over a polynucleotide or polypeptide sequence of the same size or when compared to an aligned sequence in which the alignment is done by a computer homology program known in the art. An exemplary program is the GAP program (Wisconsin Sequence Analysis Package, Version 8 for UNIX, Genetics Computer Group, University Research Park, Madison, Wis., U.S.) using the default settings, which uses the algorithm of Smith T, Waterman M, *Adv. Appl. Math.* 2: 482-9 (1981). Also included are polynucleotides capable of hybridizing to the complement of a sequence encoding the proteins of the invention under stringent conditions (see e.g. Ausubel F, et al., *Current Protocols in Molecular Biology* (John Wiley & Sons, New York, N.Y., U.S., 1993)), and below. Stringent conditions are known to those skilled in the art and may be found in *Current Protocols in Molecular Biology* (John Wiley & Sons, NY, U.S., Ch. Sec. 6.3.1-6.3.6 (1989).

Further, the present invention further provides expression vectors that comprise the polynucleotides within the scope of the invention. The polynucleotides capable of encoding the CD20-binding proteins of the invention may be inserted into known vectors, including bacterial plasmids, viral vectors and phage vectors, using material and methods well known in the art to produce expression vectors. Such expression vectors will include the polynucleotides necessary to support production of contemplated CD20-binding proteins within any host cell of choice or cell-free expression systems (e.g. pTxb1 and pIVEX2.3 described in the Examples below). The specific polynucleotides comprising expression vectors for use with specific types of host cells or cell-free expression systems are well known to one of ordinary skill in the art, can be determined using routine experimentation, or may be purchased.

The term "expression vector," as used herein, refers to a polynucleotide, linear or circular, comprising one or more expression units. The term "expression unit" denotes a polynucleotide segment encoding a polypeptide of interest and capable of providing expression of the nucleic acid segment in a host cell. An expression unit typically comprises a transcription promoter, an open reading frame encoding the polypeptide of interest, and a transcription terminator, all in operable configuration. An expression vector contains one or more expression units. Thus, in the context of the present invention, an expression vector encoding a CD20-binding protein comprising a single polypeptide chain (e.g. an scFv linked to a Shiga toxin effector region) includes at least an expression unit for the single polypeptide chain, whereas a CD20-binding protein comprising, e.g. two or more polypeptide chains (e.g. one chain comprising a $V_L$ domain and a second chain comprising a $V_H$ domain linked to a toxin effector region) includes at least two expression units, one for each of the two polypeptide chains of the CD20-binding protein. For expression of multi-chain CD20-binding proteins, an expression unit for each polypeptide chain may also be separately contained on different expression vectors (e.g. expression may be achieved with a single host cell into which expression vectors for each polypeptide chain has been introduced).

Expression vectors capable of directing transient or stable expression of polypeptides and proteins are well known in the art. The expression vectors generally include, but are not limited to, one or more of the following: a heterologous signal sequence or peptide, an origin of replication, one or more marker genes, an enhancer element, a promoter, and a transcription termination sequence, each of which is well known in the art. Optional regulatory control sequences, integration sequences, and useful markers that can be employed are known in the art.

The term "host cell" refers to a cell which can support the replication or expression of the expression vector. Host cells may be prokaryotic cells, such as *E. coli* or eukaryotic cells (e.g. yeast, insect, amphibian, bird, or mammalian cells). Creation and isolation of host cell lines comprising a polynucleotide of the invention or capable of producing a CD20-binding protein of the invention can be accomplished using standard techniques known in the art.

CD20-binding proteins within the scope of the present invention may be variants or derivatives of the CD20-binding proteins described herein that are produced by modifying the polynucleotide encoding a CD20-binding protein by altering one or more amino acids or deleting or inserting one or more amino acids that may render it more suitable to achieve desired properties, such as more optimal expression by a host cell.

Methods for Using a CD20-Binding Protein or a Pharmaceutical Composition of the Invention Generally, it is an object of the invention to provide pharmacologically active agents, as well as compositions comprising the same, that can be used in the prevention and/or treatment of diseases, disorders, and conditions, such as cancers, tumors, immune disorders, or further pathological conditions mentioned herein. Accordingly, the present invention provides methods of using the CD20-binding proteins and pharmaceutical compositions of the invention for the killing of CD20 expressing cells, delivering of additional exogenous materials into CD20 expressing cells, labeling of the interior of CD20 expressing cells, and for treating diseases, disorders, and conditions as described herein.

In particular, it is an object of the invention to provide such pharmacologically active agents, compositions, and/or methods that have certain advantages compared to the agents, compositions, and/or methods that are currently known in the art. Accordingly, the present invention provides methods of using CD20-binding proteins with specified polypeptide sequences and pharmaceutical compositions thereof. For example, any of the polypeptide sequences in SEQ ID NOs:1, 3, 4, 6-12, 14, 16, and/or 18-29, can be specifically utilized as a component of the CD20-binding protein used in the following methods.

The present invention provides methods of killing a CD20 expressing cell comprising the step of contacting the cell, either in vitro or in vivo, with a CD20-binding protein or pharmaceutical composition of the present invention. In certain embodiments, a CD20-binding protein or pharmaceutical composition of the present invention can be used to kill CD20 expressing cells in a mixture of different cell types including non-CD20 expressing cells, such as mixtures comprising cancer cells, infected cells, and/or hematological cells.

In certain embodiments, a CD20-binding protein or pharmaceutical composition of the present invention can be used to kill cancer cells in a mixture of different cell types, such as within an organism. In certain embodiments, a CD20-binding protein or pharmaceutical composition of the present invention, alone or in combination with other compounds or pharmaceutical compositions can show potent cell-kill activity when administered to a population of cells, in vitro or in vivo in a subject such as in a patient in need of treatment. By targeting the delivery of enzymatically active Shiga toxin regions using high-affinity immunoglobulin-type binding regions to CD20, this potent cell-kill activity can be restricted to specifically and selectively kill certain cell types within an organism, such as cancer cells, neoplastic cells, malignant cells, non-malignant tumor cells, or infected cells.

The term "cancer cell" or "cancerous cell" refers to various neoplastic cells which grow and divide in an abnormally accelerated fashion and will be clear to the skilled person. The term "cancer cell" includes both malignant and non-malignant cells. Generally, cancers and/or tumors can be defined as diseases, disorders, or conditions that are amenable to treatment and/or prevention. The cancers and tumors (either malignant or non-malignant) which are comprised by cancer cells and/or tumor cells will be clear to the skilled person.

The present invention provides a method of killing a CD20 expressing cell in a patient, the method comprising the step of administering to the patient at least one CD20-binding protein of the present invention or a pharmaceutical composition thereof.

Certain embodiments of the CD20-binding protein or pharmaceutical compositions thereof can be used to kill a CD20 expressing immune cell (whether healthy or malignant) in a patient.

It is within the scope of the present invention to utilize the CD20-binding protein of the invention or pharmaceutical composition thereof for the purposes of ex vivo depletion of B-cells from isolated cell populations removed from a patient.

Additionally, the present invention provides a method of treating a disease, disorder, or condition in a patient comprising the step of administering to a patient in need thereof a therapeutically effective amount of at least one of the CD20-binding proteins of the present invention or a pharmaceutical composition thereof. Contemplated diseases, disorders, and conditions that can be treated using this method include cancers, malignant tumors, non-malignant tumors, and, immune disorders. Administration of a "therapeutically effective dosage" of a compound of the invention can result in a decrease in severity of disease symptoms, an increase in frequency and duration of disease symptom-free periods, or a prevention of impairment or disability due to the disease affliction.

The therapeutically effective amount of a compound of the present invention will depend on the route of administration, the type of mammal being treated, and the physical characteristics of the specific patient under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials. An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person.

An acceptable route of administration may refer to any administration pathway known in the art, including but not limited to aerosol, enteral, nasal, ophthalmic, oral, parenteral, rectal, vaginal, or transdermal (e.g. topical administration of a cream, gel or ointment, or by means of a transdermal patch). "Parenteral administration" is typically associated with injection at or in communication with the intended site of action, including intratumoral injection, infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal administration.

For administration of a pharmaceutical composition of the invention, the dosage range will generally be from about 0.0001 to 100 milligrams per kilogram (mg/kg), and more usually 0.01 to 5 mg/kg, of the host body weight. Exemplary dosages may be 0.25 mg/kg body weight, 1 mg/kg body weight, 3 mg/kg body weight, 5 mg/kg body weight or 10 mg/kg body weight or within the range of 1-10 mg/kg. An exemplary treatment regime is a once or twice daily administration, or a once or twice weekly administration, once every two weeks, once every three weeks, once every four weeks, once a month, once every two or three months or once every three to 6 months. Dosages may be selected and readjusted by the skilled health care professional as required to maximize therapeutic benefit for a particular patient.

Pharmaceutical compositions of the invention will typically be administered to the same patient on multiple occasions. Intervals between single dosages can be, for example, 2-5 days, weekly, monthly, every two or three months, every six months, or yearly. Intervals between administrations can also be irregular, based on regulating blood levels or other markers in the subject or patient. Dosage regimens for a compound of the invention include intravenous administration of 1 mg/kg body weight or 3 mg/kg body weight with the compound administered every two to four weeks for six dosages, then every three months at 3 mg/kg body weight or 1 mg/kg body weight.

A pharmaceutical composition of the present invention may be administered via one or more routes of administration, using one or more of a variety of methods known in the art. As will be appreciated by the skilled worker, the route and/or mode of administration will vary depending upon the desired results. Routes of administration for CD20-binding proteins or pharmaceutical compositions of the invention include, e.g. intravenous, intramuscular, intradermal, intraperitoneal, subcutaneous, spinal, or other parenteral routes of administration, for example by injection or infusion at or in communication with the intended site of action (e.g. intratumoral injection). In other embodiments, a CD20-binding protein or pharmaceutical composition of the invention may be administered by a non-parenteral route, such as a topical, epidermal or mucosal route of administration, for example, intranasally, orally, vaginally, rectally, sublingually, or topically.

Therapeutic CD20-binding proteins or pharmaceutical compositions of the invention may be administered with one or more of a variety of medical devices known in the art. For example, in one embodiment, a pharmaceutical composition of the invention may be administered with a needleless hypodermic injection device. Examples of well-known implants and modules useful in the present invention are in the art, including e.g., implantable micro-infusion pumps for controlled rate delivery; devices for administering through the skin; infusion pumps for delivery at a precise infusion rate; variable flow implantable infusion devices for continuous drug delivery; and osmotic drug delivery systems. These and other such implants, delivery systems, and modules are known to those skilled in the art.

A CD20-binding protein or pharmaceutical composition of the present invention may be administered alone or in combination with one or more other therapeutic or diagnostic agents. A combination therapy may include a CD20-binding protein of the invention or pharmaceutical composition thereof combined with at least one other therapeutic agent selected based on the particular patient, disease or condition to be treated. Examples of other such agents include, inter alia, a cytotoxic, anti-cancer or chemotherapeutic agent, an anti-inflammatory or anti-proliferative agent, an antimicrobial or antiviral agent, growth factors, cytokines, an analgesic, a therapeutically active small molecule or polypeptide, a single chain antibody, a classical antibody or fragment thereof, or a nucleic acid molecule which modulates one or more signaling pathways, and similar modulating therapeutics which might complement or otherwise be beneficial in a therapeutic or prophylactic treatment regimen.

Treatment of a patient with certain embodiments of the CD20-binding proteins or pharmaceutical compositions of the present invention will lead to cell death of targeted cells and/or the inhibition of growth of targeted cells. As such, CD20-binding proteins of the invention, and pharmaceutical compositions comprising them, will be useful in methods for treating a variety of pathological disorders in which killing or depleting target cells might be beneficial, such as, inter alia, cancer, immune disorders, and infected cells. The present invention provides methods for suppressing cell proliferation, and treating cell disorders, including neoplasia and overactive B-cells.

In certain embodiments, CD20-binding proteins and pharmaceutical compositions of the invention can be used to treat or prevent cancers, tumors (malignant and non-malignant), and immune disorders.

In certain embodiments, the present invention provides methods for treating malignancies or neoplasms and other blood cell-associated cancers in a mammalian subject, such as a human, the method comprising the step of administering to a subject in need thereof a therapeutically effective amount of a CD20-binding protein or pharmaceutical composition of the invention.

The CD20-binding proteins and pharmaceutical compositions of the invention have varied applications, including, e.g., uses as anti-neoplastic agents, uses in modulating immune responses, uses in purging transplantation tissues of unwanted cell types, and uses as diagnostic agents. The CD20-binding proteins and pharmaceutical compositions of the present invention are commonly anti-neoplastic agents—meaning they are capable of treating and/or preventing the development, maturation, or spread of neoplastic or malignant cells by inhibiting the growth and/or causing the death of cancer or tumor cells.

In certain embodiments, a CD20-binding protein or pharmaceutical composition of the present invention is used to treat a B-cell-mediated disease or disorder, such as for example leukemia, lymphoma, myeloma, amyloidosis, ankylosing spondylitis, asthma, Crohn's disease, diabetes, graft rejection, graft-host disease, Hashimoto's thyroiditis, hemolytic uremic syndrome, HIV-related diseases, lupus erythematosus, multiple sclerosis, polyarteritis, psoriasis, psoriatic arthritis, rheumatoid arthritis, scleroderma, septic shock, Sjörgren's syndrome, ulcerative colitis, and vasculitis.

The CD20-binding proteins and pharmaceutical compositions of the present invention can be utilized in a method of treating cancer comprising administering to a patient, in need thereof, a therapeutically effective amount of the CD20-binding protein or a pharmaceutical composition of the present invention. Some cancers shown to have expression of CD20 include, but are not limited to, B-cell lymphomas (including both non-Hodgkin's and Hodgkin's), hairy cell leukemia, B-cell chronic lymphocytic leukemia, some T-cell lymphomas, and melanoma cancer stem cells. In certain embodiments of the methods of the present invention, the cancer being treated is selected from the group consisting of bone cancer, leukemia, lymphoma, melanoma, and myeloma.

The CD20-binding proteins and pharmaceutical compositions of the present invention can be utilized in a method of treating an immune disorder comprising administering to a patient, in need thereof, a therapeutically effective amount of the CD20-binding protein or a pharmaceutical composition of the present invention. In certain embodiments of the methods of the present invention, the immune disorder is related to an inflammation associated with a disease selected from the group consisting of: amyloidosis, ankylosing spondylitis, asthma, Crohn's disease, diabetes, graft rejection, graft-versus host disease, Hashimoto's thyroiditis, hemolytic uremic syndrome, HIV-related diseases, lupus erythematosus, multiple sclerosis, polyarteritis, psoriasis, psoriatic arthritis, rheumatoid arthritis, scleroderma, septic shock, Sjörgren's syndrome, ulcerative colitis, and vasculitis.

Among certain embodiments of the present invention is using the CD20-binding protein as a component of a medicament for the treatment or prevention of a cancer, tumor, or immune disorder. For example, immune disorders presenting on the skin of a patient may be treated with such a medicament in efforts to reduce inflammation.

Beyond the CD20-binding proteins of the present invention, the polynucleotides which encode such molecules, when applicable, are within the scope of the present invention. The term "polynucleotides" is equivalent to the term "nucleic acids" both of which include polymers of deoxyribonucleic acids and ribonucleic acids. Such polynucleotides are specifically disclosed to include all polynucleotides capable of encoding a specified CD20-binding protein, for example, taking into account the wobble known to be tolerated in the third position of amino acid codons, yet encoding for an equivalent amino acid. Further, the present invention comprises expression vectors that comprise the polynucleotides within the scope of the invention. Such expression vectors will include the polynucleotides necessary to support production of the CD20-binding proteins of the invention within any host cell of choice. The specific polynucleotides comprising expression vectors for use with specific types of host cells are well known to one of ordinary skill in the art, can be determined using routine experimentation, or may be purchased.

The present invention also provides methods of rapidly internalizing the CD20-binding protein into the interior of a cell, by contacting the cell with a CD20-binding protein of the invention either in vivo or in vitro, such as within a patient. The present invention further provides methods of killing a CD20 expressing cell, where that cell expresses a CD20 antigen on its surface, by contacting the cell with a CD20-binding protein of the invention either in vivo or in vitro, such as within a patient.

If the CD20-binding proteins of the present invention comprise or are conjugated to exogenous material, as described above, those CD20-binding proteins can be utilized in a method of delivering that exogenous material into a target cell that expresses a CD20 antigen on its cell surface. The present invention also provides methods of delivering exogenous materials into the interior of a CD20 expressing cell, by contacting the cell with a CD20-binding protein of the invention either in vivo or in vitro, such as within a patient.

Additionally, the CD20-binding proteins of the invention can be utilized in a method for treating cancer, wherein the tumor or cancer cell expresses on its surface a CD20 antigen, which method comprises administering the protein of the present invention to a patient in need of such treatment. Some cancers shown to have expression of CD20 include, but are not limited to, B-cell lymphomas (including both non-Hodgkin's and Hodgkin's), hairy cell leukemia, B-cell chronic lymphocytic leukemia, some T-cell lymphomas, and melanoma cancer stem cells.

For purposes of the present invention, the term "lymphoma" includes B-cell lymphomas (such as non-Hodgkin's and Hodgkin's types), hairy cell leukemia, B-cell chronic lymphocytic leukemia, T-cell lymphomas, and melanoma cancer stem cell type lymphomas.

Certain embodiments of the invention are below, numbered 1-40 and referring to Table C for biological sequences: (1) A CD20-binding protein for the internalization of the CD20 antigen in a cell, wherein the protein comprises a binding region specific for CD20 and a toxin effector region derived from Shiga-like toxin 1 (SLT-1), wherein the protein induces rapid internalization of CD20 present on the surface of the cell. (2) The CD20-binding protein of embodiment 1, wherein the protein induces internalization of CD20 in a B-cell lineage cell in less than about one hour. (3) The CD20-binding protein of claim 1, wherein the toxin effector region comprises amino acids 75 to 251 of NO:1 (see Table C). (4) The CD20-binding protein of embodiment 1, wherein the toxin effector region comprises amino acids 1 to 251 of NO:1. (5) The CD20-binding protein of embodiment 1, wherein the toxin effector region comprises amino acids 1 to 261 of NO:1. (6) The CD20-binding protein of embodiment 1, wherein the protein is cytotoxic.

(7) The CD20-binding protein of embodiment 1, wherein the CD20 binding region is selected from the group consisting of an Fab fragment, an F(ab')2 fragment, an Fd fragment, an Fv fragment a dAb fragment, a scFv, a diabody, a CDR3 peptide, a constrained FR3-CDR3-FR4 peptide, a nanobody, a bivalent nanobody, small modular immunopharmaceuticals (SMIPs), a shark variable IgNAR domain, a minibody, and any fragment or chemically or genetically manipulated counterparts that retain CD20 binding function. (8) The CD20-binding protein of embodiment 1, wherein the binding region is a scFv.

(9) The CD20-binding protein of embodiment 8, wherein the binding region comprises (A) (i) a heavy chain variable (VH) domain comprising HCDR1, HCDR2, HCDR3 amino acid sequences as shown in NO:6, NO:7, and NO:8, respectively, and (ii) a light chain variable (VL) domain comprising LCDR1, LCDR2, and LCDR3 amino acid sequences as shown in NO:9, NO:10, and NO:11, respectively; or (B) (i) a heavy chain variable (VH) domain comprising HCDR1, HCDR2, and HCDR3 amino acid sequences as shown in NO:21, NO:22, and NO:23, respectively, and (ii) a light chain variable (VL) domain comprising LCDR1, LCDR2, and LCDR3 amino acid sequences as shown in NO:24, NO:10, and NO:11, respectively.

(10) The CD20-binding protein of embodiment 8, wherein the CD20 binding region comprises amino acids 2 to 245 of NO:4. (11) The CD20-binding protein of embodiment 1, wherein the CD20 binding region comprises amino acids 2 to 245 of NO: 4 and the toxin effector region comprises amino acids 75 to 251 of NO:1. (12) The CD20-binding protein of embodiment 1, which comprises NO:4.

(13) A CD20-binding protein for killing a cell which expresses CD20 on its surface wherein the binding region comprises a heavy chain variable (VH) domain comprising HCDR1, HCDR2, and HCDR3 amino acid sequences as shown in NO:6, NO:7, and NO:8, respectively, and a light chain variable (VL) domain comprising LCDR1, LCDR2, and LCDR3 amino acid sequences as shown in NO:9, NO:10, and NO:11, respectively, whereby upon administration, the protein is capable of killing a cell which expresses CD20 on its surface.

(14) The CD20 binding-protein of embodiment 13, wherein the CD20 binding region comprises amino acids 2 to 245 of NO:4. (15) The CD20 binding-protein of embodiment 13, wherein the CD20 binding region comprises amino acids 2 to 245 of NO: 4 and the toxin effector region comprises amino acids 75 to 251 of NO:1. (16) The CD20 binding-protein of embodiment 13 which comprises NO:4.

(17) A CD20 binding-protein for the delivery of exogenous material into the cell that expresses CD20 on its surface, wherein the protein comprises a binding region specific for CD20, a toxin effector region wherein said toxin effector region is derived from Shiga-like toxin 1 (SLT-1), and the exogenous material, whereby upon administration, the protein is capable of delivering the exogenous material into a cell which expresses CD20 on its surface.

(18) The CD20-binding protein of embodiment 17, wherein the binding region comprises (A) (i) a heavy chain variable (VH) domain comprising HCDR1, HCDR2, HCDR3 amino acid sequences as shown in NO:6, NO:7, and NO:8, respectively, and (ii) a light chain variable (VL) domain comprising LCDR1, LCDR2, and LCDR3 amino acid sequences as shown in NO:9, NO:10, and NO:11, respectively; or (B) (i) a heavy chain variable (VH) domain comprising HCDR1, HCDR2, and HCDR3 amino acid sequences as shown in NO:21, NO:22, and NO:23, respectively, and (ii) a light chain variable (VL) domain comprising LCDR1, LCDR2, and LCDR3 amino acid sequences as shown in NO:23, NO:10, and NO:11, respectively.

(19) The CD20-binding protein of embodiment 18, wherein the exogenous material is selected from the group consisting of a peptide, a protein, and a nucleic acid. (20) The CD20 binding-protein of embodiment 19, wherein the exogenous material is a peptide and the peptide is an antigen. (21) The CD20 binding-protein of embodiment 20, wherein the antigen is encoded between the binding region and the toxin effector region of the protein. (22) The CD20 binding-protein of embodiment 19 wherein the antigen is derived from a viral protein. (23) The CD20 binding-protein of embodiment 21 wherein the antigen is NO:2. (24) The CD20 binding-protein of embodiment 21 comprising NO:5. (25) The CD20 binding-protein of embodiment 20, wherein the antigen is derived from a bacterial protein. (26) The CD20 binding-protein of embodiment 20, wherein the antigen is derived from a protein mutated in cancer. (27) The CD20 binding-protein of embodiment 20, wherein the antigen is derived from a protein aberrantly expressed in cancer. (28) The CD20 binding-protein of embodiment 20, wherein the antigen is derived from a T-cell CDR region.

(29) The CD20 binding-protein of embodiment 19, wherein the exogenous material is a protein. (30) The CD20 binding-protein of embodiment 29, wherein the protein is an enzyme. (31) The CD20 binding-protein of embodiment 19 wherein the exogenous material is a nucleic acid. (31) The CD20 binding-protein of embodiment 30 wherein the nucleic acid is a siRNA. (32) A polynucleotide that encodes the CD20 binding-protein of embodiment 1. (33) An expression vector that comprises the polynucleotide of embodiment 32. (34) A host cell comprising the expression vector of embodiment 33.

(35) A method of rapidly internalizing the CD20 antigen into the cell of a patient, the method comprising the step of administering to the patient a protein of any one of embodiments 1-12. (36) A method of killing a cell in a patient expressing the CD20 antigen on its surface, the method comprising the step of administering to a patient a protein of any of embodiments 1-16. (37) A method of delivering exogenous material into a cell of a patient that expresses CD20 on its surface, the method comprising the step of administering to the patient a protein of any one of embodiments 17-31. (39) A method of treating cancer in a patient, wherein the cancer expresses on the tumor or cancer cell surface a CD20 antigen, the method comprising the step of administering to the patient a protein of any one of embodiments 1-31. (40) The method of embodiment 39 wherein the cancer is lymphoma.

TABLE C

Sequences referred to in embodiments 1-40

| Number | Text Description | Sequence |
|---|---|---|
| NO: 1 | SLT-1 A subunit polypeptide | KEFTLDFSTAKTYVDSLNVIRSA IGTPLQTISSGGTSLLMIDSGSG DNLFAVDVRGIDPEEGFNNLRLI VERNNLYVTGFVNRTNNVFYRFA SHVTFPGTTAVTLSGDSSYTTLQ RVAGISRTGMQINRHSLTTSYLD LMSFISGTSLTQSVARAMLRFVT VTAEALRFRQIQRGFRTTLDDLS GRSYVMTAEDVDLTLNWGRLSSV LPDYHGQDSVRVGRISFGSINAT LGSVALILNCHHHARVARMASDE FPSMCPADGRVRGITHNKILWDS STLGAILMRRTISS |

TABLE C-continued Sequences referred to in embodiments 1-40

| Number | Text Description | Sequence |
|---|---|---|
| NO: 2 | SLT-1 A subunit polynucleotide (consensus) | aargarttyacnytngayttyws nacngcnaaaracntaytgtngayw snytnaaygtnathmgnwsngcn athggnacnccnytncaracnat hwsnwsnggnggnacnwsnytny tnatgathgaywsnggnwsnggn gayaaaytntttygcngtngaygt nmgnggnathgayccngargarg gnmgnttyaayaaaytnmgnytn athgtngarmgnaayaaayytnta ygtnacngggnttygtnaaymgna cnaayaaygtntttytaymgntty gcngayttywsnca TABLE C-continued Sequences referred to in embodiments 1-40

| Number | Text Description | Sequence |
|---|---|---|
| NO: 11 | Light chain CDR3 | QQWISNPPT |
| NO: 12 | B9E9-SLTA polypeptide | QVQLVQSGAELVKPGASVKMSCK ASGYTETSYNMHWVKQTPGQGLE WIGAIYPGNGDTSYNQKFKGKAT LTADKSSSTAYMQLSSLTSEDSA VYYCARAQLRPNYWYFDVWGAGT TVTVSSGGGGSGGGGSGGGGSGG GGSGGGGSDIVLSQSPAILSASP GEKVTMTCRASSSVSYMHWYQQK PGSSPKPWIYATSNLASGVPARF SGSGSGTSYSLTISRVEAEDAAT YYCQQWISNPPTEGAGTKLELKG GGGSGGKEFTLDESTAKTYVDSL NVIRSAIGTPLQTISSGGTSLLM IDSGSGDNLEAVDVRGIDPEEGR ENNLRLIVERNNLYVTGEVNRIN NVEYREADESHVTFPGITAVTLS GDSSYTTLQRVAGISRTGMQINR HSLITSYLDLNISHSGTSLTQSV ARAMERFRVTVTAEAERFRQIQRG ERTTLDDLSGRSYVMTAEDVDLT LNWGRLSSVLPDYHGQDSVRVGR ISEGSINAILGSVALILNCHMIA SRVAR |
| NO: 13 | B9E9-SLTA polynucleotide consensus | cargtncaryntngtncarwsngg ngcngarytngtnaarccnggng cnwsngtnaaratgwsntgyaar gcnwsnggntayacnttyacnws ntayaaytgcaytgggtnaarc aracnccnggncarggnytngar tggathggngcnathtayccngg naayggngayacnwsntayaayc araarttyaarggnaargcnacn ytnacngcngayaarwsnwsnws nacngctayatgcarytnwsnw snytnacnwsngargaywsngcn gtntaytaytgygcnmgngcnca rytnmgnccnaaytaytggtayt tygaygtntggggngcnggnacn acngtnacngtnwsnwsnggngg nggnggnwsnggnggnggnggnw snggnggnggnggnwsnggnggn ggnggnwsnggnggnggnggnws ngayathgtnytnwsncarwsnc cngcnathytnwsngcnwsnccn ggngaraargtnacnatgactng ymgncnwsnwsnwsngtnwsnt ayatgcaytggtaycarcaraar ccnggnwsnwsnccnaarccntg gathtaygcnacnwsnaayytng cnwsnggngtnccngcnmgnty wsnggnwsnggnwsnggnacnws ntaywsnytnacnathwsnmgng tngargcngargaygcngcnacn taytaytgycarcartggathws naayccnccnacnttyggngcng gnacnaarytngarytnaarggn ggnggnggnwsnggnggnaarga rttyacnytngayttywsnacng cnaaracntaytgngaywsnytn aaygtnathmgnwsngcnathgg nacnccnytncaracnathwsnw snggnggnacwsnytnytnatga thgaywsnggnwsnggngayaay ytnttygcngtngaygtnmgngg nathgayccngargarggnmgnt tyaayaayytnmgnytnathgtn garmgnaayaayytntaygtnac nggnttygtnaaymgnacnaaya aygtnttytaymgnttygcngay ttywsncaygtnacnttyccngg | 
| | | nacnacngcngtnacnytnwsng gngaywsnwsntayacnacnytn carmgngtngcnggnathwsnmg nacnggnatgcaratbaaymgnc aywsnytnacnacnwsntayytn gayytnatgwsncaywsnggnac nwsnytnacncarwsngtngcnm gngcnatgytnmgnttygtnacn gcngargcnytnmgnttymgnca rathcarmgnggnttymgnacna cnytngaygayytnwsnggnmgn wsntaygtnatgacngcngarga ygtngayytnacnytnaaytggg gnmgnytnwsnwsngtnytnccn gaytaycayggncargaywsngt nmgngtnggnmgnathwsntyg gnwsnathaaygcnathytnggn wsngtngcnytnathytnaaytg ycaycaycaygcnwsnmgngtng cnmgn |
| NO: 14 | C2B8-SLTA polypeptide | QVQLQQPGAELVKPGASVKMSCK ASGYTFTSYNMHWVKQTPGRGLE WIGAIYPGNGDTSYNQKFKGKAT LTADIKSSSTAYMQLSSLTSEDS AVYYCARSTYYGGDWYFNVWGAG TTVTVSAGSTSGSGKPGSGEGST KGQIVLSQSPAILSASPGEKVTM TCRASSSVSYIHWFQQKPGSSPK PWIYATSNLASGVPVRFSGSGSG TSYSLTISRVEAEDAATYYCQQW TSNPPTFGGGTKLEIKEFPKPST PPGSSGGAPKEETLDFSTAKTYV DSLNVIRSAIGTPLQTESSGGTS LLMIDSGSGDNLFAVDVRGIDPE EGRFNNLRLIVERNNLYVTGFVN RTNNVFYRFADFSHVTFPGTTAV TLSGDSSYTTLQRVAGISRTGMQ INRHSLTTSYLDLMSHSGTSLTQ SVARAMLRFVTVTAEALRFRQIQ RGFRTTLDDLSGRSYVMTAEDVD LTENWGRESSVLPDYIIGQDSVR VGRISFGSINAILGSVALILNCH HHASRVAR |
| NO: 15 | C2B8-SLTA polynucleotide consensus | cargtncaryntncarcarccngg ngcngarytngtnaarccnggng cnwsngtnaaratgwsntgyaar gcnwsnggntayacnttyacnws ntayaaytgcaytgggtnaarc aracnccnggnmgnggnytngar tggathggngcnathtayccngg naayggngayacnwsntayaayc araarttyaarggnaargcnacn ytnacngcngayaarwsnwsnws nacngctayatgcarytnwsnw snytnacnwsngargaywsngcn gtntaytaytgygcnmgnwsnna cntaytayggnggngaytggtay ttyaaygtntggggngcnggnac nacngtnacngtnwsngcnggnw snacnwsnggnwsnggnaarccn ggnwsnggngarggnwsnacnaa rggncarathgtnytnwsncarw snccngcnathytnwsngcnwsn ccngngaraargtnacnatgac ntgymgncnwsnwsnwsngtnw sntayathcaytggttycarcar aarccnggnwsnwsnccnaarcc ntgathtaygcnacnwsnaayy tngcnwsnggngtnccngtnmgn ttywsnggnwsnggnwsnggnac nwsntaywsnytnacnathwsnm gngtngargcngargaygcngcn acntaytaytgycarcartggac |

TABLE C-continued

Sequences referred to in embodiments 1-40

| Number | Text Description | Sequence |
|---|---|---|
| | | nwsnaayccnccnacnttyggng gnggnacnaarytngarathaar garttyccnaarccnwsnacncc ncngggnwsnwsnggnggngcnc cnaargarttyacnytngaytty wsnacngcnaaracntaygtnga ywsnytnaaygtnathmgnwsng cnathggnacnccnytncaracn athwsnwsnggnggnacnwsnyt nytnatgathgaywsnggnwsng gngayaayytnttygcngtngay gtnmggnggnathgayccngarga rggnmgnttyaayaayytnmgny tnathgtngarmgnaayaayytn taygtnacnggnttygtnaaymg nacnaayaaygtnttytaymgnt tygcngayttywsncaygtnacn ttyccnggnacnacngcngtnac nytnwsnggngaywsnwsntaya cnacnytncarmgngtngcnggn athwsnmgnacnggnatncarat haaymgncaywsnytnacnacnw sntayytngay TABLE C-continued Sequences referred to in embodiments 1-40

| Number | Text Description | Sequence |
|---|---|---|
| NO: 24 | Light chain CDR1 | RASSSVSYMH |

The present invention is further illustrated by the following non-limiting examples of CD20-binding proteins comprising Shiga toxin effector regions derived from A Subunits of members of the Shiga toxin family and CD20 binding regions comprising immunoglobulin-type polypeptides capable of binding extracellular parts of CD20.

EXAMPLES

The following examples demonstrate certain embodiments of the present invention. However, it is to be understood that these examples are for illustration purposes only and do not intend, nor should any be construed, to be wholly definitive as to conditions and scope of this invention. The examples were carried out using standard techniques, which are well known and routine to those of skill in the art, except where otherwise described in detail.

The following examples demonstrate the ability of exemplary CD20-binding proteins to selectively kill cells which express CD20 on their cell surfaces. The exemplary CD20-binding proteins bound to extracellular antigens on CD20 expressed by targeted cell types and entered the targeted cells. The internalized CD20-binding proteins routed their Shiga toxin effector region to the cytosol to inactivate ribosomes and subsequently caused the apoptotic death of the targeted cells. Thus, the exemplary CD20-binding proteins were capable of internalizing within CD20 expressing cell types by virtue of their Shiga toxin effector regions inducing rapid cellular internalization after the CD20-binding proteins formed a complex with cell surface CD20.

These exemplary CD20-binding proteins include αCD20scFv::SLT-1A version 1 (SEQ ID NO:4), αCD20scFv::SLT-1A version 2 (SEQ ID NO:16), B9E9-SLT-1A (SEQ ID NO:12), and C2B8-SLT-1A (SEQ ID NO:14).

Example 1—Construction, Production, and Purification of Exemplary CD20-Binding Proteins First, a CD20 binding region and a Shiga toxin effector region were designed or selected. In the examples below, the Shiga toxin effector region was derived from the A subunit of Shiga-like Toxin 1 (SLT-1A). A polynucleotide was obtained containing a fragment of SLT-1A cloned into the pECHE9A plasmid and encoding amino acids 1-251 of SLT-1A (Cheung M et al., *Mol Cancer* 9: 28 (2010)).

The CD20 binding region was designed as a recombinant scFv derived from the 1H4 CD20 monoclonal antibody (Haisma et al. (1999), *Blood* 92: 184-90). The two immunoglobulin variable regions ($V_L$ and $V_H$) were separated by a linker (SEQ ID NO:18).

Second, the binding region and Shiga toxin effector region were combined to form a single-chain, recombinant polypeptide. In this example, a polynucleotide encoding the recombinant scFv derived from 1H4 CD20 monoclonal antibody was cloned in frame with a "murine hinge" polynucleotide derived from polynucleotides encoding a murine IgG3 molecule (SEQ ID NO:20) and in frame with a polynucleotide encoding SLT-1A (residues 1-251 of SEQ ID NO:1). The full-length sequence begins with Strep-Tag® (SEQ ID NO:19) encoding polynucleotide sequence cloned in frame to facilitate detection and purification. The polynucleotide sequence of this example was codon optimized for efficient expression in *E. coli* using services from DNA 2.0, Inc. (Menlo Park, Calif., U.S.) to produce the expression vector which encoded αCD20scFv::SLT-1A version 1.

A different CD20-binding protein comprising an influenza antigen was constructed and produced in a similar manner. DNA 2.0, Inc. (Menlo Park, Calif., U.S.) synthesized the multiple polynucleotides, including the antigen sequence (SEQ ID NO:3) and the required polynucleotide components were joined in frame using vector pJ201 to create the open reading frame coding for the following single-chain polypeptide (from amino-terminus to carboxy-terminus) Strep-Tag® (SEQ ID NO:19), the 1H4-derived recombinant scFv (described above), the murine IgG3 molecule (SEQ ID NO:20), the linker (SEQ ID NO:3), and the SLT-1A-derived sequence (residues 1-251 of SEQ ID NO:1). This recombinant polynucleotide was cloned into pTXB1 for polypeptide production purposes. Again, codon optimization for efficient expression in *E. coli* was performed by DNA 2.0, Inc. (Menlo Park, Calif., U.S.) to produce the expression vector which encoded αCD20scFv::SLT-1A version 2.

Third, both versions 1 and 2 of the αCD20scFv::SLT-1A recombinant CD20-binding proteins were produced by using standard techniques for both bacterial and cell-free, protein translation systems. Then the CD20-binding proteins were purified and isolated using techniques well known in the art.

Example 2—Determining the Dissociation Constant ($K_D$) of Exemplary CD20-Binding Proteins The cell binding characteristics of both versions 1 and 2 of the αCD20scFv::SLT-1A CD20-binding proteins were determined by a fluorescence-based flow cytometry assay. Each sample contained $0.5 \times 10^6$ of either CD20 expressing cells (Raji (CD20+)) or non-expressing cells (BC1 (CD20-)) and was incubated with 1004 of various dilutions of the CD20-binding proteins in phosphate buffered saline Hyclone 1×PBS (Fisher Scientific, Waltham, Mass.) with 1% bovine serum albumin (BSA) (Calbiochem, San Diego, Calif., U.S.), hereinafter referred to as "1×PBS+1% BSA" for 1 hour at 4 degrees Celsius (° C.). The highest concentration of CD20-binding protein was selected to lead to saturation of the reaction. The cells were washed twice with 1×PBS+1% BSA. The cells were incubated for 1 hour at 4° C. with 100 μL of 1×PBS+1% BSA containing 0.3 μg of anti-Strep Tag® mAb-FITC (# A01736-100, Genscript, Piscataway, N.J., U.S.). The cells were washed twice with 1×PBS+1% BSA, suspended in 2004 of 1×PBS, and subjected to flow cytometry. The baseline corrected mean fluorescence intensity (MFI) data for all the samples was obtained by subtracting the MFI of the FITC alone sample (negative control) from each experimental sample. Graphs were plotted of MFI versus "concentration of protein" using Prism software (GraphPad Software, San Diego, Calif., U.S.). Using the Prism software function of one-site binding [$Y=B_{max}*X/(K_D+X)$] under the heading binding-saturation, the $B_{max}$ and $K_D$ were calculated using baseline corrected data. $B_{max}$ is the maximum specific binding reported in MFI. $K_D$ is the equilibrium binding constant, reported in nanomolar (nM).

Over multiple experiments, the $K_D$ of αCD20scFv::SLT-1A version 1 for Raji (CD20+) cells was determined to be about 80-100 nM. In one experiment, the $B_{max}$ for the αCD20scFv::SLT-1A version 1 CD20-binding protein binding to CD20+ cells was measured to be about 140,000 MFI with a $K_D$ of about 83 nM (Table 1), whereas there was no meaningful binding to CD20-cells observed in this assay. In one experiment, the $B_{max}$ for αCD20scFv::SLT-1A version 2 binding to CD20+ cells was measured to be about 110,000 MFI with a $K_D$ of about 101 nM (Table 1), whereas there was no meaningful binding to CD20-cells observed in this assay.

TABLE 1

Binding Characteristics: Representative values for $B_{max}$ and $K_D$ for exemplary CD20-binding proteins

| CD20-Binding Protein | target biomolecule | Target Positive Cells | | Target Negative Cells | |
|---|---|---|---|---|---|
| | | $B_{max}$ (MFI) | $K_D$ (nM) | $B_{max}$ (MFI) | $K_D$ (nM) |
| αCD20scFv::SLT-1A version 1 | CD20 | 139,000 | 82.5 | 15,800 | 1,050 |
| αCD20scFv::SLT-1A version 2 | CD20 | 112,000 | 101.0 | 8,300 | 280 |

Example 3—Determining the Half Maximal Inhibitory Concentration ($IC_{50}$) of Exemplary CD20-Binding Proteins The ribosome inactivation capabilities of both versions 1 and 2 of the αCD20scFv::SLT-1A CD20-binding proteins were determined using a cell-free, in vitro protein translation assay using the TNT® Quick Coupled Transcription/Translation kit (L1170 Promega Madison, Wis., U.S.). The kit includes Luciferase T7 Control DNA (L4821 Promega Madison, Wis., U.S.) and TNT® Quick Master Mix. The ribosome activity reaction was prepared according to the manufacturer's instructions.

A series of 10-fold dilutions of the αCD20scFv::SLT-1A version to be tested was prepared in appropriate buffer and a series of identical TNT reaction mixture components were created for each dilution. Each sample in the dilution series of the αCD20scFv::SLT-1A proteins was combined with each of the TNT reaction mixtures along with the Luciferase T7 Control DNA. The test samples were incubated for 1.5 hours at 30° C. After the incubation, Luciferase Assay Reagent (E1483 Promega, Madison, Wis., U.S.) was added to all test samples and the amount of luciferase protein translation was measured by luminescence according to the manufacturer instructions. The level of translational inhibition was determined by non-linear regression analysis of log-transformed concentrations of total protein versus relative luminescence units. Using statistical software (GraphPad Prism, San Diego, Calif., U.S.), the half maximal inhibitory concentration ($IC_{50}$) value was calculated for each sample using the Prism software function of log(inhibitor) vs. response (three parameters) [Y=Bottom+((Top−Bottom)/(1+10^(X−Log IC50)))] under the heading dose-response-inhibition. The $IC_{50}$ for experimental proteins and SLT-1A-only control protein were calculated. The percent of SLT-1A-only control protein was calculated by [(IC50 of SLT-1A control protein/IC50 of experimental protein)×100].

The inhibitory effect of both versions of αCD20scFv::SLT-1A on cell-free protein synthesis was strong. Multiple experiments determined that the $IC_{50}$ of both versions of αCD20scFv::SLT-1A was around 50 picomolar (pM). In one experiment, the $IC_{50}$ of αCD20scFv::SLT-1A version 1 on protein synthesis was about 38 pM or within 19% of the SLT-1A-only positive control (Table 2). Similarly, the $IC_{50}$ of αCD20scFv::SLT-1A version 2 on protein synthesis in this cell-free assay was about 58 pM or within 18% of the SLT-1A-only positive control (Table 2).

TABLE 2

Ribosome Inactivation: Representative half-maximal inhibitory concentrations ($IC_{50}$) for exemplary CD20-binding proteins

| CD20-Binding Protein | $IC_{50}$ (pM) | $IC_{50}$ of SLT-1A-only positive control (pM) | Percent of $IC_{50}$ of SLT-1A control |
|---|---|---|---|
| αCD20scFv::SLT-1A version 1 | 38.3 | 31.2 | 81% |
| αCD20scFv::SLT-1A version 2 | 58.3 | 47.8 | 82% |

Example 4—Determining Cellular Internalization by Immunofluorescence Assay

Immunofluorescence studies were carried out in order to analyze the binding and internalization profiles of αCD20scFv::SLT-1A version 1 in CD20+ positive cell lines (Daudi, Raji, and Ramos) as compared to CD20-cell lines (BC-1, Jurkat (J45.01), and U266). For example, 50 nM of the respective CD 20-binding proteins were incubated with $0.8\times10^6$ Raji cells for 1 hour at 37° C. to allow for binding and internalization of the CD20-binding protein. The cells were then washed with 1×PBS, fixed and permeabilized with BD cytofix/cytoperm (BD Biosciences, San Jose, Calif., U.S.), and then washed twice with 1× BD Perm/Wash™ Buffer (BD Biosciences, San Jose, Calif., U.S.). The cells were incubated with Alexa Fluor®-555 labeled mouse anti-SLT-1A antibody (BEI Resources, Manassas, Va., U.S.) in 1× BD Perm/Wash™ Buffer for 45 minutes at room temperature. Cells were then washed and fixed with BD cytofix (BD Biosciences, San Jose, Calif., U.S.) for 10 minutes at 4° C. The cells were then washed with 1×PBS and resuspended in 1×PBS, and then the cells were allowed to adhere onto poly-L-lysine coated glass slides (VWR, Radnor, Pa., U.S.). Slides were coverslipped with 4',6-diamidino-2-phenylindole (DAPI)-containing Vectashield (Fisher Scientific, Waltham, Mass., U.S.) and viewed by Zeiss Fluorescence Microscope (Zeiss, Thornwood, N.Y., U.S.).

Immunofluorescence studies showed that αCD20scFv::SLT-1A version 1 and B9E9-SLT-1A bound to cell surfaces and entered into cells expressing CD20 within one hour at 37° C.

Example 5—CD20+ Cell Kill Assay: Determining the Cytotoxic Selectivity and Half-Maximal Cytotoxic Concentrations ($CD_{50}$) of CD20-Binding Proteins The cytotoxicity profiles of both versions of αCD20scFv::SLT-1A were determined by a CD20+ cell kill assay. This assay determines the capacity of a CD20-binding protein to kill cells expressing CD20 on a cellular surface as compared to cells that do not express the target biomolecule. Cells were plated ($2\times10^3$ per well) in 20 μL media in 384 well plates. The αCD20scFv::SLT-1A protein to be tested was diluted either 5-fold or 10-fold in a 1×PBS, and 5 μL of the dilutions or buffer control were added to the cells. Control wells containing only media were used for baseline correction. The cell samples were incubated for 3 days at 37° C. and in an atmosphere of 5% carbon dioxide ($CO_2$) with the αCD20scFv::SLT-1A to be tested or only PBS buffer. The total cell survival or percent viability was determined using a luminescent readout using the CellTiter-Glo® Luminescent Cell Viability Assay (G7573 Promega Madison, Wis., U.S.) according to the manufacturer's instructions. The "percent viability" of experimental wells was calculated using the following equation: (Test RLU−Average Media RLU)/(Average Cells RLU−Average Media RLU)*100. Log polypeptide concentration versus Percent Viability was plotted using Prism software (GraphPad Prism, San Diego, Calif., U.S.) and log (inhibitor) vs. normalized response (variable slope) analysis was used to determine the half-maximal cytotoxic concentration ($CD_{50}$) value for the exemplary CD20-binding proteins. In addition, cell samples from lymphoma patients were analyzed using this cell kill assay to determine the cytotoxicity profile of αCD20scFv::SLT-1A version 1.

Over multiple experiments, both versions of αCD20scFv::SLT-1A demonstrated CD20-specific cell kill with 10 to 1000-fold specificity compared to cell kill of CD20 negative cell lines (Table 3). The CD20-specific cell kill profile of both versions of αCD20scFv::SLT-1A also contrasted to the ability of the component SLT-1A (251) to kill cells which lacked CD20-specificity (Table 3). The $CD_{50}$ values of both versions of αCD20scFv::SLT-1A protein was measured to be about 3-70 nM for CD20+ cells, depending on the cell line, as compared to over 600-2,000 for CD20- cell lines (Table 3). The $CD_{50}$ of the αCD20scFv::SLT-1A version 1 CD20-binding protein was over 100 to 400 fold greater (less cytotoxic) for cells which did not express CD20 on a cellular surface as compared to cells expressing CD20 on a cellular surface. The $CD_{50}$ of αCD20scFv::SLT-1A version toward human lymphoma cells from patient samples was about 7-40 nM (Table 3).

TABLE 3

Selective Cytotoxicity: Representative half-maximal cytotoxic concentrations ($CD_{50}$) for exemplary CD20-binding proteins

| | | $CD_{50}$ (nM) | | |
|---|---|---|---|---|
| Cell Line | CD20 status | αCD20scFv::SLT-1A version 1 | αCD20scFv::SLT-1A version 2 | SLT-1A only negative control |
| Daudi | positive | 5.6 | 67.0 | 650 |
| Raji | positive | 2.8 | 4.5 | 1,100 |
| ST486 | positive | 3.7 | 7.0 | 940 |
| Ramos | positive | 27.0 | 33.0 | 470 |
| BC-1 | negative | 2,000 | 2,100.0 | 160 |
| Jurkat | negative | 1,400 | 600.0 | 120 |
| U226 | negative | 2,500 | not determined | 960 |
| Patient Samples | | | | |
| follicular lymphoma, rituximab refractory | positive | 7.1 | 39.0 | 690,000 |
| Burkitt's lymphoma transformed by Epstein-Barr Virus | positive | 9.0 | 12.0 | 960 |

Example 6—Comparative CD20+ Cell Kill: Determining the Relative Cytotoxicities of CD20-Binding Proteins to CD20+ Cells Three potentially cytotoxic CD20-binding proteins were tested using the CD20+ cell kill assay in Raji cells (CD20+) as described above in Example 5. A set of representative results is reported in Table 4. Over multiple experiments, αCD20scFv::SLT-1A version 1 exhibited a 50 to 100-fold greater cell kill function as compared to the CD20-binding protein B9E9 (SEQ ID NO:12) (Table 4).

TABLE 4

Representative Half-Maximal Cytotoxic Concentrations ($CD_{50}$) for Exemplary CD20-Binding Proteins to CD20+ Raji Cells

| CD20-Binding Protein | $CD_{50}$ (nM) |
|---|---|
| SLT-1A only negative control | 429 |
| αCD20scFv::SLT-1A version 1 | 2 |
| αCD20scFv-B9E9::SLT-1A | 103 |

Example 7—Determining the Targeted Cytotoxicity for CD20-Binding Proteins Using In Vivo Xenograft Studies Two xenograft model systems based on an immunocompromised mouse strains were used to study the ability of exemplary CD20-binding proteins to kill CD20+ tumor cells in vivo and in a tumor environment over time and for various dosages. These xenograft model systems rely on well-characterized mouse strains that lack graft versus host responses, among other immune system deficiencies. First, an intravenous tumor model was studied using SCID (severe combined immune deficiency) mice to create disseminated tumors throughout the mice in order to test the in vivo effects of exemplary CD20-binding proteins on human tumor cells. Second, a subcutaneous tumor model was studied using BALBc/nude mice to create subcutaneous tumors on the mice, again in order to test the in vivo effects of exemplary CD20-binding proteins on human tumor cells.

For the first xenograft system, thirty-two C.B.-17 SCID mice (in four groups of eight animals) were challenged with $1\times10^7$ Raji-luc human lymphoma derived cells (Molecular Imaging, Ann Arbor, Mich., U.S.) in 200 μL PBS. On days 5-9 and 12-16 following tumor challenge, the following groups received the following through intravenous administration: Group 1: PBS; Group 2: αCD20scFv::SLT-1A version 2 at a dose of 2 mg/kg; Group 3: αCD20scFv::SLT-1A version 1 at a dose of 2 mg/kg; and Group 4: αCD20scFv::SLT-1A version 1 at a dose of 4 mg/kg (days 5-9 only). Bioluminescence, in $1\times10^6$ photons/second units (p/s), was measured on days 5, 10, 15, and 20 using a Caliper IVIS 50 optical imaging system (Perkin Elmer, Waltham, Mass., U.S.). FIG. 2 shows how both versions of αCD20scFv::SLT-1A, and αCD20scFv::SLT-1A version 1 at both dosage levels, resulted in statistically significant less total bioluminescence compared to the PBS control. The decrease in total bioluminescence was reflective of statistically significant reductions in disseminated tumor burdens after treatment with a CD20-binding protein of the invention. FIG. 3 indicates a statistically significant increase in survival with administration of either version of αCD20scFv::SLT-1A. The mean survival age was increased by five days with all treatments compared to the PBS negative control.

For the second xenograft model, twenty-eight BALBc/nude (in four groups of six or seven animals) were challenged subcutaneously with 2.5×10⁶ Raji human lymphoma cells (Washington Biotechnology, Simpsonville, Md., U.S.). Tumor volume was determined using standard methods known in the art utilizing calipers. Day 0 was set at the point when the mean tumor volume for each mouse reached approximately 160 mm³ (one mouse from each group had a tumor greater than 260 mm³ so it was excluded). On days 0-4 and 7-11 the groups received intravenous administration of the following by group: Group 1: PBS; Group 2: αCD20scFv::SLT-1A version 2 at a dose of 2 mg/kg; Group 3: αCD20scFv::SLT-1A version 1 at a dose of 2 mg/kg; Group 4: αCD20scFv::SLT-1A version 1 at a dose of 4 mg/kg. Tumor volume was measured and graphed as a function of day of study. FIG. 4 demonstrates how treatment with αCD20scFv::SLT-1A version 1 (at both dosage levels) resulted in significantly reduced tumor volume compared to the PBS control through to Day 24. This is also reflected in the tumor free mouse number through Day 54, reported in Table 5.

TABLE 5

Elimination of Tumors by Exemplary CD20-Binding Proteins in a Subcutaneous-Tumor Mouse Model

| Group | Tumor Free Mice/Total Mice |
|---|---|
| PBS | 0/7 |
| αCD20scFv::SLT-1A version 2, 2 mg/kg | 6/7 |
| αCD20scFv::SLT-1A version 1, 2 mg/kg | 5/6 |
| αCD20scFv::SLT-1A version 1, 4 mg/kg | 6/7 |

Example 8—Determining In Vivo Effects of a CD20-Binding Protein in Non-Human Primates The exemplary CD20-binding protein αCD20scFv::SLT-1A version 1 was administered to non-human primates in order to test for in vivo effects. In vivo depletion of peripheral blood B lymphocytes in cynomolgus primates was observed after parenteral administration of different doses of αCD20scFv::SLT-1A version 1.

In one experiment, ten cynomolgus primates were intravenously injected with PBS or αCD20scFv::SLT-1A version 1 at different doses (50, 150, and 450 micrograms drug/kilogram body weight (mcg/kg)) on alternative days for 2 weeks. Then, peripheral blood samples collected prior to dosing on days 3 and 8 were analyzed for the percentage of B-lymphocytes which expressed CD20 (FIGS. 5 and 6). In cynomolgus monkeys, two distinct B-cell subsets have been described by flow-cytometry: (1) CD21 negative, CD40 positive cells which express high levels of CD20, and (2) CD21 positive and CD40 positive cells which express lower levels of CD20 (Vugmeyster Y et al., *Cytometry* 52: 101-9 (2003)). Dose-dependent B-cell depletion as compared to baseline levels from blood samples collected prior to treatment was observed on day 3 (4, 14 and 45% decrease in animals dosed at 50, 150 and 450 mcg/kg) and day 8 (32, 52 and 75% decrease in animals dosed at 50, 150 and 450 mcg/kg) (Table 6). This experiment showed that αCD20scFv::SLT-1A version 1 was capable of killing CD20 positive, primate B-cells in vivo.

TABLE 6

CD20-Binding Protein Dose Dependent B-Cell Depletion in Non-Human Primates

| | Percent Decrease in CD40+, CD20+ Cells (%) | | | Percent Decrease in CD21+, CD40+, CD20+ Cells (%) | | |
|---|---|---|---|---|---|---|
| Day | 50 mcg/kg | 150 mcg/kg | 450 mcg/kg | 50 mcg/kg | 150 mcg/kg | 450 mcg/kg |
| 3 | 38 | 57 | 69 | 4 | 14 | 45 |
| 8 | 65 | 81 | 86 | 32 | 52 | 75 |

Example 9—A CD20-Binding Protein Derived from the A Subunit of Shiga-Like Toxin-1 and the Antibody Ofatumumab In this example, the Shiga toxin effector region is derived from the A subunit of Shiga-like Toxin 1 (SLT-1A). An immunoglobulin-type binding region αCD20 is derived from the monoclonal antibody ofatumumab (Gupta I, Jewell R, *Ann N Y Acad Sci* 1263: 43-56 (2012)) which comprises an immunoglobulin-type binding region capable of binding human CD20.

Construction, Production, and Purification of the CD20-Binding Protein SLT-1A::αCD20

The immunoglobulin-type binding region αCD20 and Shiga toxin effector region are linked together to form a protein. For example, a fusion protein is produced by expressing a polynucleotide encoding the CD20-binding protein SLT-1A::αCD20. Expression of the SLT-1A::αCD20 CD20-binding protein is accomplished using either bacterial and/or cell-free, protein translation systems as described in the previous examples.

Determining the In Vitro Characteristics of the CD20-Binding Protein SLT-1A::αCD20

The binding characteristics of the CD20-binding protein of this example for CD20+ cells and CD20− cells is determined by a fluorescence-based, flow-cytometry assay as described above in the previous examples. The $B_{max}$ for SLT-1A::αCD20 binding to CD20+ cells is measured to be approximately 50,000-200,000 MFI with a $K_D$ within the range of 0.01-100 nM, whereas there is no significant binding to CD20-cells in this assay.

The ribosome inactivation capabilities of the SLT-1A::αCD20 CD20-binding protein is determined in a cell-free, in vitro protein translation as described above in the previous examples. The inhibitory effect of the CD20-binding protein of this example on cell-free protein synthesis is significant. The $IC_{50}$ of SLT-1A::αCD20 on protein synthesis in this cell-free assay is approximately 0.1-100 pM.

Determining the Cytotoxicity of the CD20-Binding Protein SLT-1A::αCD20 Using a Cell-Kill Assay The cytotoxicity characteristics of SLT-1A::αCD20 are determined by the general cell-kill assay as described above in the previous examples using CD20+ cells. In addition, the selective cytotoxicity characteristics of SLT-1A::αCD20 are determined by the same general cell-kill assay using CD20− cells as a comparison to the CD20+ cells. The $CD_{50}$ of the CD20-binding protein of this example is approximately 0.01-100 nM for CD20+ cells depending on the cell line. The $CD_{50}$ of the CD20-binding protein is approximately 10-10,000 fold greater (less cytotoxic) for cells not expressing CD20 on a cellular surface as compared to cells which do express CD20 on a cellular surface.

Determining the In Vivo Effects of the CD20-Binding Protein SLT-1A::αCD20 Using Animal Models Animal models are used to determine the in vivo effects of the CD20-binding protein SLT-1A::αCD20 on neoplastic cells. Various mice strains are used to test the effect of the CD20-binding protein after intravenous administration on xenograft tumors in mice resulting from the injection into those mice of human neoplastic cells which express CD20 on their cell surfaces. Non-human primates may be used to test the effect of SLT-1A::αCD20 on peripheral blood B-cells as described above in Example 8.

Example 10—CD20-Binding Proteins Based on Various CD20 Binding Domains

In this example, the Shiga toxin effector region is derived from the A subunit of Shiga-like Toxin 1 (SLT-1A), Shiga toxin (StxA), and/or Shiga-like Toxin 2 (SLT-2A). An immunoglobulin-type binding region is derived from the immunoglobulin domain from the molecule chosen from Table 7 and which binds an extracellular part of CD20. The exemplary cytotoxic proteins of this example are created and tested as described in the previous examples using CD20+ cells expressing CD20 to a cellular surface.

TABLE 7

Exemplary CD20 Binding Domains
Source of CD20 Binding Domain ibritumomab
obinutuzumab
ocaratuzumab
ocrelizumab
obinutuzumab
ofatumumab
rituximab
tositumomab
ublituximab
CD20 binding scFv(s) in Geng S et al.,
*Cell Mol Immunol* 3: 439-43 (2006)
CD20 binding scFv(s) in Otafesn T et al,
*Protein Eng Des Sel* 23: 243-9 (2010)

While certain embodiments of the invention have been described by way of illustration, it will be apparent that the invention may be put into practice with many modifications, variations and adaptations, and with the use of numerous equivalents or alternative solutions that are within the scope of persons skilled in the art, without departing from the spirit of the invention or exceeding the scope of the claims.

All publications, patents, and patent applications are herein incorporated by reference in their entirety to the same extent as if each individual publication, patent or patent application was specifically and individually indicated to be incorporated by reference in its entirety. The U.S. provisional patent application 61/777,130 is incorporated by reference in its entirety. The complete disclosures of all electronically available biological sequence information from GenBank (National Center for Biotechnology Information, U.S.) for amino acid and nucleotide sequences cited herein are each incorporated herein by reference in their entirety.

Sequence Listings

| ID Number | Text Description | Sequence |
| --- | --- | --- |
| SEQ ID NO: 1 | Shiga-like Toxin 1 A Subunit (SLT-1A) | KEFTLDFSTAKTYVDSLN VIRSAIGTPLQTISSGGT SLLMIDSGSGDNLFAVDV RGIDPEEGRFNNLRLIVE RNNLYVTGFVNRTNNVFY RFADFSHVTFPGTTAVTL SGDSSYTTLQRVAGISRT GMQINRHSLTTSYLDLMS HSGTSLTQSVARAMLRFV TVTAEALRFRQIQRGFRT TLDDLSGRSYVMTAEDVD LTLNWGRLSSVLPDYHGQ DSVRVGRISFGSINAILG SVALILNCHHHASRVARM ASDEFPSMCPADGRVRGI THNKILWDSSTLGAILMR RTISS |
| SEQ ID NO: 2 | polynucleotide encoding SLT-1 A Subunit (consensus) | aargarttyacnytngay ttywsnacngcnaaracn taygtngaywsnytnaay gtnathmgnwsngcnath ggnacnccnytncaracn athwsnwsnggnggnacn wsnytnytnatgathgay wsnggnwsnggngayaay ytnttygcngtngaygtn mgnggnathgayccngar garggnmgnttyaayaay ytnmgnytnathgtngar mgnaayaayytntaygtn acnggnttygtnaaymgn acnaayaaygtnttytay mgnttygcngayttywsn caygtnacnttyccnggn acnacngcngtnacnytn wsnggngaywsnwsntay acnacnytncarmgngtn gcnggnathwsnmgnacn ggnatgcarathaaymgn caywsnytnacnacnwsn tayytngayytnatgwsn caywsnggnacnwsnytn acncarwsngtngcnmgn gcnatgytnmgnttygtn acngtnacngcngargcn ytnmgnttymgncarath carmgnggnttymgnacn acnytngaygayytnwsn ggnmgnwsntaygtnatg acngcngargaygtngay ytnacnytnaaytggggn mgnytnwsnwsngtnytn ccngaytaycayggncar gaywsngtnmgngtnggn mgnathwsnttyggnwsn athaaygcnathytnggn wsngtngcnytnathytn aaytgycaycaycaygcn wsnmgngtngcnmgnatg gcnwsngaygarttyccn wsnatgtgyccngcngay ggnmgngtnmgnggnath acncayaayaarathytn tgggaywsnwsnacnytn ggngcnathytnatgmgn mgnacnathwsnwsntrr |
| SEQ ID NO: 3 | linker extension for anti-CD20-scFv::SLT-1A version 2 polypeptide | GILGFVFTL |

-continued

Sequence Listings

| ID Number | Text Description | Sequence |
| --- | --- | --- |
| SEQ ID NO: 4 | anti-CD20-scFv:: SLT-1A version 1 polypeptide | MQVQLQQPGAELVKPGAS<br>VKMSCKTSGYTFTSYNVH<br>WVKQTPGQGLEWIGAIYP<br>GNGDTSFNQKFKGKATLT<br>ADKSSSTVYMQLSSLTSE<br>DSAVYYCARSNYYGSSYV<br>WFFDVWGAGTTVTVSSGS<br>TSGSGKPGSGEGSQIVLS<br>QSPTILSASPGEKVTMTC<br>RASSSVSYMDWYQQKPGS<br>SPKPWIYATSNLASGVPA<br>RFSGSGSGTSYSLTISRV<br>EAEDAATYYCQQWISNPP<br>TFGAGTKLELKEFPKPST<br>PPGSSGGAPKEFTLDFST<br>AKTYVDSLNVIRSAIGTP<br>LQTISSGGTSLLMIDSGS<br>GDNLFAVDVRGIDPEEGR<br>FNNLRLIVERNNLYVTGF<br>VNRTNNVFYRFADFSHVT<br>FPGTTAVTLSGDSSYTTL<br>QRVAGISRTGMQINRHSL<br>TTSYLDLMSHSGTSLTQS<br>VARAMLRFVTVTAEALRF<br>RQIQRGFRTTLDDLSGRS<br>YVMTAEDVDLTLNWGRLS<br>SVLPDYHGQDSVRVGRIS<br>FGSINAILGSVALILNCH<br>HHASRVAR |
| SEQ ID NO: 5 | polynucleotide encoding anti-CD20-scfv::SLT-1A version 1 | atgcargtncarytncar<br>carccnggngcngarytn<br>gtnaarccnggngcnwsn<br>gtnaaratgwsntgyaar<br>acnwsnggntayacntty<br>acnwsntayaaygtncay<br>tgggtnaarcaracnccn<br>ggncarggnytngartgg<br>athggngcnathhtaycc<br>nggnaayggngayacnws<br>nttyaaycaraarttyaa<br>rggnaargcnacnytnac<br>ngcngayaarwsnwsnws<br>nacngtntayatgcaryt<br>nwsnwsnytnacnwsnga<br>rgaywsngcngtntayta<br>ytgygcnmgnwsnaayta<br>ytayggnwsnwsntaygt<br>ntggttyttygaygtntg<br>gggngcnggnacnacngt<br>nacngtnwsnwsnggnws<br>nacnwsnggnwsnggnaa<br>rccnggnwsnggngargg<br>nwsncarathgtnytnws<br>ncarwsnccnacnathyt<br>nwsngcnwsnccnggnga<br>raargtnacnatgacntg<br>ymgngcnwsnwsnwsngt<br>nwsntayatggaytggta<br>ycarcaraarccnggnws<br>nwsnccnaarccntggat<br>htaygcnacnwsnaayyt<br>ngcnwsnggngtnccngc<br>nmgnttywsnggnwsngg<br>nwsnggnacnwsntayws<br>nytnacnathwsnmgngt<br>ngargcngargaygcngc<br>nacntaytaytgycarca<br>rtggathwsnaayccncc<br>nacnttyggngcnggnac<br>naarytngarytnaarga<br>rttyccnaarccnwsnac<br>nccnccnggnwsnwsngg<br>nggngcnccnaargartt<br>yacnytngayttywsnac<br>ngcnaaracntaygtnga<br>ywsnytnaaygtnathmg<br>nwsngcnathggnacncc<br>nytncaracnathwsnws<br>nggnggnacnwsnytnyt<br>natgathgaywsnggnws<br>nggngayaayytnttygc<br>ngtngaygtnmgnggnat<br>hgayccngargarggnmg<br>nttyaayaayytnmgnyt<br>nathgtngarmgnaayaa<br>yytntaygtnacnggntt<br>ygtnaaymgnacnaayaa<br>ygtnttytaymgnttygc<br>ngayttywsncaygtnac<br>nttyccnggnacnacngc<br>ngtnacnytnwsnggnga<br>ywsnwsntayacnacnyt<br>ncarmgngtngcnggnat<br>hwsnmgnacnggnatgca<br>rathaaymgncaywsnyt<br>nacnacnwsntayytnga<br>yytnatgwsncaywsngg<br>nacnwsnytnacncarws<br>ngtngcnmgngcnatgyt<br>nmgnttygtnacngtnac<br>ngcngargcnytnmgntt<br>ymgncarathcarmgngg<br>nttymgnacnacnytnga<br>ygayytnwsnggnmgnws<br>ntaygtnatgacngcnga<br>rgaygtngayytnacnyt<br>naaytggggnmgnytnws<br>nwsngtnytnccngayta<br>ycayggncargaywsngt<br>nmgngtnggnmgnathws<br>nttyggnwsnathaaygc<br>nathytnggnwsngtngc<br>nytnathytnaaytgyca<br>ycaycaygcnwsnmgngt<br>ngcnmgn |
| SEQ ID NO: 6 | heavy chain CDR1 | GYTFTSYNVH |
| SEQ ID NO: 7 | heavy chain CDR2 | AIYPGNGDTSFNQKFKG |
| SEQ ID NO: 8 | heavy chain CDR3 | SNYYGSSYVWFFDV |
| SEQ ID NO: 9 | light chain CDR1 | RASSSVSYMD |
| SEQ ID NO: 10 | light chain CDR2 | ATSNLAS |
| SEQ ID NO: 11 | light chain CDR3 | QQWISNPPT |
| SEQ ID NO: 12 | anti-CD20-scFv-B9E9::SLT-1A polypeptide | MQVQLVQSGAELVKPGAS<br>VKMSCKASGYTFTSYNMH<br>WVKQTPGQGLEWIGAIYP<br>GNGDTSYNQKFKGKATLT<br>ADKSSSTAYMQLSSLTSE<br>DSAVYYCARAQLRPNYWY<br>FDVWGAGTTVTVSSGGGG<br>SGGGGSGGGGSGGGGSGG<br>GGSDIVLSQSPAILSASP<br>GEKVTMTCRASSSVSYMH<br>WYQQKPGSSPKPWIYATS<br>NLASGVPARFSGSGSGTSY<br>STISRVEAEDAATYYCQQ<br>WISNPPTFGAGTKLELKG<br>GGGSGGKEFTLDFSTAKT<br>YVDSLNVIRSAIGTPLQT<br>ISSGGTSLLMIDSGSGDN<br>LFAVDVRGIDPEEGRFNN |

| ID Number | Text Description | Sequence |
|---|---|---|
| | | LRLIVERNNLYVTGFVNR TNNVFYRFADFSHVTFPG TTAVTLSGDSSYTTLQRV AGISRTGMQINRHSLTTS YLDLMSHSGTSLTQSVAR AMLRFVTVTAEALRFRQI QRGFRTTLDDLSGRSYVM TAEDVDLTLNWGRLSSVL PDYHGQDSVRVGRISFGS INAILGSVALILNCHHHA SRVA |
| SEQ ID NO: 13 | polynucleotide encoding anti-CD20-scFv-B9E9::SLT-1A (consensus) | atgcargtncarytngtn carwsnggngcngarytn gtnaarccnggngcnwsn gtnaaratgwsntgyaar gcnwsnggntayacntty acnwsntayaayatgcay tgggtnaarcaracnccn ggncarggnytngartgg athggngcnathtayccn ggnaaygngnayacnwsn tayaaycaraarttyaar ggnaargcnacnytnacn gcngayaarwsnwsnwsn acngcntayatgcarytn wsnwsnytnacnwsngar gaywsngcngtntaytay tgygcnmgngcncarytn mgnccnaaytaytggtay ttygaygtntgggngcn ggnacnacngtnacngtn wsnwsnggnggnggnggn wsnggnggnggnggnwsn ggnggnggnggnwsnggn ggnggnggnwsnggnggn ggnggnwsngayathgtn ytnwsncarwsnccngcn athytnwsngcnwsnccn ggngaraargtnacnatg acntgymgncnwsnwsn wsngtnwsntayatgcay tggtaycarcaraarccn ggnwsnwsnccnaarccn tggathtaygcnacnwsn aayytngcnwsnggngtn ccngcnmgnttywsnggn wsnggnwsnggnacnwsn tayswnsytnacnathwsn mgntgnaргcngагgay gcngcnacntaytaytgy carcartggathwsnaay ccnccnacnttyggngcn ggnacnaarytngarytn aarggnggnggnggnwsn ggnggnaargarttyacn ytngayttywsnacngcn aaracntaygtngaywsn ytnaaygtnathmgnwsn gcnathggnacnccnytn caracnathwsnwsnggn ggnacnwsnytnytnatg athgaywsnggnwsnggn gayaayytnttygcngtn gaygtnmgnggnathgay ccngargarggnmgntty aayaayytnmgnytnath gtnargmgnaayaayytn taygtnacnggnttygtn aaymgnacnaayaaygtn ttytaymgnttygcngay ttywsncaygtnacntty ccnggnacnacngcngtn acnytnwsnggngaywsn | 
| | | wsntayacnacnytncar mgngtngcnggnathwsn mgnacnggnatgcarath aaymgncaywsnytnacn acnwsntayytngayytn atgwsncaywsnggnacn wsnytcanncarwsngtn gcnmgngcnatgytnacn ttygtnacngtnacngcn gargcnytnmgnttymgn carathcarmgnggntty mgnacnacnytngaygay ytnwsnggnmgnwsntay gtnatgacngcngargay gtngayytnacnytnaay tggggnmgnytnwsnwsn gtnytnccngaytaycay ggncargaywsngtnmgn gtnggnmgnathwsntty ggnwsnathaaygcnath ytnggnwsngtngcnytn athytnaaytgycaycay caygcnwsnmgngtngcn mgn |
| SEQ ID NO: 14 | anti-CD20-scFv-C2B8::SLT-1A polypeptide | MQVQLQQPGAELVKPGAS VKMSCKASGYTFTSYNMH WVKQTPGRGLEWIGAIYP GNGDTSYNQFKGKATLT ADKSSSTAYMQLSSLTSE DSAVYYCARSTYYGGDWY FNVWGAGTTVTVSAGSTS GSGKPGSGEGSTKGQIVL SQSPAILSASPGEKVTMT CRASSSVSYIHWFQQKPG SSPKPWIYATSNLASGVP VRFSGSGSGTSYSLTISR VEAEDAATYYCQQWTSNP PTFGGGTKLEIKEFPKPS TPPGSSGGAPKEFTLDFS TAKTYVDSLNVIRSAIGT PLQTISSGGTSLLMIDSG SGDNLFAVDVRGIDPEEG RFNNLRLIVERNNLYVTG FVNRTNNVFYRFADFSHV TFPGTTAVTLSGDSSYTT LQRVAGISRTGMQINRHS LTTSYLDLMSHSGTSLTQ SVARAMLRFVTVTAEALR FRQIQRGFRTTLDDLSGR SYVMTAEDVDLTLNWGRL SSVLPDYHGQDSVRVGRI SFGSINAILGSVALILNC HHHASRVAR |
| SEQ ID NO: 15 | anti-CD20-scFv-C2B8::SLT-1A polynucleotide (consensus) | atgcargtncarytncar carccnggngcngarytn gtnaarccnggngcnwsn gtnaaratgwsntgyaar gcnwsnggntayacntty acnwsntayaayatgcay tgggtnaarcaracnccn ggnmgnggnytngartgg athggngcnathtayccn ggnaaygngnayacnwsn tayaaycaraarttyaar ggnaargcnacnytnacn gcngayaarwsnwsnwsn acngcntayatgcarytn wsnwsnytnacnwsngar gaywsngcngtntaytay tgygcnmgnwsnacntay tayggnggngaytggtay ttyaaygtntgggngcn |

| ID Number | Text Description | Sequence |
|---|---|---|
| | | ggnacnacngtnacngtn wsngcnggnwsnacnwsn ggnwsnggnaarccnggn wsnggngarggnwsnacn aarggncarathgtnytn wsncarwsnccngcnath ytnwsngcnwsnccnggn garaargtnacnatgacn tgymgngcnwsnwsnwsn gtnwsntayathcaytgg ttycarcaraarccnggn wsnwsnccnaarccnt -continued Sequence Listings

| ID Number | Text Description | Sequence |
|---|---|---|
| | | athwsnwsnggnggnacn<br>wsnytnytnatgathgay<br>wsnggnwsnggngayaay<br>ytnttygcngtngaygtn<br>mgnggnathgayccngar<br>garggnmgnttyaayaay<br>ytnmgnytnathgtngar<br>mgnaayaayytntaygtn<br>acnggnttygtnaaymgn<br>acnaayaaygtnttytay<br>mgnttygcngayttywsn<br>caygtnacnttyccnggn<br>acnacngcngtnacnytn<br>wsnggngaywsnwsntay<br>acnacnytncarmgngtn<br>gcnggnathwsnmgnacn<br>ggnatgcarathaaymgn<br>caywsnytnacnacnwsn<br>tayytngayytnatgwsn<br>caywsnggnacnwsnytn<br>acncarwsngtngcnmgn<br>gcnatgytnmgnttygtn<br>acngtnacngcngargcn<br>ytnmgnttymgncarath<br>carmgnggnttymgnacn<br>acnytngaygayytnwsn<br>ggnmgnwsntaygtnatg<br>acngcngargaytngayy<br>tnacnytnaaytggggnm<br>gnytnwsnwsngtnytnc<br>cngaytaycayggncarg<br>aywsngtnmgngtnggnm<br>gnathwsnttyggnwsna<br>thaaygcnathytnggnw<br>sngtngcnytnathytna<br>aytgycaycaycaygcnw<br>snmgngtngcnmgn |
| SEQ ID NO: 18 | linker (218) | GSTSGSGKPGSGEGS |
| SEQ ID NO: 19 | Strep-tag ® | WSHPQFEK |
| SEQ ID NO: 20 | murine hinge (murine IgG3) | EFPKPSTPPGSSGGAP |
| SEQ ID NO: 21 | heavy chain CDR1 | GYTFTSYNMH |
| SEQ ID NO: 22 | heavy chain CDR2 | AIYPGNGDTSYNQKFKG |

-continued

Sequence Listings

| ID Number | Text Description | Sequence |
|---|---|---|
| SEQ ID NO: 23 | heavy chain CDR3 | AQLRPNYWYFDV |
| SEQ ID NO: 24 | light chain CDR1 | RASSSVSYMH |
| SEQ ID NO: 25 | Shiga toxin Subunit A (StxA) | KEFTLDFSTAKTYVDSLN<br>VIRSAIGTPLQTISSGGT<br>SLLMIDSGTGDNLFAVDV<br>RGIDPEEGRFNNLRLIVE<br>RNNLYVTGFVNRTNNVFY<br>RFADFSHVTFPGTTAVTL<br>SGDSSYTTLQRVAGISRT<br>GMQINRHSLTTSYLDLMS<br>HSGTSLTQSVARAMLRFV<br>TVTAEALRFRQIQRGFRT<br>TLDDLSGRSYVMTAEDVD<br>LTLNWGRLSSVLPDYHGQ<br>DSVRVGRISFGSINAILG<br>SVALILNCHHHASRVARM<br>ASDEFPSMCPADGRVRGI<br>THNKILWDSSTLGAILMR<br>RTISS |
| SEQ ID NO: 26 | Shiga-like toxin 2 Subunit A (SLT-2A) | DEFTVDFSSQKSYVDSLN<br>SIRSAISTPLGNISQGGV<br>SVSVINHVLGGNYISLNV<br>RGLDPYSERFNHLRLIME<br>RNNLYVAGFINTETNIFY<br>RFSDFSHISVPDVITVSM<br>TTDSSYSSLQRIADLERT<br>GMQIGRHSLVGSYLDLME<br>FRGRSMTRASSRAMLRFV<br>TVIAEALRFRQIQRGFRP<br>ALSEASPLYTMTAQDVDL<br>TLNWGRISNVLPEYRGEE<br>GVRIGRISFNSLSAILGS<br>VAVILNCHSTGSYSVRSV<br>SQKQKTECQIVGDRAAIK<br>VNNVLWEANTIAALLNRK<br>PQDLTEPNQ |
| SEQ ID NO: 27 | heavy chain CDR3 | STYYGGDWYFNV |
| SEQ ID NO: 28 | light chain CDR1 | RASSSVSYIH |
| SEQ ID NO: 29 | light chain CDR3 | QWTSNPPT |

The invention is claimed as follows:

1. A CD20-binding protein comprising the amino acid sequence shown in SEQ ID NO: 4 or SEQ ID NO: 12.

2. The CD20-binding protein of claim 1, comprising the amino acid sequence shown in SEQ ID NO: 4.

3. A CD20-binding protein consisting essentially of the amino acid sequence shown in SEQ ID NO: 4 or SEQ ID NO: 12.

4. The CD20-binding protein of claim 3, consisting essentially of the polypeptide represented SEQ ID NO: 4.

5. A pharmaceutical composition comprising
  (i) a CD20-binding protein comprising the amino acid sequence shown in SEQ ID NO: 4 or SEQ ID NO: 12; and
  (ii) at least one pharmaceutically acceptable excipient or carrier.

6. The pharmaceutical composition of claim 5, wherein the excipient or carrier is a physiological acceptable: solvent, dispersion medium, coating, antimicrobial agent, isotonic agent, absorption delaying agent, aqueous solution, or powder.

7. The pharmaceutical composition of claim 5, which further comprises a pharmaceutically acceptable solvent, vehicle, aqueous solution, buffer, powder, surfactant, antioxidant, chelating agent, antimicrobial agent, preservative, isotonic agent, tonicity adjusting agent, dispersion medium, coating, adjuvant, wetting agent, emulsifying agent, dispersing agent, absorption delaying agent, stabilizer, or additive.

8. The pharmaceutical composition of claim 5, which comprises
  acetate, acetic acid, alcohol, alpha-tocopherol, aluminum monostearate, antibacterial agent, antifungal agent, ascorbic acid, ascorbyl palmitate, benzyl alcohol, butylated hydroxyanisole, butylated hydroxytoluene, chlorobutanol, citrate, citric acid, cysteine hydrochloride, dextrose, ethanol, ethylenediaminetetraacetic acid, ethyloleate, fixed oil, gelatin, glycerine, glycerol, lactic acid, lecithin, liquid polyethylene glycol, mannitol, methyl parabens, metal chelating agent, monostearate salt, organic ester, paraben, phosphate, phosphoric acid, polyalcohol, polyethylene glycol, polyol, propylene glycol, propylgallate, Ringer's solution, saline, small-molecular organic species, sodium bisulfate, sodium bisulfite, sodium chloride, sodium metabisulfite, sodium sulfite, sorbitol, sugar, synthetic solvent, tartaric acid, vegetable oil, or water.

9. The pharmaceutical composition of claim 5, which comprises citrate, propylene glycol, and sugar.

10. The pharmaceutical composition of claim 5, which comprises citrate, propylene glycol, sorbitol, and water.

11. The pharmaceutical composition of claim 5, is formulated for parenteral administration, oral administration, rectal administration, nasal administration, subcutaneous administration, intramuscular administration, intravenous administration, intradermal administration, or transdermal administration.

12. The pharmaceutical composition of claim 5, which comprises a solvate, salt, ester, or amide of the CD20-binding protein.

13. The pharmaceutical composition of any one of claims 5-10, 11-12, which comprises the CD20-binding protein comprising the amino acid sequence shown in SEQ ID NO: 4.

14. A pharmaceutical composition comprising
  (i) a CD20-binding protein consisting essentially of the amino acid sequence shown in SEQ ID NO: 4 or SEQ ID NO: 12; and
  (ii) at least one pharmaceutically acceptable excipient or carrier.

15. The pharmaceutical composition of claim 14, wherein the excipient or carrier is a physiological acceptable: solvent, dispersion medium, coating, antimicrobial agent, isotonic agent, absorption delaying agent, aqueous solution, or powder.

16. The pharmaceutical composition of claim 14, which further comprises a pharmaceutically acceptable solvent, vehicle, aqueous solution, buffer, powder, surfactant, antioxidant, chelating agent, antimicrobial agent, preservative, isotonic agent, tonicity adjusting agent, dispersion medium, coating, adjuvant, wetting agent, emulsifying agent, dispersing agent, absorption delaying agent, stabilizer, or additive.

17. The pharmaceutical composition of claim 14, which comprises
acetate, acetic acid, alcohol, alpha-tocopherol, aluminum monostearate, antibacterial agent, antifungal agent, ascorbic acid, ascorbyl palmitate, benzyl alcohol, butylated hydroxyanisole, butylated hydroxytoluene, chlorobutanol, citrate, citric acid, cysteine hydrochloride, dextrose, ethanol, ethylenediaminetetraacetic acid, ethyloleate, fixed oil, gelatin, glycerine, glycerol, lactic acid, lecithin, liquid polyethylene glycol, mannitol, methyl parabens, metal chelating agent, monostearate salt, organic ester, paraben, phosphate, phosphoric acid, polyalcohol, polyethylene glycol, polyol, propylene glycol, propylgallate, Ringer's solution, saline, small-molecular organic species, sodium bisulfate, sodium bisulfite, sodium chloride, sodium metabisulfite, sodium sulfite, sorbitol, sugar, synthetic solvent, tartaric acid, vegetable oil, or water.

18. The pharmaceutical composition of claim 14, which comprises citrate, propylene glycol, and sugar.

19. The pharmaceutical composition of claim 14, which comprises citrate, propylene glycol, sorbitol, and water.

20. The pharmaceutical composition of claim 14, which is formulated for oral, rectal, nasal parenteral subcutaneous, intramuscular, intravenous, intradermal, or transdermal administration.

21. The pharmaceutical composition of claim 14, which comprises a solvate, salt, ester, or amide of the CD20-binding protein.

22. The pharmaceutical composition of any one of claims 14-19, which comprises the CD20-binding protein consisting essentially of the amino acid sequence shown in SEQ ID NO: 4.

23. A composition comprising
(i) a CD20-binding protein comprising the amino acid sequence shown in SEQ ID NO: 4 or SEQ ID NO: 12; and
(ii) a solvent or salt.

24. The composition of claim 23, wherein the solvent is water, alcohol, saline, small-molecular organic species, fixed oil, polyethylene glycol, glycerine, propylene glycol, ethanol, polyol, glycerol, acetic acid, lactic acid, vegetable oil, organic ester, or ethyloleate.

25. The composition of claim 23, which comprises: a vehicle, aqueous solution, buffer, surfactant, antioxidant, chelating agent, antimicrobial agent, preservative, isotonic agent, dispersion medium, coating, adjuvant, tonicity adjusting agent, wetting agent, emulsifying agent, dispersing agent, absorption delaying agent, stabilizer, or additive.

26. The composition of claim 23, which comprises:
acetate, acetic acid, alcohol, alpha-tocopherol, aluminum monostearate, antibacterial agent, antifungal agent, ascorbic acid, ascorbyl palmitate, benzyl alcohol, butylated hydroxyanisole, butylated hydroxytoluene, chlorobutanol, citrate, citric acid, cysteine hydrochloride, dextrose, ethanol, ethylenediaminetetraacetic acid, ethyloleate, fixed oil, gelatin, glycerine, glycerol, lactic acid, lecithin, liquid polyethylene glycol, mannitol, metal chelating agent, methyl parabens, monostearate salt, organic ester, paraben, phosphate, phosphoric acid, polyalcohol, polyethylene glycol, polyol, propylene glycol, propylgallate, Ringer's solution, saline, small-molecular organic species, sodium bisulfate, sodium bisulfite, sodium chloride, sodium metabisulfite, sodium sulfite, sorbitol, sugar, synthetic solvent, tartaric acid, vegetable oil, or water.

27. The composition of claim 23, which comprises citrate, propylene glycol, and sugar.

28. The composition of claim 23, which comprises citrate, propylene glycol, sugar, and water.

29. The composition of claim 23, which comprises citrate, propylene glycol, and sorbitol.

30. The composition of claim 23, which comprises citrate, propylene glycol, sorbitol, and water.

31. The composition of any one of claims 23-30, which comprises the CD20-binding protein comprising the amino acid sequence shown in SEQ ID NO: 4.

32. A composition comprising
(i) a CD20-binding protein consisting essentially of the amino acid sequence shown in SEQ ID NO: 4 or SEQ ID NO: 12; and
(ii) a solvent or salt.

33. The composition of claim 32, wherein the solvent is water, alcohol, saline, small-molecular organic species, fixed oil, polyethylene glycol, glycerine, propylene glycol, ethanol, polyol, glycerol, acetic acid, lactic acid, vegetable oil, organic ester, or ethyloleate.

34. The composition of claim 33, which comprises: a vehicle, aqueous solution, buffer, surfactant, antioxidant, chelating agent, antimicrobial agent, preservative, isotonic agent, dispersion medium, coating, adjuvant, tonicity adjusting agent, wetting agent, emulsifying agent, dispersing agent, absorption delaying agent, stabilizer, or additive.

35. The composition of claim 33, which comprises:
acetate, acetic acid, alcohol, alpha-tocopherol, aluminum monostearate, antibacterial agent, antifungal agent, ascorbic acid, ascorbyl palmitate, benzyl alcohol, butylated hydroxyanisole, butylated hydroxytoluene, chlorobutanol, citrate, citric acid, cysteine hydrochloride, dextrose, ethanol, ethylenediaminetetraacetic acid, ethyloleate, fixed oil, gelatin, glycerine, glycerol, lactic acid, lecithin, liquid polyethylene glycol, mannitol, metal chelating agent, methyl parabens, monostearate salt, organic ester, paraben, phosphate, phosphoric acid, polyalcohol, polyethylene glycol, polyol, propylene glycol, propylgallate, Ringer's solution, saline, small-molecular organic species, sodium bisulfate, sodium bisulfite, sodium chloride, sodium metabisulfite, sodium sulfite, sorbitol, sugar, synthetic solvent, tartaric acid, vegetable oil, or water.

36. The composition of claim 33, which comprises citrate, propylene glycol, and sugar.

37. The composition of claim 33, which comprises citrate, propylene glycol, sugar, and water.

38. The composition of claim 33, which comprises citrate, propylene glycol, and sorbitol.

39. The composition of claim 33, which comprises citrate, propylene glycol, sorbitol, and water.

40. The composition of any one of claims 32-39, which comprises the CD20-binding protein consisting essentially of the amino acid sequence shown in SEQ ID NO: 4.

* * * * *

SEQUENCE LISTING

```
<160> NUMBER OF SEQ ID NOS: 29

<210> SEQ ID NO 1
<211> LENGTH: 293
<212> TYPE: PRT
<213> ORGANISM: Escherichia coli

<400> SEQUENCE: 1

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60
```

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg Met Ala Ser Asp Glu
                245                 250                 255

Phe Pro Ser Met Cys Pro Ala Asp Gly Arg Val Arg Gly Ile Thr His
            260                 265                 270

Asn Lys Ile Leu Trp Asp Ser Ser Thr Leu Gly Ala Ile Leu Met Arg
        275                 280                 285

Arg Thr Ile Ser Ser
    290

<210> SEQ ID NO 2
<211> LENGTH: 882
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: modified_base
<222> LOCATION: (30)..(30)
<223> OTHER INFORMATION: a, c, t, g, unknown or other
<220> FEATURE:
<221> NAME/KEY: modified_base
<222> LOCATION: (36)..(36)
<223> OTHER INFORMATION: a, c, t, g, unknown or other
<220> FEATURE:

```
<221> NAME/KEY: modified_base
<222> LOCATION: (42)..(42)
<223> OTHER INFORMATION: a, c, t, g, unknown or other
<220> FEATURE:
<221> NAME/KEY: modified_base
<222> LOCATION: (48)..(48)
<223> OTHER INFORMATION: a, c, t, g, unknown or other
<220> FEATURE:
<221> NAME/KEY: modified_base
<222> LOCATION: (51)..(51)
<223> OTHER INFORMATION: a, c, t, g, unknown or other
<220> FEATURE:
<221> NAME/KEY: modified_base
<222> LOCATION: (57)..(57)
<223> OTHER INFORMATION: a, c, t, g, unknown or other
<220> FEATURE:
<221> NAME/KEY: modified_base
<222> LOCATION: (63)..(63)
<223> OTHER INFORMATION: a, c, t, g, unknown or other
<220> FEATURE:
<221> NAME/KEY: modified_base
<222> LOCATION: (66)..(66)
<223> OTHER INFORMATION: a, c, t, g, unknown or other
<220> FEATURE:
<221> NAME/KEY: modified_base
<222> LOCATION: (69)..(69)
<223> OTHER INFORMATION: a, c, t, g, unknown or other
<220> FEATURE:
<221> NAME/KEY: modified_base
<222> LOCATION: (75)..(75)
<223> OTHER INFORMATION: a, c, t, g, unknown or other
<220> FEATURE:
<221> NAME/KEY: modified_base
<222> LOCATION: (78)..(78)
<223> OTHER INFORMATION: a, c, t, g, unknown or other
<220> FEATURE:
<221> NAME/KEY: modified_base
<222> LOCATION: (81)..(81)
<223> OTHER INFORMATION: a, c, t, g, unknown or other
<220> FEATURE:
<221> NAME/KEY: modified_base
<222> LOCATION: (84)..(84)
<223> OTHER INFORMATION: a, c, t, g, unknown or other
<220> FEATURE:
<221> NAME/KEY: modified_base
<222> LOCATION: (90)..(90)
<223> OTHER INFORMATION: a, c, t, g, unknown or other
<220> FEATURE:
<221> NAME/KEY: modified_base
<222> LOCATION: (96)..(96)
<223> OTHER INFORMATION: a, c, t, g, unknown or other
<220> FEATURE:
<221> NAME/KEY: modified_base
<222> LOCATION: (99)..(99)
<223> OTHER INFORMATION: a, c, t, g, unknown or other
<220> FEATURE:
<221> NAME/KEY: modified_base
<222> LOCATION: (102)..(102)
<223> OTHER INFORMATION: a, c, t, g, unknown or other
<220> FEATURE:
<221> NAME/KEY: modified_base
<222> LOCATION: (105)..(105)
<223> OTHER INFORMATION: a, c, t, g, unknown or other
<220> FEATURE:
<221> NAME/KEY: modified_base
<222> LOCATION: (108)..(108)
<223> OTHER INFORMATION: a, c, t, g, unknown or other
<220> FEATURE:
<221> NAME/KEY: modified_base
<222> LOCATION: (111)..(111)
<223> OTHER INFORMATION: a, c, t, g, unknown or other
<220> FEATURE:
<221> NAME/KEY: modified_base
<222> LOCATION: (114)..(114)
<223> OTHER INFORMATION: a, c, t, g, unknown or other
<220> FEATURE:
<221> NAME/KEY: modified_base
<222> LOCATION: (117)..(117)
<223> OTHER INFORMATION: a, c, t, g, unknown or other
```

-continued

```
<220> FEATURE:
<221> NAME/KEY: modified_base
<222> LOCATION: (129)..(129)
<223> OTHER INFORMATION: a, c, t, g, unknown or other
<220> FEATURE:
<221> NAME/KEY: modified_base
<222> LOCATION: (132)..(132)
<223> OTHER INFORMATION: a, c, t, g, unknown or other
<220> FEATURE:
<221> NAME/KEY: modified_base
<222> LOCATION: (135)..(135)
<223> OTHER INFORMATION: a, c, t, g, unknown or other
<220> FEATURE:
<221> NAME/KEY: modified_base
<222> LOCATION: (138)..(138)
<223> OTHER INFORMATION: a, c, t, g, unknown or other
<220> FEATURE:
<221> NAME/KEY: modified_base
<222> LOCATION: (147)..(147)
<223> OTHER INFORMATION: a, c, t, g, unknown or other
<220> FEATURE:
<221> NAME/KEY: modified_base
<222> LOCATION: (153)..(153)
<223> OTHER INFORMATION: a, c, t, g, unknown or other
<220> FEATURE:
<221> NAME/KEY: modified_base
<222> LOCATION: (156)..(156)
<223> OTHER INFORMATION: a, c, t, g, unknown or other
<220> FEATURE:
<221> NAME/KEY: modified_base
<222> LOCATION: (162)..(162)
<223> OTHER INFORMATION: a, c, t, g, unknown or other
<220> FEATURE:
<221> NAME/KEY: modified_base
<222> LOCATION: (165)..(165)
<223> OTHER INFORMATION: a, c, t, g, unknown or other
<220> FEATURE:
<221> NAME/KEY: modified_base
<222> LOCATION: (168)..(168)
<223> OTHER INFORMATION: a, c, t, g, unknown or other
<220> FEATURE:
<221> NAME/KEY: modified_base
<222> LOCATION: (177)..(177)
<223> OTHER INFORMATION: a, c, t, g, unknown or other
<220> FEATURE:
<221> NAME/KEY: modified_base
<222> LOCATION: (186)..(186)
<223> OTHER INFORMATION: a, c, t, g, unknown or other
<220> FEATURE:
<221> NAME/KEY: modified_base
<222> LOCATION: (189)..(189)
<223> OTHER INFORMATION: a, c, t, g, unknown or other
<220> FEATURE:
<221> NAME/KEY: modified_base
<222> LOCATION: (201)..(201)
<223> OTHER INFORMATION: a, c, t, g, unknown or other
<220> FEATURE:
<221> NAME/KEY: modified_base
<222> LOCATION: (204)..(204)
<223> OTHER INFORMATION: a, c, t, g, unknown or other
<220> FEATURE:
<221> NAME/KEY: modified_base
<222> LOCATION: (207)..(207)
<223> OTHER INFORMATION: a, c, t, g, unknown or other
<220> FEATURE:
<221> NAME/KEY: modified_base
<222> LOCATION: (213)..(213)
<223> OTHER INFORMATION: a, c, t, g, unknown or other
<220> FEATURE:
<221> NAME/KEY: modified_base
<222> LOCATION: (219)..(219)
<223> OTHER INFORMATION: a, c, t, g, unknown or other
<220> FEATURE:
<221> NAME/KEY: modified_base
<222> LOCATION: (228)..(228)
<223> OTHER INFORMATION: a, c, t, g, unknown or other
<220> FEATURE:
<221> NAME/KEY: modified_base
<222> LOCATION: (234)..(234)
```

```
<223> OTHER INFORMATION: a, c, t, g, unknown or other
<220> FEATURE:
<221> NAME/KEY: modified_base
<222> LOCATION: (237)..(237)
<223> OTHER INFORMATION: a, c, t, g, unknown or other
<220> FEATURE:
<221> NAME/KEY: modified_base
<222> LOCATION: (240)..(240)
<223> OTHER INFORMATION: a, c, t, g, unknown or other
<220> FEATURE:
<221> NAME/KEY: modified_base
<222> LOCATION: (246)..(246)
<223> OTHER INFORMATION: a, c, t, g, unknown or other
<220> FEATURE:
<221> NAME/KEY: modified_base
<222> LOCATION: (252)..(252)
<223> OTHER INFORMATION: a, c, t, g, unknown or other
<220> FEATURE:
<221> NAME/KEY: modified_base
<222> LOCATION: (255)..(255)
<223> OTHER INFORMATION: a, c, t, g, unknown or other
<220> FEATURE:
<221> NAME/KEY: modified_base
<222> LOCATION: (264)..(264)
<223> OTHER INFORMATION: a, c, t, g, unknown or other
<220> FEATURE:
<221> NAME/KEY: modified_base
<222> LOCATION: (273)..(273)
<223> OTHER INFORMATION: a, c, t, g, unknown or other
<220> FEATURE:
<221> NAME/KEY: modified_base
<222> LOCATION: (279)..(279)
<223> OTHER INFORMATION: a, c, t, g, unknown or other
<220> FEATURE:
<221> NAME/KEY: modified_base
<222> LOCATION: (288)..(288)
<223> OTHER INFORMATION: a, c, t, g, unknown or other
<220> FEATURE:
<221> NAME/KEY: modified_base
<222> LOCATION: (294)..(294)
<223> OTHER INFORMATION: a, c, t, g, unknown or other
<220> FEATURE:
<221> NAME/KEY: modified_base
<222> LOCATION: (297)..(297)
<223> OTHER INFORMATION: a, c, t, g, unknown or other
<220> FEATURE:
<221> NAME/KEY: modified_base
<222> LOCATION: (303)..(303)
<223> OTHER INFORMATION: a, c, t, g, unknown or other
<220> FEATURE:
<221> NAME/KEY: modified_base
<222> LOCATION: (306)..(306)
<223> OTHER INFORMATION: a, c, t, g, unknown or other
<220> FEATURE:
<221> NAME/KEY: modified_base
<222> LOCATION: (309)..(309)
<223> OTHER INFORMATION: a, c, t, g, unknown or other
<220> FEATURE:
<221> NAME/KEY: modified_base
<222> LOCATION: (312)..(312)
<223> OTHER INFORMATION: a, c, t, g, unknown or other
<220> FEATURE:
<221> NAME/KEY: modified_base
<222> LOCATION: (315)..(315)
<223> OTHER INFORMATION: a, c, t, g, unknown or other
<220> FEATURE:
<221> NAME/KEY: modified_base
<222> LOCATION: (318)..(318)
<223> OTHER INFORMATION: a, c, t, g, unknown or other
<220> FEATURE:
<221> NAME/KEY: modified_base
<222> LOCATION: (321)..(321)
<223> OTHER INFORMATION: a, c, t, g, unknown or other
<220> FEATURE:
<221> NAME/KEY: modified_base
<222> LOCATION: (324)..(324)
<223> OTHER INFORMATION: a, c, t, g, unknown or other
<220> FEATURE:
<221> NAME/KEY: modified_base
```

```
<222> LOCATION: (327)..(327)
<223> OTHER INFORMATION: a, c, t, g, unknown or other
<220> FEATURE:
<221> NAME/KEY: modified_base
<222> LOCATION: (330)..(330)
<223> OTHER INFORMATION: a, c, t, g, unknown or other
<220> FEATURE:
<221> NAME/KEY: modified_base
<222> LOCATION: (336)..(336)
<223> OTHER INFORMATION: a, c, t, g, unknown or other
<220> FEATURE:
<221> NAME/KEY: modified_base
<222> LOCATION: (339)..(339)
<223> OTHER INFORMATION: a, c, t, g, unknown or other
<220> FEATURE:
<221> NAME/KEY: modified_base
<222> LOCATION: (345)..(345)
<223> OTHER INFORMATION: a, c, t, g, unknown or other
<220> FEATURE:
<221> NAME/KEY: modified_base
<222> LOCATION: (348)..(348)
<223> OTHER INFORMATION: a, c, t, g, unknown or other
<220> FEATURE:
<221> NAME/KEY: modified_base
<222> LOCATION: (351)..(351)
<223> OTHER INFORMATION: a, c, t, g, unknown or other
<220> FEATURE:
<221> NAME/KEY: modified_base
<222> LOCATION: (357)..(357)
<223> OTHER INFORMATION: a, c, t, g, unknown or other
<220> FEATURE:
<221> NAME/KEY: modified_base
<222> LOCATION: (360)..(360)
<223> OTHER INFORMATION: a, c, t, g, unknown or other
<220> FEATURE:
<221> NAME/KEY: modified_base
<222> LOCATION: (363)..(363)
<223> OTHER INFORMATION: a, c, t, g, unknown or other
<220> FEATURE:
<221> NAME/KEY: modified_base
<222> LOCATION: (366)..(366)
<223> OTHER INFORMATION: a, c, t, g, unknown or other
<220> FEATURE:
<221> NAME/KEY: modified_base
<222> LOCATION: (372)..(372)
<223> OTHER INFORMATION: a, c, t, g, unknown or other
<220> FEATURE:
<221> NAME/KEY: modified_base
<222> LOCATION: (375)..(375)
<223> OTHER INFORMATION: a, c, t, g, unknown or other
<220> FEATURE:
<221> NAME/KEY: modified_base
<222> LOCATION: (378)..(378)
<223> OTHER INFORMATION: a, c, t, g, unknown or other
<220> FEATURE:
<221> NAME/KEY: modified_base
<222> LOCATION: (381)..(381)
<223> OTHER INFORMATION: a, c, t, g, unknown or other
<220> FEATURE:
<221> NAME/KEY: modified_base
<222> LOCATION: (396)..(396)
<223> OTHER INFORMATION: a, c, t, g, unknown or other
<220> FEATURE:
<221> NAME/KEY: modified_base
<222> LOCATION: (402)..(402)
<223> OTHER INFORMATION: a, c, t, g, unknown or other
<220> FEATURE:
<221> NAME/KEY: modified_base
<222> LOCATION: (405)..(405)
<223> OTHER INFORMATION: a, c, t, g, unknown or other
<220> FEATURE:
<221> NAME/KEY: modified_base
<222> LOCATION: (408)..(408)
<223> OTHER INFORMATION: a, c, t, g, unknown or other
<220> FEATURE:
<221> NAME/KEY: modified_base
<222> LOCATION: (411)..(411)
<223> OTHER INFORMATION: a, c, t, g, unknown or other
<220> FEATURE:
```

```
<221> NAME/KEY: modified_base
<222> LOCATION: (414)..(414)
<223> OTHER INFORMATION: a, c, t, g, unknown or other
<220> FEATURE:
<221> NAME/KEY: modified_base
<222> LOCATION: (420)..(420)
<223> OTHER INFORMATION: a, c, t, g, unknown or other
<220> FEATURE:
<221> NAME/KEY: modified_base
<222> LOCATION: (426)..(426)
<223> OTHER INFORMATION: a, c, t, g, unknown or other
<220> FEATURE:
<221> NAME/KEY: modified_base
<222> LOCATION: (432)..(432)
<223> OTHER INFORMATION: a, c, t, g, unknown or other
<220> FEATURE:
<221> NAME/KEY: modified_base
<222> LOCATION: (438)..(438)
<223> OTHER INFORMATION: a, c, t, g, unknown or other
<220> FEATURE:
<221> NAME/KEY: modified_base
<222> LOCATION: (441)..(441)
<223> OTHER INFORMATION: a, c, t, g, unknown or other
<220> FEATURE:
<221> NAME/KEY: modified_base
<222> LOCATION: (444)..(444)
<223> OTHER INFORMATION: a, c, t, g, unknown or other
<220> FEATURE:
<221> NAME/KEY: modified_base
<222> LOCATION: (447)..(447)
<223> OTHER INFORMATION: a, c, t, g, unknown or other
<220> FEATURE:
<221> NAME/KEY: modified_base
<222> LOCATION: (450)..(450)
<223> OTHER INFORMATION: a, c, t, g, unknown or other
<220> FEATURE:
<221> NAME/KEY: modified_base
<222> LOCATION: (453)..(453)
<223> OTHER INFORMATION: a, c, t, g, unknown or other
<220> FEATURE:
<221> NAME/KEY: modified_base
<222> LOCATION: (459)..(459)
<223> OTHER INFORMATION: a, c, t, g, unknown or other
<220> FEATURE:
<221> NAME/KEY: modified_base
<222> LOCATION: (462)..(462)
<223> OTHER INFORMATION: a, c, t, g, unknown or other
<220> FEATURE:
<221> NAME/KEY: modified_base
<222> LOCATION: (465)..(465)
<223> OTHER INFORMATION: a, c, t, g, unknown or other
<220> FEATURE:
<221> NAME/KEY: modified_base
<222> LOCATION: (468)..(468)
<223> OTHER INFORMATION: a, c, t, g, unknown or other
<220> FEATURE:
<221> NAME/KEY: modified_base
<222> LOCATION: (471)..(471)
<223> OTHER INFORMATION: a, c, t, g, unknown or other
<220> FEATURE:
<221> NAME/KEY: modified_base
<222> LOCATION: (477)..(477)
<223> OTHER INFORMATION: a, c, t, g, unknown or other
<220> FEATURE:
<221> NAME/KEY: modified_base
<222> LOCATION: (480)..(480)
<223> OTHER INFORMATION: a, c, t, g, unknown or other
<220> FEATURE:
<221> NAME/KEY: modified_base
<222> LOCATION: (486)..(486)
<223> OTHER INFORMATION: a, c, t, g, unknown or other
<220> FEATURE:
<221> NAME/KEY: modified_base
<222> LOCATION: (489)..(489)
<223> OTHER INFORMATION: a, c, t, g, unknown or other
<220> FEATURE:
<221> NAME/KEY: modified_base
<222> LOCATION: (492)..(492)
<223> OTHER INFORMATION: a, c, t, g, unknown or other
```

-continued

```
<220> FEATURE:
<221> NAME/KEY: modified_base
<222> LOCATION: (495)..(495)
<223> OTHER INFORMATION: a, c, t, g, unknown or other
<220> FEATURE:
<221> NAME/KEY: modified_base
<222> LOCATION: (498)..(498)
<223> OTHER INFORMATION: a, c, t, g, unknown or other
<220> FEATURE:
<221> NAME/KEY: modified_base
<222> LOCATION: (504)..(504)
<223> OTHER INFORMATION: a, c, t, g, unknown or other
<220> FEATURE:
<221> NAME/KEY: modified_base
<222> LOCATION: (507)..(507)
<223> OTHER INFORMATION: a, c, t, g, unknown or other
<220> FEATURE:
<221> NAME/KEY: modified_base
<222> LOCATION: (510)..(510)
<223> OTHER INFORMATION: a, c, t, g, unknown or other
<220> FEATURE:
<221> NAME/KEY: modified_base
<222> LOCATION: (516)..(516)
<223> OTHER INFORMATION: a, c, t, g, unknown or other
<220> FEATURE:
<221> NAME/KEY: modified_base
<222> LOCATION: (528)..(528)
<223> OTHER INFORMATION: a, c, t, g, unknown or other
<220> FEATURE:
<221> NAME/KEY: modified_base
<222> LOCATION: (531)..(531)
<223> OTHER INFORMATION: a, c, t, g, unknown or other
<220> FEATURE:
<221> NAME/KEY: modified_base
<222> LOCATION: (537)..(537)
<223> OTHER INFORMATION: a, c, t, g, unknown or other
<220> FEATURE:
<221> NAME/KEY: modified_base
<222> LOCATION: (540)..(540)
<223> OTHER INFORMATION: a, c, t, g, unknown or other
<220> FEATURE:
<221> NAME/KEY: modified_base
<222> LOCATION: (543)..(543)
<223> OTHER INFORMATION: a, c, t, g, unknown or other
<220> FEATURE:
<221> NAME/KEY: modified_base
<222> LOCATION: (546)..(546)
<223> OTHER INFORMATION: a, c, t, g, unknown or other
<220> FEATURE:
<221> NAME/KEY: modified_base
<222> LOCATION: (555)..(555)
<223> OTHER INFORMATION: a, c, t, g, unknown or other
<220> FEATURE:
<221> NAME/KEY: modified_base
<222> LOCATION: (558)..(558)
<223> OTHER INFORMATION: a, c, t, g, unknown or other
<220> FEATURE:
<221> NAME/KEY: modified_base
<222> LOCATION: (561)..(561)
<223> OTHER INFORMATION: a, c, t, g, unknown or other
<220> FEATURE:
<221> NAME/KEY: modified_base
<222> LOCATION: (564)..(564)
<223> OTHER INFORMATION: a, c, t, g, unknown or other
<220> FEATURE:
<221> NAME/KEY: modified_base
<222> LOCATION: (567)..(567)
<223> OTHER INFORMATION: a, c, t, g, unknown or other
<220> FEATURE:
<221> NAME/KEY: modified_base
<222> LOCATION: (573)..(573)
<223> OTHER INFORMATION: a, c, t, g, unknown or other
<220> FEATURE:
<221> NAME/KEY: modified_base
<222> LOCATION: (579)..(579)
<223> OTHER INFORMATION: a, c, t, g, unknown or other
<220> FEATURE:
<221> NAME/KEY: modified_base
<222> LOCATION: (582)..(582)
```

-continued

```
<223> OTHER INFORMATION: a, c, t, g, unknown or other
<220> FEATURE:
<221> NAME/KEY: modified_base
<222> LOCATION: (591)..(591)
<223> OTHER INFORMATION: a, c, t, g, unknown or other
<220> FEATURE:
<221> NAME/KEY: modified_base
<222> LOCATION: (597)..(597)
<223> OTHER INFORMATION: a, c, t, g, unknown or other
<220> FEATURE:
<221> NAME/KEY: modified_base
<222> LOCATION: (600)..(600)
<223> OTHER INFORMATION: a, c, t, g, unknown or other
<220> FEATURE:
<221> NAME/KEY: modified_base
<222> LOCATION: (603)..(603)
<223> OTHER INFORMATION: a, c, t, g, unknown or other
<220> FEATURE:
<221> NAME/KEY: modified_base
<222> LOCATION: (612)..(612)
<223> OTHER INFORMATION: a, c, t, g, unknown or other
<220> FEATURE:
<221> NAME/KEY: modified_base
<222> LOCATION: (615)..(615)
<223> OTHER INFORMATION: a, c, t, g, unknown or other
<220> FEATURE:
<221> NAME/KEY: modified_base
<222> LOCATION: (618)..(618)
<223> OTHER INFORMATION: a, c, t, g, unknown or other
<220> FEATURE:
<221> NAME/KEY: modified_base
<222> LOCATION: (621)..(621)
<223> OTHER INFORMATION: a, c, t, g, unknown or other
<220> FEATURE:
<221> NAME/KEY: modified_base
<222> LOCATION: (624)..(624)
<223> OTHER INFORMATION: a, c, t, g, unknown or other
<220> FEATURE:
<221> NAME/KEY: modified_base
<222> LOCATION: (627)..(627)
<223> OTHER INFORMATION: a, c, t, g, unknown or other
<220> FEATURE:
<221> NAME/KEY: modified_base
<222> LOCATION: (630)..(630)
<223> OTHER INFORMATION: a, c, t, g, unknown or other
<220> FEATURE:
<221> NAME/KEY: modified_base
<222> LOCATION: (633)..(633)
<223> OTHER INFORMATION: a, c, t, g, unknown or other
<220> FEATURE:
<221> NAME/KEY: modified_base
<222> LOCATION: (645)..(645)
<223> OTHER INFORMATION: a, c, t, g, unknown or other
<220> FEATURE:
<221> NAME/KEY: modified_base
<222> LOCATION: (654)..(654)
<223> OTHER INFORMATION: a, c, t, g, unknown or other
<220> FEATURE:
<221> NAME/KEY: modified_base
<222> LOCATION: (657)..(657)
<223> OTHER INFORMATION: a, c, t, g, unknown or other
<220> FEATURE:
<221> NAME/KEY: modified_base
<222> LOCATION: (660)..(660)
<223> OTHER INFORMATION: a, c, t, g, unknown or other
<220> FEATURE:
<221> NAME/KEY: modified_base
<222> LOCATION: (663)..(663)
<223> OTHER INFORMATION: a, c, t, g, unknown or other
<220> FEATURE:
<221> NAME/KEY: modified_base
<222> LOCATION: (666)..(666)
<223> OTHER INFORMATION: a, c, t, g, unknown or other
<220> FEATURE:
<221> NAME/KEY: modified_base
<222> LOCATION: (669)..(669)
<223> OTHER INFORMATION: a, c, t, g, unknown or other
<220> FEATURE:
<221> NAME/KEY: modified_base
```

-continued

```
<222> LOCATION: (675)..(675)
<223> OTHER INFORMATION: a, c, t, g, unknown or other
<220> FEATURE:
<221> NAME/KEY: modified_base
<222> LOCATION: (681)..(681)
<223> OTHER INFORMATION: a, c, t, g, unknown or other
<220> FEATURE:
<221> NAME/KEY: modified_base
<222> LOCATION: (684)..(684)
<223> OTHER INFORMATION: a, c, t, g, unknown or other
<220> FEATURE:
<221> NAME/KEY: modified_base
<222> LOCATION: (693)..(693)
<223> OTHER INFORMATION: a, c, t, g, unknown or other
<220> FEATURE:
<221> NAME/KEY: modified_base
<222> LOCATION: (699)..(699)
<223> OTHER INFORMATION: a, c, t, g, unknown or other
<220> FEATURE:
<221> NAME/KEY: modified_base
<222> LOCATION: (702)..(702)
<223> OTHER INFORMATION: a, c, t, g, unknown or other
<220> FEATURE:
<221> NAME/KEY: modified_base
<222> LOCATION: (705)..(705)
<223> OTHER INFORMATION: a, c, t, g, unknown or other
<220> FEATURE:
<221> NAME/KEY: modified_base
<222> LOCATION: (708)..(708)
<223> OTHER INFORMATION: a, c, t, g, unknown or other
<220> FEATURE:
<221> NAME/KEY: modified_base
<222> LOCATION: (711)..(711)
<223> OTHER INFORMATION: a, c, t, g, unknown or other
<220> FEATURE:
<221> NAME/KEY: modified_base
<222> LOCATION: (714)..(714)
<223> OTHER INFORMATION: a, c, t, g, unknown or other
<220> FEATURE:
<221> NAME/KEY: modified_base
<222> LOCATION: (720)..(720)
<223> OTHER INFORMATION: a, c, t, g, unknown or other
<220> FEATURE:
<221> NAME/KEY: modified_base
<222> LOCATION: (738)..(738)
<223> OTHER INFORMATION: a, c, t, g, unknown or other
<220> FEATURE:
<221> NAME/KEY: modified_base
<222> LOCATION: (741)..(741)
<223> OTHER INFORMATION: a, c, t, g, unknown or other
<220> FEATURE:
<221> NAME/KEY: modified_base
<222> LOCATION: (744)..(744)
<223> OTHER INFORMATION: a, c, t, g, unknown or other
<220> FEATURE:
<221> NAME/KEY: modified_base
<222> LOCATION: (747)..(747)
<223> OTHER INFORMATION: a, c, t, g, unknown or other
<220> FEATURE:
<221> NAME/KEY: modified_base
<222> LOCATION: (750)..(750)
<223> OTHER INFORMATION: a, c, t, g, unknown or other
<220> FEATURE:
<221> NAME/KEY: modified_base
<222> LOCATION: (753)..(753)
<223> OTHER INFORMATION: a, c, t, g, unknown or other
<220> FEATURE:
<221> NAME/KEY: modified_base
<222> LOCATION: (759)..(759)
<223> OTHER INFORMATION: a, c, t, g, unknown or other
<220> FEATURE:
<221> NAME/KEY: modified_base
<222> LOCATION: (762)..(762)
<223> OTHER INFORMATION: a, c, t, g, unknown or other
<220> FEATURE:
<221> NAME/KEY: modified_base
<222> LOCATION: (774)..(774)
<223> OTHER INFORMATION: a, c, t, g, unknown or other
<220> FEATURE:
```

```
<221> NAME/KEY: modified_base
<222> LOCATION: (777)..(777)
<223> OTHER INFORMATION: a, c, t, g, unknown or other
<220> FEATURE:
<221> NAME/KEY: modified_base
<222> LOCATION: (786)..(786)
<223> OTHER INFORMATION: a, c, t, g, unknown or other
<220> FEATURE:
<221> NAME/KEY: modified_base
<222> LOCATION: (789)..(789)
<223> OTHER INFORMATION: a, c, t, g, unknown or other
<220> FEATURE:
<221> NAME/KEY: modified_base
<222> LOCATION: (795)..(795)
<223> OTHER INFORMATION: a, c, t, g, unknown or other
<220> FEATURE:
<221> NAME/KEY: modified_base
<222> LOCATION: (798)..(798)
<223> OTHER INFORMATION: a, c, t, g, unknown or other
<220> FEATURE:
<221> NAME/KEY: modified_base
<222> LOCATION: (801)..(801)
<223> OTHER INFORMATION: a, c, t, g, unknown or other
<220> FEATURE:
<221> NAME/KEY: modified_base
<222> LOCATION: (804)..(804)
<223> OTHER INFORMATION: a, c, t, g, unknown or other
<220> FEATURE:
<221> NAME/KEY: modified_base
<222> LOCATION: (807)..(807)
<223> OTHER INFORMATION: a, c, t, g, unknown or other
<220> FEATURE:
<221> NAME/KEY: modified_base
<222> LOCATION: (813)..(813)
<223> OTHER INFORMATION: a, c, t, g, unknown or other
<220> FEATURE:
<221> NAME/KEY: modified_base
<222> LOCATION: (828)..(828)
<223> OTHER INFORMATION: a, c, t, g, unknown or other
<220> FEATURE:
<221> NAME/KEY: modified_base
<222> LOCATION: (837)..(837)
<223> OTHER INFORMATION: a, c, t, g, unknown or other
<220> FEATURE:
<221> NAME/KEY: modified_base
<222> LOCATION: (840)..(840)
<223> OTHER INFORMATION: a, c, t, g, unknown or other
<220> FEATURE:
<221> NAME/KEY: modified_base
<222> LOCATION: (843)..(843)
<223> OTHER INFORMATION: a, c, t, g, unknown or other
<220> FEATURE:
<221> NAME/KEY: modified_base
<222> LOCATION: (846)..(846)
<223> OTHER INFORMATION: a, c, t, g, unknown or other
<220> FEATURE:
<221> NAME/KEY: modified_base
<222> LOCATION: (849)..(849)
<223> OTHER INFORMATION: a, c, t, g, unknown or other
<220> FEATURE:
<221> NAME/KEY: modified_base
<222> LOCATION: (852)..(852)
<223> OTHER INFORMATION: a, c, t, g, unknown or other
<220> FEATURE:
<221> NAME/KEY: modified_base
<222> LOCATION: (858)..(858)
<223> OTHER INFORMATION: a, c, t, g, unknown or other
<220> FEATURE:
<221> NAME/KEY: modified_base
<222> LOCATION: (864)..(864)
<223> OTHER INFORMATION: a, c, t, g, unknown or other
<220> FEATURE:
<221> NAME/KEY: modified_base
<222> LOCATION: (867)..(867)
<223> OTHER INFORMATION: a, c, t, g, unknown or other
<220> FEATURE:
<221> NAME/KEY: modified_base
<222> LOCATION: (870)..(870)
<223> OTHER INFORMATION: a, c, t, g, unknown or other
```

<220> FEATURE:
<221> NAME/KEY: modified_base
<222> LOCATION: (876)..(876)
<223> OTHER INFORMATION: a, c, t, g, unknown or other
<220> FEATURE:
<221> NAME/KEY: modified_base
<222> LOCATION: (879)..(879)
<223> OTHER INFORMATION: a, c, t, g, unknown or other

<400> SEQUENCE: 2
aargarttya cnytngaytt ywsnacngcn aaracntayg tngaywsnyt naaygtnath 60
mgnwsngcna thggnacncc nytncaracn athwsnwsng gnggnacnws nytnytnatg 120
athgaywsng gnwsnggnga yaayytntty gcngtngayg tnmgnggnat hgayccngar 180
garggnmgnt tyaayaayyt nmgnytnath gtngarmgna ayaayytnta ygtnacnggn 240
ttygtnaaym gnacnaayaa ygtnttytay mgnttygcng ayttywsnca ygtnacntty 300
ccnggnacna cngcngtnac nytnwsnggn gaywsnwsnt ayacnacnyt ncarmgngtn 360
gcnggnathw snmgnacngg natgcarath aaymgncayw snytnacnac nwsntayytn 420
gayytnatgw sncaywsngg nacnwsnytn acncarwsng tngcnmgngc natgytnmgn 480
ttygtnacng tnacngcnga rgcnytnmgn ttymgncara thcarmgngg nttymgnacn 540
acnytngayg ayytnwsngg nmgnwsntay gtnatgacng cngargaygt ngayytnacn 600
ytnaaytggg gnmgnytnws nwsngtnytn ccngaytayc ayggncarga ywsngtnmgn 660
gtnggnmgna thwsnttygg nwsnathaay gcnathytng gnwsngtngc nytnathytn 720
aaytgycayc aycaygcnws nmgngtngcn mgnatggcnw sngaygartt yccnwsnatg 780
tgyccngcng ayggnmgngt nmgnggnath acncayaaya arathytntg ggaywsnwsn 840
acnytnggng cnathytnat gmgnmgnacn athwsnwsnt rr 882

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 3

Gly Ile Leu Gly Phe Val Phe Thr Leu
1 5

<210> SEQ ID NO 4
<211> LENGTH: 512
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 4

Met Gln Val Gln Leu Gln Gln Pro Gly Ala Glu Leu Val Lys Pro Gly
1 5 10 15

Ala Ser Val Lys Met Ser Cys Lys Thr Ser Gly Tyr Thr Phe Thr Ser
20 25 30

Tyr Asn Val His Trp Val Lys Gln Thr Pro Gly Gln Gly Leu Glu Trp
35 40 45

Ile Gly Ala Ile Tyr Pro Gly Asn Gly Asp Thr Ser Phe Asn Gln Lys
50 55 60

Phe Lys Gly Lys Ala Thr Leu Thr Ala Asp Lys Ser Ser Ser Thr Val

```
                65                  70                  75                  80
Tyr Met Gln Leu Ser Ser Leu Thr Ser Glu Asp Ser Ala Val Tyr Tyr
                    85                  90                  95

Cys Ala Arg Ser Asn Tyr Tyr Gly Ser Ser Tyr Val Trp Phe Phe Asp
                100                 105                 110

Val Trp Gly Ala Gly Thr Thr Val Thr Val Ser Ser Gly Ser Thr Ser
                115                 120                 125

Gly Ser Gly Lys Pro Gly Ser Gly Glu Gly Ser Gln Ile Val Leu Ser
            130                 135                 140

Gln Ser Pro Thr Ile Leu Ser Ala Ser Pro Gly Glu Lys Val Thr Met
145                 150                 155                 160

Thr Cys Arg Ala Ser Ser Ser Val Ser Tyr Met Asp Trp Tyr Gln Gln
                165                 170                 175

Lys Pro Gly Ser Ser Pro Lys Pro Trp Ile Tyr Ala Thr Ser Asn Leu
                180                 185                 190

Ala Ser Gly Val Pro Ala Arg Phe Ser Gly Ser Gly Ser Gly Thr Ser
                195                 200                 205

Tyr Ser Leu Thr Ile Ser Arg Val Glu Ala Glu Asp Ala Ala Thr Tyr
            210                 215                 220

Tyr Cys Gln Gln Trp Ile Ser Asn Pro Pro Thr Phe Gly Ala Gly Thr
225                 230                 235                 240

Lys Leu Glu Leu Lys Glu Phe Pro Lys Pro Ser Thr Pro Pro Gly Ser
                245                 250                 255

Ser Gly Gly Ala Pro Lys Glu Phe Thr Leu Asp Phe Ser Thr Ala Lys
                260                 265                 270

Thr Tyr Val Asp Ser Leu Asn Val Ile Arg Ser Ala Ile Gly Thr Pro
            275                 280                 285

Leu Gln Thr Ile Ser Ser Gly Gly Thr Ser Leu Leu Met Ile Asp Ser
            290                 295                 300

Gly Ser Gly Asp Asn Leu Phe Ala Val Asp Val Arg Gly Ile Asp Pro
305                 310                 315                 320

Glu Glu Gly Arg Phe Asn Asn Leu Arg Leu Ile Val Glu Arg Asn Asn
                325                 330                 335

Leu Tyr Val Thr Gly Phe Val Asn Arg Thr Asn Asn Val Phe Tyr Arg
                340                 345                 350

Phe Ala Asp Phe Ser His Val Thr Phe Pro Gly Thr Thr Ala Val Thr
            355                 360                 365

Leu Ser Gly Asp Ser Ser Tyr Thr Thr Leu Gln Arg Val Ala Gly Ile
            370                 375                 380

Ser Arg Thr Gly Met Gln Ile Asn Arg His Ser Leu Thr Thr Ser Tyr
385                 390                 395                 400

Leu Asp Leu Met Ser His Ser Gly Thr Ser Leu Thr Gln Ser Val Ala
                405                 410                 415

Arg Ala Met Leu Arg Phe Val Thr Val Thr Ala Glu Ala Leu Arg Phe
                420                 425                 430

Arg Gln Ile Gln Arg Gly Phe Arg Thr Thr Leu Asp Asp Leu Ser Gly
            435                 440                 445

Arg Ser Tyr Val Met Thr Ala Glu Asp Val Asp Leu Thr Leu Asn Trp
            450                 455                 460

Gly Arg Leu Ser Ser Val Leu Pro Asp Tyr His Gly Gln Asp Ser Val
465                 470                 475                 480

Arg Val Gly Arg Ile Ser Phe Gly Ser Ile Asn Ala Ile Leu Gly Ser
                485                 490                 495
```

```
Val Ala Leu Ile Leu Asn Cys His His His Ala Ser Arg Val Ala Arg
        500                 505                 510

<210> SEQ ID NO 5
<211> LENGTH: 1536
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: modified_base
<222> LOCATION: (30)..(30)
<223> OTHER INFORMATION: a, c, t, g, unknown or other
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: modified_base
<222> LOCATION: (39)..(39)
<223> OTHER INFORMATION: a, c, t, g, unknown or other
<220> FEATURE:
<221> NAME/KEY: modified_base
<222> LOCATION: (45)..(45)
<223> OTHER INFORMATION: a, c, t, g, unknown or other
<220> FEATURE:
<221> NAME/KEY: modified_base
<222> LOCATION: (48)..(48)
<223> OTHER INFORMATION: a, c, t, g, unknown or other
<220> FEATURE:
<221> NAME/KEY: modified_base
<222> LOCATION: (51)..(51)
<223> OTHER INFORMATION: a, c, t, g, unknown or other
<220> FEATURE:
<221> NAME/KEY: modified_base
<222> LOCATION: (54)..(54)
<223> OTHER INFORMATION: a, c, t, g, unknown or other
<220> FEATURE:
<221> NAME/KEY: modified_base
<222> LOCATION: (57)..(57)
<223> OTHER INFORMATION: a, c, t, g, unknown or other
<220> FEATURE:
<221> NAME/KEY: modified_base
<222> LOCATION: (66)..(66)
<223> OTHER INFORMATION: a, c, t, g, unknown or other
<220> FEATURE:
<221> NAME/KEY: modified_base
<222> LOCATION: (75)..(75)
<223> OTHER INFORMATION: a, c, t, g, unknown or other
<220> FEATURE:
<221> NAME/KEY: modified_base
<222> LOCATION: (78)..(78)
<223> OTHER INFORMATION: a, c, t, g, unknown or other
<220> FEATURE:
<221> NAME/KEY: modified_base
<222> LOCATION: (81)..(81)
<223> OTHER INFORMATION: a, c, t, g, unknown or other
<220> FEATURE:
<221> NAME/KEY: modified_base
<222> LOCATION: (87)..(87)
```

```
<223> OTHER INFORMATION: a, c, t, g, unknown or other
<220> FEATURE:
<221> NAME/KEY: modified_base
<222> LOCATION: (93)..(93)
<223> OTHER INFORMATION: a, c, t, g, unknown or other
<220> FEATURE:
<221> NAME/KEY: modified_base
<222> LOCATION: (96)..(96)
<223> OTHER INFORMATION: a, c, t, g, unknown or other
<220> FEATURE:
<221> NAME/KEY: modified_base
<222> LOCATION: (105)..(105)
<223> OTHER INFORMATION: a, c, t, g, unknown or other
<220> FEATURE:
<221> NAME/KEY: modified_base
<222> LOCATION: (114)..(114)
<223> OTHER INFORMATION: a, c, t, g, unknown or other
<220> FEATURE:
<221> NAME/KEY: modified_base
<222> LOCATION: (123)..(123)
<223> OTHER INFORMATION: a, c, t, g, unknown or other
<220> FEATURE:
<221> NAME/KEY: modified_base
<222> LOCATION: (126)..(126)
<223> OTHER INFORMATION: a, c, t, g, unknown or other
<220> FEATURE:
<221> NAME/KEY: modified_base
<222> LOCATION: (129)..(129)
<223> OTHER INFORMATION: a, c, t, g, unknown or other
<220> FEATURE:
<221> NAME/KEY: modified_base
<222> LOCATION: (135)..(135)
<223> OTHER INFORMATION: a, c, t, g, unknown or other
<220> FEATURE:
<221> NAME/KEY: modified_base
<222> LOCATION: (138)..(138)
<223> OTHER INFORMATION: a, c, t, g, unknown or other
<220> FEATURE:
<221> NAME/KEY: modified_base
<222> LOCATION: (150)..(150)
<223> OTHER INFORMATION: a, c, t, g, unknown or other
<220> FEATURE:
<221> NAME/KEY: modified_base
<222> LOCATION: (153)..(153)
<223> OTHER INFORMATION: a, c, t, g, unknown or other
<220> FEATURE:
<221> NAME/KEY: modified_base
<222> LOCATION: (162)..(162)
<223> OTHER INFORMATION: a, c, t, g, unknown or other
<220> FEATURE:
<221> NAME/KEY: modified_base
<222> LOCATION: (165)..(165)
<223> OTHER INFORMATION: a, c, t, g, unknown or other
<220> FEATURE:
<221> NAME/KEY: modified_base
<222> LOCATION: (171)..(171)
<223> OTHER INFORMATION: a, c, t, g, unknown or other
<220> FEATURE:
<221> NAME/KEY: modified_base
<222> LOCATION: (177)..(177)
<223> OTHER INFORMATION: a, c, t, g, unknown or other
<220> FEATURE:
<221> NAME/KEY: modified_base
<222> LOCATION: (180)..(180)
<223> OTHER INFORMATION: a, c, t, g, unknown or other
<220> FEATURE:
<221> NAME/KEY: modified_base
<222> LOCATION: (201)..(201)
<223> OTHER INFORMATION: a, c, t, g, unknown or other
<220> FEATURE:
<221> NAME/KEY: modified_base
<222> LOCATION: (207)..(207)
<223> OTHER INFORMATION: a, c, t, g, unknown or other
<220> FEATURE:
<221> NAME/KEY: modified_base
<222> LOCATION: (210)..(210)
<223> OTHER INFORMATION: a, c, t, g, unknown or other
<220> FEATURE:
<221> NAME/KEY: modified_base
```

-continued

```
<222> LOCATION: (213)..(213)
<223> OTHER INFORMATION: a, c, t, g, unknown or other
<220> FEATURE:
<221> NAME/KEY: modified_base
<222> LOCATION: (216)..(216)
<223> OTHER INFORMATION: a, c, t, g, unknown or other
<220> FEATURE:
<221> NAME/KEY: modified_base
<222> LOCATION: (219)..(219)
<223> OTHER INFORMATION: a, c, t, g, unknown or other
<220> FEATURE:
<221> NAME/KEY: modified_base
<222> LOCATION: (228)..(228)
<223> OTHER INFORMATION: a, c, t, g, unknown or other
<220> FEATURE:
<221> NAME/KEY: modified_base
<222> LOCATION: (231)..(231)
<223> OTHER INFORMATION: a, c, t, g, unknown or other
<220> FEATURE:
<221> NAME/KEY: modified_base
<222> LOCATION: (234)..(234)
<223> OTHER INFORMATION: a, c, t, g, unknown or other
<220> FEATURE:
<221> NAME/KEY: modified_base
<222> LOCATION: (237)..(237)
<223> OTHER INFORMATION: a, c, t, g, unknown or other
<220> FEATURE:
<221> NAME/KEY: modified_base
<222> LOCATION: (240)..(240)
<223> OTHER INFORMATION: a, c, t, g, unknown or other
<220> FEATURE:
<221> NAME/KEY: modified_base
<222> LOCATION: (252)..(252)
<223> OTHER INFORMATION: a, c, t, g, unknown or other
<220> FEATURE:
<221> NAME/KEY: modified_base
<222> LOCATION: (255)..(255)
<223> OTHER INFORMATION: a, c, t, g, unknown or other
<220> FEATURE:
<221> NAME/KEY: modified_base
<222> LOCATION: (258)..(258)
<223> OTHER INFORMATION: a, c, t, g, unknown or other
<220> FEATURE:
<221> NAME/KEY: modified_base
<222> LOCATION: (261)..(261)
<223> OTHER INFORMATION: a, c, t, g, unknown or other
<220> FEATURE:
<221> NAME/KEY: modified_base
<222> LOCATION: (264)..(264)
<223> OTHER INFORMATION: a, c, t, g, unknown or other
<220> FEATURE:
<221> NAME/KEY: modified_base
<222> LOCATION: (267)..(267)
<223> OTHER INFORMATION: a, c, t, g, unknown or other
<220> FEATURE:
<221> NAME/KEY: modified_base
<222> LOCATION: (276)..(276)
<223> OTHER INFORMATION: a, c, t, g, unknown or other
<220> FEATURE:
<221> NAME/KEY: modified_base
<222> LOCATION: (279)..(279)
<223> OTHER INFORMATION: a, c, t, g, unknown or other
<220> FEATURE:
<221> NAME/KEY: modified_base
<222> LOCATION: (282)..(282)
<223> OTHER INFORMATION: a, c, t, g, unknown or other
<220> FEATURE:
<221> NAME/KEY: modified_base
<222> LOCATION: (294)..(294)
<223> OTHER INFORMATION: a, c, t, g, unknown or other
<220> FEATURE:
<221> NAME/KEY: modified_base
<222> LOCATION: (297)..(297)
<223> OTHER INFORMATION: a, c, t, g, unknown or other
<220> FEATURE:
<221> NAME/KEY: modified_base
<222> LOCATION: (300)..(300)
<223> OTHER INFORMATION: a, c, t, g, unknown or other
<220> FEATURE:
```

```
<221> NAME/KEY: modified_base
<222> LOCATION: (312)..(312)
<223> OTHER INFORMATION: a, c, t, g, unknown or other
<220> FEATURE:
<221> NAME/KEY: modified_base
<222> LOCATION: (315)..(315)
<223> OTHER INFORMATION: a, c, t, g, unknown or other
<220> FEATURE:
<221> NAME/KEY: modified_base
<222> LOCATION: (318)..(318)
<223> OTHER INFORMATION: a, c, t, g, unknown or other
<220> FEATURE:
<221> NAME/KEY: modified_base
<222> LOCATION: (324)..(324)
<223> OTHER INFORMATION: a, c, t, g, unknown or other
<220> FEATURE:
<221> NAME/KEY: modified_base
<222> LOCATION: (339)..(339)
<223> OTHER INFORMATION: a, c, t, g, unknown or other
<220> FEATURE:
<221> NAME/KEY: modified_base
<222> LOCATION: (345)..(345)
<223> OTHER INFORMATION: a, c, t, g, unknown or other
<220> FEATURE:
<221> NAME/KEY: modified_base
<222> LOCATION: (348)..(348)
<223> OTHER INFORMATION: a, c, t, g, unknown or other
<220> FEATURE:
<221> NAME/KEY: modified_base
<222> LOCATION: (351)..(351)
<223> OTHER INFORMATION: a, c, t, g, unknown or other
<220> FEATURE:
<221> NAME/KEY: modified_base
<222> LOCATION: (354)..(354)
<223> OTHER INFORMATION: a, c, t, g, unknown or other
<220> FEATURE:
<221> NAME/KEY: modified_base
<222> LOCATION: (357)..(357)
<223> OTHER INFORMATION: a, c, t, g, unknown or other
<220> FEATURE:
<221> NAME/KEY: modified_base
<222> LOCATION: (360)..(360)
<223> OTHER INFORMATION: a, c, t, g, unknown or other
<220> FEATURE:
<221> NAME/KEY: modified_base
<222> LOCATION: (363)..(363)
<223> OTHER INFORMATION: a, c, t, g, unknown or other
<220> FEATURE:
<221> NAME/KEY: modified_base
<222> LOCATION: (366)..(366)
<223> OTHER INFORMATION: a, c, t, g, unknown or other
<220> FEATURE:
<221> NAME/KEY: modified_base
<222> LOCATION: (369)..(369)
<223> OTHER INFORMATION: a, c, t, g, unknown or other
<220> FEATURE:
<221> NAME/KEY: modified_base
<222> LOCATION: (372)..(372)
<223> OTHER INFORMATION: a, c, t, g, unknown or other
<220> FEATURE:
<221> NAME/KEY: modified_base
<222> LOCATION: (375)..(375)
<223> OTHER INFORMATION: a, c, t, g, unknown or other
<220> FEATURE:
<221> NAME/KEY: modified_base
<222> LOCATION: (378)..(378)
<223> OTHER INFORMATION: a, c, t, g, unknown or other
<220> FEATURE:
<221> NAME/KEY: modified_base
<222> LOCATION: (381)..(381)
<223> OTHER INFORMATION: a, c, t, g, unknown or other
<220> FEATURE:
<221> NAME/KEY: modified_base
<222> LOCATION: (384)..(384)
<223> OTHER INFORMATION: a, c, t, g, unknown or other
<220> FEATURE:
<221> NAME/KEY: modified_base
<222> LOCATION: (387)..(387)
<223> OTHER INFORMATION: a, c, t, g, unknown or other
```

-continued

```
<220> FEATURE:
<221> NAME/KEY: modified_base
<222> LOCATION: (390)..(390)
<223> OTHER INFORMATION: a, c, t, g, unknown or other
<220> FEATURE:
<221> NAME/KEY: modified_base
<222> LOCATION: (393)..(393)
<223> OTHER INFORMATION: a, c, t, g, unknown or other
<220> FEATURE:
<221> NAME/KEY: modified_base
<222> LOCATION: (399)..(399)
<223> OTHER INFORMATION: a, c, t, g, unknown or other
<220> FEATURE:
<221> NAME/KEY: modified_base
<222> LOCATION: (402)..(402)
<223> OTHER INFORMATION: a, c, t, g, unknown or other
<220> FEATURE:
<221> NAME/KEY: modified_base
<222> LOCATION: (405)..(405)
<223> OTHER INFORMATION: a, c, t, g, unknown or other
<220> FEATURE:
<221> NAME/KEY: modified_base
<222> LOCATION: (408)..(408)
<223> OTHER INFORMATION: a, c, t, g, unknown or other
<220> FEATURE:
<221> NAME/KEY: modified_base
<222> LOCATION: (414)..(414)
<223> OTHER INFORMATION: a, c, t, g, unknown or other
<220> FEATURE:
<221> NAME/KEY: modified_base
<222> LOCATION: (417)..(417)
<223> OTHER INFORMATION: a, c, t, g, unknown or other
<220> FEATURE:
<221> NAME/KEY: modified_base
<222> LOCATION: (426)..(426)
<223> OTHER INFORMATION: a, c, t, g, unknown or other
<220> FEATURE:
<221> NAME/KEY: modified_base
<222> LOCATION: (429)..(429)
<223> OTHER INFORMATION: a, c, t, g, unknown or other
<220> FEATURE:
<221> NAME/KEY: modified_base
<222> LOCATION: (432)..(432)
<223> OTHER INFORMATION: a, c, t, g, unknown or other
<220> FEATURE:
<221> NAME/KEY: modified_base
<222> LOCATION: (438)..(438)
<223> OTHER INFORMATION: a, c, t, g, unknown or other
<220> FEATURE:
<221> NAME/KEY: modified_base
<222> LOCATION: (441)..(441)
<223> OTHER INFORMATION: a, c, t, g, unknown or other
<220> FEATURE:
<221> NAME/KEY: modified_base
<222> LOCATION: (444)..(444)
<223> OTHER INFORMATION: a, c, t, g, unknown or other
<220> FEATURE:
<221> NAME/KEY: modified_base
<222> LOCATION: (450)..(450)
<223> OTHER INFORMATION: a, c, t, g, unknown or other
<220> FEATURE:
<221> NAME/KEY: modified_base
<222> LOCATION: (453)..(453)
<223> OTHER INFORMATION: a, c, t, g, unknown or other
<220> FEATURE:
<221> NAME/KEY: modified_base
<222> LOCATION: (456)..(456)
<223> OTHER INFORMATION: a, c, t, g, unknown or other
<220> FEATURE:
<221> NAME/KEY: modified_base
<222> LOCATION: (459)..(459)
<223> OTHER INFORMATION: a, c, t, g, unknown or other
<220> FEATURE:
<221> NAME/KEY: modified_base
<222> LOCATION: (462)..(462)
<223> OTHER INFORMATION: a, c, t, g, unknown or other
<220> FEATURE:
<221> NAME/KEY: modified_base
<222> LOCATION: (465)..(465)
```

```
<223> OTHER INFORMATION: a, c, t, g, unknown or other
<220> FEATURE:
<221> NAME/KEY: modified_base
<222> LOCATION: (474)..(474)
<223> OTHER INFORMATION: a, c, t, g, unknown or other
<220> FEATURE:
<221> NAME/KEY: modified_base
<222> LOCATION: (477)..(477)
<223> OTHER INFORMATION: a, c, t, g, unknown or other
<220> FEATURE:
<221> NAME/KEY: modified_base
<222> LOCATION: (483)..(483)
<223> OTHER INFORMATION: a, c, t, g, unknown or other
<220> FEATURE:
<221> NAME/KEY: modified_base
<222> LOCATION: (489)..(489)
<223> OTHER INFORMATION: a, c, t, g, unknown or other
<220> FEATURE:
<221> NAME/KEY: modified_base
<222> LOCATION: (492)..(492)
<223> OTHER INFORMATION: a, c, t, g, unknown or other
<220> FEATURE:
<221> NAME/KEY: modified_base
<222> LOCATION: (495)..(495)
<223> OTHER INFORMATION: a, c, t, g, unknown or other
<220> FEATURE:
<221> NAME/KEY: modified_base
<222> LOCATION: (498)..(498)
<223> OTHER INFORMATION: a, c, t, g, unknown or other
<220> FEATURE:
<221> NAME/KEY: modified_base
<222> LOCATION: (501)..(501)
<223> OTHER INFORMATION: a, c, t, g, unknown or other
<220> FEATURE:
<221> NAME/KEY: modified_base
<222> LOCATION: (504)..(504)
<223> OTHER INFORMATION: a, c, t, g, unknown or other
<220> FEATURE:
<221> NAME/KEY: modified_base
<222> LOCATION: (507)..(507)
<223> OTHER INFORMATION: a, c, t, g, unknown or other
<220> FEATURE:
<221> NAME/KEY: modified_base
<222> LOCATION: (534)..(534)
<223> OTHER INFORMATION: a, c, t, g, unknown or other
<220> FEATURE:
<221> NAME/KEY: modified_base
<222> LOCATION: (537)..(537)
<223> OTHER INFORMATION: a, c, t, g, unknown or other
<220> FEATURE:
<221> NAME/KEY: modified_base
<222> LOCATION: (540)..(540)
<223> OTHER INFORMATION: a, c, t, g, unknown or other
<220> FEATURE:
<221> NAME/KEY: modified_base
<222> LOCATION: (543)..(543)
<223> OTHER INFORMATION: a, c, t, g, unknown or other
<220> FEATURE:
<221> NAME/KEY: modified_base
<222> LOCATION: (546)..(546)
<223> OTHER INFORMATION: a, c, t, g, unknown or other
<220> FEATURE:
<221> NAME/KEY: modified_base
<222> LOCATION: (552)..(552)
<223> OTHER INFORMATION: a, c, t, g, unknown or other
<220> FEATURE:
<221> NAME/KEY: modified_base
<222> LOCATION: (564)..(564)
<223> OTHER INFORMATION: a, c, t, g, unknown or other
<220> FEATURE:
<221> NAME/KEY: modified_base
<222> LOCATION: (567)..(567)
<223> OTHER INFORMATION: a, c, t, g, unknown or other
<220> FEATURE:
<221> NAME/KEY: modified_base
<222> LOCATION: (570)..(570)
<223> OTHER INFORMATION: a, c, t, g, unknown or other
<220> FEATURE:
<221> NAME/KEY: modified_base
```

```
<222> LOCATION: (576)..(576)
<223> OTHER INFORMATION: a, c, t, g, unknown or other
<220> FEATURE:
<221> NAME/KEY: modified_base
<222> LOCATION: (579)..(579)
<223> OTHER INFORMATION: a, c, t, g, unknown or other
<220> FEATURE:
<221> NAME/KEY: modified_base
<222> LOCATION: (582)..(582)
<223> OTHER INFORMATION: a, c, t, g, unknown or other
<220> FEATURE:
<221> NAME/KEY: modified_base
<222> LOCATION: (585)..(585)
<223> OTHER INFORMATION: a, c, t, g, unknown or other
<220> FEATURE:
<221> NAME/KEY: modified_base
<222> LOCATION: (588)..(588)
<223> OTHER INFORMATION: a, c, t, g, unknown or other
<220> FEATURE:
<221> NAME/KEY: modified_base
<222> LOCATION: (591)..(591)
<223> OTHER INFORMATION: a, c, t, g, unknown or other
<220> FEATURE:
<221> NAME/KEY: modified_base
<222> LOCATION: (594)..(594)
<223> OTHER INFORMATION: a, c, t, g, unknown or other
<220> FEATURE:
<221> NAME/KEY: modified_base
<222> LOCATION: (597)..(597)
<223> OTHER INFORMATION: a, c, t, g, unknown or other
<220> FEATURE:
<221> NAME/KEY: modified_base
<222> LOCATION: (603)..(603)
<223> OTHER INFORMATION: a, c, t, g, unknown or other
<220> FEATURE:
<221> NAME/KEY: modified_base
<222> LOCATION: (606)..(606)
<223> OTHER INFORMATION: a, c, t, g, unknown or other
<220> FEATURE:
<221> NAME/KEY: modified_base
<222> LOCATION: (609)..(609)
<223> OTHER INFORMATION: a, c, t, g, unknown or other
<220> FEATURE:
<221> NAME/KEY: modified_base
<222> LOCATION: (612)..(612)
<223> OTHER INFORMATION: a, c, t, g, unknown or other
<220> FEATURE:
<221> NAME/KEY: modified_base
<222> LOCATION: (615)..(615)
<223> OTHER INFORMATION: a, c, t, g, unknown or other
<220> FEATURE:
<221> NAME/KEY: modified_base
<222> LOCATION: (618)..(618)
<223> OTHER INFORMATION: a, c, t, g, unknown or other
<220> FEATURE:
<221> NAME/KEY: modified_base
<222> LOCATION: (621)..(621)
<223> OTHER INFORMATION: a, c, t, g, unknown or other
<220> FEATURE:
<221> NAME/KEY: modified_base
<222> LOCATION: (624)..(624)
<223> OTHER INFORMATION: a, c, t, g, unknown or other
<220> FEATURE:
<221> NAME/KEY: modified_base
<222> LOCATION: (630)..(630)
<223> OTHER INFORMATION: a, c, t, g, unknown or other
<220> FEATURE:
<221> NAME/KEY: modified_base
<222> LOCATION: (633)..(633)
<223> OTHER INFORMATION: a, c, t, g, unknown or other
<220> FEATURE:
<221> NAME/KEY: modified_base
<222> LOCATION: (636)..(636)
<223> OTHER INFORMATION: a, c, t, g, unknown or other
<220> FEATURE:
<221> NAME/KEY: modified_base
<222> LOCATION: (642)..(642)
<223> OTHER INFORMATION: a, c, t, g, unknown or other
<220> FEATURE:
```

-continued

```
<221> NAME/KEY: modified_base
<222> LOCATION: (645)..(645)
<223> OTHER INFORMATION: a, c, t, g, unknown or other
<220> FEATURE:
<221> NAME/KEY: modified_base
<222> LOCATION: (648)..(648)
<223> OTHER INFORMATION: a, c, t, g, unknown or other
<220> FEATURE:
<221> NAME/KEY: modified_base
<222> LOCATION: (654)..(654)
<223> OTHER INFORMATION: a, c, t, g, unknown or other
<220> FEATURE:
<221> NAME/KEY: modified_base
<222> LOCATION: (663)..(663)
<223> OTHER INFORMATION: a, c, t, g, unknown or other
<220> FEATURE:
<221> NAME/KEY: modified_base
<222> LOCATION: (666)..(666)
<223> OTHER INFORMATION: a, c, t, g, unknown or other
<220> FEATURE:
<221> NAME/KEY: modified_base
<222> LOCATION: (669)..(669)
<223> OTHER INFORMATION: a, c, t, g, unknown or other
<220> FEATURE:
<221> NAME/KEY: modified_base
<222> LOCATION: (693)..(693)
<223> OTHER INFORMATION: a, c, t, g, unknown or other
<220> FEATURE:
<221> NAME/KEY: modified_base
<222> LOCATION: (699)..(699)
<223> OTHER INFORMATION: a, c, t, g, unknown or other
<220> FEATURE:
<221> NAME/KEY: modified_base
<222> LOCATION: (702)..(702)
<223> OTHER INFORMATION: a, c, t, g, unknown or other
<220> FEATURE:
<221> NAME/KEY: modified_base
<222> LOCATION: (705)..(705)
<223> OTHER INFORMATION: a, c, t, g, unknown or other
<220> FEATURE:
<221> NAME/KEY: modified_base
<222> LOCATION: (711)..(711)
<223> OTHER INFORMATION: a, c, t, g, unknown or other
<220> FEATURE:
<221> NAME/KEY: modified_base
<222> LOCATION: (714)..(714)
<223> OTHER INFORMATION: a, c, t, g, unknown or other
<220> FEATURE:
<221> NAME/KEY: modified_base
<222> LOCATION: (717)..(717)
<223> OTHER INFORMATION: a, c, t, g, unknown or other
<220> FEATURE:
<221> NAME/KEY: modified_base
<222> LOCATION: (720)..(720)
<223> OTHER INFORMATION: a, c, t, g, unknown or other
<220> FEATURE:
<221> NAME/KEY: modified_base
<222> LOCATION: (726)..(726)
<223> OTHER INFORMATION: a, c, t, g, unknown or other
<220> FEATURE:
<221> NAME/KEY: modified_base
<222> LOCATION: (732)..(732)
<223> OTHER INFORMATION: a, c, t, g, unknown or other
<220> FEATURE:
<221> NAME/KEY: modified_base
<222> LOCATION: (744)..(744)
<223> OTHER INFORMATION: a, c, t, g, unknown or other
<220> FEATURE:
<221> NAME/KEY: modified_base
<222> LOCATION: (750)..(750)
<223> OTHER INFORMATION: a, c, t, g, unknown or other
<220> FEATURE:
<221> NAME/KEY: modified_base
<222> LOCATION: (753)..(753)
<223> OTHER INFORMATION: a, c, t, g, unknown or other
<220> FEATURE:
<221> NAME/KEY: modified_base
<222> LOCATION: (756)..(756)
<223> OTHER INFORMATION: a, c, t, g, unknown or other
```

-continued

```
<220> FEATURE:
<221> NAME/KEY: modified_base
<222> LOCATION: (759)..(759)
<223> OTHER INFORMATION: a, c, t, g, unknown or other
<220> FEATURE:
<221> NAME/KEY: modified_base
<222> LOCATION: (762)..(762)
<223> OTHER INFORMATION: a, c, t, g, unknown or other
<220> FEATURE:
<221> NAME/KEY: modified_base
<222> LOCATION: (765)..(765)
<223> OTHER INFORMATION: a, c, t, g, unknown or other
<220> FEATURE:
<221> NAME/KEY: modified_base
<222> LOCATION: (768)..(768)
<223> OTHER INFORMATION: a, c, t, g, unknown or other
<220> FEATURE:
<221> NAME/KEY: modified_base
<222> LOCATION: (771)..(771)
<223> OTHER INFORMATION: a, c, t, g, unknown or other
<220> FEATURE:
<221> NAME/KEY: modified_base
<222> LOCATION: (774)..(774)
<223> OTHER INFORMATION: a, c, t, g, unknown or other
<220> FEATURE:
<221> NAME/KEY: modified_base
<222> LOCATION: (777)..(777)
<223> OTHER INFORMATION: a, c, t, g, unknown or other
<220> FEATURE:
<221> NAME/KEY: modified_base
<222> LOCATION: (780)..(780)
<223> OTHER INFORMATION: a, c, t, g, unknown or other
<220> FEATURE:
<221> NAME/KEY: modified_base
<222> LOCATION: (783)..(783)
<223> OTHER INFORMATION: a, c, t, g, unknown or other
<220> FEATURE:
<221> NAME/KEY: modified_base
<222> LOCATION: (795)..(795)
<223> OTHER INFORMATION: a, c, t, g, unknown or other
<220> FEATURE:
<221> NAME/KEY: modified_base
<222> LOCATION: (798)..(798)
<223> OTHER INFORMATION: a, c, t, g, unknown or other
<220> FEATURE:
<221> NAME/KEY: modified_base
<222> LOCATION: (807)..(807)
<223> OTHER INFORMATION: a, c, t, g, unknown or other
<220> FEATURE:
<221> NAME/KEY: modified_base
<222> LOCATION: (810)..(810)
<223> OTHER INFORMATION: a, c, t, g, unknown or other
<220> FEATURE:
<221> NAME/KEY: modified_base
<222> LOCATION: (813)..(813)
<223> OTHER INFORMATION: a, c, t, g, unknown or other
<220> FEATURE:
<221> NAME/KEY: modified_base
<222> LOCATION: (819)..(819)
<223> OTHER INFORMATION: a, c, t, g, unknown or other
<220> FEATURE:
<221> NAME/KEY: modified_base
<222> LOCATION: (825)..(825)
<223> OTHER INFORMATION: a, c, t, g, unknown or other
<220> FEATURE:
<221> NAME/KEY: modified_base
<222> LOCATION: (831)..(831)
<223> OTHER INFORMATION: a, c, t, g, unknown or other
<220> FEATURE:
<221> NAME/KEY: modified_base
<222> LOCATION: (834)..(834)
<223> OTHER INFORMATION: a, c, t, g, unknown or other
<220> FEATURE:
<221> NAME/KEY: modified_base
<222> LOCATION: (840)..(840)
<223> OTHER INFORMATION: a, c, t, g, unknown or other
<220> FEATURE:
<221> NAME/KEY: modified_base
<222> LOCATION: (846)..(846)
```

```
<223> OTHER INFORMATION: a, c, t, g, unknown or other
<220> FEATURE:
<221> NAME/KEY: modified_base
<222> LOCATION: (849)..(849)
<223> OTHER INFORMATION: a, c, t, g, unknown or other
<220> FEATURE:
<221> NAME/KEY: modified_base
<222> LOCATION: (852)..(852)
<223> OTHER INFORMATION: a, c, t, g, unknown or other
<220> FEATURE:
<221> NAME/KEY: modified_base
<222> LOCATION: (858)..(858)
<223> OTHER INFORMATION: a, c, t, g, unknown or other
<220> FEATURE:
<221> NAME/KEY: modified_base
<222> LOCATION: (861)..(861)
<223> OTHER INFORMATION: a, c, t, g, unknown or other
<220> FEATURE:
<221> NAME/KEY: modified_base
<222> LOCATION: (864)..(864)
<223> OTHER INFORMATION: a, c, t, g, unknown or other
<220> FEATURE:
<221> NAME/KEY: modified_base
<222> LOCATION: (867)..(867)
<223> OTHER INFORMATION: a, c, t, g, unknown or other
<220> FEATURE:
<221> NAME/KEY: modified_base
<222> LOCATION: (873)..(873)
<223> OTHER INFORMATION: a, c, t, g, unknown or other
<220> FEATURE:
<221> NAME/KEY: modified_base
<222> LOCATION: (879)..(879)
<223> OTHER INFORMATION: a, c, t, g, unknown or other
<220> FEATURE:
<221> NAME/KEY: modified_base
<222> LOCATION: (882)..(882)
<223> OTHER INFORMATION: a, c, t, g, unknown or other
<220> FEATURE:
<221> NAME/KEY: modified_base
<222> LOCATION: (885)..(885)
<223> OTHER INFORMATION: a, c, t, g, unknown or other
<220> FEATURE:
<221> NAME/KEY: modified_base
<222> LOCATION: (888)..(888)
<223> OTHER INFORMATION: a, c, t, g, unknown or other
<220> FEATURE:
<221> NAME/KEY: modified_base
<222> LOCATION: (891)..(891)
<223> OTHER INFORMATION: a, c, t, g, unknown or other
<220> FEATURE:
<221> NAME/KEY: modified_base
<222> LOCATION: (894)..(894)
<223> OTHER INFORMATION: a, c, t, g, unknown or other
<220> FEATURE:
<221> NAME/KEY: modified_base
<222> LOCATION: (897)..(897)
<223> OTHER INFORMATION: a, c, t, g, unknown or other
<220> FEATURE:
<221> NAME/KEY: modified_base
<222> LOCATION: (900)..(900)
<223> OTHER INFORMATION: a, c, t, g, unknown or other
<220> FEATURE:
<221> NAME/KEY: modified_base
<222> LOCATION: (912)..(912)
<223> OTHER INFORMATION: a, c, t, g, unknown or other
<220> FEATURE:
<221> NAME/KEY: modified_base
<222> LOCATION: (915)..(915)
<223> OTHER INFORMATION: a, c, t, g, unknown or other
<220> FEATURE:
<221> NAME/KEY: modified_base
<222> LOCATION: (918)..(918)
<223> OTHER INFORMATION: a, c, t, g, unknown or other
<220> FEATURE:
<221> NAME/KEY: modified_base
<222> LOCATION: (921)..(921)
<223> OTHER INFORMATION: a, c, t, g, unknown or other
<220> FEATURE:
<221> NAME/KEY: modified_base
```

```
<222> LOCATION: (930)..(930)
<223> OTHER INFORMATION: a, c, t, g, unknown or other
<220> FEATURE:
<221> NAME/KEY: modified_base
<222> LOCATION: (936)..(936)
<223> OTHER INFORMATION: a, c, t, g, unknown or other
<220> FEATURE:
<221> NAME/KEY: modified_base
<222> LOCATION: (939)..(939)
<223> OTHER INFORMATION: a, c, t, g, unknown or other
<220> FEATURE:
<221> NAME/KEY: modified_base
<222> LOCATION: (945)..(945)
<223> OTHER INFORMATION: a, c, t, g, unknown or other
<220> FEATURE:
<221> NAME/KEY: modified_base
<222> LOCATION: (948)..(948)
<223> OTHER INFORMATION: a, c, t, g, unknown or other
<220> FEATURE:
<221> NAME/KEY: modified_base
<222> LOCATION: (951)..(951)
<223> OTHER INFORMATION: a, c, t, g, unknown or other
<220> FEATURE:
<221> NAME/KEY: modified_base
<222> LOCATION: (960)..(960)
<223> OTHER INFORMATION: a, c, t, g, unknown or other
<220> FEATURE:
<221> NAME/KEY: modified_base
<222> LOCATION: (969)..(969)
<223> OTHER INFORMATION: a, c, t, g, unknown or other
<220> FEATURE:
<221> NAME/KEY: modified_base
<222> LOCATION: (972)..(972)
<223> OTHER INFORMATION: a, c, t, g, unknown or other
<220> FEATURE:
<221> NAME/KEY: modified_base
<222> LOCATION: (984)..(984)
<223> OTHER INFORMATION: a, c, t, g, unknown or other
<220> FEATURE:
<221> NAME/KEY: modified_base
<222> LOCATION: (987)..(987)
<223> OTHER INFORMATION: a, c, t, g, unknown or other
<220> FEATURE:
<221> NAME/KEY: modified_base
<222> LOCATION: (990)..(990)
<223> OTHER INFORMATION: a, c, t, g, unknown or other
<220> FEATURE:
<221> NAME/KEY: modified_base
<222> LOCATION: (996)..(996)
<223> OTHER INFORMATION: a, c, t, g, unknown or other
<220> FEATURE:
<221> NAME/KEY: modified_base
<222> LOCATION: (1002)..(1002)
<223> OTHER INFORMATION: a, c, t, g, unknown or other
<220> FEATURE:
<221> NAME/KEY: modified_base
<222> LOCATION: (1011)..(1011)
<223> OTHER INFORMATION: a, c, t, g, unknown or other
<220> FEATURE:
<221> NAME/KEY: modified_base
<222> LOCATION: (1017)..(1017)
<223> OTHER INFORMATION: a, c, t, g, unknown or other
<220> FEATURE:
<221> NAME/KEY: modified_base
<222> LOCATION: (1020)..(1020)
<223> OTHER INFORMATION: a, c, t, g, unknown or other
<220> FEATURE:
<221> NAME/KEY: modified_base
<222> LOCATION: (1023)..(1023)
<223> OTHER INFORMATION: a, c, t, g, unknown or other
<220> FEATURE:
<221> NAME/KEY: modified_base
<222> LOCATION: (1029)..(1029)
<223> OTHER INFORMATION: a, c, t, g, unknown or other
<220> FEATURE:
<221> NAME/KEY: modified_base
<222> LOCATION: (1035)..(1035)
<223> OTHER INFORMATION: a, c, t, g, unknown or other
<220> FEATURE:
```

```
<221> NAME/KEY: modified_base
<222> LOCATION: (1038)..(1038)
<223> OTHER INFORMATION: a, c, t, g, unknown or other
<220> FEATURE:
<221> NAME/KEY: modified_base
<222> LOCATION: (1047)..(1047)
<223> OTHER INFORMATION: a, c, t, g, unknown or other
<220> FEATURE:
<221> NAME/KEY: modified_base
<222> LOCATION: (1056)..(1056)
<223> OTHER INFORMATION: a, c, t, g, unknown or other
<220> FEATURE:
<221> NAME/KEY: modified_base
<222> LOCATION: (1062)..(1062)
<223> OTHER INFORMATION: a, c, t, g, unknown or other
<220> FEATURE:
<221> NAME/KEY: modified_base
<222> LOCATION: (1071)..(1071)
<223> OTHER INFORMATION: a, c, t, g, unknown or other
<220> FEATURE:
<221> NAME/KEY: modified_base
<222> LOCATION: (1077)..(1077)
<223> OTHER INFORMATION: a, c, t, g, unknown or other
<220> FEATURE:
<221> NAME/KEY: modified_base
<222> LOCATION: (1080)..(1080)
<223> OTHER INFORMATION: a, c, t, g, unknown or other
<220> FEATURE:
<221> NAME/KEY: modified_base
<222> LOCATION: (1086)..(1086)
<223> OTHER INFORMATION: a, c, t, g, unknown or other
<220> FEATURE:
<221> NAME/KEY: modified_base
<222> LOCATION: (1089)..(1089)
<223> OTHER INFORMATION: a, c, t, g, unknown or other
<220> FEATURE:
<221> NAME/KEY: modified_base
<222> LOCATION: (1092)..(1092)
<223> OTHER INFORMATION: a, c, t, g, unknown or other
<220> FEATURE:
<221> NAME/KEY: modified_base
<222> LOCATION: (1095)..(1095)
<223> OTHER INFORMATION: a, c, t, g, unknown or other
<220> FEATURE:
<221> NAME/KEY: modified_base
<222> LOCATION: (1098)..(1098)
<223> OTHER INFORMATION: a, c, t, g, unknown or other
<220> FEATURE:
<221> NAME/KEY: modified_base
<222> LOCATION: (1101)..(1101)
<223> OTHER INFORMATION: a, c, t, g, unknown or other
<220> FEATURE:
<221> NAME/KEY: modified_base
<222> LOCATION: (1104)..(1104)
<223> OTHER INFORMATION: a, c, t, g, unknown or other
<220> FEATURE:
<221> NAME/KEY: modified_base
<222> LOCATION: (1107)..(1107)
<223> OTHER INFORMATION: a, c, t, g, unknown or other
<220> FEATURE:
<221> NAME/KEY: modified_base
<222> LOCATION: (1110)..(1110)
<223> OTHER INFORMATION: a, c, t, g, unknown or other
<220> FEATURE:
<221> NAME/KEY: modified_base
<222> LOCATION: (1113)..(1113)
<223> OTHER INFORMATION: a, c, t, g, unknown or other
<220> FEATURE:
<221> NAME/KEY: modified_base
<222> LOCATION: (1119)..(1119)
<223> OTHER INFORMATION: a, c, t, g, unknown or other
<220> FEATURE:
<221> NAME/KEY: modified_base
<222> LOCATION: (1122)..(1122)
<223> OTHER INFORMATION: a, c, t, g, unknown or other
<220> FEATURE:
<221> NAME/KEY: modified_base
<222> LOCATION: (1128)..(1128)
<223> OTHER INFORMATION: a, c, t, g, unknown or other
```

-continued

```
<220> FEATURE:
<221> NAME/KEY: modified_base
<222> LOCATION: (1131)..(1131)
<223> OTHER INFORMATION: a, c, t, g, unknown or other
<220> FEATURE:
<221> NAME/KEY: modified_base
<222> LOCATION: (1134)..(1134)
<223> OTHER INFORMATION: a, c, t, g, unknown or other
<220> FEATURE:
<221> NAME/KEY: modified_base
<222> LOCATION: (1140)..(1140)
<223> OTHER INFORMATION: a, c, t, g, unknown or other
<220> FEATURE:
<221> NAME/KEY: modified_base
<222> LOCATION: (1143)..(1143)
<223> OTHER INFORMATION: a, c, t, g, unknown or other
<220> FEATURE:
<221> NAME/KEY: modified_base
<222> LOCATION: (1146)..(1146)
<223> OTHER INFORMATION: a, c, t, g, unknown or other
<220> FEATURE:
<221> NAME/KEY: modified_base
<222> LOCATION: (1149)..(1149)
<223> OTHER INFORMATION: a, c, t, g, unknown or other
<220> FEATURE:
<221> NAME/KEY: modified_base
<222> LOCATION: (1155)..(1155)
<223> OTHER INFORMATION: a, c, t, g, unknown or other
<220> FEATURE:
<221> NAME/KEY: modified_base
<222> LOCATION: (1158)..(1158)
<223> OTHER INFORMATION: a, c, t, g, unknown or other
<220> FEATURE:
<221> NAME/KEY: modified_base
<222> LOCATION: (1161)..(1161)
<223> OTHER INFORMATION: a, c, t, g, unknown or other
<220> FEATURE:
<221> NAME/KEY: modified_base
<222> LOCATION: (1164)..(1164)
<223> OTHER INFORMATION: a, c, t, g, unknown or other
<220> FEATURE:
<221> NAME/KEY: modified_base
<222> LOCATION: (1179)..(1179)
<223> OTHER INFORMATION: a, c, t, g, unknown or other
<220> FEATURE:
<221> NAME/KEY: modified_base
<222> LOCATION: (1185)..(1185)
<223> OTHER INFORMATION: a, c, t, g, unknown or other
<220> FEATURE:
<221> NAME/KEY: modified_base
<222> LOCATION: (1188)..(1188)
<223> OTHER INFORMATION: a, c, t, g, unknown or other
<220> FEATURE:
<221> NAME/KEY: modified_base
<222> LOCATION: (1191)..(1191)
<223> OTHER INFORMATION: a, c, t, g, unknown or other
<220> FEATURE:
<221> NAME/KEY: modified_base
<222> LOCATION: (1194)..(1194)
<223> OTHER INFORMATION: a, c, t, g, unknown or other
<220> FEATURE:
<221> NAME/KEY: modified_base
<222> LOCATION: (1197)..(1197)
<223> OTHER INFORMATION: a, c, t, g, unknown or other
<220> FEATURE:
<221> NAME/KEY: modified_base
<222> LOCATION: (1203)..(1203)
<223> OTHER INFORMATION: a, c, t, g, unknown or other
<220> FEATURE:
<221> NAME/KEY: modified_base
<222> LOCATION: (1209)..(1209)
<223> OTHER INFORMATION: a, c, t, g, unknown or other
<220> FEATURE:
<221> NAME/KEY: modified_base
<222> LOCATION: (1215)..(1215)
<223> OTHER INFORMATION: a, c, t, g, unknown or other
<220> FEATURE:
<221> NAME/KEY: modified_base
<222> LOCATION: (1221)..(1221)
```

-continued

```
<223> OTHER INFORMATION: a, c, t, g, unknown or other
<220> FEATURE:
<221> NAME/KEY: modified_base
<222> LOCATION: (1224)..(1224)
<223> OTHER INFORMATION: a, c, t, g, unknown or other
<220> FEATURE:
<221> NAME/KEY: modified_base
<222> LOCATION: (1227)..(1227)
<223> OTHER INFORMATION: a, c, t, g, unknown or other
<220> FEATURE:
<221> NAME/KEY: modified_base
<222> LOCATION: (1230)..(1230)
<223> OTHER INFORMATION: a, c, t, g, unknown or other
<220> FEATURE:
<221> NAME/KEY: modified_base
<222> LOCATION: (1233)..(1233)
<223> OTHER INFORMATION: a, c, t, g, unknown or other
<220> FEATURE:
<221> NAME/KEY: modified_base
<222> LOCATION: (1236)..(1236)
<223> OTHER INFORMATION: a, c, t, g, unknown or other
<220> FEATURE:
<221> NAME/KEY: modified_base
<222> LOCATION: (1242)..(1242)
<223> OTHER INFORMATION: a, c, t, g, unknown or other
<220> FEATURE:
<221> NAME/KEY: modified_base
<222> LOCATION: (1245)..(1245)
<223> OTHER INFORMATION: a, c, t, g, unknown or other
<220> FEATURE:
<221> NAME/KEY: modified_base
<222> LOCATION: (1248)..(1248)
<223> OTHER INFORMATION: a, c, t, g, unknown or other
<220> FEATURE:
<221> NAME/KEY: modified_base
<222> LOCATION: (1251)..(1251)
<223> OTHER INFORMATION: a, c, t, g, unknown or other
<220> FEATURE:
<221> NAME/KEY: modified_base
<222> LOCATION: (1254)..(1254)
<223> OTHER INFORMATION: a, c, t, g, unknown or other
<220> FEATURE:
<221> NAME/KEY: modified_base
<222> LOCATION: (1260)..(1260)
<223> OTHER INFORMATION: a, c, t, g, unknown or other
<220> FEATURE:
<221> NAME/KEY: modified_base
<222> LOCATION: (1263)..(1263)
<223> OTHER INFORMATION: a, c, t, g, unknown or other
<220> FEATURE:
<221> NAME/KEY: modified_base
<222> LOCATION: (1269)..(1269)
<223> OTHER INFORMATION: a, c, t, g, unknown or other
<220> FEATURE:
<221> NAME/KEY: modified_base
<222> LOCATION: (1272)..(1272)
<223> OTHER INFORMATION: a, c, t, g, unknown or other
<220> FEATURE:
<221> NAME/KEY: modified_base
<222> LOCATION: (1275)..(1275)
<223> OTHER INFORMATION: a, c, t, g, unknown or other
<220> FEATURE:
<221> NAME/KEY: modified_base
<222> LOCATION: (1278)..(1278)
<223> OTHER INFORMATION: a, c, t, g, unknown or other
<220> FEATURE:
<221> NAME/KEY: modified_base
<222> LOCATION: (1281)..(1281)
<223> OTHER INFORMATION: a, c, t, g, unknown or other
<220> FEATURE:
<221> NAME/KEY: modified_base
<222> LOCATION: (1287)..(1287)
<223> OTHER INFORMATION: a, c, t, g, unknown or other
<220> FEATURE:
<221> NAME/KEY: modified_base
<222> LOCATION: (1290)..(1290)
<223> OTHER INFORMATION: a, c, t, g, unknown or other
<220> FEATURE:
<221> NAME/KEY: modified_base
```

-continued

```
<222> LOCATION: (1293)..(1293)
<223> OTHER INFORMATION: a, c, t, g, unknown or other
<220> FEATURE:
<221> NAME/KEY: modified_base
<222> LOCATION: (1299)..(1299)
<223> OTHER INFORMATION: a, c, t, g, unknown or other
<220> FEATURE:
<221> NAME/KEY: modified_base
<222> LOCATION: (1311)..(1311)
<223> OTHER INFORMATION: a, c, t, g, unknown or other
<220> FEATURE:
<221> NAME/KEY: modified_base
<222> LOCATION: (1314)..(1314)
<223> OTHER INFORMATION: a, c, t, g, unknown or other
<220> FEATURE:
<221> NAME/KEY: modified_base
<222> LOCATION: (1320)..(1320)
<223> OTHER INFORMATION: a, c, t, g, unknown or other
<220> FEATURE:
<221> NAME/KEY: modified_base
<222> LOCATION: (1323)..(1323)
<223> OTHER INFORMATION: a, c, t, g, unknown or other
<220> FEATURE:
<221> NAME/KEY: modified_base
<222> LOCATION: (1326)..(1326)
<223> OTHER INFORMATION: a, c, t, g, unknown or other
<220> FEATURE:
<221> NAME/KEY: modified_base
<222> LOCATION: (1329)..(1329)
<223> OTHER INFORMATION: a, c, t, g, unknown or other
<220> FEATURE:
<221> NAME/KEY: modified_base
<222> LOCATION: (1338)..(1338)
<223> OTHER INFORMATION: a, c, t, g, unknown or other
<220> FEATURE:
<221> NAME/KEY: modified_base
<222> LOCATION: (1341)..(1341)
<223> OTHER INFORMATION: a, c, t, g, unknown or other
<220> FEATURE:
<221> NAME/KEY: modified_base
<222> LOCATION: (1344)..(1344)
<223> OTHER INFORMATION: a, c, t, g, unknown or other
<220> FEATURE:
<221> NAME/KEY: modified_base
<222> LOCATION: (1347)..(1347)
<223> OTHER INFORMATION: a, c, t, g, unknown or other
<220> FEATURE:
<221> NAME/KEY: modified_base
<222> LOCATION: (1350)..(1350)
<223> OTHER INFORMATION: a, c, t, g, unknown or other
<220> FEATURE:
<221> NAME/KEY: modified_base
<222> LOCATION: (1356)..(1356)
<223> OTHER INFORMATION: a, c, t, g, unknown or other
<220> FEATURE:
<221> NAME/KEY: modified_base
<222> LOCATION: (1362)..(1362)
<223> OTHER INFORMATION: a, c, t, g, unknown or other
<220> FEATURE:
<221> NAME/KEY: modified_base
<222> LOCATION: (1365)..(1365)
<223> OTHER INFORMATION: a, c, t, g, unknown or other
<220> FEATURE:
<221> NAME/KEY: modified_base
<222> LOCATION: (1374)..(1374)
<223> OTHER INFORMATION: a, c, t, g, unknown or other
<220> FEATURE:
<221> NAME/KEY: modified_base
<222> LOCATION: (1380)..(1380)
<223> OTHER INFORMATION: a, c, t, g, unknown or other
<220> FEATURE:
<221> NAME/KEY: modified_base
<222> LOCATION: (1383)..(1383)
<223> OTHER INFORMATION: a, c, t, g, unknown or other
<220> FEATURE:
<221> NAME/KEY: modified_base
<222> LOCATION: (1386)..(1386)
<223> OTHER INFORMATION: a, c, t, g, unknown or other
<220> FEATURE:
```

```
<221> NAME/KEY: modified_base
<222> LOCATION: (1395)..(1395)
<223> OTHER INFORMATION: a, c, t, g, unknown or other
<220> FEATURE:
<221> NAME/KEY: modified_base
<222> LOCATION: (1398)..(1398)
<223> OTHER INFORMATION: a, c, t, g, unknown or other
<220> FEATURE:
<221> NAME/KEY: modified_base
<222> LOCATION: (1401)..(1401)
<223> OTHER INFORMATION: a, c, t, g, unknown or other
<220> FEATURE:
<221> NAME/KEY: modified_base
<222> LOCATION: (1404)..(1404)
<223> OTHER INFORMATION: a, c, t, g, unknown or other
<220> FEATURE:
<221> NAME/KEY: modified_base
<222> LOCATION: (1407)..(1407)
<223> OTHER INFORMATION: a, c, t, g, unknown or other
<220> FEATURE:
<221> NAME/KEY: modified_base
<222> LOCATION: (1410)..(1410)
<223> OTHER INFORMATION: a, c, t, g, unknown or other
<220> FEATURE:
<221> NAME/KEY: modified_base
<222> LOCATION: (1413)..(1413)
<223> OTHER INFORMATION: a, c, t, g, unknown or other
<220> FEATURE:
<221> NAME/KEY: modified_base
<222> LOCATION: (1416)..(1416)
<223> OTHER INFORMATION: a, c, t, g, unknown or other
<220> FEATURE:
<221> NAME/KEY: modified_base
<222> LOCATION: (1428)..(1428)
<223> OTHER INFORMATION: a, c, t, g, unknown or other
<220> FEATURE:
<221> NAME/KEY: modified_base
<222> LOCATION: (1437)..(1437)
<223> OTHER INFORMATION: a, c, t, g, unknown or other
<220> FEATURE:
<221> NAME/KEY: modified_base
<222> LOCATION: (1440)..(1440)
<223> OTHER INFORMATION: a, c, t, g, unknown or other
<220> FEATURE:
<221> NAME/KEY: modified_base
<222> LOCATION: (1443)..(1443)
<223> OTHER INFORMATION: a, c, t, g, unknown or other
<220> FEATURE:
<221> NAME/KEY: modified_base
<222> LOCATION: (1446)..(1446)
<223> OTHER INFORMATION: a, c, t, g, unknown or other
<220> FEATURE:
<221> NAME/KEY: modified_base
<222> LOCATION: (1449)..(1449)
<223> OTHER INFORMATION: a, c, t, g, unknown or other
<220> FEATURE:
<221> NAME/KEY: modified_base
<222> LOCATION: (1452)..(1452)
<223> OTHER INFORMATION: a, c, t, g, unknown or other
<220> FEATURE:
<221> NAME/KEY: modified_base
<222> LOCATION: (1458)..(1458)
<223> OTHER INFORMATION: a, c, t, g, unknown or other
<220> FEATURE:
<221> NAME/KEY: modified_base
<222> LOCATION: (1464)..(1464)
<223> OTHER INFORMATION: a, c, t, g, unknown or other
<220> FEATURE:
<221> NAME/KEY: modified_base
<222> LOCATION: (1467)..(1467)
<223> OTHER INFORMATION: a, c, t, g, unknown or other
<220> FEATURE:
<221> NAME/KEY: modified_base
<222> LOCATION: (1476)..(1476)
<223> OTHER INFORMATION: a, c, t, g, unknown or other
<220> FEATURE:
<221> NAME/KEY: modified_base
<222> LOCATION: (1482)..(1482)
<223> OTHER INFORMATION: a, c, t, g, unknown or other
```

<220> FEATURE:
<221> NAME/KEY: modified_base
<222> LOCATION: (1485)..(1485)
<223> OTHER INFORMATION: a, c, t, g, unknown or other
<220> FEATURE:
<221> NAME/KEY: modified_base
<222> LOCATION: (1488)..(1488)
<223> OTHER INFORMATION: a, c, t, g, unknown or other
<220> FEATURE:
<221> NAME/KEY: modified_base
<222> LOCATION: (1491)..(1491)
<223> OTHER INFORMATION: a, c, t, g, unknown or other
<220> FEATURE:
<221> NAME/KEY: modified_base
<222> LOCATION: (1494)..(1494)
<223> OTHER INFORMATION: a, c, t, g, unknown or other
<220> FEATURE:
<221> NAME/KEY: modified_base
<222> LOCATION: (1497)..(1497)
<223> OTHER INFORMATION: a, c, t, g, unknown or other
<220> FEATURE:
<221> NAME/KEY: modified_base
<222> LOCATION: (1503)..(1503)
<223> OTHER INFORMATION: a, c, t, g, unknown or other
<220> FEATURE:
<221> NAME/KEY: modified_base
<222> LOCATION: (1521)..(1521)
<223> OTHER INFORMATION: a, c, t, g, unknown or other
<220> FEATURE:
<221> NAME/KEY: modified_base
<222> LOCATION: (1524)..(1524)
<223> OTHER INFORMATION: a, c, t, g, unknown or other
<220> FEATURE:
<221> NAME/KEY: modified_base
<222> LOCATION: (1527)..(1527)
<223> OTHER INFORMATION: a, c, t, g, unknown or other
<220> FEATURE:
<221> NAME/KEY: modified_base
<222> LOCATION: (1530)..(1530)
<223> OTHER INFORMATION: a, c, t, g, unknown or other
<220> FEATURE:
<221> NAME/KEY: modified_base
<222> LOCATION: (1533)..(1533)
<223> OTHER INFORMATION: a, c, t, g, unknown or other
<220> FEATURE:
<221> NAME/KEY: modified_base
<222> LOCATION: (1536)..(1536)
<223> OTHER INFORMATION: a, c, t, g, unknown or other

<400> SEQUENCE: 5
atgcargtnc arytncarca rccnggngcn garytngtna arccnggngc nwsngtnaar 60
atgwsntgya aracnwsngg ntayacntty acnwsntaya aygtncaytg ggtnaarcar 120
acnccnggnc arggnytnga rtggathggn gcnathtayc cnggnaaygg ngayacnwsn 180
ttyaaycara arttyaargg naargcnacn ytnacngcng ayaarwsnws nwsnacngtn 240
tayatgcary tnwsnwsnyt nacnwsngar gaywsngcng tntaytaytg ygcnmgnwsn 300
aaytaytayg gnwsnwsnta ygtntggtty ttygaygtnt ggggngcngg nacnacngtn 360
acngtnwsnw snggnwsnac nwsnggnwsn ggnaarccng gnwsnggnga rggnwsncar 420
athgtnytnw sncarwsncc nacnathytn wsngcnwsnc cnggngaraa rgtnacnatg 480
acntgymgng cnwsnwsnws ngtnwsntay atggaytggt aycarcaraa rccnggnwsn 540
wsnccnaarc cntggathta ygcnacnwsn aayytngcnw snggngtncc ngcnmgntty 600
wsnggnwsng gnwsnggnac nwsntaywsn ytnacnathw snmgngtnga rgcngargay 660
gcngcnacnt aytaytgyca rcartggath wsnaayccnc cnacnttygg ngcnggnacn 720
aarytngary tnaargartt yccnaarccn wsnacnccnc cnggnwsnws nggnggngcn 780
ccnaargart tyacnytnga yttywsnacn gcnaaracnt aygtngayws nytnaaygtn 840

```
athmgnwsng cnathggnac nccnytncar acnathwsnw sn

Arg Ala Ser Ser Ser Val Ser Tyr Met Asp
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Thr Ser Asn Leu Ala Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gln Gln Trp Ile Ser Asn Pro Pro Thr
1               5

<210> SEQ ID NO 12
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Gln Val Gln Leu Val Gln Ser Gly Ala Glu Leu Val Lys Pro Gly
1               5                   10                  15

Ala Ser Val Lys Met Ser Cys Lys Ala Ser Gly Tyr Thr Phe Thr Ser
            20                  25                  30

Tyr Asn Met His Trp Val Lys Gln Thr Pro Gly Gln Gly Leu Glu Trp
        35                  40                  45

Ile Gly Ala Ile Tyr Pro Gly Asn Gly Asp Thr Ser Tyr Asn Gln Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Ser Glu Asp Ser Ala Val Tyr Tyr
                85                  90                  95

Cys Ala Arg Ala Gln Leu Arg Pro Asn Tyr Trp Tyr Phe Asp Val Trp
            100                 105                 110

Gly Ala Gly Thr Thr Val Thr Val Ser Ser Gly Gly Gly Gly Ser Gly
        115                 120                 125

Gly Gly Gly Ser Gly Gly Gly Ser Gly Gly Gly Ser Gly Gly
    130                 135                 140

Gly Gly Ser Asp Ile Val Leu Ser Gln Ser Pro Ala Ile Leu Ser Ala
145                 150                 155                 160

Ser Pro Gly Glu Lys Val Thr Met Thr Cys Arg Ala Ser Ser Ser Val
                165                 170                 175

Ser Tyr Met His Trp Tyr Gln Gln Lys Pro Gly Ser Ser Pro Lys Pro
            180                 185                 190

Trp Ile Tyr Ala Thr Ser Asn Leu Ala Ser Gly Val Pro Ala Arg Phe

```
            195                 200                 205
Ser Gly Ser Gly Ser Gly Thr Ser Tyr Ser Leu Thr Ile Ser Arg Val
210                 215                 220
Glu Ala Glu Asp Ala Ala Thr Tyr Tyr Cys Gln Gln Trp Ile Ser Asn
225                 230                 235                 240
Pro Pro Thr Phe Gly Ala Gly Thr Lys Leu Glu Leu Lys Gly Gly Gly
                245                 250                 255
Gly Ser Gly Gly Lys Glu Phe Thr Leu Asp Phe Ser Thr Ala Lys Thr
            260                 265                 270
Tyr Val Asp Ser Leu Asn Val Ile Arg Ser Ala Ile Gly Thr Pro Leu
        275                 280                 285
Gln Thr Ile Ser Ser Gly Gly Thr Ser Leu Leu Met Ile Asp Ser Gly
290                 295                 300
Ser Gly Asp Asn Leu Phe Ala Val Asp Val Arg Gly Ile Asp Pro Glu
305                 310                 315                 320
Glu Gly Arg Phe Asn Asn Leu Arg Leu Ile Val Glu Arg Asn Asn Leu
                325                 330                 335
Tyr Val Thr Gly Phe Val Asn Arg Thr Asn Asn Val Phe Tyr Arg Phe
            340                 345                 350
Ala Asp Phe Ser His Val Thr Phe Pro Gly Thr Thr Ala Val Thr Leu
        355                 360                 365
Ser Gly Asp Ser Ser Tyr Thr Thr Leu Gln Arg Val Ala Gly Ile Ser
370                 375                 380
Arg Thr Gly Met Gln Ile Asn Arg His Ser Leu Thr Thr Ser Tyr Leu
385                 390                 395                 400
Asp Leu Met Ser His Ser Gly Thr Ser Leu Thr Gln Ser Val Ala Arg
                405                 410                 415
Ala Met Leu Arg Phe Val Thr Val Thr Ala Glu Ala Leu Arg Phe Arg
            420                 425                 430
Gln Ile Gln Arg Gly Phe Arg Thr Thr Leu Asp Asp Leu Ser Gly Arg
        435                 440                 445
Ser Tyr Val Met Thr Ala Glu Asp Val Asp Leu Thr Leu Asn Trp Gly
450                 455                 460
Arg Leu Ser Ser Val Leu Pro Asp Tyr His Gly Gln Asp Ser Val Arg
465                 470                 475                 480
Val Gly Arg Ile Ser Phe Gly Ser Ile Asn Ala Ile Leu Gly Ser Val
                485                 490                 495
Ala Leu Ile Leu Asn Cys His His His Ala Ser Arg Val Ala Arg
            500                 505                 510
```

<210> SEQ ID NO 13
<211> LENGTH: 1533
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (18)..(18)
<223> OTHER INFORMATION: a, c, t, g, unknown or other

```
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: modified_base
<222> LOCATION: (30)..(30)
<223> OTHER INFORMATION: a, c, t, g, unknown or other
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: modified_base
<222> LOCATION: (39)..(39)
<223> OTHER INFORMATION: a, c, t, g, unknown or other
<220> FEATURE:
<221> NAME/KEY: modified_base
<222> LOCATION: (45)..(45)
<223> OTHER INFORMATION: a, c, t, g, unknown or other
<220> FEATURE:
<221> NAME/KEY: modified_base
<222> LOCATION: (48)..(48)
<223> OTHER INFORMATION: a, c, t, g, unknown or other
<220> FEATURE:
<221> NAME/KEY: modified_base
<222> LOCATION: (51)..(51)
<223> OTHER INFORMATION: a, c, t, g, unknown or other
<220> FEATURE:
<221> NAME/KEY: modified_base
<222> LOCATION: (54)..(54)
<223> OTHER INFORMATION: a, c, t, g, unknown or other
<220> FEATURE:
<221> NAME/KEY: modified_base
<222> LOCATION: (57)..(57)
<223> OTHER INFORMATION: a, c, t, g, unknown or other
<220> FEATURE:
<221> NAME/KEY: modified_base
<222> LOCATION: (66)..(66)
<223> OTHER INFORMATION: a, c, t, g, unknown or other
<220> FEATURE:
<221> NAME/KEY: modified_base
<222> LOCATION: (75)..(75)
<223> OTHER INFORMATION: a, c, t, g, unknown or other
<220> FEATURE:
<221> NAME/KEY: modified_base
<222> LOCATION: (78)..(78)
<223> OTHER INFORMATION: a, c, t, g, unknown or other
<220> FEATURE:
<221> NAME/KEY: modified_base
<222> LOCATION: (81)..(81)
<223> OTHER INFORMATION: a, c, t, g, unknown or other
<220> FEATURE:
<221> NAME/KEY: modified_base
<222> LOCATION: (87)..(87)
<223> OTHER INFORMATION: a, c, t, g, unknown or other
<220> FEATURE:
<221> NAME/KEY: modified_base
<222> LOCATION: (93)..(93)
<223> OTHER INFORMATION: a, c, t, g, unknown or other
<220> FEATURE:
<221> NAME/KEY: modified_base
<222> LOCATION: (96)..(96)
<223> OTHER INFORMATION: a, c, t, g, unknown or other
<220> FEATURE:
<221> NAME/KEY: modified_base
<222> LOCATION: (114)..(114)
<223> OTHER INFORMATION: a, c, t, g, unknown or other
<220> FEATURE:
<221> NAME/KEY: modified_base
<222> LOCATION: (123)..(123)
<223> OTHER INFORMATION: a, c, t, g, unknown or other
<220> FEATURE:
<221> NAME/KEY: modified_base
<222> LOCATION: (126)..(126)
```

```
<223> OTHER INFORMATION: a, c, t, g, unknown or other
<220> FEATURE:
<221> NAME/KEY: modified_base
<222> LOCATION: (129)..(129)
<223> OTHER INFORMATION: a, c, t, g, unknown or other
<220> FEATURE:
<221> NAME/KEY: modified_base
<222> LOCATION: (135)..(135)
<223> OTHER INFORMATION: a, c, t, g, unknown or other
<220> FEATURE:
<221> NAME/KEY: modified_base
<222> LOCATION: (138)..(138)
<223> OTHER INFORMATION: a, c, t, g, unknown or other
<220> FEATURE:
<221> NAME/KEY: modified_base
<222> LOCATION: (150)..(150)
<223> OTHER INFORMATION: a, c, t, g, unknown or other
<220> FEATURE:
<221> NAME/KEY: modified_base
<222> LOCATION: (153)..(153)
<223> OTHER INFORMATION: a, c, t, g, unknown or other
<220> FEATURE:
<221> NAME/KEY: modified_base
<222> LOCATION: (162)..(162)
<223> OTHER INFORMATION: a, c, t, g, unknown or other
<220> FEATURE:
<221> NAME/KEY: modified_base
<222> LOCATION: (165)..(165)
<223> OTHER INFORMATION: a, c, t, g, unknown or other
<220> FEATURE:
<221> NAME/KEY: modified_base
<222> LOCATION: (171)..(171)
<223> OTHER INFORMATION: a, c, t, g, unknown or other
<220> FEATURE:
<221> NAME/KEY: modified_base
<222> LOCATION: (177)..(177)
<223> OTHER INFORMATION: a, c, t, g, unknown or other
<220> FEATURE:
<221> NAME/KEY: modified_base
<222> LOCATION: (180)..(180)
<223> OTHER INFORMATION: a, c, t, g, unknown or other
<220> FEATURE:
<221> NAME/KEY: modified_base
<222> LOCATION: (201)..(201)
<223> OTHER INFORMATION: a, c, t, g, unknown or other
<220> FEATURE:
<221> NAME/KEY: modified_base
<222> LOCATION: (207)..(207)
<223> OTHER INFORMATION: a, c, t, g, unknown or other
<220> FEATURE:
<221> NAME/KEY: modified_base
<222> LOCATION: (210)..(210)
<223> OTHER INFORMATION: a, c, t, g, unknown or other
<220> FEATURE:
<221> NAME/KEY: modified_base
<222> LOCATION: (213)..(213)
<223> OTHER INFORMATION: a, c, t, g, unknown or other
<220> FEATURE:
<221> NAME/KEY: modified_base
<222> LOCATION: (216)..(216)
<223> OTHER INFORMATION: a, c, t, g, unknown or other
<220> FEATURE:
<221> NAME/KEY: modified_base
<222> LOCATION: (219)..(219)
<223> OTHER INFORMATION: a, c, t, g, unknown or other
<220> FEATURE:
<221> NAME/KEY: modified_base
<222> LOCATION: (228)..(228)
<223> OTHER INFORMATION: a, c, t, g, unknown or other
<220> FEATURE:
<221> NAME/KEY: modified_base
<222> LOCATION: (231)..(231)
<223> OTHER INFORMATION: a, c, t, g, unknown or other
<220> FEATURE:
<221> NAME/KEY: modified_base
<222> LOCATION: (234)..(234)
<223> OTHER INFORMATION: a, c, t, g, unknown or other
<220> FEATURE:
<221> NAME/KEY: modified_base
```

-continued

```
<222> LOCATION: (237)..(237)
<223> OTHER INFORMATION: a, c, t, g, unknown or other
<220> FEATURE:
<221> NAME/KEY: modified_base
<222> LOCATION: (240)..(240)
<223> OTHER INFORMATION: a, c, t, g, unknown or other
<220> FEATURE:
<221> NAME/KEY: modified_base
<222> LOCATION: (252)..(252)
<223> OTHER INFORMATION: a, c, t, g, unknown or other
<220> FEATURE:
<221> NAME/KEY: modified_base
<222> LOCATION: (255)..(255)
<223> OTHER INFORMATION: a, c, t, g, unknown or other
<220> FEATURE:
<221> NAME/KEY: modified_base
<222> LOCATION: (258)..(258)
<223> OTHER INFORMATION: a, c, t, g, unknown or other
<220> FEATURE:
<221> NAME/KEY: modified_base
<222> LOCATION: (261)..(261)
<223> OTHER INFORMATION: a, c, t, g, unknown or other
<220> FEATURE:
<221> NAME/KEY: modified_base
<222> LOCATION: (264)..(264)
<223> OTHER INFORMATION: a, c, t, g, unknown or other
<220> FEATURE:
<221> NAME/KEY: modified_base
<222> LOCATION: (267)..(267)
<223> OTHER INFORMATION: a, c, t, g, unknown or other
<220> FEATURE:
<221> NAME/KEY: modified_base
<222> LOCATION: (276)..(276)
<223> OTHER INFORMATION: a, c, t, g, unknown or other
<220> FEATURE:
<221> NAME/KEY: modified_base
<222> LOCATION: (279)..(279)
<223> OTHER INFORMATION: a, c, t, g, unknown or other
<220> FEATURE:
<221> NAME/KEY: modified_base
<222> LOCATION: (282)..(282)
<223> OTHER INFORMATION: a, c, t, g, unknown or other
<220> FEATURE:
<221> NAME/KEY: modified_base
<222> LOCATION: (294)..(294)
<223> OTHER INFORMATION: a, c, t, g, unknown or other
<220> FEATURE:
<221> NAME/KEY: modified_base
<222> LOCATION: (297)..(297)
<223> OTHER INFORMATION: a, c, t, g, unknown or other
<220> FEATURE:
<221> NAME/KEY: modified_base
<222> LOCATION: (300)..(300)
<223> OTHER INFORMATION: a, c, t, g, unknown or other
<220> FEATURE:
<221> NAME/KEY: modified_base
<222> LOCATION: (306)..(306)
<223> OTHER INFORMATION: a, c, t, g, unknown or other
<220> FEATURE:
<221> NAME/KEY: modified_base
<222> LOCATION: (309)..(309)
<223> OTHER INFORMATION: a, c, t, g, unknown or other
<220> FEATURE:
<221> NAME/KEY: modified_base
<222> LOCATION: (312)..(312)
<223> OTHER INFORMATION: a, c, t, g, unknown or other
<220> FEATURE:
<221> NAME/KEY: modified_base
<222> LOCATION: (333)..(333)
<223> OTHER INFORMATION: a, c, t, g, unknown or other
<220> FEATURE:
<221> NAME/KEY: modified_base
<222> LOCATION: (339)..(339)
<223> OTHER INFORMATION: a, c, t, g, unknown or other
<220> FEATURE:
<221> NAME/KEY: modified_base
<222> LOCATION: (342)..(342)
<223> OTHER INFORMATION: a, c, t, g, unknown or other
<220> FEATURE:
```

```
<221> NAME/KEY: modified_base
<222> LOCATION: (345)..(345)
<223> OTHER INFORMATION: a, c, t, g, unknown or other
<220> FEATURE:
<221> NAME/KEY: modified_base
<222> LOCATION: (348)..(348)
<223> OTHER INFORMATION: a, c, t, g, unknown or other
<220> FEATURE:
<221> NAME/KEY: modified_base
<222> LOCATION: (351)..(351)
<223> OTHER INFORMATION: a, c, t, g, unknown or other
<220> FEATURE:
<221> NAME/KEY: modified_base
<222> LOCATION: (354)..(354)
<223> OTHER INFORMATION: a, c, t, g, unknown or other
<220> FEATURE:
<221> NAME/KEY: modified_base
<222> LOCATION: (357)..(357)
<223> OTHER INFORMATION: a, c, t, g, unknown or other
<220> FEATURE:
<221> NAME/KEY: modified_base
<222> LOCATION: (360)..(360)
<223> OTHER INFORMATION: a, c, t, g, unknown or other
<220> FEATURE:
<221> NAME/KEY: modified_base
<222> LOCATION: (363)..(363)
<223> OTHER INFORMATION: a, c, t, g, unknown or other
<220> FEATURE:
<221> NAME/KEY: modified_base
<222> LOCATION: (366)..(366)
<223> OTHER INFORMATION: a, c, t, g, unknown or other
<220> FEATURE:
<221> NAME/KEY: modified_base
<222> LOCATION: (369)..(369)
<223> OTHER INFORMATION: a, c, t, g, unknown or other
<220> FEATURE:
<221> NAME/KEY: modified_base
<222> LOCATION: (372)..(372)
<223> OTHER INFORMATION: a, c, t, g, unknown or other
<220> FEATURE:
<221> NAME/KEY: modified_base
<222> LOCATION: (375)..(375)
<223> OTHER INFORMATION: a, c, t, g, unknown or other
<220> FEATURE:
<221> NAME/KEY: modified_base
<222> LOCATION: (378)..(378)
<223> OTHER INFORMATION: a, c, t, g, unknown or other
<220> FEATURE:
<221> NAME/KEY: modified_base
<222> LOCATION: (381)..(381)
<223> OTHER INFORMATION: a, c, t, g, unknown or other
<220> FEATURE:
<221> NAME/KEY: modified_base
<222> LOCATION: (384)..(384)
<223> OTHER INFORMATION: a, c, t, g, unknown or other
<220> FEATURE:
<221> NAME/KEY: modified_base
<222> LOCATION: (387)..(387)
<223> OTHER INFORMATION: a, c, t, g, unknown or other
<220> FEATURE:
<221> NAME/KEY: modified_base
<222> LOCATION: (390)..(390)
<223> OTHER INFORMATION: a, c, t, g, unknown or other
<220> FEATURE:
<221> NAME/KEY: modified_base
<222> LOCATION: (393)..(393)
<223> OTHER INFORMATION: a, c, t, g, unknown or other
<220> FEATURE:
<221> NAME/KEY: modified_base
<222> LOCATION: (396)..(396)
<223> OTHER INFORMATION: a, c, t, g, unknown or other
<220> FEATURE:
<221> NAME/KEY: modified_base
<222> LOCATION: (399)..(399)
<223> OTHER INFORMATION: a, c, t, g, unknown or other
<220> FEATURE:
<221> NAME/KEY: modified_base
<222> LOCATION: (402)..(402)
<223> OTHER INFORMATION: a, c, t, g, unknown or other
```

```
<220> FEATURE:
<221> NAME/KEY: modified_base
<222> LOCATION: (405)..(405)
<223> OTHER INFORMATION: a, c, t, g, unknown or other
<220> FEATURE:
<221> NAME/KEY: modified_base
<222> LOCATION: (408)..(408)
<223> OTHER INFORMATION: a, c, t, g, unknown or other
<220> FEATURE:
<221> NAME/KEY: modified_base
<222> LOCATION: (411)..(411)
<223> OTHER INFORMATION: a, c, t, g, unknown or other
<220> FEATURE:
<221> NAME/KEY: modified_base
<222> LOCATION: (414)..(414)
<223> OTHER INFORMATION: a, c, t, g, unknown or other
<220> FEATURE:
<221> NAME/KEY: modified_base
<222> LOCATION: (417)..(417)
<223> OTHER INFORMATION: a, c, t, g, unknown or other
<220> FEATURE:
<221> NAME/KEY: modified_base
<222> LOCATION: (420)..(420)
<223> OTHER INFORMATION: a, c, t, g, unknown or other
<220> FEATURE:
<221> NAME/KEY: modified_base
<222> LOCATION: (423)..(423)
<223> OTHER INFORMATION: a, c, t, g, unknown or other
<220> FEATURE:
<221> NAME/KEY: modified_base
<222> LOCATION: (426)..(426)
<223> OTHER INFORMATION: a, c, t, g, unknown or other
<220> FEATURE:
<221> NAME/KEY: modified_base
<222> LOCATION: (429)..(429)
<223> OTHER INFORMATION: a, c, t, g, unknown or other
<220> FEATURE:
<221> NAME/KEY: modified_base
<222> LOCATION: (432)..(432)
<223> OTHER INFORMATION: a, c, t, g, unknown or other
<220> FEATURE:
<221> NAME/KEY: modified_base
<222> LOCATION: (435)..(435)
<223> OTHER INFORMATION: a, c, t, g, unknown or other
<220> FEATURE:
<221> NAME/KEY: modified_base
<222> LOCATION: (438)..(438)
<223> OTHER INFORMATION: a, c, t, g, unknown or other
<220> FEATURE:
<221> NAME/KEY: modified_base
<222> LOCATION: (441)..(441)
<223> OTHER INFORMATION: a, c, t, g, unknown or other
<220> FEATURE:
<221> NAME/KEY: modified_base
<222> LOCATION: (450)..(450)
<223> OTHER INFORMATION: a, c, t, g, unknown or other
<220> FEATURE:
<221> NAME/KEY: modified_base
<222> LOCATION: (453)..(453)
<223> OTHER INFORMATION: a, c, t, g, unknown or other
<220> FEATURE:
<221> NAME/KEY: modified_base
<222> LOCATION: (456)..(456)
<223> OTHER INFORMATION: a, c, t, g, unknown or other
<220> FEATURE:
<221> NAME/KEY: modified_base
<222> LOCATION: (462)..(462)
<223> OTHER INFORMATION: a, c, t, g, unknown or other
<220> FEATURE:
<221> NAME/KEY: modified_base
<222> LOCATION: (465)..(465)
<223> OTHER INFORMATION: a, c, t, g, unknown or other
<220> FEATURE:
<221> NAME/KEY: modified_base
<222> LOCATION: (468)..(468)
<223> OTHER INFORMATION: a, c, t, g, unknown or other
<220> FEATURE:
<221> NAME/KEY: modified_base
<222> LOCATION: (474)..(474)
```

-continued

```
<223> OTHER INFORMATION: a, c, t, g, unknown or other
<220> FEATURE:
<221> NAME/KEY: modified_base
<222> LOCATION: (477)..(477)
<223> OTHER INFORMATION: a, c, t, g, unknown or other
<220> FEATURE:
<221> NAME/KEY: modified_base
<222> LOCATION: (480)..(480)
<223> OTHER INFORMATION: a, c, t, g, unknown or other
<220> FEATURE:
<221> NAME/KEY: modified_base
<222> LOCATION: (483)..(483)
<223> OTHER INFORMATION: a, c, t, g, unknown or other
<220> FEATURE:
<221> NAME/KEY: modified_base
<222> LOCATION: (486)..(486)
<223> OTHER INFORMATION: a, c, t, g, unknown or other
<220> FEATURE:
<221> NAME/KEY: modified_base
<222> LOCATION: (489)..(489)
<223> OTHER INFORMATION: a, c, t, g, unknown or other
<220> FEATURE:
<221> NAME/KEY: modified_base
<222> LOCATION: (498)..(498)
<223> OTHER INFORMATION: a, c, t, g, unknown or other
<220> FEATURE:
<221> NAME/KEY: modified_base
<222> LOCATION: (501)..(501)
<223> OTHER INFORMATION: a, c, t, g, unknown or other
<220> FEATURE:
<221> NAME/KEY: modified_base
<222> LOCATION: (507)..(507)
<223> OTHER INFORMATION: a, c, t, g, unknown or other
<220> FEATURE:
<221> NAME/KEY: modified_base
<222> LOCATION: (513)..(513)
<223> OTHER INFORMATION: a, c, t, g, unknown or other
<220> FEATURE:
<221> NAME/KEY: modified_base
<222> LOCATION: (516)..(516)
<223> OTHER INFORMATION: a, c, t, g, unknown or other
<220> FEATURE:
<221> NAME/KEY: modified_base
<222> LOCATION: (519)..(519)
<223> OTHER INFORMATION: a, c, t, g, unknown or other
<220> FEATURE:
<221> NAME/KEY: modified_base
<222> LOCATION: (522)..(522)
<223> OTHER INFORMATION: a, c, t, g, unknown or other
<220> FEATURE:
<221> NAME/KEY: modified_base
<222> LOCATION: (525)..(525)
<223> OTHER INFORMATION: a, c, t, g, unknown or other
<220> FEATURE:
<221> NAME/KEY: modified_base
<222> LOCATION: (528)..(528)
<223> OTHER INFORMATION: a, c, t, g, unknown or other
<220> FEATURE:
<221> NAME/KEY: modified_base
<222> LOCATION: (531)..(531)
<223> OTHER INFORMATION: a, c, t, g, unknown or other
<220> FEATURE:
<221> NAME/KEY: modified_base
<222> LOCATION: (558)..(558)
<223> OTHER INFORMATION: a, c, t, g, unknown or other
<220> FEATURE:
<221> NAME/KEY: modified_base
<222> LOCATION: (561)..(561)
<223> OTHER INFORMATION: a, c, t, g, unknown or other
<220> FEATURE:
<221> NAME/KEY: modified_base
<222> LOCATION: (564)..(564)
<223> OTHER INFORMATION: a, c, t, g, unknown or other
<220> FEATURE:
<221> NAME/KEY: modified_base
<222> LOCATION: (567)..(567)
<223> OTHER INFORMATION: a, c, t, g, unknown or other
<220> FEATURE:
<221> NAME/KEY: modified_base
```

-continued

```
<222> LOCATION: (570)..(570)
<223> OTHER INFORMATION: a, c, t, g, unknown or other
<220> FEATURE:
<221> NAME/KEY: modified_base
<222> LOCATION: (576)..(576)
<223> OTHER INFORMATION: a, c, t, g, unknown or other
<220> FEATURE:
<221> NAME/KEY: modified_base
<222> LOCATION: (588)..(588)
<223> OTHER INFORMATION: a, c, t, g, unknown or other
<220> FEATURE:
<221> NAME/KEY: modified_base
<222> LOCATION: (591)..(591)
<223> OTHER INFORMATION: a, c, t, g, unknown or other
<220> FEATURE:
<221> NAME/KEY: modified_base
<222> LOCATION: (594)..(594)
<223> OTHER INFORMATION: a, c, t, g, unknown or other
<220> FEATURE:
<221> NAME/KEY: modified_base
<222> LOCATION: (600)..(600)
<223> OTHER INFORMATION: a, c, t, g, unknown or other
<220> FEATURE:
<221> NAME/KEY: modified_base
<222> LOCATION: (603)..(603)
<223> OTHER INFORMATION: a, c, t, g, unknown or other
<220> FEATURE:
<221> NAME/KEY: modified_base
<222> LOCATION: (606)..(606)
<223> OTHER INFORMATION: a, c, t, g, unknown or other
<220> FEATURE:
<221> NAME/KEY: modified_base
<222> LOCATION: (609)..(609)
<223> OTHER INFORMATION: a, c, t, g, unknown or other
<220> FEATURE:
<221> NAME/KEY: modified_base
<222> LOCATION: (612)..(612)
<223> OTHER INFORMATION: a, c, t, g, unknown or other
<220> FEATURE:
<221> NAME/KEY: modified_base
<222> LOCATION: (615)..(615)
<223> OTHER INFORMATION: a, c, t, g, unknown or other
<220> FEATURE:
<221> NAME/KEY: modified_base
<222> LOCATION: (618)..(618)
<223> OTHER INFORMATION: a, c, t, g, unknown or other
<220> FEATURE:
<221> NAME/KEY: modified_base
<222> LOCATION: (621)..(621)
<223> OTHER INFORMATION: a, c, t, g, unknown or other
<220> FEATURE:
<221> NAME/KEY: modified_base
<222> LOCATION: (627)..(627)
<223> OTHER INFORMATION: a, c, t, g, unknown or other
<220> FEATURE:
<221> NAME/KEY: modified_base
<222> LOCATION: (630)..(630)
<223> OTHER INFORMATION: a, c, t, g, unknown or other
<220> FEATURE:
<221> NAME/KEY: modified_base
<222> LOCATION: (633)..(633)
<223> OTHER INFORMATION: a, c, t, g, unknown or other
<220> FEATURE:
<221> NAME/KEY: modified_base
<222> LOCATION: (636)..(636)
<223> OTHER INFORMATION: a, c, t, g, unknown or other
<220> FEATURE:
<221> NAME/KEY: modified_base
<222> LOCATION: (639)..(639)
<223> OTHER INFORMATION: a, c, t, g, unknown or other
<220> FEATURE:
<221> NAME/KEY: modified_base
<222> LOCATION: (642)..(642)
<223> OTHER INFORMATION: a, c, t, g, unknown or other
<220> FEATURE:
<221> NAME/KEY: modified_base
<222> LOCATION: (645)..(645)
<223> OTHER INFORMATION: a, c, t, g, unknown or other
<220> FEATURE:
```

```
<221> NAME/KEY: modified_base
<222> LOCATION: (648)..(648)
<223> OTHER INFORMATION: a, c, t, g, unknown or other
<220> FEATURE:
<221> NAME/KEY: modified_base
<222> LOCATION: (654)..(654)
<223> OTHER INFORMATION: a, c, t, g, unknown or other
<220> FEATURE:
<221> NAME/KEY: modified_base
<222> LOCATION: (657)..(657)
<223> OTHER INFORMATION: a, c, t, g, unknown or other
<220> FEATURE:
<221> NAME/KEY: modified_base
<222> LOCATION: (660)..(660)
<223> OTHER INFORMATION: a, c, t, g, unknown or other
<220> FEATURE:
<221> NAME/KEY: modified_base
<222> LOCATION: (666)..(666)
<223> OTHER INFORMATION: a, c, t, g, unknown or other
<220> FEATURE:
<221> NAME/KEY: modified_base
<222> LOCATION: (669)..(669)
<223> OTHER INFORMATION: a, c, t, g, unknown or other
<220> FEATURE:
<221> NAME/KEY: modified_base
<222> LOCATION: (672)..(672)
<223> OTHER INFORMATION: a, c, t, g, unknown or other
<220> FEATURE:
<221> NAME/KEY: modified_base
<222> LOCATION: (678)..(678)
<223> OTHER INFORMATION: a, c, t, g, unknown or other
<220> FEATURE:
<221> NAME/KEY: modified_base
<222> LOCATION: (687)..(687)
<223> OTHER INFORMATION: a, c, t, g, unknown or other
<220> FEATURE:
<221> NAME/KEY: modified_base
<222> LOCATION: (690)..(690)
<223> OTHER INFORMATION: a, c, t, g, unknown or other
<220> FEATURE:
<221> NAME/KEY: modified_base
<222> LOCATION: (693)..(693)
<223> OTHER INFORMATION: a, c, t, g, unknown or other
<220> FEATURE:
<221> NAME/KEY: modified_base
<222> LOCATION: (717)..(717)
<223> OTHER INFORMATION: a, c, t, g, unknown or other
<220> FEATURE:
<221> NAME/KEY: modified_base
<222> LOCATION: (723)..(723)
<223> OTHER INFORMATION: a, c, t, g, unknown or other
<220> FEATURE:
<221> NAME/KEY: modified_base
<222> LOCATION: (726)..(726)
<223> OTHER INFORMATION: a, c, t, g, unknown or other
<220> FEATURE:
<221> NAME/KEY: modified_base
<222> LOCATION: (729)..(729)
<223> OTHER INFORMATION: a, c, t, g, unknown or other
<220> FEATURE:
<221> NAME/KEY: modified_base
<222> LOCATION: (735)..(735)
<223> OTHER INFORMATION: a, c, t, g, unknown or other
<220> FEATURE:
<221> NAME/KEY: modified_base
<222> LOCATION: (738)..(738)
<223> OTHER INFORMATION: a, c, t, g, unknown or other
<220> FEATURE:
<221> NAME/KEY: modified_base
<222> LOCATION: (741)..(741)
<223> OTHER INFORMATION: a, c, t, g, unknown or other
<220> FEATURE:
<221> NAME/KEY: modified_base
<222> LOCATION: (744)..(744)
<223> OTHER INFORMATION: a, c, t, g, unknown or other
<220> FEATURE:
<221> NAME/KEY: modified_base
<222> LOCATION: (750)..(750)
<223> OTHER INFORMATION: a, c, t, g, unknown or other
```

```
<220> FEATURE:
<221> NAME/KEY: modified_base
<222> LOCATION: (756)..(756)
<223> OTHER INFORMATION: a, c, t, g, unknown or other
<220> FEATURE:
<221> NAME/KEY: modified_base
<222> LOCATION: (762)..(762)
<223> OTHER INFORMATION: a, c, t, g, unknown or other
<220> FEATURE:
<221> NAME/KEY: modified_base
<222> LOCATION: (765)..(765)
<223> OTHER INFORMATION: a, c, t, g, unknown or other
<220> FEATURE:
<221> NAME/KEY: modified_base
<222> LOCATION: (768)..(768)
<223> OTHER INFORMATION: a, c, t, g, unknown or other
<220> FEATURE:
<221> NAME/KEY: modified_base
<222> LOCATION: (771)..(771)
<223> OTHER INFORMATION: a, c, t, g, unknown or other
<220> FEATURE:
<221> NAME/KEY: modified_base
<222> LOCATION: (774)..(774)
<223> OTHER INFORMATION: a, c, t, g, unknown or other
<220> FEATURE:
<221> NAME/KEY: modified_base
<222> LOCATION: (777)..(777)
<223> OTHER INFORMATION: a, c, t, g, unknown or other
<220> FEATURE:
<221> NAME/KEY: modified_base
<222> LOCATION: (780)..(780)
<223> OTHER INFORMATION: a, c, t, g, unknown or other
<220> FEATURE:
<221> NAME/KEY: modified_base
<222> LOCATION: (792)..(792)
<223> OTHER INFORMATION: a, c, t, g, unknown or other
<220> FEATURE:
<221> NAME/KEY: modified_base
<222> LOCATION: (795)..(795)
<223> OTHER INFORMATION: a, c, t, g, unknown or other
<220> FEATURE:
<221> NAME/KEY: modified_base
<222> LOCATION: (804)..(804)
<223> OTHER INFORMATION: a, c, t, g, unknown or other
<220> FEATURE:
<221> NAME/KEY: modified_base
<222> LOCATION: (807)..(807)
<223> OTHER INFORMATION: a, c, t, g, unknown or other
<220> FEATURE:
<221> NAME/KEY: modified_base
<222> LOCATION: (810)..(810)
<223> OTHER INFORMATION: a, c, t, g, unknown or other
<220> FEATURE:
<221> NAME/KEY: modified_base
<222> LOCATION: (816)..(816)
<223> OTHER INFORMATION: a, c, t, g, unknown or other
<220> FEATURE:
<221> NAME/KEY: modified_base
<222> LOCATION: (822)..(822)
<223> OTHER INFORMATION: a, c, t, g, unknown or other
<220> FEATURE:
<221> NAME/KEY: modified_base
<222> LOCATION: (828)..(828)
<223> OTHER INFORMATION: a, c, t, g, unknown or other
<220> FEATURE:
<221> NAME/KEY: modified_base
<222> LOCATION: (831)..(831)
<223> OTHER INFORMATION: a, c, t, g, unknown or other
<220> FEATURE:
<221> NAME/KEY: modified_base
<222> LOCATION: (837)..(837)
<223> OTHER INFORMATION: a, c, t, g, unknown or other
<220> FEATURE:
<221> NAME/KEY: modified_base
<222> LOCATION: (843)..(843)
<223> OTHER INFORMATION: a, c, t, g, unknown or other
<220> FEATURE:
<221> NAME/KEY: modified_base
<222> LOCATION: (846)..(846)
```

-continued

```
<223> OTHER INFORMATION: a, c, t, g, unknown or other
<220> FEATURE:
<221> NAME/KEY: modified_base
<222> LOCATION: (849)..(849)
<223> OTHER INFORMATION: a, c, t, g, unknown or other
<220> FEATURE:
<221> NAME/KEY: modified_base
<222> LOCATION: (855)..(855)
<223> OTHER INFORMATION: a, c, t, g, unknown or other
<220> FEATURE:
<221> NAME/KEY: modified_base
<222> LOCATION: (858)..(858)
<223> OTHER INFORMATION: a, c, t, g, unknown or other
<220> FEATURE:
<221> NAME/KEY: modified_base
<222> LOCATION: (861)..(861)
<223> OTHER INFORMATION: a, c, t, g, unknown or other
<220> FEATURE:
<221> NAME/KEY: modified_base
<222> LOCATION: (864)..(864)
<223> OTHER INFORMATION: a, c, t, g, unknown or other
<220> FEATURE:
<221> NAME/KEY: modified_base
<222> LOCATION: (870)..(870)
<223> OTHER INFORMATION: a, c, t, g, unknown or other
<220> FEATURE:
<221> NAME/KEY: modified_base
<222> LOCATION: (876)..(876)
<223> OTHER INFORMATION: a, c, t, g, unknown or other
<220> FEATURE:
<221> NAME/KEY: modified_base
<222> LOCATION: (879)..(879)
<223> OTHER INFORMATION: a, c, t, g, unknown or other
<220> FEATURE:
<221> NAME/KEY: modified_base
<222> LOCATION: (882)..(882)
<223> OTHER INFORMATION: a, c, t, g, unknown or other
<220> FEATURE:
<221> NAME/KEY: modified_base
<222> LOCATION: (885)..(885)
<223> OTHER INFORMATION: a, c, t, g, unknown or other
<220> FEATURE:
<221> NAME/KEY: modified_base
<222> LOCATION: (888)..(888)
<223> OTHER INFORMATION: a, c, t, g, unknown or other
<220> FEATURE:
<221> NAME/KEY: modified_base
<222> LOCATION: (891)..(891)
<223> OTHER INFORMATION: a, c, t, g, unknown or other
<220> FEATURE:
<221> NAME/KEY: modified_base
<222> LOCATION: (894)..(894)
<223> OTHER INFORMATION: a, c, t, g, unknown or other
<220> FEATURE:
<221> NAME/KEY: modified_base
<222> LOCATION: (897)..(897)
<223> OTHER INFORMATION: a, c, t, g, unknown or other
<220> FEATURE:
<221> NAME/KEY: modified_base
<222> LOCATION: (909)..(909)
<223> OTHER INFORMATION: a, c, t, g, unknown or other
<220> FEATURE:
<221> NAME/KEY: modified_base
<222> LOCATION: (912)..(912)
<223> OTHER INFORMATION: a, c, t, g, unknown or other
<220> FEATURE:
<221> NAME/KEY: modified_base
<222> LOCATION: (915)..(915)
<223> OTHER INFORMATION: a, c, t, g, unknown or other
<220> FEATURE:
<221> NAME/KEY: modified_base
<222> LOCATION: (918)..(918)
<223> OTHER INFORMATION: a, c, t, g, unknown or other
<220> FEATURE:
<221> NAME/KEY: modified_base
<222> LOCATION: (927)..(927)
<223> OTHER INFORMATION: a, c, t, g, unknown or other
<220> FEATURE:
<221> NAME/KEY: modified_base
```

```
<222> LOCATION: (933)..(933)
<223> OTHER INFORMATION: a, c, t, g, unknown or other
<220> FEATURE:
<221> NAME/KEY: modified_base
<222> LOCATION: (936)..(936)
<223> OTHER INFORMATION: a, c, t, g, unknown or other
<220> FEATURE:
<221> NAME/KEY: modified_base
<222> LOCATION: (942)..(942)
<223> OTHER INFORMATION: a, c, t, g, unknown or other
<220> FEATURE:
<221> NAME/KEY: modified_base
<222> LOCATION: (945)..(945)
<223> OTHER INFORMATION: a, c, t, g, unknown or other
<220> FEATURE:
<221> NAME/KEY: modified_base
<222> LOCATION: (948)..(948)
<223> OTHER INFORMATION: a, c, t, g, unknown or other
<220> FEATURE:
<221> NAME/KEY: modified_base
<222> LOCATION: (957)..(957)
<223> OTHER INFORMATION: a, c, t, g, unknown or other
<220> FEATURE:
<221> NAME/KEY: modified_base
<222> LOCATION: (966)..(966)
<223> OTHER INFORMATION: a, c, t, g, unknown or other
<220> FEATURE:
<221> NAME/KEY: modified_base
<222> LOCATION: (969)..(969)
<223> OTHER INFORMATION: a, c, t, g, unknown or other
<220> FEATURE:
<221> NAME/KEY: modified_base
<222> LOCATION: (981)..(981)
<223> OTHER INFORMATION: a, c, t, g, unknown or other
<220> FEATURE:
<221> NAME/KEY: modified_base
<222> LOCATION: (984)..(984)
<223> OTHER INFORMATION: a, c, t, g, unknown or other
<220> FEATURE:
<221> NAME/KEY: modified_base
<222> LOCATION: (987)..(987)
<223> OTHER INFORMATION: a, c, t, g, unknown or other
<220> FEATURE:
<221> NAME/KEY: modified_base
<222> LOCATION: (993)..(993)
<223> OTHER INFORMATION: a, c, t, g, unknown or other
<220> FEATURE:
<221> NAME/KEY: modified_base
<222> LOCATION: (999)..(999)
<223> OTHER INFORMATION: a, c, t, g, unknown or other
<220> FEATURE:
<221> NAME/KEY: modified_base
<222> LOCATION: (1008)..(1008)
<223> OTHER INFORMATION: a, c, t, g, unknown or other
<220> FEATURE:
<221> NAME/KEY: modified_base
<222> LOCATION: (1014)..(1014)
<223> OTHER INFORMATION: a, c, t, g, unknown or other
<220> FEATURE:
<221> NAME/KEY: modified_base
<222> LOCATION: (1017)..(1017)
<223> OTHER INFORMATION: a, c, t, g, unknown or other
<220> FEATURE:
<221> NAME/KEY: modified_base
<222> LOCATION: (1020)..(1020)
<223> OTHER INFORMATION: a, c, t, g, unknown or other
<220> FEATURE:
<221> NAME/KEY: modified_base
<222> LOCATION: (1026)..(1026)
<223> OTHER INFORMATION: a, c, t, g, unknown or other
<220> FEATURE:
<221> NAME/KEY: modified_base
<222> LOCATION: (1032)..(1032)
<223> OTHER INFORMATION: a, c, t, g, unknown or other
<220> FEATURE:
<221> NAME/KEY: modified_base
<222> LOCATION: (1035)..(1035)
<223> OTHER INFORMATION: a, c, t, g, unknown or other
<220> FEATURE:
```

```
<221> NAME/KEY: modified_base
<222> LOCATION: (1044)..(1044)
<223> OTHER INFORMATION: a, c, t, g, unknown or other
<220> FEATURE:
<221> NAME/KEY: modified_base
<222> LOCATION: (1053)..(1053)
<223> OTHER INFORMATION: a, c, t, g, unknown or other
<220> FEATURE:
<221> NAME/KEY: modified_base
<222> LOCATION: (1059)..(1059)
<223> OTHER INFORMATION: a, c, t, g, unknown or other
<220> FEATURE:
<221> NAME/KEY: modified_base
<222> LOCATION: (1068)..(1068)
<223> OTHER INFORMATION: a, c, t, g, unknown or other
<220> FEATURE:
<221> NAME/KEY: modified_base
<222> LOCATION: (1074)..(1074)
<223> OTHER INFORMATION: a, c, t, g, unknown or other
<220> FEATURE:
<221> NAME/KEY: modified_base
<222> LOCATION: (1077)..(1077)
<223> OTHER INFORMATION: a, c, t, g, unknown or other
<220> FEATURE:
<221> NAME/KEY: modified_base
<222> LOCATION: (1083)..(1083)
<223> OTHER INFORMATION: a, c, t, g, unknown or other
<220> FEATURE:
<221> NAME/KEY: modified_base
<222> LOCATION: (1086)..(1086)
<223> OTHER INFORMATION: a, c, t, g, unknown or other
<220> FEATURE:
<221> NAME/KEY: modified_base
<222> LOCATION: (1089)..(1089)
<223> OTHER INFORMATION: a, c, t, g, unknown or other
<220> FEATURE:
<221> NAME/KEY: modified_base
<222> LOCATION: (1092)..(1092)
<223> OTHER INFORMATION: a, c, t, g, unknown or other
<220> FEATURE:
<221> NAME/KEY: modified_base
<222> LOCATION: (1095)..(1095)
<223> OTHER INFORMATION: a, c, t, g, unknown or other
<220> FEATURE:
<221> NAME/KEY: modified_base
<222> LOCATION: (1098)..(1098)
<223> OTHER INFORMATION: a, c, t, g, unknown or other
<220> FEATURE:
<221> NAME/KEY: modified_base
<222> LOCATION: (1101)..(1101)
<223> OTHER INFORMATION: a, c, t, g, unknown or other
<220> FEATURE:
<221> NAME/KEY: modified_base
<222> LOCATION: (1104)..(1104)
<223> OTHER INFORMATION: a, c, t, g, unknown or other
<220> FEATURE:
<221> NAME/KEY: modified_base
<222> LOCATION: (1107)..(1107)
<223> OTHER INFORMATION: a, c, t, g, unknown or other
<220> FEATURE:
<221> NAME/KEY: modified_base
<222> LOCATION: (1110)..(1110)
<223> OTHER INFORMATION: a, c, t, g, unknown or other
<220> FEATURE:
<221> NAME/KEY: modified_base
<222> LOCATION: (1116)..(1116)
<223> OTHER INFORMATION: a, c, t, g, unknown or other
<220> FEATURE:
<221> NAME/KEY: modified_base
<222> LOCATION: (1119)..(1119)
<223> OTHER INFORMATION: a, c, t, g, unknown or other
<220> FEATURE:
<221> NAME/KEY: modified_base
<222> LOCATION: (1125)..(1125)
<223> OTHER INFORMATION: a, c, t, g, unknown or other
<220> FEATURE:
<221> NAME/KEY: modified_base
<222> LOCATION: (1128)..(1128)
<223> OTHER INFORMATION: a, c, t, g, unknown or other
```

```
<220> FEATURE:
<221> NAME/KEY: modified_base
<222> LOCATION: (1131)..(1131)
<223> OTHER INFORMATION: a, c, t, g, unknown or other
<220> FEATURE:
<221> NAME/KEY: modified_base
<222> LOCATION: (1137)..(1137)
<223> OTHER INFORMATION: a, c, t, g, unknown or other
<220> FEATURE:
<221> NAME/KEY: modified_base
<222> LOCATION: (1140)..(1140)
<223> OTHER INFORMATION: a, c, t, g, unknown or other
<220> FEATURE:
<221> NAME/KEY: modified_base
<222> LOCATION: (1143)..(1143)
<223> OTHER INFORMATION: a, c, t, g, unknown or other
<220> FEATURE:
<221> NAME/KEY: modified_base
<222> LOCATION: (1146)..(1146)
<223> OTHER INFORMATION: a, c, t, g, unknown or other
<220> FEATURE:
<221> NAME/KEY: modified_base
<222> LOCATION: (1152)..(1152)
<223> OTHER INFORMATION: a, c, t, g, unknown or other
<220> FEATURE:
<221> NAME/KEY: modified_base
<222> LOCATION: (1155)..(1155)
<223> OTHER INFORMATION: a, c, t, g, unknown or other
<220> FEATURE:
<221> NAME/KEY: modified_base
<222> LOCATION: (1158)..(1158)
<223> OTHER INFORMATION: a, c, t, g, unknown or other
<220> FEATURE:
<221> NAME/KEY: modified_base
<222> LOCATION: (1161)..(1161)
<223> OTHER INFORMATION: a, c, t, g, unknown or other
<220> FEATURE:
<221> NAME/KEY: modified_base
<222> LOCATION: (1176)..(1176)
<223> OTHER INFORMATION: a, c, t, g, unknown or other
<220> FEATURE:
<221> NAME/KEY: modified_base
<222> LOCATION: (1182)..(1182)
<223> OTHER INFORMATION: a, c, t, g, unknown or other
<220> FEATURE:
<221> NAME/KEY: modified_base
<222> LOCATION: (1185)..(1185)
<223> OTHER INFORMATION: a, c, t, g, unknown or other
<220> FEATURE:
<221> NAME/KEY: modified_base
<222> LOCATION: (1188)..(1188)
<223> OTHER INFORMATION: a, c, t, g, unknown or other
<220> FEATURE:
<221> NAME/KEY: modified_base
<222> LOCATION: (1191)..(1191)
<223> OTHER INFORMATION: a, c, t, g, unknown or other
<220> FEATURE:
<221> NAME/KEY: modified_base
<222> LOCATION: (1194)..(1194)
<223> OTHER INFORMATION: a, c, t, g, unknown or other
<220> FEATURE:
<221> NAME/KEY: modified_base
<222> LOCATION: (1200)..(1200)
<223> OTHER INFORMATION: a, c, t, g, unknown or other
<220> FEATURE:
<221> NAME/KEY: modified_base
<222> LOCATION: (1206)..(1206)
<223> OTHER INFORMATION: a, c, t, g, unknown or other
<220> FEATURE:
<221> NAME/KEY: modified_base
<222> LOCATION: (1212)..(1212)
<223> OTHER INFORMATION: a, c, t, g, unknown or other
<220> FEATURE:
<221> NAME/KEY: modified_base
<222> LOCATION: (1218)..(1218)
<223> OTHER INFORMATION: a, c, t, g, unknown or other
<220> FEATURE:
<221> NAME/KEY: modified_base
<222> LOCATION: (1221)..(1221)
```

```
<223> OTHER INFORMATION: a, c, t, g, unknown or other
<220> FEATURE:
<221> NAME/KEY: modified_base
<222> LOCATION: (1224)..(1224)
<223> OTHER INFORMATION: a, c, t, g, unknown or other
<220> FEATURE:
<221> NAME/KEY: modified_base
<222> LOCATION: (1227)..(1227)
<223> OTHER INFORMATION: a, c, t, g, unknown or other
<220> FEATURE:
<221> NAME/KEY: modified_base
<222> LOCATION: (1230)..(1230)
<223> OTHER INFORMATION: a, c, t, g, unknown or other
<220> FEATURE:
<221> NAME/KEY: modified_base
<222> LOCATION: (1233)..(1233)
<223> OTHER INFORMATION: a, c, t, g, unknown or other
<220> FEATURE:
<221> NAME/KEY: modified_base
<222> LOCATION: (1239)..(1239)
<223> OTHER INFORMATION: a, c, t, g, unknown or other
<220> FEATURE:
<221> NAME/KEY: modified_base
<222> LOCATION: (1242)..(1242)
<223> OTHER INFORMATION: a, c, t, g, unknown or other
<220> FEATURE:
<221> NAME/KEY: modified_base
<222> LOCATION: (1245)..(1245)
<223> OTHER INFORMATION: a, c, t, g, unknown or other
<220> FEATURE:
<221> NAME/KEY: modified_base
<222> LOCATION: (1248)..(1248)
<223> OTHER INFORMATION: a, c, t, g, unknown or other
<220> FEATURE:
<221> NAME/KEY: modified_base
<222> LOCATION: (1251)..(1251)
<223> OTHER INFORMATION: a, c, t, g, unknown or other
<220> FEATURE:
<221> NAME/KEY: modified_base
<222> LOCATION: (1257)..(1257)
<223> OTHER INFORMATION: a, c, t, g, unknown or other
<220> FEATURE:
<221> NAME/KEY: modified_base
<222> LOCATION: (1260)..(1260)
<223> OTHER INFORMATION: a, c, t, g, unknown or other
<220> FEATURE:
<221> NAME/KEY: modified_base
<222> LOCATION: (1266)..(1266)
<223> OTHER INFORMATION: a, c, t, g, unknown or other
<220> FEATURE:
<221> NAME/KEY: modified_base
<222> LOCATION: (1269)..(1269)
<223> OTHER INFORMATION: a, c, t, g, unknown or other
<220> FEATURE:
<221> NAME/KEY: modified_base
<222> LOCATION: (1272)..(1272)
<223> OTHER INFORMATION: a, c, t, g, unknown or other
<220> FEATURE:
<221> NAME/KEY: modified_base
<222> LOCATION: (1275)..(1275)
<223> OTHER INFORMATION: a, c, t, g, unknown or other
<220> FEATURE:
<221> NAME/KEY: modified_base
<222> LOCATION: (1278)..(1278)
<223> OTHER INFORMATION: a, c, t, g, unknown or other
<220> FEATURE:
<221> NAME/KEY: modified_base
<222> LOCATION: (1284)..(1284)
<223> OTHER INFORMATION: a, c, t, g, unknown or other
<220> FEATURE:
<221> NAME/KEY: modified_base
<222> LOCATION: (1287)..(1287)
<223> OTHER INFORMATION: a, c, t, g, unknown or other
<220> FEATURE:
<221> NAME/KEY: modified_base
<222> LOCATION: (1290)..(1290)
<223> OTHER INFORMATION: a, c, t, g, unknown or other
<220> FEATURE:
<221> NAME/KEY: modified_base
```

```
<222> LOCATION: (1296)..(1296)
<223> OTHER INFORMATION: a, c, t, g, unknown or other
<220> FEATURE:
<221> NAME/KEY: modified_base
<222> LOCATION: (1308)..(1308)
<223> OTHER INFORMATION: a, c, t, g, unknown or other
<220> FEATURE:
<221> NAME/KEY: modified_base
<222> LOCATION: (1311)..(1311)
<223> OTHER INFORMATION: a, c, t, g, unknown or other
<220> FEATURE:
<221> NAME/KEY: modified_base
<222> LOCATION: (1317)..(1317)
<223> OTHER INFORMATION: a, c, t, g, unknown or other
<220> FEATURE:
<221> NAME/KEY: modified_base
<222> LOCATION: (1320)..(1320)
<223> OTHER INFORMATION: a, c, t, g, unknown or other
<220> FEATURE:
<221> NAME/KEY: modified_base
<222> LOCATION: (1323)..(1323)
<223> OTHER INFORMATION: a, c, t, g, unknown or other
<220> FEATURE:
<221> NAME/KEY: modified_base
<222> LOCATION: (1326)..(1326)
<223> OTHER INFORMATION: a, c, t, g, unknown or other
<220> FEATURE:
<221> NAME/KEY: modified_base
<222> LOCATION: (1335)..(1335)
<223> OTHER INFORMATION: a, c, t, g, unknown or other
<220> FEATURE:
<221> NAME/KEY: modified_base
<222> LOCATION: (1338)..(1338)
<223> OTHER INFORMATION: a, c, t, g, unknown or other
<220> FEATURE:
<221> NAME/KEY: modified_base
<222> LOCATION: (1341)..(1341)
<223> OTHER INFORMATION: a, c, t, g, unknown or other
<220> FEATURE:
<221> NAME/KEY: modified_base
<222> LOCATION: (1344)..(1344)
<223> OTHER INFORMATION: a, c, t, g, unknown or other
<220> FEATURE:
<221> NAME/KEY: modified_base
<222> LOCATION: (1347)..(1347)
<223> OTHER INFORMATION: a, c, t, g, unknown or other
<220> FEATURE:
<221> NAME/KEY: modified_base
<222> LOCATION: (1353)..(1353)
<223> OTHER INFORMATION: a, c, t, g, unknown or other
<220> FEATURE:
<221> NAME/KEY: modified_base
<222> LOCATION: (1359)..(1359)
<223> OTHER INFORMATION: a, c, t, g, unknown or other
<220> FEATURE:
<221> NAME/KEY: modified_base
<222> LOCATION: (1362)..(1362)
<223> OTHER INFORMATION: a, c, t, g, unknown or other
<220> FEATURE:
<221> NAME/KEY: modified_base
<222> LOCATION: (1371)..(1371)
<223> OTHER INFORMATION: a, c, t, g, unknown or other
<220> FEATURE:
<221> NAME/KEY: modified_base
<222> LOCATION: (1377)..(1377)
<223> OTHER INFORMATION: a, c, t, g, unknown or other
<220> FEATURE:
<221> NAME/KEY: modified_base
<222> LOCATION: (1380)..(1380)
<223> OTHER INFORMATION: a, c, t, g, unknown or other
<220> FEATURE:
<221> NAME/KEY: modified_base
<222> LOCATION: (1383)..(1383)
<223> OTHER INFORMATION: a, c, t, g, unknown or other
<220> FEATURE:
<221> NAME/KEY: modified_base
<222> LOCATION: (1392)..(1392)
<223> OTHER INFORMATION: a, c, t, g, unknown or other
<220> FEATURE:
```

-continued

```
<221> NAME/KEY: modified_base
<222> LOCATION: (1395)..(1395)
<223> OTHER INFORMATION: a, c, t, g, unknown or other
<220> FEATURE:
<221> NAME/KEY: modified_base
<222> LOCATION: (1398)..(1398)
<223> OTHER INFORMATION: a, c, t, g, unknown or other
<220> FEATURE:
<221> NAME/KEY: modified_base
<222> LOCATION: (1401)..(1401)
<223> OTHER INFORMATION: a, c, t, g, unknown or other
<220> FEATURE:
<221> NAME/KEY: modified_base
<222> LOCATION: (1404)..(1404)
<223> OTHER INFORMATION: a, c, t, g, unknown or other
<220> FEATURE:
<221> NAME/KEY: modified_base
<222> LOCATION: (1407)..(1407)
<223> OTHER INFORMATION: a, c, t, g, unknown or other
<220> FEATURE:
<221> NAME/KEY: modified_base
<222> LOCATION: (1410)..(1410)
<223> OTHER INFORMATION: a, c, t, g, unknown or other
<220> FEATURE:
<221> NAME/KEY: modified_base
<222> LOCATION: (1413)..(1413)
<223> OTHER INFORMATION: a, c, t, g, unknown or other
<220> FEATURE:
<221> NAME/KEY: modified_base
<222> LOCATION: (1425)..(1425)
<223> OTHER INFORMATION: a, c, t, g, unknown or other
<220> FEATURE:
<221> NAME/KEY: modified_base
<222> LOCATION: (1434)..(1434)
<223> OTHER INFORMATION: a, c, t, g, unknown or other
<220> FEATURE:
<221> NAME/KEY: modified_base
<222> LOCATION: (1437)..(1437)
<223> OTHER INFORMATION: a, c, t, g, unknown or other
<220> FEATURE:
<221> NAME/KEY: modified_base
<222> LOCATION: (1440)..(1440)
<223> OTHER INFORMATION: a, c, t, g, unknown or other
<220> FEATURE:
<221> NAME/KEY: modified_base
<222> LOCATION: (1443)..(1443)
<223> OTHER INFORMATION: a, c, t, g, unknown or other
<220> FEATURE:
<221> NAME/KEY: modified_base
<222> LOCATION: (1446)..(1446)
<223> OTHER INFORMATION: a, c, t, g, unknown or other
<220> FEATURE:
<221> NAME/KEY: modified_base
<222> LOCATION: (1449)..(1449)
<223> OTHER INFORMATION: a, c, t, g, unknown or other
<220> FEATURE:
<221> NAME/KEY: modified_base
<222> LOCATION: (1455)..(1455)
<223> OTHER INFORMATION: a, c, t, g, unknown or other
<220> FEATURE:
<221> NAME/KEY: modified_base
<222> LOCATION: (1461)..(1461)
<223> OTHER INFORMATION: a, c, t, g, unknown or other
<220> FEATURE:
<221> NAME/KEY: modified_base
<222> LOCATION: (1464)..(1464)
<223> OTHER INFORMATION: a, c, t, g, unknown or other
<220> FEATURE:
<221> NAME/KEY: modified_base
<222> LOCATION: (1473)..(1473)
<223> OTHER INFORMATION: a, c, t, g, unknown or other
<220> FEATURE:
<221> NAME/KEY: modified_base
<222> LOCATION: (1479)..(1479)
<223> OTHER INFORMATION: a, c, t, g, unknown or other
<220> FEATURE:
<221> NAME/KEY: modified_base
<222> LOCATION: (1482)..(1482)
<223> OTHER INFORMATION: a, c, t, g, unknown or other
```

<220> FEATURE:
<221> NAME/KEY: modified_base
<222> LOCATION: (1485)..(1485)
<223> OTHER INFORMATION: a, c, t, g, unknown or other
<220> FEATURE:
<221> NAME/KEY: modified_base
<222> LOCATION: (1488)..(1488)
<223> OTHER INFORMATION: a, c, t, g, unknown or other
<220> FEATURE:
<221> NAME/KEY: modified_base
<222> LOCATION: (1491)..(1491)
<223> OTHER INFORMATION: a, c, t, g, unknown or other
<220> FEATURE:
<221> NAME/KEY: modified_base
<222> LOCATION: (1494)..(1494)
<223> OTHER INFORMATION: a, c, t, g, unknown or other
<220> FEATURE:
<221> NAME/KEY: modified_base
<222> LOCATION: (1500)..(1500)
<223> OTHER INFORMATION: a, c, t, g, unknown or other
<220> FEATURE:
<221> NAME/KEY: modified_base
<222> LOCATION: (1518)..(1518)
<223> OTHER INFORMATION: a, c, t, g, unknown or other
<220> FEATURE:
<221> NAME/KEY: modified_base
<222> LOCATION: (1521)..(1521)
<223> OTHER INFORMATION: a, c, t, g, unknown or other
<220> FEATURE:
<221> NAME/KEY: modified_base
<222> LOCATION: (1524)..(1524)
<223> OTHER INFORMATION: a, c, t, g, unknown or other
<220> FEATURE:
<221> NAME/KEY: modified_base
<222> LOCATION: (1527)..(1527)
<223> OTHER INFORMATION: a, c, t, g, unknown or other
<220> FEATURE:
<221> NAME/KEY: modified_base
<222> LOCATION: (1530)..(1530)
<223> OTHER INFORMATION: a, c, t, g, unknown or other
<220> FEATURE:
<221> NAME/KEY: modified_base
<222> LOCATION: (1533)..(1533)
<223> OTHER INFORMATION: a, c, t, g, unknown or other

<400> SEQUENCE: 13
atgcargtnc arytngtnca rwsnggngcn garytngtna arccnggngc nwsngtnaar 60
atgwsntgya argcnwsngg ntayacntty acnwsntaya ayatgcaytg ggtnaarcar 120
acnccnggnc arggnytnga rtggathggn gcnathtayc cnggnaaygg ngayacnwsn 180
tayaaycara arttyaargg naargcnacn ytnacngcng ayaarwsnws nwsnacngcn 240
tayatgcary tnwsnwsnyt nacnwsngar gaywsngcng tntaytaytg ygcnmgngcn 300
carytnmgnc cnaaytaytg gtayttygay gtntggggng cnggnacnac ngtnacngtn 360
wsnwsnggng gnggnggnws nggnggnggn ggnwsnggng gnggnggnws nggnggnggn 420
ggnwsnggng gnggnggnws ngayathgtn ytnwsncarw snccngcnat hytnwsngcn 480
wsnccnggng araargtnac natgacntgy mgngcnwsnw snwsngtnws ntayatgcay 540
tggtaycarc araarccngg nwsnwsnccn aarccntgga thtaygcnac nwsnaayytn 600
gcnwsnggng tnccngcnmg nttywsnggn wsnggnwsng gnacnwsnta ywsnytnacn 660
athwsnmgng tngargcnga rgaygcngcn acntaytayt gycarcartg gathwsnaay 720
ccnccnacnt tyggngcngg nacnaarytn garytnaarg gnggnggngg nwsnggnggn 780
aargarttya cnytngaytt ywsnacngcn aaracntayg tngaywsnyt naaygtnath 840
mgnwsngcna thggnacncc nytncaracn athwsnwsng gnggnacnws nytnytnatg 900
athgaywsng gnwsnggnga yaayytntty gcngtngayg tnmgnggnat hgayccngar 960

```
garggnmgnt tyaayaayyt nmgnytnath gtngarmgna ayaayytnta ygtnacnggn    1020
ttygtnaaym gnacnaayaa ygtnttytay mgnttygcng ayttywsnca ygtnacntty    1080
ccnggnacna cngcngtnac nytnwsnggn gaywsnwsnt ayacnacnyt ncarmgngtn    1140
gcnggnathw snmgnacngg natgcarath aaymgncayw snytnacnac nwsntayytn    1200
gayytnatgw sncaywsngg nacnwsnytn acncarwsng tngcnmgngc natgytnmgn    1260
ttygtnacng tnacngcnga rgcnytnmgn ttymgncara thcarmgngg nttymgnacn    1320
acnytngayg ayytnwsngg nmgnwsntay gtnatgacng cngargaygt ngayytnacn    1380
ytnaaytggg gnmgnytnws nwsngtnytn ccngaytayc ayggncarga ywsngtnmgn    1440
gtnggnmgna thwsnttygg nwsnathaay gcnathytng gnwsngtngc nytnathytn    1500
aaytgycayc aycaygcnws nmgngtngcn mgn                                1533
```

<210> SEQ ID NO 14
<211> LENGTH: 513
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 14

```
Met Gln Val Gln Leu Gln Gln Pro Gly Ala Glu Leu Val Lys Pro Gly
1               5                   10                  15

Ala Ser Val Lys Met Ser Cys Lys Ala Ser Gly Tyr Thr Phe Thr Ser
            20                  25                  30

Tyr Asn Met His Trp Val Lys Gln Thr Pro Gly Arg Gly Leu Glu Trp
        35                  40                  45

Ile Gly Ala Ile Tyr Pro Gly Asn Gly Asp Thr Ser Tyr Asn Gln Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Ser Glu Asp Ser Ala Val Tyr Tyr
                85                  90                  95

Cys Ala Arg Ser Thr Tyr Tyr Gly Gly Asp Trp Tyr Phe Asn Val Trp
            100                 105                 110

Gly Ala Gly Thr Thr Val Thr Val Ser Ala Gly Ser Thr Ser Gly Ser
        115                 120                 125

Gly Lys Pro Gly Ser Gly Glu Gly Ser Thr Lys Gly Gln Ile Val Leu
    130                 135                 140

Ser Gln Ser Pro Ala Ile Leu Ser Ala Ser Pro Gly Glu Lys Val Thr
145                 150                 155                 160

Met Thr Cys Arg Ala Ser Ser Ser Val Ser Tyr Ile His Trp Phe Gln
                165                 170                 175

Gln Lys Pro Gly Ser Ser Pro Lys Pro Trp Ile Tyr Ala Thr Ser Asn
            180                 185                 190

Leu Ala Ser Gly Val Pro Val Arg Phe Ser Gly Ser Gly Ser Gly Thr
        195                 200                 205

Ser Tyr Ser Leu Thr Ile Ser Arg Val Glu Ala Glu Asp Ala Ala Thr
    210                 215                 220

Tyr Tyr Cys Gln Gln Trp Thr Ser Asn Pro Pro Thr Phe Gly Gly Gly
225                 230                 235                 240

Thr Lys Leu Glu Ile Lys Glu Pro Lys Pro Ser Thr Pro Pro Gly
                245                 250                 255
```

-continued

Ser Ser Gly Gly Ala Pro Lys Glu Phe Thr Leu Asp Phe Ser Thr Ala
            260                 265                 270
Lys Thr Tyr Val Asp Ser Leu Asn Val Ile Arg Ser Ala Ile Gly Thr
        275                 280                 285
Pro Leu Gln Thr Ile Ser Ser Gly Thr Ser Leu Leu Met Ile Asp
    290                 295                 300
Ser Gly Ser Gly Asp Asn Leu Phe Ala Val Asp Val Arg Gly Ile Asp
305                 310                 315                 320
Pro Glu Glu Gly Arg Phe Asn Asn Leu Arg Leu Ile Val Glu Arg Asn
                325                 330                 335
Asn Leu Tyr Val Thr Gly Phe Val Asn Arg Thr Asn Asn Val Phe Tyr
            340                 345                 350
Arg Phe Ala Asp Phe Ser His Val Thr Phe Pro Gly Thr Thr Ala Val
        355                 360                 365
Thr Leu Ser Gly Asp Ser Ser Tyr Thr Thr Leu Gln Arg Val Ala Gly
    370                 375                 380
Ile Ser Arg Thr Gly Met Gln Ile Asn Arg His Ser Leu Thr Thr Ser
385                 390                 395                 400
Tyr Leu Asp Leu Met Ser His Ser Gly Thr Ser Leu Thr Gln Ser Val
                405                 410                 415
Ala Arg Ala Met Leu Arg Phe Val Thr Val Thr Ala Glu Ala Leu Arg
            420                 425                 430
Phe Arg Gln Ile Gln Arg Gly Phe Arg Thr Thr Leu Asp Asp Leu Ser
        435                 440                 445
Gly Arg Ser Tyr Val Met Thr Ala Glu Asp Val Asp Leu Thr Leu Asn
    450                 455                 460
Trp Gly Arg Leu Ser Ser Val Leu Pro Asp Tyr His Gly Gln Asp Ser
465                 470                 475                 480
Val Arg Val Gly Arg Ile Ser Phe Gly Ser Ile Asn Ala Ile Leu Gly
                485                 490                 495
Ser Val Ala Leu Ile Leu Asn Cys His His Ala Ser Arg Val Ala
            500                 505                 510
Arg

<210> SEQ ID NO 15
<211> LENGTH: 1539
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: modified_base
<222> LOCATION: (30)..(30)
<223> OTHER INFORMATION: a, c, t, g, unknown or other
<220> FEATURE:

```
<221> NAME/KEY: modified_base
<222> LOCATION: (36)..(36)
<223> OTHER INFORMATION: a, c, t, g, unknown or other
<220> FEATURE:
<221> NAME/KEY: modified_base
<222> LOCATION: (39)..(39)
<223> OTHER INFORMATION: a, c, t, g, unknown or other
<220> FEATURE:
<221> NAME/KEY: modified_base
<222> LOCATION: (45)..(45)
<223> OTHER INFORMATION: a, c, t, g, unknown or other
<220> FEATURE:
<221> NAME/KEY: modified_base
<222> LOCATION: (48)..(48)
<223> OTHER INFORMATION: a, c, t, g, unknown or other
<220> FEATURE:
<221> NAME/KEY: modified_base
<222> LOCATION: (51)..(51)
<223> OTHER INFORMATION: a, c, t, g, unknown or other
<220> FEATURE:
<221> NAME/KEY: modified_base
<222> LOCATION: (54)..(54)
<223> OTHER INFORMATION: a, c, t, g, unknown or other
<220> FEATURE:
<221> NAME/KEY: modified_base
<222> LOCATION: (57)..(57)
<223> OTHER INFORMATION: a, c, t, g, unknown or other
<220> FEATURE:
<221> NAME/KEY: modified_base
<222> LOCATION: (66)..(66)
<223> OTHER INFORMATION: a, c, t, g, unknown or other
<220> FEATURE:
<221> NAME/KEY: modified_base
<222> LOCATION: (75)..(75)
<223> OTHER INFORMATION: a, c, t, g, unknown or other
<220> FEATURE:
<221> NAME/KEY: modified_base
<222> LOCATION: (78)..(78)
<223> OTHER INFORMATION: a, c, t, g, unknown or other
<220> FEATURE:
<221> NAME/KEY: modified_base
<222> LOCATION: (81)..(81)
<223> OTHER INFORMATION: a, c, t, g, unknown or other
<220> FEATURE:
<221> NAME/KEY: modified_base
<222> LOCATION: (87)..(87)
<223> OTHER INFORMATION: a, c, t, g, unknown or other
<220> FEATURE:
<221> NAME/KEY: modified_base
<222> LOCATION: (93)..(93)
<223> OTHER INFORMATION: a, c, t, g, unknown or other
<220> FEATURE:
<221> NAME/KEY: modified_base
<222> LOCATION: (96)..(96)
<223> OTHER INFORMATION: a, c, t, g, unknown or other
<220> FEATURE:
<221> NAME/KEY: modified_base
<222> LOCATION: (114)..(114)
<223> OTHER INFORMATION: a, c, t, g, unknown or other
<220> FEATURE:
<221> NAME/KEY: modified_base
<222> LOCATION: (123)..(123)
<223> OTHER INFORMATION: a, c, t, g, unknown or other
<220> FEATURE:
<221> NAME/KEY: modified_base
<222> LOCATION: (126)..(126)
<223> OTHER INFORMATION: a, c, t, g, unknown or other
<220> FEATURE:
<221> NAME/KEY: modified_base
<222> LOCATION: (129)..(129)
<223> OTHER INFORMATION: a, c, t, g, unknown or other
<220> FEATURE:
<221> NAME/KEY: modified_base
<222> LOCATION: (132)..(132)
<223> OTHER INFORMATION: a, c, t, g, unknown or other
<220> FEATURE:
<221> NAME/KEY: modified_base
<222> LOCATION: (135)..(135)
<223> OTHER INFORMATION: a, c, t, g, unknown or other
```

-continued

```
<220> FEATURE:
<221> NAME/KEY: modified_base
<222> LOCATION: (138)..(138)
<223> OTHER INFORMATION: a, c, t, g, unknown or other
<220> FEATURE:
<221> NAME/KEY: modified_base
<222> LOCATION: (150)..(150)
<223> OTHER INFORMATION: a, c, t, g, unknown or other
<220> FEATURE:
<221> NAME/KEY: modified_base
<222> LOCATION: (153)..(153)
<223> OTHER INFORMATION: a, c, t, g, unknown or other
<220> FEATURE:
<221> NAME/KEY: modified_base
<222> LOCATION: (162)..(162)
<223> OTHER INFORMATION: a, c, t, g, unknown or other
<220> FEATURE:
<221> NAME/KEY: modified_base
<222> LOCATION: (165)..(165)
<223> OTHER INFORMATION: a, c, t, g, unknown or other
<220> FEATURE:
<221> NAME/KEY: modified_base
<222> LOCATION: (171)..(171)
<223> OTHER INFORMATION: a, c, t, g, unknown or other
<220> FEATURE:
<221> NAME/KEY: modified_base
<222> LOCATION: (177)..(177)
<223> OTHER INFORMATION: a, c, t, g, unknown or other
<220> FEATURE:
<221> NAME/KEY: modified_base
<222> LOCATION: (180)..(180)
<223> OTHER INFORMATION: a, c, t, g, unknown or other
<220> FEATURE:
<221> NAME/KEY: modified_base
<222> LOCATION: (201)..(201)
<223> OTHER INFORMATION: a, c, t, g, unknown or other
<220> FEATURE:
<221> NAME/KEY: modified_base
<222> LOCATION: (207)..(207)
<223> OTHER INFORMATION: a, c, t, g, unknown or other
<220> FEATURE:
<221> NAME/KEY: modified_base
<222> LOCATION: (210)..(210)
<223> OTHER INFORMATION: a, c, t, g, unknown or other
<220> FEATURE:
<221> NAME/KEY: modified_base
<222> LOCATION: (213)..(213)
<223> OTHER INFORMATION: a, c, t, g, unknown or other
<220> FEATURE:
<221> NAME/KEY: modified_base
<222> LOCATION: (216)..(216)
<223> OTHER INFORMATION: a, c, t, g, unknown or other
<220> FEATURE:
<221> NAME/KEY: modified_base
<222> LOCATION: (219)..(219)
<223> OTHER INFORMATION: a, c, t, g, unknown or other
<220> FEATURE:
<221> NAME/KEY: modified_base
<222> LOCATION: (228)..(228)
<223> OTHER INFORMATION: a, c, t, g, unknown or other
<220> FEATURE:
<221> NAME/KEY: modified_base
<222> LOCATION: (231)..(231)
<223> OTHER INFORMATION: a, c, t, g, unknown or other
<220> FEATURE:
<221> NAME/KEY: modified_base
<222> LOCATION: (234)..(234)
<223> OTHER INFORMATION: a, c, t, g, unknown or other
<220> FEATURE:
<221> NAME/KEY: modified_base
<222> LOCATION: (237)..(237)
<223> OTHER INFORMATION: a, c, t, g, unknown or other
<220> FEATURE:
<221> NAME/KEY: modified_base
<222> LOCATION: (240)..(240)
<223> OTHER INFORMATION: a, c, t, g, unknown or other
<220> FEATURE:
<221> NAME/KEY: modified_base
<222> LOCATION: (252)..(252)
```

```
<223> OTHER INFORMATION: a, c, t, g, unknown or other
<220> FEATURE:
<221> NAME/KEY: modified_base
<222> LOCATION: (255)..(255)
<223> OTHER INFORMATION: a, c, t, g, unknown or other
<220> FEATURE:
<221> NAME/KEY: modified_base
<222> LOCATION: (258)..(258)
<223> OTHER INFORMATION: a, c, t, g, unknown or other
<220> FEATURE:
<221> NAME/KEY: modified_base
<222> LOCATION: (261)..(261)
<223> OTHER INFORMATION: a, c, t, g, unknown or other
<220> FEATURE:
<221> NAME/KEY: modified_base
<222> LOCATION: (264)..(264)
<223> OTHER INFORMATION: a, c, t, g, unknown or other
<220> FEATURE:
<221> NAME/KEY: modified_base
<222> LOCATION: (267)..(267)
<223> OTHER INFORMATION: a, c, t, g, unknown or other
<220> FEATURE:
<221> NAME/KEY: modified_base
<222> LOCATION: (276)..(276)
<223> OTHER INFORMATION: a, c, t, g, unknown or other
<220> FEATURE:
<221> NAME/KEY: modified_base
<222> LOCATION: (279)..(279)
<223> OTHER INFORMATION: a, c, t, g, unknown or other
<220> FEATURE:
<221> NAME/KEY: modified_base
<222> LOCATION: (282)..(282)
<223> OTHER INFORMATION: a, c, t, g, unknown or other
<220> FEATURE:
<221> NAME/KEY: modified_base
<222> LOCATION: (294)..(294)
<223> OTHER INFORMATION: a, c, t, g, unknown or other
<220> FEATURE:
<221> NAME/KEY: modified_base
<222> LOCATION: (297)..(297)
<223> OTHER INFORMATION: a, c, t, g, unknown or other
<220> FEATURE:
<221> NAME/KEY: modified_base
<222> LOCATION: (300)..(300)
<223> OTHER INFORMATION: a, c, t, g, unknown or other
<220> FEATURE:
<221> NAME/KEY: modified_base
<222> LOCATION: (303)..(303)
<223> OTHER INFORMATION: a, c, t, g, unknown or other
<220> FEATURE:
<221> NAME/KEY: modified_base
<222> LOCATION: (312)..(312)
<223> OTHER INFORMATION: a, c, t, g, unknown or other
<220> FEATURE:
<221> NAME/KEY: modified_base
<222> LOCATION: (315)..(315)
<223> OTHER INFORMATION: a, c, t, g, unknown or other
<220> FEATURE:
<221> NAME/KEY: modified_base
<222> LOCATION: (333)..(333)
<223> OTHER INFORMATION: a, c, t, g, unknown or other
<220> FEATURE:
<221> NAME/KEY: modified_base
<222> LOCATION: (339)..(339)
<223> OTHER INFORMATION: a, c, t, g, unknown or other
<220> FEATURE:
<221> NAME/KEY: modified_base
<222> LOCATION: (342)..(342)
<223> OTHER INFORMATION: a, c, t, g, unknown or other
<220> FEATURE:
<221> NAME/KEY: modified_base
<222> LOCATION: (345)..(345)
<223> OTHER INFORMATION: a, c, t, g, unknown or other
<220> FEATURE:
<221> NAME/KEY: modified_base
<222> LOCATION: (348)..(348)
<223> OTHER INFORMATION: a, c, t, g, unknown or other
<220> FEATURE:
<221> NAME/KEY: modified_base
```

-continued

```
<222> LOCATION: (351)..(351)
<223> OTHER INFORMATION: a, c, t, g, unknown or other
<220> FEATURE:
<221> NAME/KEY: modified_base
<222> LOCATION: (354)..(354)
<223> OTHER INFORMATION: a, c, t, g, unknown or other
<220> FEATURE:
<221> NAME/KEY: modified_base
<222> LOCATION: (357)..(357)
<223> OTHER INFORMATION: a, c, t, g, unknown or other
<220> FEATURE:
<221> NAME/KEY: modified_base
<222> LOCATION: (360)..(360)
<223> OTHER INFORMATION: a, c, t, g, unknown or other
<220> FEATURE:
<221> NAME/KEY: modified_base
<222> LOCATION: (363)..(363)
<223> OTHER INFORMATION: a, c, t, g, unknown or other
<220> FEATURE:
<221> NAME/KEY: modified_base
<222> LOCATION: (366)..(366)
<223> OTHER INFORMATION: a, c, t, g, unknown or other
<220> FEATURE:
<221> NAME/KEY: modified_base
<222> LOCATION: (369)..(369)
<223> OTHER INFORMATION: a, c, t, g, unknown or other
<220> FEATURE:
<221> NAME/KEY: modified_base
<222> LOCATION: (372)..(372)
<223> OTHER INFORMATION: a, c, t, g, unknown or other
<220> FEATURE:
<221> NAME/KEY: modified_base
<222> LOCATION: (375)..(375)
<223> OTHER INFORMATION: a, c, t, g, unknown or other
<220> FEATURE:
<221> NAME/KEY: modified_base
<222> LOCATION: (378)..(378)
<223> OTHER INFORMATION: a, c, t, g, unknown or other
<220> FEATURE:
<221> NAME/KEY: modified_base
<222> LOCATION: (381)..(381)
<223> OTHER INFORMATION: a, c, t, g, unknown or other
<220> FEATURE:
<221> NAME/KEY: modified_base
<222> LOCATION: (384)..(384)
<223> OTHER INFORMATION: a, c, t, g, unknown or other
<220> FEATURE:
<221> NAME/KEY: modified_base
<222> LOCATION: (387)..(387)
<223> OTHER INFORMATION: a, c, t, g, unknown or other
<220> FEATURE:
<221> NAME/KEY: modified_base
<222> LOCATION: (393)..(393)
<223> OTHER INFORMATION: a, c, t, g, unknown or other
<220> FEATURE:
<221> NAME/KEY: modified_base
<222> LOCATION: (396)..(396)
<223> OTHER INFORMATION: a, c, t, g, unknown or other
<220> FEATURE:
<221> NAME/KEY: modified_base
<222> LOCATION: (399)..(399)
<223> OTHER INFORMATION: a, c, t, g, unknown or other
<220> FEATURE:
<221> NAME/KEY: modified_base
<222> LOCATION: (402)..(402)
<223> OTHER INFORMATION: a, c, t, g, unknown or other
<220> FEATURE:
<221> NAME/KEY: modified_base
<222> LOCATION: (408)..(408)
<223> OTHER INFORMATION: a, c, t, g, unknown or other
<220> FEATURE:
<221> NAME/KEY: modified_base
<222> LOCATION: (411)..(411)
<223> OTHER INFORMATION: a, c, t, g, unknown or other
<220> FEATURE:
<221> NAME/KEY: modified_base
<222> LOCATION: (414)..(414)
<223> OTHER INFORMATION: a, c, t, g, unknown or other
<220> FEATURE:
```

-continued

```
<221> NAME/KEY: modified_base
<222> LOCATION: (420)..(420)
<223> OTHER INFORMATION: a, c, t, g, unknown or other
<220> FEATURE:
<221> NAME/KEY: modified_base
<222> LOCATION: (429)..(429)
<223> OTHER INFORMATION: a, c, t, g, unknown or other
<220> FEATURE:
<221> NAME/KEY: modified_base
<222> LOCATION: (432)..(432)
<223> OTHER INFORMATION: a, c, t, g, unknown or other
<220> FEATURE:
<221> NAME/KEY: modified_base
<222> LOCATION: (435)..(435)
<223> OTHER INFORMATION: a, c, t, g, unknown or other
<220> FEATURE:
<221> NAME/KEY: modified_base
<222> LOCATION: (441)..(441)
<223> OTHER INFORMATION: a, c, t, g, unknown or other
<220> FEATURE:
<221> NAME/KEY: modified_base
<222> LOCATION: (444)..(444)
<223> OTHER INFORMATION: a, c, t, g, unknown or other
<220> FEATURE:
<221> NAME/KEY: modified_base
<222> LOCATION: (447)..(447)
<223> OTHER INFORMATION: a, c, t, g, unknown or other
<220> FEATURE:
<221> NAME/KEY: modified_base
<222> LOCATION: (453)..(453)
<223> OTHER INFORMATION: a, c, t, g, unknown or other
<220> FEATURE:
<221> NAME/KEY: modified_base
<222> LOCATION: (456)..(456)
<223> OTHER INFORMATION: a, c, t, g, unknown or other
<220> FEATURE:
<221> NAME/KEY: modified_base
<222> LOCATION: (459)..(459)
<223> OTHER INFORMATION: a, c, t, g, unknown or other
<220> FEATURE:
<221> NAME/KEY: modified_base
<222> LOCATION: (462)..(462)
<223> OTHER INFORMATION: a, c, t, g, unknown or other
<220> FEATURE:
<221> NAME/KEY: modified_base
<222> LOCATION: (465)..(465)
<223> OTHER INFORMATION: a, c, t, g, unknown or other
<220> FEATURE:
<221> NAME/KEY: modified_base
<222> LOCATION: (468)..(468)
<223> OTHER INFORMATION: a, c, t, g, unknown or other
<220> FEATURE:
<221> NAME/KEY: modified_base
<222> LOCATION: (477)..(477)
<223> OTHER INFORMATION: a, c, t, g, unknown or other
<220> FEATURE:
<221> NAME/KEY: modified_base
<222> LOCATION: (480)..(480)
<223> OTHER INFORMATION: a, c, t, g, unknown or other
<220> FEATURE:
<221> NAME/KEY: modified_base
<222> LOCATION: (486)..(486)
<223> OTHER INFORMATION: a, c, t, g, unknown or other
<220> FEATURE:
<221> NAME/KEY: modified_base
<222> LOCATION: (492)..(492)
<223> OTHER INFORMATION: a, c, t, g, unknown or other
<220> FEATURE:
<221> NAME/KEY: modified_base
<222> LOCATION: (495)..(495)
<223> OTHER INFORMATION: a, c, t, g, unknown or other
<220> FEATURE:
<221> NAME/KEY: modified_base
<222> LOCATION: (498)..(498)
<223> OTHER INFORMATION: a, c, t, g, unknown or other
<220> FEATURE:
<221> NAME/KEY: modified_base
<222> LOCATION: (501)..(501)
<223> OTHER INFORMATION: a, c, t, g, unknown or other
```

-continued

```
<220> FEATURE:
<221> NAME/KEY: modified_base
<222> LOCATION: (504)..(504)
<223> OTHER INFORMATION: a, c, t, g, unknown or other
<220> FEATURE:
<221> NAME/KEY: modified_base
<222> LOCATION: (507)..(507)
<223> OTHER INFORMATION: a, c, t, g, unknown or other
<220> FEATURE:
<221> NAME/KEY: modified_base
<222> LOCATION: (510)..(510)
<223> OTHER INFORMATION: a, c, t, g, unknown or other
<220> FEATURE:
<221> NAME/KEY: modified_base
<222> LOCATION: (537)..(537)
<223> OTHER INFORMATION: a, c, t, g, unknown or other
<220> FEATURE:
<221> NAME/KEY: modified_base
<222> LOCATION: (540)..(540)
<223> OTHER INFORMATION: a, c, t, g, unknown or other
<220> FEATURE:
<221> NAME/KEY: modified_base
<222> LOCATION: (543)..(543)
<223> OTHER INFORMATION: a, c, t, g, unknown or other
<220> FEATURE:
<221> NAME/KEY: modified_base
<222> LOCATION: (546)..(546)
<223> OTHER INFORMATION: a, c, t, g, unknown or other
<220> FEATURE:
<221> NAME/KEY: modified_base
<222> LOCATION: (549)..(549)
<223> OTHER INFORMATION: a, c, t, g, unknown or other
<220> FEATURE:
<221> NAME/KEY: modified_base
<222> LOCATION: (555)..(555)
<223> OTHER INFORMATION: a, c, t, g, unknown or other
<220> FEATURE:
<221> NAME/KEY: modified_base
<222> LOCATION: (567)..(567)
<223> OTHER INFORMATION: a, c, t, g, unknown or other
<220> FEATURE:
<221> NAME/KEY: modified_base
<222> LOCATION: (570)..(570)
<223> OTHER INFORMATION: a, c, t, g, unknown or other
<220> FEATURE:
<221> NAME/KEY: modified_base
<222> LOCATION: (573)..(573)
<223> OTHER INFORMATION: a, c, t, g, unknown or other
<220> FEATURE:
<221> NAME/KEY: modified_base
<222> LOCATION: (579)..(579)
<223> OTHER INFORMATION: a, c, t, g, unknown or other
<220> FEATURE:
<221> NAME/KEY: modified_base
<222> LOCATION: (582)..(582)
<223> OTHER INFORMATION: a, c, t, g, unknown or other
<220> FEATURE:
<221> NAME/KEY: modified_base
<222> LOCATION: (585)..(585)
<223> OTHER INFORMATION: a, c, t, g, unknown or other
<220> FEATURE:
<221> NAME/KEY: modified_base
<222> LOCATION: (588)..(588)
<223> OTHER INFORMATION: a, c, t, g, unknown or other
<220> FEATURE:
<221> NAME/KEY: modified_base
<222> LOCATION: (591)..(591)
<223> OTHER INFORMATION: a, c, t, g, unknown or other
<220> FEATURE:
<221> NAME/KEY: modified_base
<222> LOCATION: (594)..(594)
<223> OTHER INFORMATION: a, c, t, g, unknown or other
<220> FEATURE:
<221> NAME/KEY: modified_base
<222> LOCATION: (597)..(597)
<223> OTHER INFORMATION: a, c, t, g, unknown or other
<220> FEATURE:
<221> NAME/KEY: modified_base
<222> LOCATION: (600)..(600)
```

```
<223> OTHER INFORMATION: a, c, t, g, unknown or other
<220> FEATURE:
<221> NAME/KEY: modified_base
<222> LOCATION: (606)..(606)
<223> OTHER INFORMATION: a, c, t, g, unknown or other
<220> FEATURE:
<221> NAME/KEY: modified_base
<222> LOCATION: (609)..(609)
<223> OTHER INFORMATION: a, c, t, g, unknown or other
<220> FEATURE:
<221> NAME/KEY: modified_base
<222> LOCATION: (612)..(612)
<223> OTHER INFORMATION: a, c, t, g, unknown or other
<220> FEATURE:
<221> NAME/KEY: modified_base
<222> LOCATION: (615)..(615)
<223> OTHER INFORMATION: a, c, t, g, unknown or other
<220> FEATURE:
<221> NAME/KEY: modified_base
<222> LOCATION: (618)..(618)
<223> OTHER INFORMATION: a, c, t, g, unknown or other
<220> FEATURE:
<221> NAME/KEY: modified_base
<222> LOCATION: (621)..(621)
<223> OTHER INFORMATION: a, c, t, g, unknown or other
<220> FEATURE:
<221> NAME/KEY: modified_base
<222> LOCATION: (624)..(624)
<223> OTHER INFORMATION: a, c, t, g, unknown or other
<220> FEATURE:
<221> NAME/KEY: modified_base
<222> LOCATION: (627)..(627)
<223> OTHER INFORMATION: a, c, t, g, unknown or other
<220> FEATURE:
<221> NAME/KEY: modified_base
<222> LOCATION: (633)..(633)
<223> OTHER INFORMATION: a, c, t, g, unknown or other
<220> FEATURE:
<221> NAME/KEY: modified_base
<222> LOCATION: (636)..(636)
<223> OTHER INFORMATION: a, c, t, g, unknown or other
<220> FEATURE:
<221> NAME/KEY: modified_base
<222> LOCATION: (639)..(639)
<223> OTHER INFORMATION: a, c, t, g, unknown or other
<220> FEATURE:
<221> NAME/KEY: modified_base
<222> LOCATION: (645)..(645)
<223> OTHER INFORMATION: a, c, t, g, unknown or other
<220> FEATURE:
<221> NAME/KEY: modified_base
<222> LOCATION: (648)..(648)
<223> OTHER INFORMATION: a, c, t, g, unknown or other
<220> FEATURE:
<221> NAME/KEY: modified_base
<222> LOCATION: (651)..(651)
<223> OTHER INFORMATION: a, c, t, g, unknown or other
<220> FEATURE:
<221> NAME/KEY: modified_base
<222> LOCATION: (657)..(657)
<223> OTHER INFORMATION: a, c, t, g, unknown or other
<220> FEATURE:
<221> NAME/KEY: modified_base
<222> LOCATION: (666)..(666)
<223> OTHER INFORMATION: a, c, t, g, unknown or other
<220> FEATURE:
<221> NAME/KEY: modified_base
<222> LOCATION: (669)..(669)
<223> OTHER INFORMATION: a, c, t, g, unknown or other
<220> FEATURE:
<221> NAME/KEY: modified_base
<222> LOCATION: (672)..(672)
<223> OTHER INFORMATION: a, c, t, g, unknown or other
<220> FEATURE:
<221> NAME/KEY: modified_base
<222> LOCATION: (693)..(693)
<223> OTHER INFORMATION: a, c, t, g, unknown or other
<220> FEATURE:
<221> NAME/KEY: modified_base
```

-continued

```
<222> LOCATION: (696)..(696)
<223> OTHER INFORMATION: a, c, t, g, unknown or other
<220> FEATURE:
<221> NAME/KEY: modified_base
<222> LOCATION: (702)..(702)
<223> OTHER INFORMATION: a, c, t, g, unknown or other
<220> FEATURE:
<221> NAME/KEY: modified_base
<222> LOCATION: (705)..(705)
<223> OTHER INFORMATION: a, c, t, g, unknown or other
<220> FEATURE:
<221> NAME/KEY: modified_base
<222> LOCATION: (708)..(708)
<223> OTHER INFORMATION: a, c, t, g, unknown or other
<220> FEATURE:
<221> NAME/KEY: modified_base
<222> LOCATION: (714)..(714)
<223> OTHER INFORMATION: a, c, t, g, unknown or other
<220> FEATURE:
<221> NAME/KEY: modified_base
<222> LOCATION: (717)..(717)
<223> OTHER INFORMATION: a, c, t, g, unknown or other
<220> FEATURE:
<221> NAME/KEY: modified_base
<222> LOCATION: (720)..(720)
<223> OTHER INFORMATION: a, c, t, g, unknown or other
<220> FEATURE:
<221> NAME/KEY: modified_base
<222> LOCATION: (723)..(723)
<223> OTHER INFORMATION: a, c, t, g, unknown or other
<220> FEATURE:
<221> NAME/KEY: modified_base
<222> LOCATION: (729)..(729)
<223> OTHER INFORMATION: a, c, t, g, unknown or other
<220> FEATURE:
<221> NAME/KEY: modified_base
<222> LOCATION: (747)..(747)
<223> OTHER INFORMATION: a, c, t, g, unknown or other
<220> FEATURE:
<221> NAME/KEY: modified_base
<222> LOCATION: (753)..(753)
<223> OTHER INFORMATION: a, c, t, g, unknown or other
<220> FEATURE:
<221> NAME/KEY: modified_base
<222> LOCATION: (756)..(756)
<223> OTHER INFORMATION: a, c, t, g, unknown or other
<220> FEATURE:
<221> NAME/KEY: modified_base
<222> LOCATION: (759)..(759)
<223> OTHER INFORMATION: a, c, t, g, unknown or other
<220> FEATURE:
<221> NAME/KEY: modified_base
<222> LOCATION: (762)..(762)
<223> OTHER INFORMATION: a, c, t, g, unknown or other
<220> FEATURE:
<221> NAME/KEY: modified_base
<222> LOCATION: (765)..(765)
<223> OTHER INFORMATION: a, c, t, g, unknown or other
<220> FEATURE:
<221> NAME/KEY: modified_base
<222> LOCATION: (768)..(768)
<223> OTHER INFORMATION: a, c, t, g, unknown or other
<220> FEATURE:
<221> NAME/KEY: modified_base
<222> LOCATION: (771)..(771)
<223> OTHER INFORMATION: a, c, t, g, unknown or other
<220> FEATURE:
<221> NAME/KEY: modified_base
<222> LOCATION: (774)..(774)
<223> OTHER INFORMATION: a, c, t, g, unknown or other
<220> FEATURE:
<221> NAME/KEY: modified_base
<222> LOCATION: (777)..(777)
<223> OTHER INFORMATION: a, c, t, g, unknown or other
<220> FEATURE:
<221> NAME/KEY: modified_base
<222> LOCATION: (780)..(780)
<223> OTHER INFORMATION: a, c, t, g, unknown or other
<220> FEATURE:
```

```
<221> NAME/KEY: modified_base
<222> LOCATION: (783)..(783)
<223> OTHER INFORMATION: a, c, t, g, unknown or other
<220> FEATURE:
<221> NAME/KEY: modified_base
<222> LOCATION: (786)..(786)
<223> OTHER INFORMATION: a, c, t, g, unknown or other
<220> FEATURE:
<221> NAME/KEY: modified_base
<222> LOCATION: (798)..(798)
<223> OTHER INFORMATION: a, c, t, g, unknown or other
<220> FEATURE:
<221> NAME/KEY: modified_base
<222> LOCATION: (801)..(801)
<223> OTHER INFORMATION: a, c, t, g, unknown or other
<220> FEATURE:
<221> NAME/KEY: modified_base
<222> LOCATION: (810)..(810)
<223> OTHER INFORMATION: a, c, t, g, unknown or other
<220> FEATURE:
<221> NAME/KEY: modified_base
<222> LOCATION: (813)..(813)
<223> OTHER INFORMATION: a, c, t, g, unknown or other
<220> FEATURE:
<221> NAME/KEY: modified_base
<222> LOCATION: (816)..(816)
<223> OTHER INFORMATION: a, c, t, g, unknown or other
<220> FEATURE:
<221> NAME/KEY: modified_base
<222> LOCATION: (822)..(822)
<223> OTHER INFORMATION: a, c, t, g, unknown or other
<220> FEATURE:
<221> NAME/KEY: modified_base
<222> LOCATION: (828)..(828)
<223> OTHER INFORMATION: a, c, t, g, unknown or other
<220> FEATURE:
<221> NAME/KEY: modified_base
<222> LOCATION: (834)..(834)
<223> OTHER INFORMATION: a, c, t, g, unknown or other
<220> FEATURE:
<221> NAME/KEY: modified_base
<222> LOCATION: (837)..(837)
<223> OTHER INFORMATION: a, c, t, g, unknown or other
<220> FEATURE:
<221> NAME/KEY: modified_base
<222> LOCATION: (843)..(843)
<223> OTHER INFORMATION: a, c, t, g, unknown or other
<220> FEATURE:
<221> NAME/KEY: modified_base
<222> LOCATION: (849)..(849)
<223> OTHER INFORMATION: a, c, t, g, unknown or other
<220> FEATURE:
<221> NAME/KEY: modified_base
<222> LOCATION: (852)..(852)
<223> OTHER INFORMATION: a, c, t, g, unknown or other
<220> FEATURE:
<221> NAME/KEY: modified_base
<222> LOCATION: (855)..(855)
<223> OTHER INFORMATION: a, c, t, g, unknown or other
<220> FEATURE:
<221> NAME/KEY: modified_base
<222> LOCATION: (861)..(861)
<223> OTHER INFORMATION: a, c, t, g, unknown or other
<220> FEATURE:
<221> NAME/KEY: modified_base
<222> LOCATION: (864)..(864)
<223> OTHER INFORMATION: a, c, t, g, unknown or other
<220> FEATURE:
<221> NAME/KEY: modified_base
<222> LOCATION: (867)..(867)
<223> OTHER INFORMATION: a, c, t, g, unknown or other
<220> FEATURE:
<221> NAME/KEY: modified_base
<222> LOCATION: (870)..(870)
<223> OTHER INFORMATION: a, c, t, g, unknown or other
<220> FEATURE:
<221> NAME/KEY: modified_base
<222> LOCATION: (876)..(876)
<223> OTHER INFORMATION: a, c, t, g, unknown or other
```

```
-continued

<220> FEATURE:
<221> NAME/KEY: modified_base
<222> LOCATION: (882)..(882)
<223> OTHER INFORMATION: a, c, t, g, unknown or other
<220> FEATURE:
<221> NAME/KEY: modified_base
<222> LOCATION: (885)..(885)
<223> OTHER INFORMATION: a, c, t, g, unknown or other
<220> FEATURE:
<221> NAME/KEY: modified_base
<222> LOCATION: (888)..(888)
<223> OTHER INFORMATION: a, c, t, g, unknown or other
<220> FEATURE:
<221> NAME/KEY: modified_base
<222> LOCATION: (891)..(891)
<223> OTHER INFORMATION: a, c, t, g, unknown or other
<220> FEATURE:
<221> NAME/KEY: modified_base
<222> LOCATION: (894)..(894)
<223> OTHER INFORMATION: a, c, t, g, unknown or other
<220> FEATURE:
<221> NAME/KEY: modified_base
<222> LOCATION: (897)..(897)
<223> OTHER INFORMATION: a, c, t, g, unknown or other
<220> FEATURE:
<221> NAME/KEY: modified_base
<222> LOCATION: (900)..(900)
<223> OTHER INFORMATION: a, c, t, g, unknown or other
<220> FEATURE:
<221> NAME/KEY: modified_base
<222> LOCATION: (903)..(903)
<223> OTHER INFORMATION: a, c, t, g, unknown or other
<220> FEATURE:
<221> NAME/KEY: modified_base
<222> LOCATION: (915)..(915)
<223> OTHER INFORMATION: a, c, t, g, unknown or other
<220> FEATURE:
<221> NAME/KEY: modified_base
<222> LOCATION: (918)..(918)
<223> OTHER INFORMATION: a, c, t, g, unknown or other
<220> FEATURE:
<221> NAME/KEY: modified_base
<222> LOCATION: (921)..(921)
<223> OTHER INFORMATION: a, c, t, g, unknown or other
<220> FEATURE:
<221> NAME/KEY: modified_base
<222> LOCATION: (924)..(924)
<223> OTHER INFORMATION: a, c, t, g, unknown or other
<220> FEATURE:
<221> NAME/KEY: modified_base
<222> LOCATION: (933)..(933)
<223> OTHER INFORMATION: a, c, t, g, unknown or other
<220> FEATURE:
<221> NAME/KEY: modified_base
<222> LOCATION: (939)..(939)
<223> OTHER INFORMATION: a, c, t, g, unknown or other
<220> FEATURE:
<221> NAME/KEY: modified_base
<222> LOCATION: (942)..(942)
<223> OTHER INFORMATION: a, c, t, g, unknown or other
<220> FEATURE:
<221> NAME/KEY: modified_base
<222> LOCATION: (948)..(948)
<223> OTHER INFORMATION: a, c, t, g, unknown or other
<220> FEATURE:
<221> NAME/KEY: modified_base
<222> LOCATION: (951)..(951)
<223> OTHER INFORMATION: a, c, t, g, unknown or other
<220> FEATURE:
<221> NAME/KEY: modified_base
<222> LOCATION: (954)..(954)
<223> OTHER INFORMATION: a, c, t, g, unknown or other
<220> FEATURE:
<221> NAME/KEY: modified_base
<222> LOCATION: (963)..(963)
<223> OTHER INFORMATION: a, c, t, g, unknown or other
<220> FEATURE:
<221> NAME/KEY: modified_base
<222> LOCATION: (972)..(972)
```

-continued

```
<223> OTHER INFORMATION: a, c, t, g, unknown or other
<220> FEATURE:
<221> NAME/KEY: modified_base
<222> LOCATION: (975)..(975)
<223> OTHER INFORMATION: a, c, t, g, unknown or other
<220> FEATURE:
<221> NAME/KEY: modified_base
<222> LOCATION: (987)..(987)
<223> OTHER INFORMATION: a, c, t, g, unknown or other
<220> FEATURE:
<221> NAME/KEY: modified_base
<222> LOCATION: (990)..(990)
<223> OTHER INFORMATION: a, c, t, g, unknown or other
<220> FEATURE:
<221> NAME/KEY: modified_base
<222> LOCATION: (993)..(993)
<223> OTHER INFORMATION: a, c, t, g, unknown or other
<220> FEATURE:
<221> NAME/KEY: modified_base
<222> LOCATION: (999)..(999)
<223> OTHER INFORMATION: a, c, t, g, unknown or other
<220> FEATURE:
<221> NAME/KEY: modified_base
<222> LOCATION: (1005)..(1005)
<223> OTHER INFORMATION: a, c, t, g, unknown or other
<220> FEATURE:
<221> NAME/KEY: modified_base
<222> LOCATION: (1014)..(1014)
<223> OTHER INFORMATION: a, c, t, g, unknown or other
<220> FEATURE:
<221> NAME/KEY: modified_base
<222> LOCATION: (1020)..(1020)
<223> OTHER INFORMATION: a, c, t, g, unknown or other
<220> FEATURE:
<221> NAME/KEY: modified_base
<222> LOCATION: (1023)..(1023)
<223> OTHER INFORMATION: a, c, t, g, unknown or other
<220> FEATURE:
<221> NAME/KEY: modified_base
<222> LOCATION: (1026)..(1026)
<223> OTHER INFORMATION: a, c, t, g, unknown or other
<220> FEATURE:
<221> NAME/KEY: modified_base
<222> LOCATION: (1032)..(1032)
<223> OTHER INFORMATION: a, c, t, g, unknown or other
<220> FEATURE:
<221> NAME/KEY: modified_base
<222> LOCATION: (1038)..(1038)
<223> OTHER INFORMATION: a, c, t, g, unknown or other
<220> FEATURE:
<221> NAME/KEY: modified_base
<222> LOCATION: (1041)..(1041)
<223> OTHER INFORMATION: a, c, t, g, unknown or other
<220> FEATURE:
<221> NAME/KEY: modified_base
<222> LOCATION: (1050)..(1050)
<223> OTHER INFORMATION: a, c, t, g, unknown or other
<220> FEATURE:
<221> NAME/KEY: modified_base
<222> LOCATION: (1059)..(1059)
<223> OTHER INFORMATION: a, c, t, g, unknown or other
<220> FEATURE:
<221> NAME/KEY: modified_base
<222> LOCATION: (1065)..(1065)
<223> OTHER INFORMATION: a, c, t, g, unknown or other
<220> FEATURE:
<221> NAME/KEY: modified_base
<222> LOCATION: (1074)..(1074)
<223> OTHER INFORMATION: a, c, t, g, unknown or other
<220> FEATURE:
<221> NAME/KEY: modified_base
<222> LOCATION: (1080)..(1080)
<223> OTHER INFORMATION: a, c, t, g, unknown or other
<220> FEATURE:
<221> NAME/KEY: modified_base
<222> LOCATION: (1083)..(1083)
<223> OTHER INFORMATION: a, c, t, g, unknown or other
<220> FEATURE:
<221> NAME/KEY: modified_base
```

```
<222> LOCATION: (1089)..(1089)
<223> OTHER INFORMATION: a, c, t, g, unknown or other
<220> FEATURE:
<221> NAME/KEY: modified_base
<222> LOCATION: (1092)..(1092)
<223> OTHER INFORMATION: a, c, t, g, unknown or other
<220> FEATURE:
<221> NAME/KEY: modified_base
<222> LOCATION: (1095)..(1095)
<223> OTHER INFORMATION: a, c, t, g, unknown or other
<220> FEATURE:
<221> NAME/KEY: modified_base
<222> LOCATION: (1098)..(1098)
<223> OTHER INFORMATION: a, c, t, g, unknown or other
<220> FEATURE:
<221> NAME/KEY: modified_base
<222> LOCATION: (1101)..(1101)
<223> OTHER INFORMATION: a, c, t, g, unknown or other
<220> FEATURE:
<221> NAME/KEY: modified_base
<222> LOCATION: (1104)..(1104)
<223> OTHER INFORMATION: a, c, t, g, unknown or other
<220> FEATURE:
<221> NAME/KEY: modified_base
<222> LOCATION: (1107)..(1107)
<223> OTHER INFORMATION: a, c, t, g, unknown or other
<220> FEATURE:
<221> NAME/KEY: modified_base
<222> LOCATION: (1110)..(1110)
<223> OTHER INFORMATION: a, c, t, g, unknown or other
<220> FEATURE:
<221> NAME/KEY: modified_base
<222> LOCATION: (1113)..(1113)
<223> OTHER INFORMATION: a, c, t, g, unknown or other
<220> FEATURE:
<221> NAME/KEY: modified_base
<222> LOCATION: (1116)..(1116)
<223> OTHER INFORMATION: a, c, t, g, unknown or other
<220> FEATURE:
<221> NAME/KEY: modified_base
<222> LOCATION: (1122)..(1122)
<223> OTHER INFORMATION: a, c, t, g, unknown or other
<220> FEATURE:
<221> NAME/KEY: modified_base
<222> LOCATION: (1125)..(1125)
<223> OTHER INFORMATION: a, c, t, g, unknown or other
<220> FEATURE:
<221> NAME/KEY: modified_base
<222> LOCATION: (1131)..(1131)
<223> OTHER INFORMATION: a, c, t, g, unknown or other
<220> FEATURE:
<221> NAME/KEY: modified_base
<222> LOCATION: (1134)..(1134)
<223> OTHER INFORMATION: a, c, t, g, unknown or other
<220> FEATURE:
<221> NAME/KEY: modified_base
<222> LOCATION: (1137)..(1137)
<223> OTHER INFORMATION: a, c, t, g, unknown or other
<220> FEATURE:
<221> NAME/KEY: modified_base
<222> LOCATION: (1143)..(1143)
<223> OTHER INFORMATION: a, c, t, g, unknown or other
<220> FEATURE:
<221> NAME/KEY: modified_base
<222> LOCATION: (1146)..(1146)
<223> OTHER INFORMATION: a, c, t, g, unknown or other
<220> FEATURE:
<221> NAME/KEY: modified_base
<222> LOCATION: (1149)..(1149)
<223> OTHER INFORMATION: a, c, t, g, unknown or other
<220> FEATURE:
<221> NAME/KEY: modified_base
<222> LOCATION: (1152)..(1152)
<223> OTHER INFORMATION: a, c, t, g, unknown or other
<220> FEATURE:
<221> NAME/KEY: modified_base
<222> LOCATION: (1158)..(1158)
<223> OTHER INFORMATION: a, c, t, g, unknown or other
<220> FEATURE:
```

```
<221> NAME/KEY: modified_base
<222> LOCATION: (1161)..(1161)
<223> OTHER INFORMATION: a, c, t, g, unknown or other
<220> FEATURE:
<221> NAME/KEY: modified_base
<222> LOCATION: (1164)..(1164)
<223> OTHER INFORMATION: a, c, t, g, unknown or other
<220> FEATURE:
<221> NAME/KEY: modified_base
<222> LOCATION: (1167)..(1167)
<223> OTHER INFORMATION: a, c, t, g, unknown or other
<220> FEATURE:
<221> NAME/KEY: modified_base
<222> LOCATION: (1182)..(1182)
<223> OTHER INFORMATION: a, c, t, g, unknown or other
<220> FEATURE:
<221> NAME/KEY: modified_base
<222> LOCATION: (1188)..(1188)
<223> OTHER INFORMATION: a, c, t, g, unknown or other
<220> FEATURE:
<221> NAME/KEY: modified_base
<222> LOCATION: (1191)..(1191)
<223> OTHER INFORMATION: a, c, t, g, unknown or other
<220> FEATURE:
<221> NAME/KEY: modified_base
<222> LOCATION: (1194)..(1194)
<223> OTHER INFORMATION: a, c, t, g, unknown or other
<220> FEATURE:
<221> NAME/KEY: modified_base
<222> LOCATION: (1197)..(1197)
<223> OTHER INFORMATION: a, c, t, g, unknown or other
<220> FEATURE:
<221> NAME/KEY: modified_base
<222> LOCATION: (1200)..(1200)
<223> OTHER INFORMATION: a, c, t, g, unknown or other
<220> FEATURE:
<221> NAME/KEY: modified_base
<222> LOCATION: (1206)..(1206)
<223> OTHER INFORMATION: a, c, t, g, unknown or other
<220> FEATURE:
<221> NAME/KEY: modified_base
<222> LOCATION: (1212)..(1212)
<223> OTHER INFORMATION: a, c, t, g, unknown or other
<220> FEATURE:
<221> NAME/KEY: modified_base
<222> LOCATION: (1218)..(1218)
<223> OTHER INFORMATION: a, c, t, g, unknown or other
<220> FEATURE:
<221> NAME/KEY: modified_base
<222> LOCATION: (1224)..(1224)
<223> OTHER INFORMATION: a, c, t, g, unknown or other
<220> FEATURE:
<221> NAME/KEY: modified_base
<222> LOCATION: (1227)..(1227)
<223> OTHER INFORMATION: a, c, t, g, unknown or other
<220> FEATURE:
<221> NAME/KEY: modified_base
<222> LOCATION: (1230)..(1230)
<223> OTHER INFORMATION: a, c, t, g, unknown or other
<220> FEATURE:
<221> NAME/KEY: modified_base
<222> LOCATION: (1233)..(1233)
<223> OTHER INFORMATION: a, c, t, g, unknown or other
<220> FEATURE:
<221> NAME/KEY: modified_base
<222> LOCATION: (1236)..(1236)
<223> OTHER INFORMATION: a, c, t, g, unknown or other
<220> FEATURE:
<221> NAME/KEY: modified_base
<222> LOCATION: (1239)..(1239)
<223> OTHER INFORMATION: a, c, t, g, unknown or other
<220> FEATURE:
<221> NAME/KEY: modified_base
<222> LOCATION: (1245)..(1245)
<223> OTHER INFORMATION: a, c, t, g, unknown or other
<220> FEATURE:
<221> NAME/KEY: modified_base
<222> LOCATION: (1248)..(1248)
<223> OTHER INFORMATION: a, c, t, g, unknown or other
```

-continued

```
<220> FEATURE:
<221> NAME/KEY: modified_base
<222> LOCATION: (1251)..(1251)
<223> OTHER INFORMATION: a, c, t, g, unknown or other
<220> FEATURE:
<221> NAME/KEY: modified_base
<222> LOCATION: (1254)..(1254)
<223> OTHER INFORMATION: a, c, t, g, unknown or other
<220> FEATURE:
<221> NAME/KEY: modified_base
<222> LOCATION: (1257)..(1257)
<223> OTHER INFORMATION: a, c, t, g, unknown or other
<220> FEATURE:
<221> NAME/KEY: modified_base
<222> LOCATION: (1263)..(1263)
<223> OTHER INFORMATION: a, c, t, g, unknown or other
<220> FEATURE:
<221> NAME/KEY: modified_base
<222> LOCATION: (1266)..(1266)
<223> OTHER INFORMATION: a, c, t, g, unknown or other
<220> FEATURE:
<221> NAME/KEY: modified_base
<222> LOCATION: (1272)..(1272)
<223> OTHER INFORMATION: a, c, t, g, unknown or other
<220> FEATURE:
<221> NAME/KEY: modified_base
<222> LOCATION: (1275)..(1275)
<223> OTHER INFORMATION: a, c, t, g, unknown or other
<220> FEATURE:
<221> NAME/KEY: modified_base
<222> LOCATION: (1278)..(1278)
<223> OTHER INFORMATION: a, c, t, g, unknown or other
<220> FEATURE:
<221> NAME/KEY: modified_base
<222> LOCATION: (1281)..(1281)
<223> OTHER INFORMATION: a, c, t, g, unknown or other
<220> FEATURE:
<221> NAME/KEY: modified_base
<222> LOCATION: (1284)..(1284)
<223> OTHER INFORMATION: a, c, t, g, unknown or other
<220> FEATURE:
<221> NAME/KEY: modified_base
<222> LOCATION: (1290)..(1290)
<223> OTHER INFORMATION: a, c, t, g, unknown or other
<220> FEATURE:
<221> NAME/KEY: modified_base
<222> LOCATION: (1293)..(1293)
<223> OTHER INFORMATION: a, c, t, g, unknown or other
<220> FEATURE:
<221> NAME/KEY: modified_base
<222> LOCATION: (1296)..(1296)
<223> OTHER INFORMATION: a, c, t, g, unknown or other
<220> FEATURE:
<221> NAME/KEY: modified_base
<222> LOCATION: (1302)..(1302)
<223> OTHER INFORMATION: a, c, t, g, unknown or other
<220> FEATURE:
<221> NAME/KEY: modified_base
<222> LOCATION: (1314)..(1314)
<223> OTHER INFORMATION: a, c, t, g, unknown or other
<220> FEATURE:
<221> NAME/KEY: modified_base
<222> LOCATION: (1317)..(1317)
<223> OTHER INFORMATION: a, c, t, g, unknown or other
<220> FEATURE:
<221> NAME/KEY: modified_base
<222> LOCATION: (1323)..(1323)
<223> OTHER INFORMATION: a, c, t, g, unknown or other
<220> FEATURE:
<221> NAME/KEY: modified_base
<222> LOCATION: (1326)..(1326)
<223> OTHER INFORMATION: a, c, t, g, unknown or other
<220> FEATURE:
<221> NAME/KEY: modified_base
<222> LOCATION: (1329)..(1329)
<223> OTHER INFORMATION: a, c, t, g, unknown or other
<220> FEATURE:
<221> NAME/KEY: modified_base
<222> LOCATION: (1332)..(1332)
```

```
<223> OTHER INFORMATION: a, c, t, g, unknown or other
<220> FEATURE:
<221> NAME/KEY: modified_base
<222> LOCATION: (1341)..(1341)
<223> OTHER INFORMATION: a, c, t, g, unknown or other
<220> FEATURE:
<221> NAME/KEY: modified_base
<222> LOCATION: (1344)..(1344)
<223> OTHER INFORMATION: a, c, t, g, unknown or other
<220> FEATURE:
<221> NAME/KEY: modified_base
<222> LOCATION: (1347)..(1347)
<223> OTHER INFORMATION: a, c, t, g, unknown or other
<220> FEATURE:
<221> NAME/KEY: modified_base
<222> LOCATION: (1350)..(1350)
<223> OTHER INFORMATION: a, c, t, g, unknown or other
<220> FEATURE:
<221> NAME/KEY: modified_base
<222> LOCATION: (1353)..(1353)
<223> OTHER INFORMATION: a, c, t, g, unknown or other
<220> FEATURE:
<221> NAME/KEY: modified_base
<222> LOCATION: (1359)..(1359)
<223> OTHER INFORMATION: a, c, t, g, unknown or other
<220> FEATURE:
<221> NAME/KEY: modified_base
<222> LOCATION: (1365)..(1365)
<223> OTHER INFORMATION: a, c, t, g, unknown or other
<220> FEATURE:
<221> NAME/KEY: modified_base
<222> LOCATION: (1368)..(1368)
<223> OTHER INFORMATION: a, c, t, g, unknown or other
<220> FEATURE:
<221> NAME/KEY: modified_base
<222> LOCATION: (1377)..(1377)
<223> OTHER INFORMATION: a, c, t, g, unknown or other
<220> FEATURE:
<221> NAME/KEY: modified_base
<222> LOCATION: (1383)..(1383)
<223> OTHER INFORMATION: a, c, t, g, unknown or other
<220> FEATURE:
<221> NAME/KEY: modified_base
<222> LOCATION: (1386)..(1386)
<223> OTHER INFORMATION: a, c, t, g, unknown or other
<220> FEATURE:
<221> NAME/KEY: modified_base
<222> LOCATION: (1389)..(1389)
<223> OTHER INFORMATION: a, c, t, g, unknown or other
<220> FEATURE:
<221> NAME/KEY: modified_base
<222> LOCATION: (1398)..(1398)
<223> OTHER INFORMATION: a, c, t, g, unknown or other
<220> FEATURE:
<221> NAME/KEY: modified_base
<222> LOCATION: (1401)..(1401)
<223> OTHER INFORMATION: a, c, t, g, unknown or other
<220> FEATURE:
<221> NAME/KEY: modified_base
<222> LOCATION: (1404)..(1404)
<223> OTHER INFORMATION: a, c, t, g, unknown or other
<220> FEATURE:
<221> NAME/KEY: modified_base
<222> LOCATION: (1407)..(1407)
<223> OTHER INFORMATION: a, c, t, g, unknown or other
<220> FEATURE:
<221> NAME/KEY: modified_base
<222> LOCATION: (1410)..(1410)
<223> OTHER INFORMATION: a, c, t, g, unknown or other
<220> FEATURE:
<221> NAME/KEY: modified_base
<222> LOCATION: (1413)..(1413)
<223> OTHER INFORMATION: a, c, t, g, unknown or other
<220> FEATURE:
<221> NAME/KEY: modified_base
<222> LOCATION: (1416)..(1416)
<223> OTHER INFORMATION: a, c, t, g, unknown or other
<220> FEATURE:
<221> NAME/KEY: modified_base
```

```
<222> LOCATION: (1419)..(1419)
<223> OTHER INFORMATION: a, c, t, g, unknown or other
<220> FEATURE:
<221> NAME/KEY: modified_base
<222> LOCATION: (1431)..(1431)
<223> OTHER INFORMATION: a, c, t, g, unknown or other
<220> FEATURE:
<221> NAME/KEY: modified_base
<222> LOCATION: (1440)..(1440)
<223> OTHER INFORMATION: a, c, t, g, unknown or other
<220> FEATURE:
<221> NAME/KEY: modified_base
<222> LOCATION: (1443)..(1443)
<223> OTHER INFORMATION: a, c, t, g, unknown or other
<220> FEATURE:
<221> NAME/KEY: modified_base
<222> LOCATION: (1446)..(1446)
<223> OTHER INFORMATION: a, c, t, g, unknown or other
<220> FEATURE:
<221> NAME/KEY: modified_base
<222> LOCATION: (1449)..(1449)
<223> OTHER INFORMATION: a, c, t, g, unknown or other
<220> FEATURE:
<221> NAME/KEY: modified_base
<222> LOCATION: (1452)..(1452)
<223> OTHER INFORMATION: a, c, t, g, unknown or other
<220> FEATURE:
<221> NAME/KEY: modified_base
<222> LOCATION: (1455)..(1455)
<223> OTHER INFORMATION: a, c, t, g, unknown or other
<220> FEATURE:
<221> NAME/KEY: modified_base
<222> LOCATION: (1461)..(1461)
<223> OTHER INFORMATION: a, c, t, g, unknown or other
<220> FEATURE:
<221> NAME/KEY: modified_base
<222> LOCATION: (1467)..(1467)
<223> OTHER INFORMATION: a, c, t, g, unknown or other
<220> FEATURE:
<221> NAME/KEY: modified_base
<222> LOCATION: (1470)..(1470)
<223> OTHER INFORMATION: a, c, t, g, unknown or other
<220> FEATURE:
<221> NAME/KEY: modified_base
<222> LOCATION: (1479)..(1479)
<223> OTHER INFORMATION: a, c, t, g, unknown or other
<220> FEATURE:
<221> NAME/KEY: modified_base
<222> LOCATION: (1485)..(1485)
<223> OTHER INFORMATION: a, c, t, g, unknown or other
<220> FEATURE:
<221> NAME/KEY: modified_base
<222> LOCATION: (1488)..(1488)
<223> OTHER INFORMATION: a, c, t, g, unknown or other
<220> FEATURE:
<221> NAME/KEY: modified_base
<222> LOCATION: (1491)..(1491)
<223> OTHER INFORMATION: a, c, t, g, unknown or other
<220> FEATURE:
<221> NAME/KEY: modified_base
<222> LOCATION: (1494)..(1494)
<223> OTHER INFORMATION: a, c, t, g, unknown or other
<220> FEATURE:
<221> NAME/KEY: modified_base
<222> LOCATION: (1497)..(1497)
<223> OTHER INFORMATION: a, c, t, g, unknown or other
<220> FEATURE:
<221> NAME/KEY: modified_base
<222> LOCATION: (1500)..(1500)
<223> OTHER INFORMATION: a, c, t, g, unknown or other
<220> FEATURE:
<221> NAME/KEY: modified_base
<222> LOCATION: (1506)..(1506)
<223> OTHER INFORMATION: a, c, t, g, unknown or other
<220> FEATURE:
<221> NAME/KEY: modified_base
<222> LOCATION: (1524)..(1524)
<223> OTHER INFORMATION: a, c, t, g, unknown or other
<220> FEATURE:
```

<221> NAME/KEY: modified_base
<222> LOCATION: (1527)..(1527)
<223> OTHER INFORMATION: a, c, t, g, unknown or other
<220> FEATURE:
<221> NAME/KEY: modified_base
<222> LOCATION: (1530)..(1530)
<223> OTHER INFORMATION: a, c, t, g, unknown or other
<220> FEATURE:
<221> NAME/KEY: modified_base
<222> LOCATION: (1533)..(1533)
<223> OTHER INFORMATION: a, c, t, g, unknown or other
<220> FEATURE:
<221> NAME/KEY: modified_base
<222> LOCATION: (1536)..(1536)
<223> OTHER INFORMATION: a, c, t, g, unknown or other
<220> FEATURE:
<221> NAME/KEY: modified_base
<222> LOCATION: (1539)..(1539)
<223> OTHER INFORMATION: a, c, t, g, unknown or other

<400> SEQUENCE: 15
atgcargtnc arytncarca rccnggngcn garytngtna arccnggngc nwsngtnaar 60
atgwsntgya argcnwsngg ntayacntty acnwsntaya ayatgcaytg ggtnaarcar 120
acnccnggnm gnggnytnga rtggathggn gcnathtayc cnggnaaygg ngayacnwsn 180
tayaaycara arttyaargg naargcnacn ytnacngcng ayaarwsnws nwsnacngcn 240
tayatgcary tnwsnwsnyt nacnwsngar gaywsngcng tntaytaytg ygcnmgnwsn 300
acntaytayg gnggngaytg gtayttyaay gtntggggng cnggnacnac ngtnacngtn 360
wsngcnggnw snacnwsngg nwsnggnaar ccnggnwsng gngarggnws nacnaarggn 420
carathgtny tnwsncarws nccngcnath ytnwsngcnw snccnggnga raargtnacn 480
atgacntgym gngcnwsnws nwsngtnwsn tayathcayt ggttycarca raarccnggn 540
wsnwsnccna arccntggat htaygcnacn wsnaayytng cnwsnggngt nccngtnmgn 600
ttywsnggnw snggnwsngg nacnwsntay wsnytnacna thwsnmgngt ngargcngar 660
gaygcngcna cntaytaytg ycarcartgg acnwsnaayc cnccnacntt yggnggnggn 720
acnaarytng arathaarga rttyccnaar ccnwsnacnc cnccnggnws nwsnggnggn 780
gcnccnaarg arttyacnyt ngayttywsn acngcnaara cntaygtnga ywsnytnaay 840
gtnathmgnw sngcnathgg nacnccnytn caracnathw snwsnggngg nacnwsnytn 900
ytnatgathg aywsnggnws nggngayaay ytnttygcng tngaygtnmg nggnathgay 960
ccngargarg gnmgnttyaa yaayytnmgn ytnathgtng armgnaayaa yytntaygtn 1020
acnggnttyg tnaaymgnac naayaaygtn ttytaymgnt tygcngaytt ywsncaygtn 1080
acnttyccng gnacnacngc ngtnacnytn wsnggngayw snwsntayac nacnytncar 1140
mgngtngcng gnathwsnmg nacnggnatg carathaaym gncaywsnyt nacnacnwsn 1200
tayytngayy tnatgwsnca ywsnggnacn wsnytnacnc arwsngtngc nmgngcnatg 1260
ytnmgnttyg tnacngtnac ngcngargcn ytnmgnttym gncarathca rmgnggntty 1320
mgnacnacny tngaygayyt nwsnggnmgn wsntaygtna tgacngcnga rgaygtngay 1380
ytnacnytna aytggggnmg nytnwsnwsn gtnytnccng aytaycaygg ncargaywsn 1440
gtnmgngtng gnmgnathws nttyggnwsn athaaygcna thytnggnws ngtngcnytn 1500
athytnaayt gycaycayca ygcnwsnmgn gtngcnmgn 1539

<210> SEQ ID NO 16
<211> LENGTH: 521
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Gln Val Gln Leu Gln Gln Pro Gly Ala Glu Leu Val Lys Pro Gly
1               5                   10                  15

Ala Ser Val Lys Met Ser Cys Lys Thr Ser Gly Tyr Thr Phe Thr Ser
            20                  25                  30

Tyr Asn Val His Trp Val Lys Gln Thr Pro Gly Gln Gly Leu Glu Trp
        35                  40                  45

Ile Gly Ala Ile Tyr Pro Gly Asn Gly Asp Thr Ser Phe Asn Gln Lys
50                  55                  60

Phe Lys Gly Lys Ala Thr Leu Thr Ala Asp Lys Ser Ser Ser Thr Val
65                  70                  75                  80

Tyr Met Gln Leu Ser Ser Leu Thr Ser Glu Asp Ser Ala Val Tyr Tyr
                85                  90                  95

Cys Ala Arg Ser Asn Tyr Tyr Gly Ser Ser Tyr Val Trp Phe Phe Asp
            100                 105                 110

Val Trp Gly Ala Gly Thr Thr Val Thr Val Ser Ser Gly Ser Thr Ser
        115                 120                 125

Gly Ser Gly Lys Pro Gly Ser Gly Glu Gly Ser Gln Ile Val Leu Ser
130                 135                 140

Gln Ser Pro Thr Ile Leu Ser Ala Ser Pro Gly Glu Lys Val Thr Met
145                 150                 155                 160

Thr Cys Arg Ala Ser Ser Ser Val Ser Tyr Met Asp Trp Tyr Gln Gln
                165                 170                 175

Lys Pro Gly Ser Ser Pro Lys Pro Trp Ile Tyr Ala Thr Ser Asn Leu
            180                 185                 190

Ala Ser Gly Val Pro Ala Arg Phe Ser Gly Ser Gly Ser Gly Thr Ser
        195                 200                 205

Tyr Ser Leu Thr Ile Ser Arg Val Glu Ala Glu Asp Ala Ala Thr Tyr
210                 215                 220

Tyr Cys Gln Gln Trp Ile Ser Asn Pro Pro Thr Phe Gly Ala Gly Thr
225                 230                 235                 240

Lys Leu Glu Leu Lys Glu Phe Pro Lys Pro Ser Thr Pro Pro Gly Ser
                245                 250                 255

Ser Gly Gly Ala Pro Gly Ile Leu Gly Phe Val Phe Thr Leu Lys Glu
            260                 265                 270

Phe Thr Leu Asp Phe Ser Thr Ala Lys Thr Tyr Val Asp Ser Leu Asn
        275                 280                 285

Val Ile Arg Ser Ala Ile Gly Thr Pro Leu Gln Thr Ile Ser Ser Gly
290                 295                 300

Gly Thr Ser Leu Leu Met Ile Asp Ser Gly Ser Gly Asp Asn Leu Phe
305                 310                 315                 320

Ala Val Asp Val Arg Gly Ile Asp Pro Glu Glu Gly Arg Phe Asn Asn
                325                 330                 335

Leu Arg Leu Ile Val Glu Arg Asn Asn Leu Tyr Val Thr Gly Phe Val
            340                 345                 350

Asn Arg Thr Asn Asn Val Phe Tyr Arg Phe Ala Asp Phe Ser His Val
        355                 360                 365

Thr Phe Pro Gly Thr Thr Ala Val Thr Leu Ser Gly Asp Ser Ser Tyr
370                 375                 380

Thr Thr Leu Gln Arg Val Ala Gly Ile Ser Arg Thr Gly Met Gln Ile

```
                385                 390                 395                 400
Asn Arg His Ser Leu Thr Thr Ser Tyr Leu Asp Leu Met Ser His Ser
                405                 410                 415

Gly Thr Ser Leu Thr Gln Ser Val Ala Arg Ala Met Leu Arg Phe Val
            420                 425                 430

Thr Val Thr Ala Glu Ala Leu Arg Phe Arg Gln Ile Gln Arg Gly Phe
        435                 440                 445

Arg Thr Thr Leu Asp Asp Leu Ser Gly Arg Ser Tyr Val Met Thr Ala
    450                 455                 460

Glu Asp Val Asp Leu Thr Leu Asn Trp Gly Arg Leu Ser Ser Val Leu
465                 470                 475                 480

Pro Asp Tyr His Gly Gln Asp Ser Val Arg Val Gly Arg Ile Ser Phe
                485                 490                 495

Gly Ser Ile Asn Ala Ile Leu Gly Ser Val Ala Leu Ile Leu Asn Cys
            500                 505                 510

His His His Ala Ser Arg Val Ala Arg
        515                 520

<210> SEQ ID NO 17
<211> LENGTH: 1563
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: modified_base
<222> LOCATION: (27)..(27)
<223> OTHER INFORMATION: a, c, t, g, unknown or other
<220> FEATURE:
<221> NAME/KEY: modified_base
<222> LOCATION: (30)..(30)
<223> OTHER INFORMATION: a, c, t, g, unknown or other
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: modified_base
<222> LOCATION: (39)..(39)
<223> OTHER INFORMATION: a, c, t, g, unknown or other
<220> FEATURE:
<221> NAME/KEY: modified_base
<222> LOCATION: (45)..(45)
<223> OTHER INFORMATION: a, c, t, g, unknown or other
<220> FEATURE:
<221> NAME/KEY: modified_base
<222> LOCATION: (48)..(48)
<223> OTHER INFORMATION: a, c, t, g, unknown or other
<220> FEATURE:
<221> NAME/KEY: modified_base
<222> LOCATION: (51)..(51)
<223> OTHER INFORMATION: a, c, t, g, unknown or other
<220> FEATURE:
<221> NAME/KEY: modified_base
<222> LOCATION: (54)..(54)
<223> OTHER INFORMATION: a, c, t, g, unknown or other
<220> FEATURE:
```

```
<221> NAME/KEY: modified_base
<222> LOCATION: (57)..(57)
<223> OTHER INFORMATION: a, c, t, g, unknown or other
<220> FEATURE:
<221> NAME/KEY: modified_base
<222> LOCATION: (66)..(66)
<223> OTHER INFORMATION: a, c, t, g, unknown or other
<220> FEATURE:
<221> NAME/KEY: modified_base
<222> LOCATION: (75)..(75)
<223> OTHER INFORMATION: a, c, t, g, unknown or other
<220> FEATURE:
<221> NAME/KEY: modified_base
<222> LOCATION: (78)..(78)
<223> OTHER INFORMATION: a, c, t, g, unknown or other
<220> FEATURE:
<221> NAME/KEY: modified_base
<222> LOCATION: (81)..(81)
<223> OTHER INFORMATION: a, c, t, g, unknown or other
<220> FEATURE:
<221> NAME/KEY: modified_base
<222> LOCATION: (87)..(87)
<223> OTHER INFORMATION: a, c, t, g, unknown or other
<220> FEATURE:
<221> NAME/KEY: modified_base
<222> LOCATION: (93)..(93)
<223> OTHER INFORMATION: a, c, t, g, unknown or other
<220> FEATURE:
<221> NAME/KEY: modified_base
<222> LOCATION: (96)..(96)
<223> OTHER INFORMATION: a, c, t, g, unknown or other
<220> FEATURE:
<221> NAME/KEY: modified_base
<222> LOCATION: (105)..(105)
<223> OTHER INFORMATION: a, c, t, g, unknown or other
<220> FEATURE:
<221> NAME/KEY: modified_base
<222> LOCATION: (114)..(114)
<223> OTHER INFORMATION: a, c, t, g, unknown or other
<220> FEATURE:
<221> NAME/KEY: modified_base
<222> LOCATION: (123)..(123)
<223> OTHER INFORMATION: a, c, t, g, unknown or other
<220> FEATURE:
<221> NAME/KEY: modified_base
<222> LOCATION: (126)..(126)
<223> OTHER INFORMATION: a, c, t, g, unknown or other
<220> FEATURE:
<221> NAME/KEY: modified_base
<222> LOCATION: (129)..(129)
<223> OTHER INFORMATION: a, c, t, g, unknown or other
<220> FEATURE:
<221> NAME/KEY: modified_base
<222> LOCATION: (135)..(135)
<223> OTHER INFORMATION: a, c, t, g, unknown or other
<220> FEATURE:
<221> NAME/KEY: modified_base
<222> LOCATION: (138)..(138)
<223> OTHER INFORMATION: a, c, t, g, unknown or other
<220> FEATURE:
<221> NAME/KEY: modified_base
<222> LOCATION: (150)..(150)
<223> OTHER INFORMATION: a, c, t, g, unknown or other
<220> FEATURE:
<221> NAME/KEY: modified_base
<222> LOCATION: (153)..(153)
<223> OTHER INFORMATION: a, c, t, g, unknown or other
<220> FEATURE:
<221> NAME/KEY: modified_base
<222> LOCATION: (162)..(162)
<223> OTHER INFORMATION: a, c, t, g, unknown or other
<220> FEATURE:
<221> NAME/KEY: modified_base
<222> LOCATION: (165)..(165)
<223> OTHER INFORMATION: a, c, t, g, unknown or other
<220> FEATURE:
<221> NAME/KEY: modified_base
<222> LOCATION: (171)..(171)
<223> OTHER INFORMATION: a, c, t, g, unknown or other
```

```
<220> FEATURE:
<221> NAME/KEY: modified_base
<222> LOCATION: (177)..(177)
<223> OTHER INFORMATION: a, c, t, g, unknown or other
<220> FEATURE:
<221> NAME/KEY: modified_base
<222> LOCATION: (180)..(180)
<223> OTHER INFORMATION: a, c, t, g, unknown or other
<220> FEATURE:
<221> NAME/KEY: modified_base
<222> LOCATION: (201)..(201)
<223> OTHER INFORMATION: a, c, t, g, unknown or other
<220> FEATURE:
<221> NAME/KEY: modified_base
<222> LOCATION: (207)..(207)
<223> OTHER INFORMATION: a, c, t, g, unknown or other
<220> FEATURE:
<221> NAME/KEY: modified_base
<222> LOCATION: (210)..(210)
<223> OTHER INFORMATION: a, c, t, g, unknown or other
<220> FEATURE:
<221> NAME/KEY: modified_base
<222> LOCATION: (213)..(213)
<223> OTHER INFORMATION: a, c, t, g, unknown or other
<220> FEATURE:
<221> NAME/KEY: modified_base
<222> LOCATION: (216)..(216)
<223> OTHER INFORMATION: a, c, t, g, unknown or other
<220> FEATURE:
<221> NAME/KEY: modified_base
<222> LOCATION: (219)..(219)
<223> OTHER INFORMATION: a, c, t, g, unknown or other
<220> FEATURE:
<221> NAME/KEY: modified_base
<222> LOCATION: (228)..(228)
<223> OTHER INFORMATION: a, c, t, g, unknown or other
<220> FEATURE:
<221> NAME/KEY: modified_base
<222> LOCATION: (231)..(231)
<223> OTHER INFORMATION: a, c, t, g, unknown or other
<220> FEATURE:
<221> NAME/KEY: modified_base
<222> LOCATION: (234)..(234)
<223> OTHER INFORMATION: a, c, t, g, unknown or other
<220> FEATURE:
<221> NAME/KEY: modified_base
<222> LOCATION: (237)..(237)
<223> OTHER INFORMATION: a, c, t, g, unknown or other
<220> FEATURE:
<221> NAME/KEY: modified_base
<222> LOCATION: (240)..(240)
<223> OTHER INFORMATION: a, c, t, g, unknown or other
<220> FEATURE:
<221> NAME/KEY: modified_base
<222> LOCATION: (252)..(252)
<223> OTHER INFORMATION: a, c, t, g, unknown or other
<220> FEATURE:
<221> NAME/KEY: modified_base
<222> LOCATION: (255)..(255)
<223> OTHER INFORMATION: a, c, t, g, unknown or other
<220> FEATURE:
<221> NAME/KEY: modified_base
<222> LOCATION: (258)..(258)
<223> OTHER INFORMATION: a, c, t, g, unknown or other
<220> FEATURE:
<221> NAME/KEY: modified_base
<222> LOCATION: (261)..(261)
<223> OTHER INFORMATION: a, c, t, g, unknown or other
<220> FEATURE:
<221> NAME/KEY: modified_base
<222> LOCATION: (264)..(264)
<223> OTHER INFORMATION: a, c, t, g, unknown or other
<220> FEATURE:
<221> NAME/KEY: modified_base
<222> LOCATION: (267)..(267)
<223> OTHER INFORMATION: a, c, t, g, unknown or other
<220> FEATURE:
<221> NAME/KEY: modified_base
<222> LOCATION: (276)..(276)
```

-continued

```
<223> OTHER INFORMATION: a, c, t, g, unknown or other
<220> FEATURE:
<221> NAME/KEY: modified_base
<222> LOCATION: (279)..(279)
<223> OTHER INFORMATION: a, c, t, g, unknown or other
<220> FEATURE:
<221> NAME/KEY: modified_base
<222> LOCATION: (282)..(282)
<223> OTHER INFORMATION: a, c, t, g, unknown or other
<220> FEATURE:
<221> NAME/KEY: modified_base
<222> LOCATION: (294)..(294)
<223> OTHER INFORMATION: a, c, t, g, unknown or other
<220> FEATURE:
<221> NAME/KEY: modified_base
<222> LOCATION: (297)..(297)
<223> OTHER INFORMATION: a, c, t, g, unknown or other
<220> FEATURE:
<221> NAME/KEY: modified_base
<222> LOCATION: (300)..(300)
<223> OTHER INFORMATION: a, c, t, g, unknown or other
<220> FEATURE:
<221> NAME/KEY: modified_base
<222> LOCATION: (312)..(312)
<223> OTHER INFORMATION: a, c, t, g, unknown or other
<220> FEATURE:
<221> NAME/KEY: modified_base
<222> LOCATION: (315)..(315)
<223> OTHER INFORMATION: a, c, t, g, unknown or other
<220> FEATURE:
<221> NAME/KEY: modified_base
<222> LOCATION: (318)..(318)
<223> OTHER INFORMATION: a, c, t, g, unknown or other
<220> FEATURE:
<221> NAME/KEY: modified_base
<222> LOCATION: (324)..(324)
<223> OTHER INFORMATION: a, c, t, g, unknown or other
<220> FEATURE:
<221> NAME/KEY: modified_base
<222> LOCATION: (339)..(339)
<223> OTHER INFORMATION: a, c, t, g, unknown or other
<220> FEATURE:
<221> NAME/KEY: modified_base
<222> LOCATION: (345)..(345)
<223> OTHER INFORMATION: a, c, t, g, unknown or other
<220> FEATURE:
<221> NAME/KEY: modified_base
<222> LOCATION: (348)..(348)
<223> OTHER INFORMATION: a, c, t, g, unknown or other
<220> FEATURE:
<221> NAME/KEY: modified_base
<222> LOCATION: (351)..(351)
<223> OTHER INFORMATION: a, c, t, g, unknown or other
<220> FEATURE:
<221> NAME/KEY: modified_base
<222> LOCATION: (354)..(354)
<223> OTHER INFORMATION: a, c, t, g, unknown or other
<220> FEATURE:
<221> NAME/KEY: modified_base
<222> LOCATION: (357)..(357)
<223> OTHER INFORMATION: a, c, t, g, unknown or other
<220> FEATURE:
<221> NAME/KEY: modified_base
<222> LOCATION: (360)..(360)
<223> OTHER INFORMATION: a, c, t, g, unknown or other
<220> FEATURE:
<221> NAME/KEY: modified_base
<222> LOCATION: (363)..(363)
<223> OTHER INFORMATION: a, c, t, g, unknown or other
<220> FEATURE:
<221> NAME/KEY: modified_base
<222> LOCATION: (366)..(366)
<223> OTHER INFORMATION: a, c, t, g, unknown or other
<220> FEATURE:
<221> NAME/KEY: modified_base
<222> LOCATION: (369)..(369)
<223> OTHER INFORMATION: a, c, t, g, unknown or other
<220> FEATURE:
<221> NAME/KEY: modified_base
```

```
<222> LOCATION: (372)..(372)
<223> OTHER INFORMATION: a, c, t, g, unknown or other
<220> FEATURE:
<221> NAME/KEY: modified_base
<222> LOCATION: (375)..(375)
<223> OTHER INFORMATION: a, c, t, g, unknown or other
<220> FEATURE:
<221> NAME/KEY: modified_base
<222> LOCATION: (378)..(378)
<223> OTHER INFORMATION: a, c, t, g, unknown or other
<220> FEATURE:
<221> NAME/KEY: modified_base
<222> LOCATION: (381)..(381)
<223> OTHER INFORMATION: a, c, t, g, unknown or other
<220> FEATURE:
<221> NAME/KEY: modified_base
<222> LOCATION: (384)..(384)
<223> OTHER INFORMATION: a, c, t, g, unknown or other
<220> FEATURE:
<221> NAME/KEY: modified_base
<222> LOCATION: (387)..(387)
<223> OTHER INFORMATION: a, c, t, g, unknown or other
<220> FEATURE:
<221> NAME/KEY: modified_base
<222> LOCATION: (390)..(390)
<223> OTHER INFORMATION: a, c, t, g, unknown or other
<220> FEATURE:
<221> NAME/KEY: modified_base
<222> LOCATION: (393)..(393)
<223> OTHER INFORMATION: a, c, t, g, unknown or other
<220> FEATURE:
<221> NAME/KEY: modified_base
<222> LOCATION: (399)..(399)
<223> OTHER INFORMATION: a, c, t, g, unknown or other
<220> FEATURE:
<221> NAME/KEY: modified_base
<222> LOCATION: (402)..(402)
<223> OTHER INFORMATION: a, c, t, g, unknown or other
<220> FEATURE:
<221> NAME/KEY: modified_base
<222> LOCATION: (405)..(405)
<223> OTHER INFORMATION: a, c, t, g, unknown or other
<220> FEATURE:
<221> NAME/KEY: modified_base
<222> LOCATION: (408)..(408)
<223> OTHER INFORMATION: a, c, t, g, unknown or other
<220> FEATURE:
<221> NAME/KEY: modified_base
<222> LOCATION: (414)..(414)
<223> OTHER INFORMATION: a, c, t, g, unknown or other
<220> FEATURE:
<221> NAME/KEY: modified_base
<222> LOCATION: (417)..(417)
<223> OTHER INFORMATION: a, c, t, g, unknown or other
<220> FEATURE:
<221> NAME/KEY: modified_base
<222> LOCATION: (426)..(426)
<223> OTHER INFORMATION: a, c, t, g, unknown or other
<220> FEATURE:
<221> NAME/KEY: modified_base
<222> LOCATION: (429)..(429)
<223> OTHER INFORMATION: a, c, t, g, unknown or other
<220> FEATURE:
<221> NAME/KEY: modified_base
<222> LOCATION: (432)..(432)
<223> OTHER INFORMATION: a, c, t, g, unknown or other
<220> FEATURE:
<221> NAME/KEY: modified_base
<222> LOCATION: (438)..(438)
<223> OTHER INFORMATION: a, c, t, g, unknown or other
<220> FEATURE:
<221> NAME/KEY: modified_base
<222> LOCATION: (441)..(441)
<223> OTHER INFORMATION: a, c, t, g, unknown or other
<220> FEATURE:
<221> NAME/KEY: modified_base
<222> LOCATION: (444)..(444)
<223> OTHER INFORMATION: a, c, t, g, unknown or other
<220> FEATURE:
```

-continued

```
<221> NAME/KEY: modified_base
<222> LOCATION: (450)..(450)
<223> OTHER INFORMATION: a, c, t, g, unknown or other
<220> FEATURE:
<221> NAME/KEY: modified_base
<222> LOCATION: (453)..(453)
<223> OTHER INFORMATION: a, c, t, g, unknown or other
<220> FEATURE:
<221> NAME/KEY: modified_base
<222> LOCATION: (456)..(456)
<223> OTHER INFORMATION: a, c, t, g, unknown or other
<220> FEATURE:
<221> NAME/KEY: modified_base
<222> LOCATION: (459)..(459)
<223> OTHER INFORMATION: a, c, t, g, unknown or other
<220> FEATURE:
<221> NAME/KEY: modified_base
<222> LOCATION: (462)..(462)
<223> OTHER INFORMATION: a, c, t, g, unknown or other
<220> FEATURE:
<221> NAME/KEY: modified_base
<222> LOCATION: (465)..(465)
<223> OTHER INFORMATION: a, c, t, g, unknown or other
<220> FEATURE:
<221> NAME/KEY: modified_base
<222> LOCATION: (474)..(474)
<223> OTHER INFORMATION: a, c, t, g, unknown or other
<220> FEATURE:
<221> NAME/KEY: modified_base
<222> LOCATION: (477)..(477)
<223> OTHER INFORMATION: a, c, t, g, unknown or other
<220> FEATURE:
<221> NAME/KEY: modified_base
<222> LOCATION: (483)..(483)
<223> OTHER INFORMATION: a, c, t, g, unknown or other
<220> FEATURE:
<221> NAME/KEY: modified_base
<222> LOCATION: (489)..(489)
<223> OTHER INFORMATION: a, c, t, g, unknown or other
<220> FEATURE:
<221> NAME/KEY: modified_base
<222> LOCATION: (492)..(492)
<223> OTHER INFORMATION: a, c, t, g, unknown or other
<220> FEATURE:
<221> NAME/KEY: modified_base
<222> LOCATION: (495)..(495)
<223> OTHER INFORMATION: a, c, t, g, unknown or other
<220> FEATURE:
<221> NAME/KEY: modified_base
<222> LOCATION: (498)..(498)
<223> OTHER INFORMATION: a, c, t, g, unknown or other
<220> FEATURE:
<221> NAME/KEY: modified_base
<222> LOCATION: (501)..(501)
<223> OTHER INFORMATION: a, c, t, g, unknown or other
<220> FEATURE:
<221> NAME/KEY: modified_base
<222> LOCATION: (504)..(504)
<223> OTHER INFORMATION: a, c, t, g, unknown or other
<220> FEATURE:
<221> NAME/KEY: modified_base
<222> LOCATION: (507)..(507)
<223> OTHER INFORMATION: a, c, t, g, unknown or other
<220> FEATURE:
<221> NAME/KEY: modified_base
<222> LOCATION: (534)..(534)
<223> OTHER INFORMATION: a, c, t, g, unknown or other
<220> FEATURE:
<221> NAME/KEY: modified_base
<222> LOCATION: (537)..(537)
<223> OTHER INFORMATION: a, c, t, g, unknown or other
<220> FEATURE:
<221> NAME/KEY: modified_base
<222> LOCATION: (540)..(540)
<223> OTHER INFORMATION: a, c, t, g, unknown or other
<220> FEATURE:
<221> NAME/KEY: modified_base
<222> LOCATION: (543)..(543)
<223> OTHER INFORMATION: a, c, t, g, unknown or other
```

-continued

```
<220> FEATURE:
<221> NAME/KEY: modified_base
<222> LOCATION: (546)..(546)
<223> OTHER INFORMATION: a, c, t, g, unknown or other
<220> FEATURE:
<221> NAME/KEY: modified_base
<222> LOCATION: (552)..(552)
<223> OTHER INFORMATION: a, c, t, g, unknown or other
<220> FEATURE:
<221> NAME/KEY: modified_base
<222> LOCATION: (564)..(564)
<223> OTHER INFORMATION: a, c, t, g, unknown or other
<220> FEATURE:
<221> NAME/KEY: modified_base
<222> LOCATION: (567)..(567)
<223> OTHER INFORMATION: a, c, t, g, unknown or other
<220> FEATURE:
<221> NAME/KEY: modified_base
<222> LOCATION: (570)..(570)
<223> OTHER INFORMATION: a, c, t, g, unknown or other
<220> FEATURE:
<221> NAME/KEY: modified_base
<222> LOCATION: (576)..(576)
<223> OTHER INFORMATION: a, c, t, g, unknown or other
<220> FEATURE:
<221> NAME/KEY: modified_base
<222> LOCATION: (579)..(579)
<223> OTHER INFORMATION: a, c, t, g, unknown or other
<220> FEATURE:
<221> NAME/KEY: modified_base
<222> LOCATION: (582)..(582)
<223> OTHER INFORMATION: a, c, t, g, unknown or other
<220> FEATURE:
<221> NAME/KEY: modified_base
<222> LOCATION: (585)..(585)
<223> OTHER INFORMATION: a, c, t, g, unknown or other
<220> FEATURE:
<221> NAME/KEY: modified_base
<222> LOCATION: (588)..(588)
<223> OTHER INFORMATION: a, c, t, g, unknown or other
<220> FEATURE:
<221> NAME/KEY: modified_base
<222> LOCATION: (591)..(591)
<223> OTHER INFORMATION: a, c, t, g, unknown or other
<220> FEATURE:
<221> NAME/KEY: modified_base
<222> LOCATION: (594)..(594)
<223> OTHER INFORMATION: a, c, t, g, unknown or other
<220> FEATURE:
<221> NAME/KEY: modified_base
<222> LOCATION: (597)..(597)
<223> OTHER INFORMATION: a, c, t, g, unknown or other
<220> FEATURE:
<221> NAME/KEY: modified_base
<222> LOCATION: (603)..(603)
<223> OTHER INFORMATION: a, c, t, g, unknown or other
<220> FEATURE:
<221> NAME/KEY: modified_base
<222> LOCATION: (606)..(606)
<223> OTHER INFORMATION: a, c, t, g, unknown or other
<220> FEATURE:
<221> NAME/KEY: modified_base
<222> LOCATION: (609)..(609)
<223> OTHER INFORMATION: a, c, t, g, unknown or other
<220> FEATURE:
<221> NAME/KEY: modified_base
<222> LOCATION: (612)..(612)
<223> OTHER INFORMATION: a, c, t, g, unknown or other
<220> FEATURE:
<221> NAME/KEY: modified_base
<222> LOCATION: (615)..(615)
<223> OTHER INFORMATION: a, c, t, g, unknown or other
<220> FEATURE:
<221> NAME/KEY: modified_base
<222> LOCATION: (618)..(618)
<223> OTHER INFORMATION: a, c, t, g, unknown or other
<220> FEATURE:
<221> NAME/KEY: modified_base
<222> LOCATION: (621)..(621)
```

```
<223> OTHER INFORMATION: a, c, t, g, unknown or other
<220> FEATURE:
<221> NAME/KEY: modified_base
<222> LOCATION: (624)..(624)
<223> OTHER INFORMATION: a, c, t, g, unknown or other
<220> FEATURE:
<221> NAME/KEY: modified_base
<222> LOCATION: (630)..(630)
<223> OTHER INFORMATION: a, c, t, g, unknown or other
<220> FEATURE:
<221> NAME/KEY: modified_base
<222> LOCATION: (633)..(633)
<223> OTHER INFORMATION: a, c, t, g, unknown or other
<220> FEATURE:
<221> NAME/KEY: modified_base
<222> LOCATION: (636)..(636)
<223> OTHER INFORMATION: a, c, t, g, unknown or other
<220> FEATURE:
<221> NAME/KEY: modified_base
<222> LOCATION: (642)..(642)
<223> OTHER INFORMATION: a, c, t, g, unknown or other
<220> FEATURE:
<221> NAME/KEY: modified_base
<222> LOCATION: (645)..(645)
<223> OTHER INFORMATION: a, c, t, g, unknown or other
<220> FEATURE:
<221> NAME/KEY: modified_base
<222> LOCATION: (648)..(648)
<223> OTHER INFORMATION: a, c, t, g, unknown or other
<220> FEATURE:
<221> NAME/KEY: modified_base
<222> LOCATION: (654)..(654)
<223> OTHER INFORMATION: a, c, t, g, unknown or other
<220> FEATURE:
<221> NAME/KEY: modified_base
<222> LOCATION: (663)..(663)
<223> OTHER INFORMATION: a, c, t, g, unknown or other
<220> FEATURE:
<221> NAME/KEY: modified_base
<222> LOCATION: (666)..(666)
<223> OTHER INFORMATION: a, c, t, g, unknown or other
<220> FEATURE:
<221> NAME/KEY: modified_base
<222> LOCATION: (669)..(669)
<223> OTHER INFORMATION: a, c, t, g, unknown or other
<220> FEATURE:
<221> NAME/KEY: modified_base
<222> LOCATION: (693)..(693)
<223> OTHER INFORMATION: a, c, t, g, unknown or other
<220> FEATURE:
<221> NAME/KEY: modified_base
<222> LOCATION: (699)..(699)
<223> OTHER INFORMATION: a, c, t, g, unknown or other
<220> FEATURE:
<221> NAME/KEY: modified_base
<222> LOCATION: (702)..(702)
<223> OTHER INFORMATION: a, c, t, g, unknown or other
<220> FEATURE:
<221> NAME/KEY: modified_base
<222> LOCATION: (705)..(705)
<223> OTHER INFORMATION: a, c, t, g, unknown or other
<220> FEATURE:
<221> NAME/KEY: modified_base
<222> LOCATION: (711)..(711)
<223> OTHER INFORMATION: a, c, t, g, unknown or other
<220> FEATURE:
<221> NAME/KEY: modified_base
<222> LOCATION: (714)..(714)
<223> OTHER INFORMATION: a, c, t, g, unknown or other
<220> FEATURE:
<221> NAME/KEY: modified_base
<222> LOCATION: (717)..(717)
<223> OTHER INFORMATION: a, c, t, g, unknown or other
<220> FEATURE:
<221> NAME/KEY: modified_base
<222> LOCATION: (720)..(720)
<223> OTHER INFORMATION: a, c, t, g, unknown or other
<220> FEATURE:
<221> NAME/KEY: modified_base
```

```
<222> LOCATION: (726)..(726)
<223> OTHER INFORMATION: a, c, t, g, unknown or other
<220> FEATURE:
<221> NAME/KEY: modified_base
<222> LOCATION: (732)..(732)
<223> OTHER INFORMATION: a, c, t, g, unknown or other
<220> FEATURE:
<221> NAME/KEY: modified_base
<222> LOCATION: (744)..(744)
<223> OTHER INFORMATION: a, c, t, g, unknown or other
<220> FEATURE:
<221> NAME/KEY: modified_base
<222> LOCATION: (750)..(750)
<223> OTHER INFORMATION: a, c, t, g, unknown or other
<220> FEATURE:
<221> NAME/KEY: modified_base
<222> LOCATION: (753)..(753)
<223> OTHER INFORMATION: a, c, t, g, unknown or other
<220> FEATURE:
<221> NAME/KEY: modified_base
<222> LOCATION: (756)..(756)
<223> OTHER INFORMATION: a, c, t, g, unknown or other
<220> FEATURE:
<221> NAME/KEY: modified_base
<222> LOCATION: (759)..(759)
<223> OTHER INFORMATION: a, c, t, g, unknown or other
<220> FEATURE:
<221> NAME/KEY: modified_base
<222> LOCATION: (762)..(762)
<223> OTHER INFORMATION: a, c, t, g, unknown or other
<220> FEATURE:
<221> NAME/KEY: modified_base
<222> LOCATION: (765)..(765)
<223> OTHER INFORMATION: a, c, t, g, unknown or other
<220> FEATURE:
<221> NAME/KEY: modified_base
<222> LOCATION: (768)..(768)
<223> OTHER INFORMATION: a, c, t, g, unknown or other
<220> FEATURE:
<221> NAME/KEY: modified_base
<222> LOCATION: (771)..(771)
<223> OTHER INFORMATION: a, c, t, g, unknown or other
<220> FEATURE:
<221> NAME/KEY: modified_base
<222> LOCATION: (774)..(774)
<223> OTHER INFORMATION: a, c, t, g, unknown or other
<220> FEATURE:
<221> NAME/KEY: modified_base
<222> LOCATION: (777)..(777)
<223> OTHER INFORMATION: a, c, t, g, unknown or other
<220> FEATURE:
<221> NAME/KEY: modified_base
<222> LOCATION: (780)..(780)
<223> OTHER INFORMATION: a, c, t, g, unknown or other
<220> FEATURE:
<221> NAME/KEY: modified_base
<222> LOCATION: (783)..(783)
<223> OTHER INFORMATION: a, c, t, g, unknown or other
<220> FEATURE:
<221> NAME/KEY: modified_base
<222> LOCATION: (786)..(786)
<223> OTHER INFORMATION: a, c, t, g, unknown or other
<220> FEATURE:
<221> NAME/KEY: modified_base
<222> LOCATION: (792)..(792)
<223> OTHER INFORMATION: a, c, t, g, unknown or other
<220> FEATURE:
<221> NAME/KEY: modified_base
<222> LOCATION: (795)..(795)
<223> OTHER INFORMATION: a, c, t, g, unknown or other
<220> FEATURE:
<221> NAME/KEY: modified_base
<222> LOCATION: (801)..(801)
<223> OTHER INFORMATION: a, c, t, g, unknown or other
<220> FEATURE:
<221> NAME/KEY: modified_base
<222> LOCATION: (807)..(807)
<223> OTHER INFORMATION: a, c, t, g, unknown or other
<220> FEATURE:
```

```
<221> NAME/KEY: modified_base
<222> LOCATION: (810)..(810)
<223> OTHER INFORMATION: a, c, t, g, unknown or other
<220> FEATURE:
<221> NAME/KEY: modified_base
<222> LOCATION: (822)..(822)
<223> OTHER INFORMATION: a, c, t, g, unknown or other
<220> FEATURE:
<221> NAME/KEY: modified_base
<222> LOCATION: (825)..(825)
<223> OTHER INFORMATION: a, c, t, g, unknown or other
<220> FEATURE:
<221> NAME/KEY: modified_base
<222> LOCATION: (834)..(834)
<223> OTHER INFORMATION: a, c, t, g, unknown or other
<220> FEATURE:
<221> NAME/KEY: modified_base
<222> LOCATION: (837)..(837)
<223> OTHER INFORMATION: a, c, t, g, unknown or other
<220> FEATURE:
<221> NAME/KEY: modified_base
<222> LOCATION: (840)..(840)
<223> OTHER INFORMATION: a, c, t, g, unknown or other
<220> FEATURE:
<221> NAME/KEY: modified_base
<222> LOCATION: (846)..(846)
<223> OTHER INFORMATION: a, c, t, g, unknown or other
<220> FEATURE:
<221> NAME/KEY: modified_base
<222> LOCATION: (852)..(852)
<223> OTHER INFORMATION: a, c, t, g, unknown or other
<220> FEATURE:
<221> NAME/KEY: modified_base
<222> LOCATION: (858)..(858)
<223> OTHER INFORMATION: a, c, t, g, unknown or other
<220> FEATURE:
<221> NAME/KEY: modified_base
<222> LOCATION: (861)..(861)
<223> OTHER INFORMATION: a, c, t, g, unknown or other
<220> FEATURE:
<221> NAME/KEY: modified_base
<222> LOCATION: (867)..(867)
<223> OTHER INFORMATION: a, c, t, g, unknown or other
<220> FEATURE:
<221> NAME/KEY: modified_base
<222> LOCATION: (873)..(873)
<223> OTHER INFORMATION: a, c, t, g, unknown or other
<220> FEATURE:
<221> NAME/KEY: modified_base
<222> LOCATION: (876)..(876)
<223> OTHER INFORMATION: a, c, t, g, unknown or other
<220> FEATURE:
<221> NAME/KEY: modified_base
<222> LOCATION: (879)..(879)
<223> OTHER INFORMATION: a, c, t, g, unknown or other
<220> FEATURE:
<221> NAME/KEY: modified_base
<222> LOCATION: (885)..(885)
<223> OTHER INFORMATION: a, c, t, g, unknown or other
<220> FEATURE:
<221> NAME/KEY: modified_base
<222> LOCATION: (888)..(888)
<223> OTHER INFORMATION: a, c, t, g, unknown or other
<220> FEATURE:
<221> NAME/KEY: modified_base
<222> LOCATION: (891)..(891)
<223> OTHER INFORMATION: a, c, t, g, unknown or other
<220> FEATURE:
<221> NAME/KEY: modified_base
<222> LOCATION: (894)..(894)
<223> OTHER INFORMATION: a, c, t, g, unknown or other
<220> FEATURE:
<221> NAME/KEY: modified_base
<222> LOCATION: (900)..(900)
<223> OTHER INFORMATION: a, c, t, g, unknown or other
<220> FEATURE:
<221> NAME/KEY: modified_base
<222> LOCATION: (906)..(906)
<223> OTHER INFORMATION: a, c, t, g, unknown or other
```

```
<220> FEATURE:
<221> NAME/KEY: modified_base
<222> LOCATION: (909)..(909)
<223> OTHER INFORMATION: a, c, t, g, unknown or other
<220> FEATURE:
<221> NAME/KEY: modified_base
<222> LOCATION: (912)..(912)
<223> OTHER INFORMATION: a, c, t, g, unknown or other
<220> FEATURE:
<221> NAME/KEY: modified_base
<222> LOCATION: (915)..(915)
<223> OTHER INFORMATION: a, c, t, g, unknown or other
<220> FEATURE:
<221> NAME/KEY: modified_base
<222> LOCATION: (918)..(918)
<223> OTHER INFORMATION: a, c, t, g, unknown or other
<220> FEATURE:
<221> NAME/KEY: modified_base
<222> LOCATION: (921)..(921)
<223> OTHER INFORMATION: a, c, t, g, unknown or other
<220> FEATURE:
<221> NAME/KEY: modified_base
<222> LOCATION: (924)..(924)
<223> OTHER INFORMATION: a, c, t, g, unknown or other
<220> FEATURE:
<221> NAME/KEY: modified_base
<222> LOCATION: (927)..(927)
<223> OTHER INFORMATION: a, c, t, g, unknown or other
<220> FEATURE:
<221> NAME/KEY: modified_base
<222> LOCATION: (939)..(939)
<223> OTHER INFORMATION: a, c, t, g, unknown or other
<220> FEATURE:
<221> NAME/KEY: modified_base
<222> LOCATION: (942)..(942)
<223> OTHER INFORMATION: a, c, t, g, unknown or other
<220> FEATURE:
<221> NAME/KEY: modified_base
<222> LOCATION: (945)..(945)
<223> OTHER INFORMATION: a, c, t, g, unknown or other
<220> FEATURE:
<221> NAME/KEY: modified_base
<222> LOCATION: (948)..(948)
<223> OTHER INFORMATION: a, c, t, g, unknown or other
<220> FEATURE:
<221> NAME/KEY: modified_base
<222> LOCATION: (957)..(957)
<223> OTHER INFORMATION: a, c, t, g, unknown or other
<220> FEATURE:
<221> NAME/KEY: modified_base
<222> LOCATION: (963)..(963)
<223> OTHER INFORMATION: a, c, t, g, unknown or other
<220> FEATURE:
<221> NAME/KEY: modified_base
<222> LOCATION: (966)..(966)
<223> OTHER INFORMATION: a, c, t, g, unknown or other
<220> FEATURE:
<221> NAME/KEY: modified_base
<222> LOCATION: (972)..(972)
<223> OTHER INFORMATION: a, c, t, g, unknown or other
<220> FEATURE:
<221> NAME/KEY: modified_base
<222> LOCATION: (975)..(975)
<223> OTHER INFORMATION: a, c, t, g, unknown or other
<220> FEATURE:
<221> NAME/KEY: modified_base
<222> LOCATION: (978)..(978)
<223> OTHER INFORMATION: a, c, t, g, unknown or other
<220> FEATURE:
<221> NAME/KEY: modified_base
<222> LOCATION: (987)..(987)
<223> OTHER INFORMATION: a, c, t, g, unknown or other
<220> FEATURE:
<221> NAME/KEY: modified_base
<222> LOCATION: (996)..(996)
<223> OTHER INFORMATION: a, c, t, g, unknown or other
<220> FEATURE:
<221> NAME/KEY: modified_base
<222> LOCATION: (999)..(999)
```

```
<223> OTHER INFORMATION: a, c, t, g, unknown or other
<220> FEATURE:
<221> NAME/KEY: modified_base
<222> LOCATION: (1011)..(1011)
<223> OTHER INFORMATION: a, c, t, g, unknown or other
<220> FEATURE:
<221> NAME/KEY: modified_base
<222> LOCATION: (1014)..(1014)
<223> OTHER INFORMATION: a, c, t, g, unknown or other
<220> FEATURE:
<221> NAME/KEY: modified_base
<222> LOCATION: (1017)..(1017)
<223> OTHER INFORMATION: a, c, t, g, unknown or other
<220> FEATURE:
<221> NAME/KEY: modified_base
<222> LOCATION: (1023)..(1023)
<223> OTHER INFORMATION: a, c, t, g, unknown or other
<220> FEATURE:
<221> NAME/KEY: modified_base
<222> LOCATION: (1029)..(1029)
<223> OTHER INFORMATION: a, c, t, g, unknown or other
<220> FEATURE:
<221> NAME/KEY: modified_base
<222> LOCATION: (1038)..(1038)
<223> OTHER INFORMATION: a, c, t, g, unknown or other
<220> FEATURE:
<221> NAME/KEY: modified_base
<222> LOCATION: (1044)..(1044)
<223> OTHER INFORMATION: a, c, t, g, unknown or other
<220> FEATURE:
<221> NAME/KEY: modified_base
<222> LOCATION: (1047)..(1047)
<223> OTHER INFORMATION: a, c, t, g, unknown or other
<220> FEATURE:
<221> NAME/KEY: modified_base
<222> LOCATION: (1050)..(1050)
<223> OTHER INFORMATION: a, c, t, g, unknown or other
<220> FEATURE:
<221> NAME/KEY: modified_base
<222> LOCATION: (1056)..(1056)
<223> OTHER INFORMATION: a, c, t, g, unknown or other
<220> FEATURE:
<221> NAME/KEY: modified_base
<222> LOCATION: (1062)..(1062)
<223> OTHER INFORMATION: a, c, t, g, unknown or other
<220> FEATURE:
<221> NAME/KEY: modified_base
<222> LOCATION: (1065)..(1065)
<223> OTHER INFORMATION: a, c, t, g, unknown or other
<220> FEATURE:
<221> NAME/KEY: modified_base
<222> LOCATION: (1074)..(1074)
<223> OTHER INFORMATION: a, c, t, g, unknown or other
<220> FEATURE:
<221> NAME/KEY: modified_base
<222> LOCATION: (1083)..(1083)
<223> OTHER INFORMATION: a, c, t, g, unknown or other
<220> FEATURE:
<221> NAME/KEY: modified_base
<222> LOCATION: (1089)..(1089)
<223> OTHER INFORMATION: a, c, t, g, unknown or other
<220> FEATURE:
<221> NAME/KEY: modified_base
<222> LOCATION: (1098)..(1098)
<223> OTHER INFORMATION: a, c, t, g, unknown or other
<220> FEATURE:
<221> NAME/KEY: modified_base
<222> LOCATION: (1104)..(1104)
<223> OTHER INFORMATION: a, c, t, g, unknown or other
<220> FEATURE:
<221> NAME/KEY: modified_base
<222> LOCATION: (1107)..(1107)
<223> OTHER INFORMATION: a, c, t, g, unknown or other
<220> FEATURE:
<221> NAME/KEY: modified_base
<222> LOCATION: (1113)..(1113)
<223> OTHER INFORMATION: a, c, t, g, unknown or other
<220> FEATURE:
<221> NAME/KEY: modified_base
```

```
<222> LOCATION: (1116)..(1116)
<223> OTHER INFORMATION: a, c, t, g, unknown or other
<220> FEATURE:
<221> NAME/KEY: modified_base
<222> LOCATION: (1119)..(1119)
<223> OTHER INFORMATION: a, c, t, g, unknown or other
<220> FEATURE:
<221> NAME/KEY: modified_base
<222> LOCATION: (1122)..(1122)
<223> OTHER INFORMATION: a, c, t, g, unknown or other
<220> FEATURE:
<221> NAME/KEY: modified_base
<222> LOCATION: (1125)..(1125)
<223> OTHER INFORMATION: a, c, t, g, unknown or other
<220> FEATURE:
<221> NAME/KEY: modified_base
<222> LOCATION: (1128)..(1128)
<223> OTHER INFORMATION: a, c, t, g, unknown or other
<220> FEATURE:
<221> NAME/KEY: modified_base
<222> LOCATION: (1131)..(1131)
<223> OTHER INFORMATION: a, c, t, g, unknown or other
<220> FEATURE:
<221> NAME/KEY: modified_base
<222> LOCATION: (1134)..(1134)
<223> OTHER INFORMATION: a, c, t, g, unknown or other
<220> FEATURE:
<221> NAME/KEY: modified_base
<222> LOCATION: (1137)..(1137)
<223> OTHER INFORMATION: a, c, t, g, unknown or other
<220> FEATURE:
<221> NAME/KEY: modified_base
<222> LOCATION: (1140)..(1140)
<223> OTHER INFORMATION: a, c, t, g, unknown or other
<220> FEATURE:
<221> NAME/KEY: modified_base
<222> LOCATION: (1146)..(1146)
<223> OTHER INFORMATION: a, c, t, g, unknown or other
<220> FEATURE:
<221> NAME/KEY: modified_base
<222> LOCATION: (1149)..(1149)
<223> OTHER INFORMATION: a, c, t, g, unknown or other
<220> FEATURE:
<221> NAME/KEY: modified_base
<222> LOCATION: (1155)..(1155)
<223> OTHER INFORMATION: a, c, t, g, unknown or other
<220> FEATURE:
<221> NAME/KEY: modified_base
<222> LOCATION: (1158)..(1158)
<223> OTHER INFORMATION: a, c, t, g, unknown or other
<220> FEATURE:
<221> NAME/KEY: modified_base
<222> LOCATION: (1161)..(1161)
<223> OTHER INFORMATION: a, c, t, g, unknown or other
<220> FEATURE:
<221> NAME/KEY: modified_base
<222> LOCATION: (1167)..(1167)
<223> OTHER INFORMATION: a, c, t, g, unknown or other
<220> FEATURE:
<221> NAME/KEY: modified_base
<222> LOCATION: (1170)..(1170)
<223> OTHER INFORMATION: a, c, t, g, unknown or other
<220> FEATURE:
<221> NAME/KEY: modified_base
<222> LOCATION: (1173)..(1173)
<223> OTHER INFORMATION: a, c, t, g, unknown or other
<220> FEATURE:
<221> NAME/KEY: modified_base
<222> LOCATION: (1176)..(1176)
<223> OTHER INFORMATION: a, c, t, g, unknown or other
<220> FEATURE:
<221> NAME/KEY: modified_base
<222> LOCATION: (1182)..(1182)
<223> OTHER INFORMATION: a, c, t, g, unknown or other
<220> FEATURE:
<221> NAME/KEY: modified_base
<222> LOCATION: (1185)..(1185)
<223> OTHER INFORMATION: a, c, t, g, unknown or other
<220> FEATURE:
```

```
<221> NAME/KEY: modified_base
<222> LOCATION: (1188)..(1188)
<223> OTHER INFORMATION: a, c, t, g, unknown or other
<220> FEATURE:
<221> NAME/KEY: modified_base
<222> LOCATION: (1191)..(1191)
<223> OTHER INFORMATION: a, c, t, g, unknown or other
<220> FEATURE:
<221> NAME/KEY: modified_base
<222> LOCATION: (1206)..(1206)
<223> OTHER INFORMATION: a, c, t, g, unknown or other
<220> FEATURE:
<221> NAME/KEY: modified_base
<222> LOCATION: (1212)..(1212)
<223> OTHER INFORMATION: a, c, t, g, unknown or other
<220> FEATURE:
<221> NAME/KEY: modified_base
<222> LOCATION: (1215)..(1215)
<223> OTHER INFORMATION: a, c, t, g, unknown or other
<220> FEATURE:
<221> NAME/KEY: modified_base
<222> LOCATION: (1218)..(1218)
<223> OTHER INFORMATION: a, c, t, g, unknown or other
<220> FEATURE:
<221> NAME/KEY: modified_base
<222> LOCATION: (1221)..(1221)
<223> OTHER INFORMATION: a, c, t, g, unknown or other
<220> FEATURE:
<221> NAME/KEY: modified_base
<222> LOCATION: (1224)..(1224)
<223> OTHER INFORMATION: a, c, t, g, unknown or other
<220> FEATURE:
<221> NAME/KEY: modified_base
<222> LOCATION: (1230)..(1230)
<223> OTHER INFORMATION: a, c, t, g, unknown or other
<220> FEATURE:
<221> NAME/KEY: modified_base
<222> LOCATION: (1236)..(1236)
<223> OTHER INFORMATION: a, c, t, g, unknown or other
<220> FEATURE:
<221> NAME/KEY: modified_base
<222> LOCATION: (1242)..(1242)
<223> OTHER INFORMATION: a, c, t, g, unknown or other
<220> FEATURE:
<221> NAME/KEY: modified_base
<222> LOCATION: (1248)..(1248)
<223> OTHER INFORMATION: a, c, t, g, unknown or other
<220> FEATURE:
<221> NAME/KEY: modified_base
<222> LOCATION: (1251)..(1251)
<223> OTHER INFORMATION: a, c, t, g, unknown or other
<220> FEATURE:
<221> NAME/KEY: modified_base
<222> LOCATION: (1254)..(1254)
<223> OTHER INFORMATION: a, c, t, g, unknown or other
<220> FEATURE:
<221> NAME/KEY: modified_base
<222> LOCATION: (1257)..(1257)
<223> OTHER INFORMATION: a, c, t, g, unknown or other
<220> FEATURE:
<221> NAME/KEY: modified_base
<222> LOCATION: (1260)..(1260)
<223> OTHER INFORMATION: a, c, t, g, unknown or other
<220> FEATURE:
<221> NAME/KEY: modified_base
<222> LOCATION: (1263)..(1263)
<223> OTHER INFORMATION: a, c, t, g, unknown or other
<220> FEATURE:
<221> NAME/KEY: modified_base
<222> LOCATION: (1269)..(1269)
<223> OTHER INFORMATION: a, c, t, g, unknown or other
<220> FEATURE:
<221> NAME/KEY: modified_base
<222> LOCATION: (1272)..(1272)
<223> OTHER INFORMATION: a, c, t, g, unknown or other
<220> FEATURE:
<221> NAME/KEY: modified_base
<222> LOCATION: (1275)..(1275)
<223> OTHER INFORMATION: a, c, t, g, unknown or other
```

```
<220> FEATURE:
<221> NAME/KEY: modified_base
<222> LOCATION: (1278)..(1278)
<223> OTHER INFORMATION: a, c, t, g, unknown or other
<220> FEATURE:
<221> NAME/KEY: modified_base
<222> LOCATION: (1281)..(1281)
<223> OTHER INFORMATION: a, c, t, g, unknown or other
<220> FEATURE:
<221> NAME/KEY: modified_base
<222> LOCATION: (1287)..(1287)
<223> OTHER INFORMATION: a, c, t, g, unknown or other
<220> FEATURE:
<221> NAME/KEY: modified_base
<222> LOCATION: (1290)..(1290)
<223> OTHER INFORMATION: a, c, t, g, unknown or other
<220> FEATURE:
<221> NAME/KEY: modified_base
<222> LOCATION: (1296)..(1296)
<223> OTHER INFORMATION: a, c, t, g, unknown or other
<220> FEATURE:
<221> NAME/KEY: modified_base
<222> LOCATION: (1299)..(1299)
<223> OTHER INFORMATION: a, c, t, g, unknown or other
<220> FEATURE:
<221> NAME/KEY: modified_base
<222> LOCATION: (1302)..(1302)
<223> OTHER INFORMATION: a, c, t, g, unknown or other
<220> FEATURE:
<221> NAME/KEY: modified_base
<222> LOCATION: (1305)..(1305)
<223> OTHER INFORMATION: a, c, t, g, unknown or other
<220> FEATURE:
<221> NAME/KEY: modified_base
<222> LOCATION: (1308)..(1308)
<223> OTHER INFORMATION: a, c, t, g, unknown or other
<220> FEATURE:
<221> NAME/KEY: modified_base
<222> LOCATION: (1314)..(1314)
<223> OTHER INFORMATION: a, c, t, g, unknown or other
<220> FEATURE:
<221> NAME/KEY: modified_base
<222> LOCATION: (1317)..(1317)
<223> OTHER INFORMATION: a, c, t, g, unknown or other
<220> FEATURE:
<221> NAME/KEY: modified_base
<222> LOCATION: (1320)..(1320)
<223> OTHER INFORMATION: a, c, t, g, unknown or other
<220> FEATURE:
<221> NAME/KEY: modified_base
<222> LOCATION: (1326)..(1326)
<223> OTHER INFORMATION: a, c, t, g, unknown or other
<220> FEATURE:
<221> NAME/KEY: modified_base
<222> LOCATION: (1338)..(1338)
<223> OTHER INFORMATION: a, c, t, g, unknown or other
<220> FEATURE:
<221> NAME/KEY: modified_base
<222> LOCATION: (1341)..(1341)
<223> OTHER INFORMATION: a, c, t, g, unknown or other
<220> FEATURE:
<221> NAME/KEY: modified_base
<222> LOCATION: (1347)..(1347)
<223> OTHER INFORMATION: a, c, t, g, unknown or other
<220> FEATURE:
<221> NAME/KEY: modified_base
<222> LOCATION: (1350)..(1350)
<223> OTHER INFORMATION: a, c, t, g, unknown or other
<220> FEATURE:
<221> NAME/KEY: modified_base
<222> LOCATION: (1353)..(1353)
<223> OTHER INFORMATION: a, c, t, g, unknown or other
<220> FEATURE:
<221> NAME/KEY: modified_base
<222> LOCATION: (1356)..(1356)
<223> OTHER INFORMATION: a, c, t, g, unknown or other
<220> FEATURE:
<221> NAME/KEY: modified_base
<222> LOCATION: (1365)..(1365)
```

```
<223> OTHER INFORMATION: a, c, t, g, unknown or other
<220> FEATURE:
<221> NAME/KEY: modified_base
<222> LOCATION: (1368)..(1368)
<223> OTHER INFORMATION: a, c, t, g, unknown or other
<220> FEATURE:
<221> NAME/KEY: modified_base
<222> LOCATION: (1371)..(1371)
<223> OTHER INFORMATION: a, c, t, g, unknown or other
<220> FEATURE:
<221> NAME/KEY: modified_base
<222> LOCATION: (1374)..(1374)
<223> OTHER INFORMATION: a, c, t, g, unknown or other
<220> FEATURE:
<221> NAME/KEY: modified_base
<222> LOCATION: (1377)..(1377)
<223> OTHER INFORMATION: a, c, t, g, unknown or other
<220> FEATURE:
<221> NAME/KEY: modified_base
<222> LOCATION: (1383)..(1383)
<223> OTHER INFORMATION: a, c, t, g, unknown or other
<220> FEATURE:
<221> NAME/KEY: modified_base
<222> LOCATION: (1389)..(1389)
<223> OTHER INFORMATION: a, c, t, g, unknown or other
<220> FEATURE:
<221> NAME/KEY: modified_base
<222> LOCATION: (1392)..(1392)
<223> OTHER INFORMATION: a, c, t, g, unknown or other
<220> FEATURE:
<221> NAME/KEY: modified_base
<222> LOCATION: (1401)..(1401)
<223> OTHER INFORMATION: a, c, t, g, unknown or other
<220> FEATURE:
<221> NAME/KEY: modified_base
<222> LOCATION: (1407)..(1407)
<223> OTHER INFORMATION: a, c, t, g, unknown or other
<220> FEATURE:
<221> NAME/KEY: modified_base
<222> LOCATION: (1410)..(1410)
<223> OTHER INFORMATION: a, c, t, g, unknown or other
<220> FEATURE:
<221> NAME/KEY: modified_base
<222> LOCATION: (1413)..(1413)
<223> OTHER INFORMATION: a, c, t, g, unknown or other
<220> FEATURE:
<221> NAME/KEY: modified_base
<222> LOCATION: (1422)..(1422)
<223> OTHER INFORMATION: a, c, t, g, unknown or other
<220> FEATURE:
<221> NAME/KEY: modified_base
<222> LOCATION: (1425)..(1425)
<223> OTHER INFORMATION: a, c, t, g, unknown or other
<220> FEATURE:
<221> NAME/KEY: modified_base
<222> LOCATION: (1428)..(1428)
<223> OTHER INFORMATION: a, c, t, g, unknown or other
<220> FEATURE:
<221> NAME/KEY: modified_base
<222> LOCATION: (1431)..(1431)
<223> OTHER INFORMATION: a, c, t, g, unknown or other
<220> FEATURE:
<221> NAME/KEY: modified_base
<222> LOCATION: (1434)..(1434)
<223> OTHER INFORMATION: a, c, t, g, unknown or other
<220> FEATURE:
<221> NAME/KEY: modified_base
<222> LOCATION: (1437)..(1437)
<223> OTHER INFORMATION: a, c, t, g, unknown or other
<220> FEATURE:
<221> NAME/KEY: modified_base
<222> LOCATION: (1440)..(1440)
<223> OTHER INFORMATION: a, c, t, g, unknown or other
<220> FEATURE:
<221> NAME/KEY: modified_base
<222> LOCATION: (1443)..(1443)
<223> OTHER INFORMATION: a, c, t, g, unknown or other
<220> FEATURE:
<221> NAME/KEY: modified_base
```

```
<222> LOCATION: (1455)..(1455)
<223> OTHER INFORMATION: a, c, t, g, unknown or other
<220> FEATURE:
<221> NAME/KEY: modified_base
<222> LOCATION: (1464)..(1464)
<223> OTHER INFORMATION: a, c, t, g, unknown or other
<220> FEATURE:
<221> NAME/KEY: modified_base
<222> LOCATION: (1467)..(1467)
<223> OTHER INFORMATION: a, c, t, g, unknown or other
<220> FEATURE:
<221> NAME/KEY: modified_base
<222> LOCATION: (1470)..(1470)
<223> OTHER INFORMATION: a, c, t, g, unknown or other
<220> FEATURE:
<221> NAME/KEY: modified_base
<222> LOCATION: (1473)..(1473)
<223> OTHER INFORMATION: a, c, t, g, unknown or other
<220> FEATURE:
<221> NAME/KEY: modified_base
<222> LOCATION: (1476)..(1476)
<223> OTHER INFORMATION: a, c, t, g, unknown or other
<220> FEATURE:
<221> NAME/KEY: modified_base
<222> LOCATION: (1479)..(1479)
<223> OTHER INFORMATION: a, c, t, g, unknown or other
<220> FEATURE:
<221> NAME/KEY: modified_base
<222> LOCATION: (1485)..(1485)
<223> OTHER INFORMATION: a, c, t, g, unknown or other
<220> FEATURE:
<221> NAME/KEY: modified_base
<222> LOCATION: (1491)..(1491)
<223> OTHER INFORMATION: a, c, t, g, unknown or other
<220> FEATURE:
<221> NAME/KEY: modified_base
<222> LOCATION: (1494)..(1494)
<223> OTHER INFORMATION: a, c, t, g, unknown or other
<220> FEATURE:
<221> NAME/KEY: modified_base
<222> LOCATION: (1503)..(1503)
<223> OTHER INFORMATION: a, c, t, g, unknown or other
<220> FEATURE:
<221> NAME/KEY: modified_base
<222> LOCATION: (1509)..(1509)
<223> OTHER INFORMATION: a, c, t, g, unknown or other
<220> FEATURE:
<221> NAME/KEY: modified_base
<222> LOCATION: (1512)..(1512)
<223> OTHER INFORMATION: a, c, t, g, unknown or other
<220> FEATURE:
<221> NAME/KEY: modified_base
<222> LOCATION: (1515)..(1515)
<223> OTHER INFORMATION: a, c, t, g, unknown or other
<220> FEATURE:
<221> NAME/KEY: modified_base
<222> LOCATION: (1518)..(1518)
<223> OTHER INFORMATION: a, c, t, g, unknown or other
<220> FEATURE:
<221> NAME/KEY: modified_base
<222> LOCATION: (1521)..(1521)
<223> OTHER INFORMATION: a, c, t, g, unknown or other
<220> FEATURE:
<221> NAME/KEY: modified_base
<222> LOCATION: (1524)..(1524)
<223> OTHER INFORMATION: a, c, t, g, unknown or other
<220> FEATURE:
<221> NAME/KEY: modified_base
<222> LOCATION: (1530)..(1530)
<223> OTHER INFORMATION: a, c, t, g, unknown or other
<220> FEATURE:
<221> NAME/KEY: modified_base
<222> LOCATION: (1548)..(1548)
<223> OTHER INFORMATION: a, c, t, g, unknown or other
<220> FEATURE:
<221> NAME/KEY: modified_base
<222> LOCATION: (1551)..(1551)
<223> OTHER INFORMATION: a, c, t, g, unknown or other
<220> FEATURE:
```

<221> NAME/KEY: modified_base
<222> LOCATION: (1554)..(1554)
<223> OTHER INFORMATION: a, c, t, g, unknown or other
<220> FEATURE:
<221> NAME/KEY: modified_base
<222> LOCATION: (1557)..(1557)
<223> OTHER INFORMATION: a, c, t, g, unknown or other
<220> FEATURE:
<221> NAME/KEY: modified_base
<222> LOCATION: (1560)..(1560)
<223> OTHER INFORMATION: a, c, t, g, unknown or other
<220> FEATURE:
<221> NAME/KEY: modified_base
<222> LOCATION: (1563)..(1563)
<223> OTHER INFORMATION: a, c, t, g, unknown or other

<400> SEQUENCE: 17

```
atgcargtnc arytncarca rccnggngcn garytngtna arccnggngc nwsngtnaar      60
atgwsntgya aracnwsngg ntayacntty acnwsntaya aygtncaytg ggtnaarcar     120
acnccnggnc arggnytnga rtggathggn gcnathtayc cnggnaaygg ngayacnwsn     180
ttyaaycara arttyaargg naargcnacn ytnacngcng ayaarwsnws nwsnacngtn     240
tayatgcary tnwsnwsnyt nacnwsngar gaywsngcng tntaytaytg ygcnmgnwsn     300
aaytaytayg gnwsnwsnta ygtntggtty ttygaygtnt ggggngcngg nacnacngtn     360
acngtnwsnw snggnwsnac nwsnggnwsn ggnaarccng gnwsnggnga rggnwsncar     420
athgtnytnw sncarwsncc nacnathytn wsngcnwsnc cnggngaraa rgtnacnatg     480
acntgymgng cnwsnwsnws ngtnwsntay atggaytggt aycarcaraa rccnggnwsn     540
wsnccnaarc cntggathta ygcnacnwsn aayytngcnw snggngtncc ngcnmgntty     600
wsnggnwsng gnwsnggnac nwsntaywsn ytnacnathw snmgngtnga rgcngargay     660
gcngcnacnt aytaytgyca rcartggath wsnaayccnc cnacnttygg ngcnggnacn     720
aarytngary tnaargartt yccnaarccn wsnacnccnc cnggnwsnws nggnggngcn     780
ccnggnathy tnggnttygt nttyacnytn aargarttya cnytngaytt ywsnacngcn     840
aaracntayg tngaywsnyt naaygtnath mgnwsngcna thggnacncc nytncaracn     900
athwsnwsng gnggnacnws nytnytnatg athgaywsng gnwsnggnga yaayytntty     960
gcngtngayg tnmgnggnat hgayccngar garggnmgnt tyaayaayyt nmgnytnath    1020
gtngarmgna ayaayytnta ygtnacnggn ttygtnaaym gnacnaayaa ygtnttytay    1080
mgnttygcng ayttywsnca ygtnacntty ccnggnacna cngcngtnac nytnwsnggn    1140
gaywsnwsnt ayacnacnyt ncarmgngtn gcnggnathw snmgnacngg natgcarath    1200
aaymgncayw snytnacnac nwsntayytn gayytnatgw sncaywsngg nacnwsnytn    1260
acncarwsng tngcnmgngc natgytnmgn ttygtnacng tnacngcnga rgcnytnmgn    1320
ttymgncara thcarmgngg nttymgnacn acnytngayg ayytnwsngg nmgnwsntay    1380
gtnatgacng cngargaygt ngayytnacn ytnaaytggg gnmgnytnws nwsngtnytn    1440
ccngaytayc ayggncarga ywsngtnmgn gtnggnmgna thwsnttygg nwsnathaay    1500
gcnathytng gnwsngtngc nytnathytn aaytgycayc aycaygcnws nmgngtngcn    1560
mgn                                                                 1563
```

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic

```
                              peptide

<400> SEQUENCE: 18

Gly Ser Thr Ser Gly Ser Gly Lys Pro Gly Ser Gly Glu Gly Ser
1               5                   10                  15

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Trp Ser His Pro Gln Phe Glu Lys
1               5

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Glu Phe Pro Lys Pro Ser Thr Pro Pro Gly Ser Ser Gly Gly Ala Pro
1               5                   10                  15

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Tyr Thr Phe Thr Ser Tyr Asn Met His
1               5                   10

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Ile Tyr Pro Gly Asn Gly Asp Thr Ser Tyr Asn Gln Lys Phe Lys
1               5                   10                  15

Gly

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Gln Leu Arg Pro Asn Tyr Trp Tyr Phe Asp Val
1               5                   10
```

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Arg Ala Ser Ser Ser Val Ser Tyr Met His
1               5                   10

<210> SEQ ID NO 25
<211> LENGTH: 293
<212> TYPE: PRT
<213> ORGANISM: Shigella dysenteriae

<400> SEQUENCE: 25

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Thr Gly Asp Asn
            35                  40                  45

Leu Phe Ala Val Asp Val Arg Gly Ile Asp Pro Glu Glu Gly Arg Phe
        50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg Met Ala Ser Asp Glu
                245                 250                 255

Phe Pro Ser Met Cys Pro Ala Asp Gly Arg Val Arg Gly Ile Thr His
            260                 265                 270

Asn Lys Ile Leu Trp Asp Ser Ser Thr Leu Gly Ala Ile Leu Met Arg
        275                 280                 285

Arg Thr Ile Ser Ser
        290

<210> SEQ ID NO 26
<211> LENGTH: 297
<212> TYPE: PRT
<213> ORGANISM: Escherichia coli

<400> SEQUENCE: 26

Asp Glu Phe Thr Val Asp Phe Ser Ser Gln Lys Ser Tyr Val Asp Ser
1               5                   10                  15

Leu Asn Ser Ile Arg Ser Ala Ile Ser Thr Pro Leu Gly Asn Ile Ser
            20                  25                  30

Gln Gly Gly Val Ser Val Ser Val Ile Asn His Val Leu Gly Gly Asn
        35                  40                  45

Tyr Ile Ser Leu Asn Val Arg Gly Leu Asp Pro Tyr Ser Glu Arg Phe
    50                  55                  60

Asn His Leu Arg Leu Ile Met Glu Arg Asn Asn Leu Tyr Val Ala Gly
65                  70                  75                  80

Phe Ile Asn Thr Glu Thr Asn Ile Phe Tyr Arg Phe Ser Asp Phe Ser
                85                  90                  95

His Ile Ser Val Pro Asp Val Ile Thr Val Ser Met Thr Thr Asp Ser
            100                 105                 110

Ser Tyr Ser Ser Leu Gln Arg Ile Ala Asp Leu Glu Arg Thr Gly Met
        115                 120                 125

Gln Ile Gly Arg His Ser Leu Val Gly Ser Tyr Leu Asp Leu Met Glu
    130                 135                 140

Phe Arg Gly Arg Ser Met Thr Arg Ala Ser Ser Arg Ala Met Leu Arg
145                 150                 155                 160

Phe Val Thr Val Ile Ala Glu Ala Leu Arg Phe Arg Gln Ile Gln Arg
                165                 170                 175

Gly Phe Arg Pro Ala Leu Ser Glu Ala Ser Pro Leu Tyr Thr Met Thr
            180                 185                 190

Ala Gln Asp Val Asp Leu Thr Leu Asn Trp Gly Arg Ile Ser Asn Val
        195                 200                 205

Leu Pro Glu Tyr Arg Gly Glu Glu Gly Val Arg Ile Gly Arg Ile Ser
    210                 215                 220

Phe Asn Ser Leu Ser Ala Ile Leu Gly Ser Val Ala Val Ile Leu Asn
225                 230                 235                 240

Cys His Ser Thr Gly Ser Tyr Ser Val Arg Ser Val Ser Gln Lys Gln
                245                 250                 255

Lys Thr Glu Cys Gln Ile Val Gly Asp Arg Ala Ala Ile Lys Val Asn
            260                 265                 270

Asn Val Leu Trp Glu Ala Asn Thr Ile Ala Ala Leu Leu Asn Arg Lys
        275                 280                 285

Pro Gln Asp Leu Thr Glu Pro Asn Gln
    290                 295

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Thr Tyr Tyr Gly Gly Asp Trp Tyr Phe Asn Val
1               5                   10

```
<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Ala Ser Ser Ser Val Ser Tyr Ile His
1               5                   10

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Trp Thr Ser Asn Pro Pro Thr
1               5
```